US005783701A

United States Patent [19]

Tung et al.

[11] Patent Number: 5,783,701

[45] Date of Patent: Jul. 21, 1998

[54] SULFONAMIDE INHIBITORS OF ASPARTYL PROTEASE

[75] Inventors: Roger D. Tung, Arlington; Mark A. Murcko, Holliston; Govinda Rao Bhisetti, Lexington, all of Mass.

[73] Assignee: Vertex Pharmaceuticals, Incorporated, Cambridge, Mass.

[21] Appl. No.: 393,460

[22] Filed: Feb. 23, 1995

Related U.S. Application Data

[63] Continuation-in-part of Ser. No. 142,327, Sep. 7, 1993, Pat. No. 5,585,397, which is a continuation-in-part of Ser. No. 941,982, Sep. 8, 1992, abandoned.

[51] Int. Cl.$^6$ .......... C07D 215/12

[52] U.S. Cl. .......... 546/169; 548/550; 548/228; 514/424; 514/376; 514/464; 549/475; 549/448

[58] Field of Search .......... 546/169; 548/550, 548/228; 514/424; 549/475

[56] References Cited

U.S. PATENT DOCUMENTS

| | | | |
|---|---|---|---|
| 3,743,722 | 7/1973 | Mohrs et al. | 424/98 |
| 4,330,542 | 5/1982 | Descamps et al. | 424/248.5 |
| 4,629,724 | 12/1986 | Ryono et al. | 514/18 |
| 5,196,438 | 3/1993 | Martin et al. | 514/311 |
| 5,354,866 | 10/1994 | Kempf et al. | 546/265 |

FOREIGN PATENT DOCUMENTS

| | | |
|---|---|---|
| 0 022 118 | 1/1981 | European Pat. Off. . |
| 0 181 071 | 3/1986 | European Pat. Off. . |
| 0 264 795 | 4/1988 | European Pat. Off. . |
| 0 346 847 | 12/1989 | European Pat. Off. . |
| 0 364 804 | 4/1990 | European Pat. Off. . |
| 0 468 641 | 1/1992 | European Pat. Off. . |
| 0 486 948 | 5/1992 | European Pat. Off. . |
| 0 541 168 | 5/1993 | European Pat. Off. . |
| 3542567 | 6/1986 | Germany . |
| 59-046252 | 3/1984 | Japan . |
| 59-048449 | 3/1984 | Japan . |
| 61-071830 | 4/1986 | Japan . |
| 2167759 | 6/1986 | United Kingdom . |
| 2200115 | 7/1988 | United Kingdom . |
| WO 90/07329 | 7/1990 | WIPO . |
| WO 91/00725 | 1/1991 | WIPO . |
| WO 91/18866 | 12/1991 | WIPO . |
| WO 92/08688 | 5/1992 | WIPO . |
| WO 92/08698 | 5/1992 | WIPO . |
| WO 92/08699 | 5/1992 | WIPO . |
| WO 92/08700 | 5/1992 | WIPO . |
| WO 92/08701 | 5/1992 | WIPO . |
| WO 92/17176 | 10/1992 | WIPO . |
| WO 93/23368 | 11/1993 | WIPO . |
| WO 93/23379 | 11/1993 | WIPO . |
| WO 93/23388 | 11/1993 | WIPO . |
| WO 94/04491 | 3/1994 | WIPO . |
| WO 94/04492 | 3/1994 | WIPO . |
| WO 94/04493 | 3/1994 | WIPO . |
| WO 94/10134 | 5/1994 | WIPO . |
| WO 94/10136 | 5/1994 | WIPO . |
| WO 94/18192 | 8/1994 | WIPO . |
| WO 94/19322 | 9/1994 | WIPO . |

OTHER PUBLICATIONS

R.D. Bindal et al., "Ab Initio Calculations on N-Methylmethanesulfonamide and Methyl Methanesulfonate for the Development of Force Field Torsional Parameters and Their Use in the Conformational Analysis of Some Novel Estrogens", *J. Am. Chem. Soc.*, 112, pp. 7861–7868 (1990).

R. Bone et al., "X-ray Crystal Structure of the HIV Protease Complex with L-700,417, an Inhibitor with Pseudo $C_2$ Symmetry", *J. Am. Chem. Soc.*, 113, pp. 9382–9384 (1991).

R.F. Borch et al., "The Cyanohydridoborate Anion as a Selective Reducing Agent", *J. Am. Chem. Soc.*, 93, pp. 2897–2904 (1971).

J.C. Craig et al., "Antiviral Synergy Between Inhibitors of HIV Proteinase and Reverse Transcriptase", *Antiviral Chem. and Chemotherapy*, 4(3), pp. 161–166 (1990).

S. Crawford et al., "A Deletion Mutation in the 5' Part of the pol Gene of Moloney Murine Leukemia Virus Blocks Proteolytic Processing of the gag and pol Polyproteins", *J. Virol.*, 53, pp. 899–907 (1985).

M. Cushman et al., "Delvelopment of Methodology for the Synthesis of Stereochemically Pure Pheψ[$CH_2N$]Pro Linkages in HIV Protease Inhibitors", *J. Org. Chem.*, 56, pp. 4161–4167 (1991).

D.S. Dhanoa et al., "The Synthesis of Potent Macrocyclic Renin Inhibitors", *Tetrahedron Lett.*, 33, pp. 1725–1728 (1992).

G.B. Dreyer et al., "Hydroxyethylene Isostere Inhibitors of Human Immunodeficiency Virus-1 Protease: Structure-Activity Analysis Using Enzyme Kinetics, X-ray Crystallography, and Infected T-Cell Assays", *Biochemistry*, 31, pp. 6646–6659 (1992).

B.E. Evans et al., "A Stereocontrolled Synthesis of Hydroxyethylene Dipeptide Isosteres Using Novel, Chiral Aminoalkyl Epoxides and γ-(Aminoalkyl) γ-Lactones", *J. Org. Chem.*, 50, pp. 4615–4625 (1985).

(List continued on next page.)

*Primary Examiner*—Johann Richter
*Assistant Examiner*—Dominic Keating
*Attorney, Agent, or Firm*—Fish & Neave; James F. Haley, Jr.; Barbara A. Ruskin

[57] ABSTRACT

The present invention relates to a novel class of sulfonamides which are aspartyl protease inhibitors. In one embodiment, this invention relates to a novel class of HIV aspartyl protease inhibitors characterized by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting the activity of HIV aspartyl protease using the compounds of this invention and methods for screening compounds for anti-HIV activity.

18 Claims, 3 Drawing Sheets

OTHER PUBLICATIONS

G.A. Flynn et al., "An Acyl-Iminium Ion Cyclization Route to a Novel Conformationally Restricted Dipeptide Mimic: Applications to Angiotensin-Converting Enzyme Inhibition", *J. Am. Chem. Soc.*, 109, pp., 7914-7915 (1989).

G. Fontenot et al., "PCR Amplification of HIV-1 Proteinase Sequences Directly form Lab Isolates Allows Determination of Five Conserved Domains", *Virology*, 190, pp. 1-10 (1992).

P.G. Gassman and T.L. Guggenheim, "Opening of Epoxides with Trimethylsilyl Cyanide to Produce β-Amino Alcohols", *J. Am. Chem. Soc.*, 104, pp. 5849-5850 (1982).

E.E. Gilbert, "Recent Developments in Preparative Sulfonation and Sulfation", *Synthesis*, 1969, pp. 3-10 (1969).

A. Goldblum, "Modulation of the Affinity of Aspartic Proteases by the Mutated Residues in Active Site Models", *FEBS*, 261, pp. 241-244 (1990).

D. Grobelny et al., "Selective Phosphinate Transition-State Analogue Inhibitors of the Protease of Human Immunodeficiency Virus", *Biochem. Biophys. Res. Commun.*, 169, pp. 1111-1116 (1990).

G.D. Hartman et al., "4-Substituted Thiophene-and Furan-2-sulfonamides as Topical Carbonic Anhydrase Inhibitors", *J. Med. Chem.*, 35, pp. 3822-3831 (1992).

J.R. Huff, "HIV Protease: A Novel Chemotherapeutic Target for AIDS", *Journal of Medicinal Chemistry*, 34(8), pp. 2305-2314 (1991).

K.Y. Hui et al., "A Rational Approach in the Search for Potent Inhibitors Against HIV Proteinase", *FASEB*, 5, pp. 2606-2610 (1991).

N.E. Kohl et al., "Active HIV Protease Is Required for Viral Infectivity", *Proc. Natl. Acad. Sci. USA*, 85, pp. 4686-4690 (1988).

X. Lin et al., "Enzymic Activities of Two-Chain Pepsinogen, Two-Chain Pepsin, and the Amino-Terminal Lobe of Pepsinogen", *J. Biol. Chem.*, 267(24), pp. 17257-17263 (1992).

K.P. Manfredi et al., "Examination of HIV-1 Protease Secondary Structure Specificty Using Conformationally Constrained Inhibitors", *J. Med. Chem.*, 34, pp. 3395-3399 (1991).

F.R. Marshall, "Computer-Aided Drug Design", *Ann. Ref. Pharmacol. Toxicol.*, 27, pp. 193-213 (1987).

J.A. Martin, "Recent Advances in the Design of HIV Proteinase Inhibitors", *Antiviral Research*, 17, pp. 265-278 (1992).

T.D. Meek et al., "Inhibition of HIV-1 Protease in Infected T-Lymphocytes by Synthetic Peptide Analogues", *Nature*, 343, pp. 90-92 (1990).

M. Miller et al., "Structure of Complex of Synthetic HIV-1 Protease with a Substrate-Based Inhibitor at 2.3 Å Resolution", *Science*, 246, pp. 1149-1152 (1989).

M. Miller et al., "Crystal Structure of a Retroviral Protease Proves Relationship to Aspartic Protease Family", *Nature*, 337, pp. 576-579 (1989).

H. Mitsuya and S. Broder, "Inhibition of the in vitro Infectivity and Cytopathic Effect of Human T-Lymphotropic Virus Type III/Lymphoadenopathy-Associated Virus (HTLV-III/LAV) by 2',3'-Dideoxynucleosides", *Proc. Natl. Acad. Sci. USA*, 83, pp. 1911-1915 (1986).

K.H.M. Murthy et al., "Crystal Structures at 2.2-Å Resolution of Hydroxyethylene-Based Inhibitors Bound to Human Immunodeficiency Virus Type 1 Protease Show That the Inhibitors Are Present in Two Distinct Orientations", *J. Biol. Chem.*, 267, pp. 22770-22778 (1992).

J.B. Nichols et al., "A Molecular Mechanics Valence Force Field for Sulfonamides Derived by *ab initio* Methods", *J. Phys. Chem.*, 95, pp. 9803-9811 (1991).

L.E. Overman and L.A. Flippin, "Facile Aminolysis of Epoxides with Diethylaluminum Amides", *Tetrahedron Letters*, 195, pp. 195-198 (1981).

J. Palca, "Shooting at a New HIV Target", *Science*, 247, p. 410 (1990).

L.H. Pearl et al., "A Structural Model for the Retroviral Proteases", *Nature*, 329, pp. 329-351 (1987).

M. Popvic et al., "Detection, Isolation, and Continuos Production of Cytopathic Retroviruses (HTLV-III) from Patients with AIDS and Pre-AIDS", *Science*, 224, pp. 497-500 (1984).

G.H. Posner and D.Z. Rogers, "Organic Reactions at Alumina Surfaces. Mild and Selective Opening of Epoxides by Alcohols, Thiols, Benzeneselenol, Amines, and Acetic Acid", *J. Am. Chem. Soc.*, 99, 8208-18 (1977).

M.D. Power et al., "Nucleotide Sequence of SRV-1, a Type D Simian Acquired Immune Deficiency Syndrome Retrovirus" *Science*, 231, pp. 1567-1573 (1986).

N.A. Roberts, "Rational Design of Peptide-Based HIV Proteinase Inhibitors", *Science*, 248, pp. 358-361 (1990).

S. Scharpe et al., "Proteases and Their Inhibitors: Today and Tomorrow", *Biochimie*, 73, pp. 121-126 (1991).

S.K. Sharma et al., "Could Angiotensin I Be Produced from a Renin Substrate by the HIV-1 Protease?", *Anal. Biochem.*, 198, pp. 363-367 (1991).

H. Toh et al., "Close Structural Resemblance Between Putative Polymerase of a Drosophila Transposable Genetic Element 17.6 and pol Gene Product of Moloney Murine Leukemia Virus", *EMBO J.*, 4, pp. 1267-1272 (1985).

SULFONAMIDE INHIBITORS OF ASPARTYL PROTEASE

CROSS-REFERENCE TO RELATED APPLICATIONS

This application is a continuation-in-part of U.S. patent application Ser. No. 08/142,327, filed Sep. 7, 1993, now U.S. Pat. No. 5,585,397 which is a continuation-in-part of U.S. patent application Ser. No. 07/941,982, filed Sep. 8, 1992, now abandoned.

TECHNICAL FIELD OF THE INVENTION

The present invention relates to a novel class of sulfonamides which are aspartyl protease inhibitors. In one embodiment, this invention relates to a novel class of HIV aspartyl protease inhibitors characterized by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting the activity of HIV aspartyl protease using the compounds of this invention and methods for screening compounds for anti-HIV activity.

BACKGROUND OF THE INVENTION

The human immunodeficiency virus ("HIV") is the causative agent for acquired immunodeficiency syndrome ("AIDS")—a disease characterized by the destruction of the immune system, particularly of $CD4^+$ T-cells, with attendant susceptibility to opportunistic infections—and its precursor AIDS-related complex ("ARC")—a syndrome characterized by symptoms such as persistent generalized lymphadenopathy, fever and weight loss.

As in the case of several other retroviruses, HIV encodes the production of a protease which carries out post-translational cleavage of precursor polypeptides in a process necessary for the formation of infectious virions (S. Crawford et al., "A Deletion Mutation in the 5' Part of the pol Gene of Moloney Murine Leukemia Virus Blocks Proteolytic Processing of the gag and pol Polyproteins", *J. Virol.*, 53, p. 899 (1985)). These gene products include pol, which encodes the virion RNA-dependent DNA polymerase (reverse transcriptase), an endonuclease, HIV protease, and gag, which encodes the core-proteins of the virion (H. Toh et al., "Close Structural Resemblance Between Putative Polymerase of a Drosophila Transposable Genetic Element 17.6 and pol gene product of Moloney Murine Leukemia Virus", *EMBO J.*, 4, p. 1267 (1985); L. H. Pearl et al., "A Structural Model for the Retroviral Proteases", *Nature*, pp. 329–351 (1987); M. D. Power et al., "Nucleotide Sequence of SRV-1, a Type D Simian Acquired Immune Deficiency Syndrome Retrovirus", *Science*, 231, p 1567 (1986)).

A number of synthetic anti-viral agents have been designed to target various stages in the replication cycle of HIV. These agents include compounds which block viral binding to $CD4^+$ T-lymphocytes (for example, soluble CD4), and compounds which interfere with viral replication by inhibiting viral reverse transcriptase (for example, didanosine and zidovudine (AZT)) and inhibit integration of viral DNA into cellular DNA (M. S. Hirsh and R. T. D'Aqulia, "Therapy for Human Immunodeficiency Virus Infection", *N. Eng. J. Med.*, 328, p 1686 (1993)). However, such agents, which are directed primarily to early stages of viral replication, do not prevent the production of infectious virions in chronically infected cells. Furthermore, administration of some of these agents in effective amounts has led to cell-toxicity and unwanted side effects, such as anemia and bone marrow suppression.

More recently, the focus of anti-viral drug design has been to create compounds which inhibit the formation of infectious virions by interfering with the processing of viral polyprotein precursors. Processing of these precursor proteins requires the action of virus-encoded proteases which are essential for replication (Kohl, N. E. et al. "Active HIV Protease is Required for Viral Infectivity" *Proc. Natl. Acad. Sci. USA*, 85, p. 4686 (1988)). The anti-viral potential of HIV protease inhibition has been demonstrated using peptidal inhibitors. Such peptidal compounds, however, are typically large and complex molecules that tend to exhibit poor bioavailability and are not generally consistent with oral administration. Accordingly, the need still exists for compounds that can effectively inhibit the action of viral proteases, for use as agents for preventing and treating chronic and acute viral infections.

SUMMARY OF THE INVENTION

The present invention provides a novel class of compounds, and pharmaceutically acceptable derivatives thereof, that are useful as inhibitors of aspartyl proteases, in particular, HIV aspartyl protease. These compounds can be used alone or in combination with other therapeutic or prophylactic agents, such as anti-virals, antibiotics, immunomodulators or vaccines, for the treatment or prophylaxis of viral infection.

According to a preferred embodiment, the compounds of this invention are capable of inhibiting HIV viral replication in human $CD_4^+$ T-cells. These compounds are useful as therapeutic and prophylactic agents to treat or prevent infection by HIV-1 and related viruses which may result in asymptomatic infection, AIDS-related complex ("ARC"), acquired immunodeficiency syndrome ("AIDS"), or similar disease of the immune system.

It is a principal object of this invention to provide a novel class of sulfonamides which are aspartyl protease inhibitors, and particularly, HIV aspartyl protease inhibitors. This novel class of sulfonamides is represented by formula I:

$$A-(B)_x-\underset{H}{\underset{|}{N}}-\overset{D}{\overset{|}{CH}}-\underset{OH}{\underset{|}{CH}}-CH_2-\underset{D'}{\underset{|}{N}}-SO_2-E \qquad (I)$$

wherein;

A is selected from the group consisting of H; Ht; $-R^1-Ht$; $-R^1-C_1-C_6$ alkyl, which may be optionally substituted with one or more groups selected from the group consisting of hydroxy, $C_1-C_4$ alkoxy, Ht, $-O-Ht$, $-NR^2-CO-N(R^2)(R^2)$ and $-CO-N(R^2)(R^2)$; and $-R^1-C_2-C_6$ alkenyl, which may be optionally substituted with one or more groups selected from the group consisting of hydroxy, $C_1-C_4$ alkoxy, Ht, $-O-Ht$, $-NR^2-CO-N(R^2)(R^2)$ and $-CO-N(R^2)(R^2)$;

each $R^1$ is independently selected from the group consisting of $-C(O)-$, $-S(O)_2-$, $-C(O)-C(O)-$, $-O-C(O)-$, $-O-S(O)_2$, $-NR^2-S(O)_2-$, $-NR^2-C(O)-$ and $-NR^2-C(O)-C(O)-$;

each Ht is independently selected from the group consisting of $C_3-C_7$ cycloalkyl; $C_5-C_7$ cycloalkenyl;

$C_6$–$C_{10}$ aryl; and 5–7 membered saturated or unsaturated heterocycle, containing one or more heteroatoms selected from N, $N(R^2)$, O, S and $S(O)_n$, wherein said heterocycle may optionally be benzofused; and wherein any member of said Ht may be optionally substituted with one or more substituents selected from the group consisting of oxo, $—OR^2$, $—R^2$, $—N(R^2)(R^2)$, $—R^2—OH$, —CN, $—CO_2R^2$, $—C(O)—N(R^2)(R^2)$, $—S(O)_2—N(R^2)(R^2)$, $—N(R^2)—C(O)—R^2$, $—C(O)—R^2$, $—S(O)_n—R^2$, $—OCF_3$, $—S(O)_n—R^7$, methylenedioxy, $—N(R^2)—S(O)_2(R^2)$, halo, $—CF_3$, $—NO_2$, $R^7$ and $—O—R^7$;

each $R^2$ is independently selected from the group consisting of H and $C_1$–$C_3$ alkyl optionally substituted with $R^7$;

B, when present, is $—N(R^2)—C(R^3)(R^3)—C(O)—$;

x is 0 or 1;

each $R^3$ is independently selected from the group consisting of H, Ht, $C_1$–$C_6$ alkyl, $C_2$–$C_6$ alkenyl, $C_3$–$C_6$ cycloalkyl and $C_5$–$C_6$ cycloalkenyl, wherein any member of said $R^3$, except H, may be optionally substituted with one or more substituents selected from the group consisting of $—OR^2$, $—C(O)—NH—R^2$, $—S(O)_n—N(R^2)(R^2)$, Ht, —CN, $—SR^2$, $—CO_2R^2$, $NR^2—C(O)—R^2$;

each n is independently 1 or 2;

D and D' are independently selected from the group consisting of $R^7$; $C_1$–$C_4$ alkyl, which may be optionally substituted with one or more groups selected from $C_3$–$C_6$ cycloalkyl, $—OR^2$, $—R^3$, $—O—R^7$ and $R^7$; $C_2$–$C_4$ alkenyl, which may be optionally substituted with one or more groups selected from the group consisting of $C_3$–$C_6$ cycloalkyl, $—OR^2$, $—R^3$, $—O—R^7$ and $R^7$; $C_3$–$C_6$ cycloalkyl, which may be optionally substituted with or fused with $R^7$; and $C_5$–$C_6$ cycloalkenyl, which may be optionally substituted with or fused with $R^7$;

each $R^7$ is independently selected from the group consisting of phenyl; 3–6 membered carbocyclic ring and 5–6 membered heterocyclic ring containing one or more heteroatoms selected from O, N, S, $S(O)_n$ and $N(R^2)$, wherein said carbocyclic or heterocyclic ring may be saturated or unsaturated and optionally substituted with one or more groups selected from the group consisting of oxo, $—OR^2$, $—R^2$, $—N(R^2)(R^2)$, $—N(R^2)—C(O)—R^2$, $—R^2—OH$, —CN, $—CO_2R^2$, $—C(O)—N(R^2)(R^2)$, halo and $—CF_3$;

E is selected from the group consisting of Ht; O—Ht; Ht—Ht; $—O—R^3$; $—NR^2R^3$; $C_1$–$C_6$ alkyl, which may be optionally substituted with one or more groups selected from the group consisting of $R^4$ and Ht; $C_2$–$C_6$ alkenyl, which may be optionally substituted with one or more groups selected from the group consisting of $R^4$ and Ht; $C_3$–$C_6$ saturated carbocycle, which may optionally be substituted with one or more groups selected from the group consisting of $R^4$ and Ht; and $C_5$–$C_6$ unsaturated carbocycle, which may optionally be substituted with one or more groups selected from the group consisting of $R^4$ and Ht; and each $R^4$ is independently selected from the group consisting of $—OR^2$, $—C(O)—NHR^2$, $—S(O)_2—NHR^2$, halo, $—NR^2—C(O)—R^2$ and —CN.

It is a also an object of this invention to provide pharmaceutical compositions comprising the sulfonamides of formula I and methods for their use as inhibitors of HIV aspartyl protease.

It is a further object of this invention to provide a novel class of HIV aspartyl protease inhibitor compounds characterized by the following novel combination of structural and physicochemical features:

(1) a first and a second hydrogen bond acceptor moiety, at least one of which is more highly polarizable than a carbonyl, said moieties being the same or different, and being capable of hydrogen bonding with the hydrogen atoms of the flap water molecule of an HIV aspartyl protease when the compound is bound thereto;

(2) substantially hydrophobic moieties which associate with the $P_1$ and $P_1'$ binding pockets of said HIV aspartyl protease when the compound is bound thereto;

(3) a third hydrogen bonding moiety, which may be either a hydrogen bond donor or acceptor, capable of simultaneously hydrogen bonding to Asp25 and Asp25' of said HIV aspartyl protease when the compound is bound thereto;

(4) an additional occupied volume of space of at least 100 $Å^3$ when the compound is bound to the active site of said HIV aspartyl protease, said space overlapping with the volume of space that would be filled by a native substrate of said HIV aspartyl protease or a nonhyrolyzable isostere thereof;

(5) a deformation energy of binding of the compound to said HIV aspartyl protease of not greater than 10 kcal/mole; and (6) a neutral or favorable enthalpic contribution from the sum of all electrostatic interactions between the compound and the protease when the compound is bound to said HIV aspartyl protease.

It is also an object of this invention to provide pharmaceutical compositions comprising compounds having the above-mentioned features and methods for their use as inhibitors of HIV aspartyl protease.

It is a further object of this invention to provide a method for identification, design, or prediction of HIV aspartyl protease inhibitors comprising the steps of:

(a) selecting a candidate compound of defined chemical structure containing a first and a second hydrogen bond acceptor moiety, at least one of which is more highly polarizable than a carbonyl, said moieties being the same or different; a third hydrogen bonding moiety, which may be either a hydrogen bond donor or acceptor; and at least two substantially hydrophobic moieties;

(b) determining a low-energy conformation for binding of said compound to the active site of an HIV aspartyl protease;

(c) evaluating the capability of said first and second hydrogen bond acceptor moieties to form hydrogen bonds to the flap water molecule of said HIV aspartyl protease when said compound is bound thereto in said conformation;

(d) evaluating the capability of said substantially hydrophobic moieties to associate with the $P_1$ and $P_1'$ binding pockets of said HIV aspartyl protease when said compound is bound thereto in said conformation;

(e) evaluating the capability of said third hydrogen bonding moiety to form hydrogen bonds to Asp25 and Asp25' of said HIV aspartyl protease when said compound is bound thereto in said conformation;

(f) evaluating the overlap of the occupied volume of said compound when said compound is bound to said HIV aspartyl protease in said conformation and the occupied volume of a native substrate of HIV aspartyl protease or a nonhydrolyzable isostere thereof, when said polypeptide is bound to said HIV aspartyl protease;

(g) evaluating the deformation energy of binding of said compound to said HIV aspartyl protease;

(h) evaluating the enthalpic contribution of the sum of all electrostatic interactions between said compound and said HIV aspartyl protease when said compound is bound thereto in said conformation; and (i) accepting or rejecting said candidate compound as an HIV protease inhbitor based upon the determinations and evaluations carried out in steps (b) through (h).

DETAILED DESCRIPTION OF THE DRAWINGS

Figure 1:
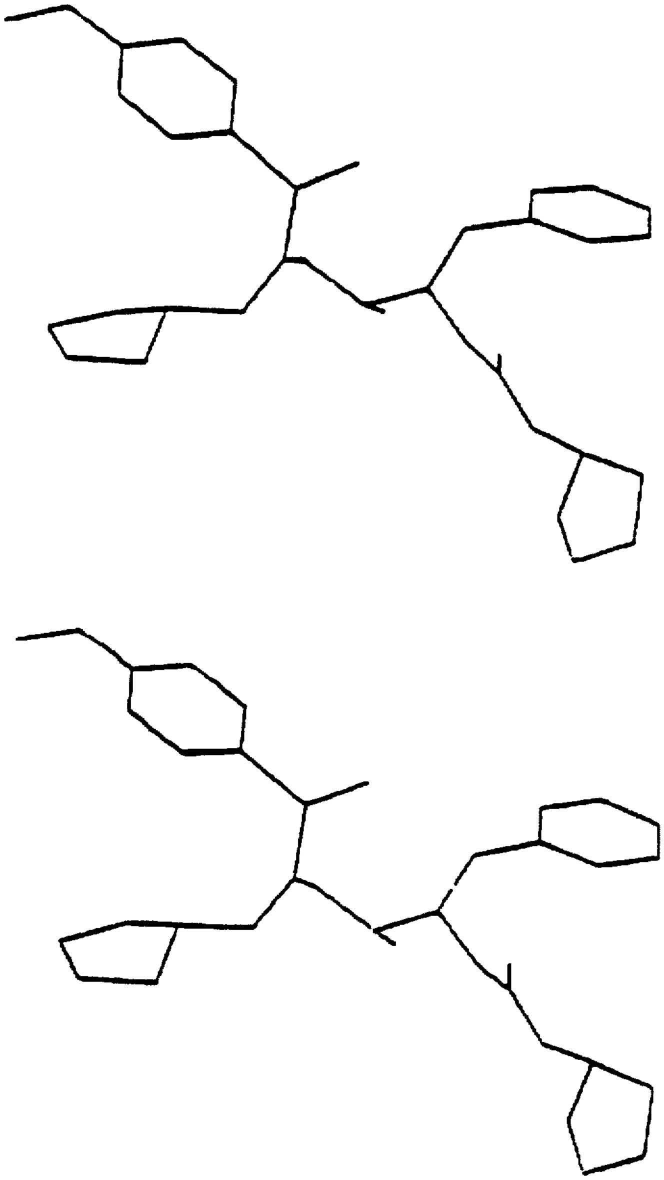
FIG. 1 depicts a stereo drawing of a low-energy conformation of Compound 140, as predicted by computer-modelling.

In order that the invention herein described may be more fully understood, the following detailed description is set forth. In the description, the following abbreviations are used:

| Designation | Reagent or Fragment |
|---|---|
| Ac | acetyl |
| Me | methyl |
| Et | ethyl |
| Bzl | benzyl |
| Trityl | triphenylmethyl |
| Asn | D- or L-asparagine |
| Ile | D- or L-isoleucine |
| Phe | D- or L-phenylalanine |
| Val | D- or L-valine |
| Boc | tert-butoxycarbonyl |
| Cbz | benzyloxycarbonyl (carbobenzyloxy) |
| Fmoc | 9-fluorenylmethoxycarbonyl |
| DCC | dicyclohexylcarbodiimide |
| DIC | diisopropylcarbodiimide |
| EDC | 1-(3-dimethylaminopropyl)-3-ethylcarbodiimide hydrochloride |
| HOBt | 1-hydroxybenzotriazole |
| HOSu | 1-hydroxysuccinimide |
| TFA | trifluoroacetic acid |
| DIEA | diisopropylethylamine |
| DBU | 1,8-diazabicyclo(5.4.0)undec-7-ene |
| EtOAc | ethyl acetate |

The following terms are employed herein:

Unless expressly stated to the contrary, the terms "—$SO_2$—" and "—$S(O)_2$—" as used herein refer to a sulfone or sulfone derivative (i.e., both appended groups linked to the S), and not a sulfinate ester.

For the compounds of formula I, and intermediates thereof, the stereochemistry of the explicitly shown hydroxyl is defined relative to D on the adjacent carbon atom, when the molecule is drawn in an extended zig-zag representation (such as that drawn for compounds of formula XI, XV, XXII, XXIII and XXXI). If both OH and D reside on the same side of the plane defined by the extended backbone of the compound, the stereochemistry of the hydroxyl will be referred to as "syn". If OH and D reside on opposite sides of that plane, the stereochemistry of the hydroxyl will be referred to as "anti".

The term "heterocyclic" refers to a stable 5–7 membered monocycle or 8–11 membered bicyclic heterocycle which is either saturated or unsaturated, and which may be optionally benzofused if monocyclic. Each heterocycle consists of carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. The heterocyclic ring may be attached by any heteroatom of the cycle which results in the creation of a stable structure. Preferred heterocycles defined above include, for example, benzimidazolyl, imidazolyl, imidazolinoyl, imidazolidinyl, quinolyl, isoquinolyl, indolyl, pyridyl, pyrrolyl, pyrrolinyl, pyrazolyl, pyrazinyl, quinoxolyl, piperidinyl, morpholinyl, thiamorpholinyl, furyl, thienyl, triazolyl, thiazolyl, β-carbolinyl, tetrazolyl, thiazolidinyl, benzofuanoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazoyl, benzodioxolyl, thiophenyl, tetrahydrothiophenyl and sulfolanyl.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "hydrophobic" refers to a moiety which tends not to dissolve readily in water and is often fat-soluble. Hydrophobic moieties include, but are not limited to, hydrocarbons, such as alkanes, alkenes, alkynes, cycloalkanes, cycloalkenes, cycloalkynes and aromatic hydrocarbons, such as aryls, certain saturated and unsaturated heterocycles and moieties that are substantially similar to the side chains of hydrophobic natural and unnatural α-amino acids, including valine, leucine, isoleucine, methionine, phenylalanine, α-amino isobutyric acid, alloisoleucine, tyrosine, and tryptophan.

The term "substantially hydrophobic" refers to a hydrophobic moiety which may optionally contain polar atoms or groups in the region of the moiety which are solvent exposed when the compound is bound in the active site of an aspartyl protease.

The term "linker moiety" refers to a group within a compound, said group consisting of a backbone of 1–6 atoms selected from the group consisting of C, N, O, S and P, said backbone being substituted with, fused to or otherwise associated with a substantially hydrophobic group capable of associating with the $P_1$ or $P_1'$ binding pocket of an HIV aspartyl protease when said compound is bound thereto. In alternative embodiments of this invention, such linker moieties may optionally be substituted with a group or groups which occupy a volume of space overlapping with the volume of space that would be filled by a native substrate of HIV aspartyl protease or a nonhydrolyzable isostere thereof.

The term "more highly polarizable than a carbonyl" refers to a moiety having a polarizability (α) greater than that of a carbonyl group of a corresponding aldehyde, ketone, ester or amide moiety.

The term "pharmaceutically effective amount" refers to an amount effective in treating HIV infection in a patient. The term "prophylactically effective amount" refers to an amount effective in preventing HIV infection in a patient. As used herein, the term "patient" refers to a mammal, including a human.

The term "pharmaceutically acceptable carrier or adjuvant" refers to a non-toxic carrier or adjuvant that may be administered to a patient, together with a compound of this invention, and which does not destroy the pharmacological activity thereof.

As used herein, the compounds of this invention, including the compounds of formula I, are defined to include pharmaceutically acceptable derivatives thereof. A "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an anti-virally active metabolite or residue thereof.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds or the invention and their pharmaceutically acceptable acid addition salts.

Salts derived from appropriate bases include alkali metal (e.g., sodium), alkaline earth metal (e.g., magnesium), ammonium and N-$(C_{1-4}$ alkyl$)_4{}^+$ salts.

The term "thiocarbamates" refers to compounds containing the functional group N—$SO_2$—O.

The compounds of this invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. The explicitly shown hydroxyl is also preferred to be syn to D, in the extended zig-zag conformation between the nitrogens shown in compounds of formula I.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

The compounds of the present invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentaneprqpionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The novel sulfonamides of this invention are those of formula I:

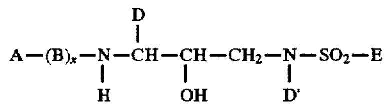
(I)

wherein:

A is selected from the group consisting of H; Ht; —$R^1$—Ht; —$R^1$—$C_1$–$C_6$ alkyl, which may be optionally substituted with one or more groups selected from the group consisting of hydroxy, $C_1$–$C_4$ alkoxy, Ht, —O—Ht, —$NR^2$—CO—$N(R^2)(R^2)$ and —CO—N$(R^2)(R^2)$; and —$R^1$—$C_2$–$C_6$ alkenyl, which may be optionally substituted with one or more groups selected from the group consisting of hydroxy, $C_1$–$C_4$ alkoxy, Ht, —O—Ht, —$NR^2$—CO—$N(R^2)(R^2)$ and —CO—$N(R^2)(R^2)$;

each $R^1$ is independently selected from the group consisting of —C(O)—, —$S(O)_2$—, —C(O)—C(O)—, —O—C(O)—, —O—$S(O)_2$, —$NR^2$—$S(O)_2$—, —NR—C(O)— and —$NR^2$—C(O)—C(O)—;

each Ht is independently selected from the group consisting of $C_3$–$C_7$ cycloalkyl; $C_5$–$C_7$ cycloalkenyl; $C_6$–$C_{10}$ aryl; and 5–7 membered saturated or unsaturated heterocycle, containing one or more heteroatoms selected from N, $N(R^2)$, O, S and $S(O)_n$, wherein said heterocycle may optionally be benzofused; and wherein any member of said Ht may be optionally substituted with one or more substituents selected from the group consisting of oxo, —$OR^2$, —$R^2$, —$N(R^2)(R^2)$, —$R^2$—OH, —CN, —$CO_2R^2$, —C(O)—$N(R^2)(R^2)$, —$S(O)_2$—$N(R^2)(R^2)$, —$N(R^2)$—C(O)—$R^2$, —C(O)—$R^2$, —$S(O)_n$—$R^2$, —$OCF_3$, —$S(O)_n$—$R^7$, methylenedioxy, —$N(R^2)$—$S(O)_2(R^2)$, halo, —$CF_3$, —$NO_2$, $R^7$ and —O—$R^7$;

each $R^2$ is independently selected from the group consisting of H and $C_1$–$C_3$ alkyl optionally substituted with $R^7$;

B, when present, is —$N(R^2)$—$C(R^3)(R^3)$—C(O)—;

x is 0 or 1;

each $R^3$ is independently selected from the group consisting of H, Ht, $C_1$–$C_6$ alkyl, $C_2$–$C_6$ alkenyl, $C_3$–$C_6$ cycloalkyl and $C_5$–$C_6$ cycloalkenyl, wherein any member of said $R^3$, except H, may be optionally substituted with one or more substituents selected from the group consisting of —$OR^2$, —C(O)—NH—$R^2$, —$S(O)_n$—N$(R^2)(R^2)$, Ht, —CN, —$SR^2$, —$CO_2R^2$, $NR^2$—C(O)—$R^2$;

each n is independently 1 or 2;

D and D' are independently selected from the group consisting of $R^7$; $C_1$–$C_4$ alkyl, which may be optionally substituted with one or more groups selected from $C_3$–$C_6$ cycloalkyl, —$OR^2$, —$R^3$, —O—$R^7$ and $R^7$; $C_2$–$C_4$ alkenyl, which may be optionally substituted with one or more groups selected from the group consisting of $C_3$–$C_6$ cycloalkyl, —$OR^2$, —$R^3$, —O—$R^7$ and $R^7$; $C_3$–$C_6$ cycloalkyl, which may be optionally substituted with or fused with $R^7$; and $C_5$–$C_6$ cycloalkenyl, which may be optionally substituted with or fused with $R^7$;

each $R^7$ is independently selected from the group consisting of phenyl; 3–6 membered carbocyclic ring and 5–6 membered heterocyclic ring containing one or more heteroatoms selected from O, N, S, $S(O)_n$ and $N(R^2)$, wherein said carbocyclic or heterocyclic ring may be saturated or unsaturated and optionally substituted with one or more groups selected from the group consisting of oxo, —$OR^2$, —$R^2$, —$N(R^2)(R^2)$, —$N(R^2)$—C(O)—$R^2$, —$R^2$—OH, —CN, —$CO_2R^2$, —C(O)—$N(R^2)(R^2)$, halo and —$CF_3$;

E is selected from the group consisting of Ht; O—Ht; Ht—Ht; —O—$R^3$; —$NR^2R^3$; $C_1$–$C_6$ alkyl, which may be optionally substituted with one or more groups selected from the group consisting of $R^4$ and Ht; $C_2$–$C_6$ alkenyl, which may be optionally substituted with one or more groups selected from the group consisting of $R^4$ and Ht; $C_3$–$C_6$ saturated carbocycle, which may optionally be substituted with one or more groups selected from the group consisting of $R^4$ and Ht; and $C_5$–$C_6$ unsaturated carbocycle, which may optionally be substituted with one or more groups selected from the group consisting of $R^4$ and Ht; and each $R^4$ is independently selected from the group consisting of —$OR^2$, —C(O)—$NHR^7$, —$S(O)_2$—$NHR^2$, halo, —$NR^2$—C(O)—$R^2$ and —CN.

Except where expressly provided to the contrary, as used herein, the definitions of variables A, $R^1$–$R^4$, Ht, B, x, n, D, D', $R^7$ and E are to be taken as they are defined above for the compounds of formula I.

According to one embodiment of this invention, a subclass of compounds are those compounds of formula I, and pharmaceutically acceptable salts thereof, wherein:

A is selected from the group consisting of H; —$R^1$—Ht; —$R^1$—$C_1$–$C_6$ alkyl, which may be optionally substituted with one or more groups selected from the group consisting of hydroxy, $C_1$–$C_4$ alkoxy, Ht and —O—Ht; and —$R^1$—$C_2$–$C_6$ alkenyl, which may be optionally substituted with one or more groups selected from hydroxy, $C_1$–$C_4$ alkoxy, Ht and —O—Ht;

each $R^1$ is independently selected from the group consisting of —C(O)—, —$S(O)_2$—, —C(O)—C(O)—, —O—CO—, —O—$S(O)_2$— and —$NR^2$—$S(O)_2$—;

each Ht is independently selected from the group consisting of $C_3$–$C_7$ cycloalkyl; $C_5$–$C_7$ cycloalkehyl; $C_6$–$C_{10}$ aryl; and 5–7 membered saturated or unsaturated heterocycle, containing one or more heteroatoms selected from N, O and S, which may optionally be benzofused; wherein any member of said Ht may be optionally substituted with one or more substituents selected from the group consisting of oxo, —$OR^2$, —$R^2$, —$N(R^2)_2$, —$R^2$—OH, —CN, —$CO_2R^2$, —C(O)—$N(R^2)_2$ and —$S(O)_2$—$N(R^2)_2$;

each $R^2$ is independently selected from the group consisting of H and $C_1$–$C_3$ alkyl;

B, when present, is —NH—$CH(R^3)$—C(O)—;

x is 0 or 1;

$R^3$ is selected from the group consisting of Ht, $C_1$–$C_6$ alkyl, $C_2$–$C_6$ alkenyl, $C_3$–$C_6$ cycloalkyl and $C_5$–$C_6$ cycloalkenyl, wherein any member of said $R^3$ may be optionally substituted with one or more substituents selected from the group consisting of —$OR^2$, —C(O)—NH—$R^2$, —$S(O)_n$—$N(R^2)_2$, Ht and —CN;

n is 1 or 2;

D and D' are independently selected from the group consisting of $R^7$; $C_1$–$C_4$ alkyl, which may be optionally substituted with $C_3$–$C_6$ cycloalkyl or $R^7$; $C_2$–$C_4$ alkenyl, which may be optionally substituted with $C_3$–$C_6$ cycloalkyl or $R^7$; $C_3$–$C_6$ cycloalkyl, which may be optionally substituted or fused with $R^7$; and $C_5$–$C_6$ cycloalkenyl, which may be optionally substituted or fused with $R^7$; with the proviso that when D is attached to N, D may not be methyl or $C_2$ alkenyl;

$R^7$ is selected from the group consisting of phenyl; 3–6 membered carbocyclic ring and 5–6 membered heterocyclic ring containing one or more heteroatoms selected from O, N and S, wherein said carbocyclic or heterocyclic ring may be saturated or unsaturated and optionally substituted with one or more groups selected from the group consisting of oxo, —$OR^2$, —$R^2$, —$N(R^2)_2$, —$N(R^2)$—$C(O)R^2$, —$R^2$—OH, —CN, —$CO_2R^2$, —C(O)—$N(R^2)_2$, halo and —$CF_3$;

E is selected from the group consisting of Ht; —O—$R^3$; —$NR^2R^5$; $C_1$–$C_6$ alkyl, which may be optionally substituted with one or more $R^4$ or Ht; $C_2$–$C_6$ alkenyl, which may be optionally substituted with one or more $R^4$ or Ht; $C_3$–$C_6$ saturated carbocycle, which may optionally be substituted with one or more $R^4$ or Ht; and $C_5$–$C_6$ unsaturated carbocycle, which may optionally be substituted with one or more $R^4$ or Ht;

each $R^4$ is independently selected from the group consisting of —$OR^2$, —C(O)—$NHR^2$, —$S(O)_2$—$NHR^2$, halo and —CN; and each $R^5$ is independently selected from the group consisting of H and $R^3$, with the proviso that at least one $R^5$ is not H.

A preferred subclass of compounds of this invention are those compounds of formula I having a molecular weight of less than about 700 g/mole. More preferably, the subclass of compounds of formula I have a molecular weight of less than about 600 g/mole.

Other preferred subclasses of this invention are those compounds of formulas XXII, XXIII and XXXI:

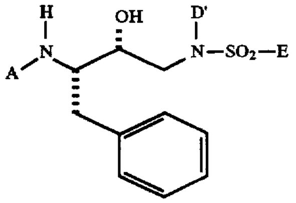

(XXII)

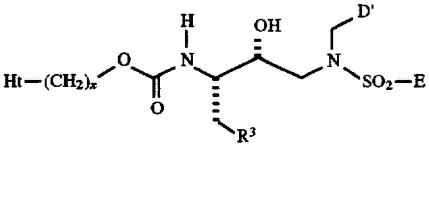

(XXIII)

-continued

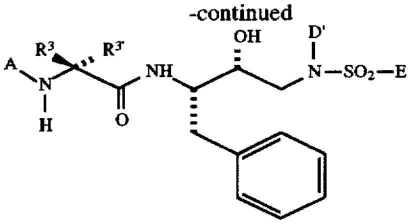

(XXXI)

wherein A, $R^3$, Ht, D, D', x and E are as defined above for compounds of formula I. For ease of reference, the two $R^3$ moieties present in formula XXXI have been labeled $R^3$ and $R^{3'}$.

For compounds of formula XXII, most preferred compounds are those wherein A is $R^1$—Ht and D' is $C_1$–$C_3$ alkyl or $C_3$ alkenyl, wherein said alkyl or alkenyl may optionally be substituted with one or more groups selected from the group consisting of $C_3$–$C_6$ cycloalkyl, —$OR^2$, —O—$R^7$ and $R^7$ (with all other variables being defined as above for compounds of formula I). For compounds of formula XXIII, most preferred compounds are those wherein $R^3$ is $C_1$–$C_6$ alkyl, $C_2$–$C_6$ alkenyl, $C_5$–$C_6$ cycloalkyl, $C_5$–$C_6$ cycloalkenyl or a 5–6 membered saturated or unsaturated heterocycle, wherein any member of said $R^3$ may be optionally substituted with one or more substituents selected from the group consisting of —$OR^2$, —C(O)—NH—$R^2$, —$S(O)_nN(R^2)(R^2)$, Ht, —CN, —$SR^2$, —$C(O)_2R^2$ and $NR^2$—C(O)—$R^2$ and D' is $C_1$–$C_3$ alkyl or $C_3$ alkenyl, wherein said alkyl or alkenyl may optionally be substituted with one or more groups selected from the group consisting of $C_3$–$C_6$ cycloalkyl, —$OR^2$, —O—$R^7$ and $R^7$ (with all other variables being defined as above for compounds of formula I).

For compounds of formula XXXI, most preferred compounds are those wherein A is $R^1$—Ht, each $R^3$ is independently $C_1$–$C_6$ alkyl which may be optionally substituted with a substituent selected from the group consisting of —$OR^2$, —C(O)—NH—$R^2$, —$S(O)_nN(R^2)(R^2)$, Ht, —CN, —$SR^2$, —$CO_2R^2$ and —$NR^2$—C(O)—$R^2$; D' is $C_1$–$C_4$ alkyl, which may be optionally substituted with a group selected from the group consisting of $C_3$–$C_6$ cycloalkyl, —$OR^2$, —O—$R^7$; and E is Ht, Ht—Ht and —$NR^2R^3$.

Sulfonamides of this invention include the following specific compounds contained in Tables I–VI. In Tables I–IV and VI, A is attached through the right-most bond, unless otherwise expressly noted. All other substituents in Tables I–VI are attached via the left-most bond, unless otherwise expressly noted.

TABLE I

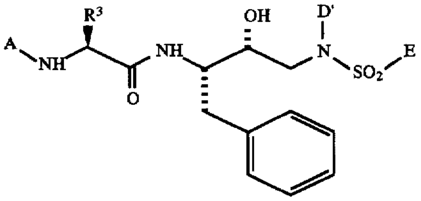

| COMPOUND | A | $R^3$ | D' | E |
| --- | --- | --- | --- | --- |
| 1 | 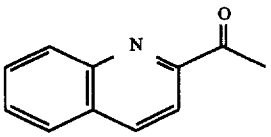 | 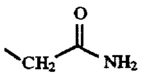 | 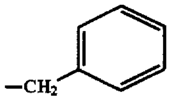 | 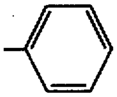 |
| 2 | 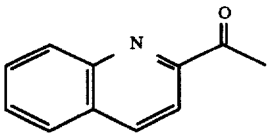 | 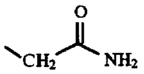 | 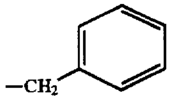 | 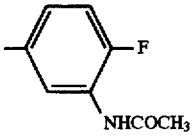 + 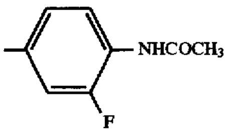 (2:1) |
| 3 | 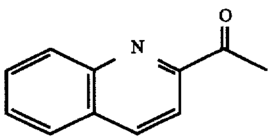 | 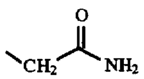 | 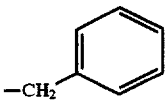 | 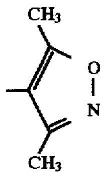 |

TABLE I-continued
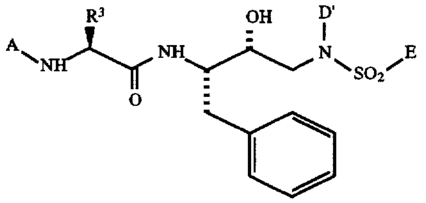
| COMPOUND | A | $R^3$ | D' | E |
|---|---|---|---|---|
| 4 | 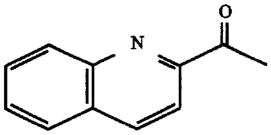 | 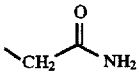 | 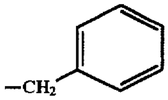 | 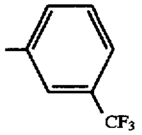 |
| 5 | 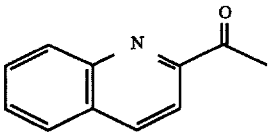 | 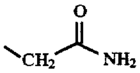 | 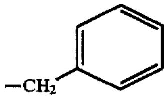 | 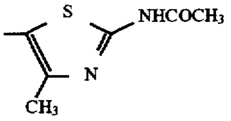 |
| 6 | 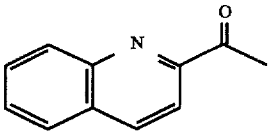 | 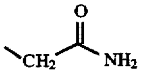 | 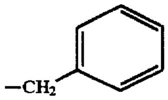 | 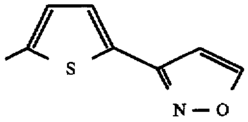 |
| 7 | 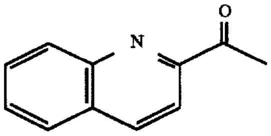 | 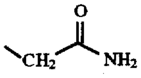 | 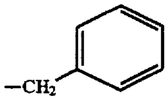 | 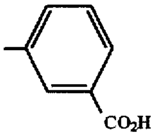 |
| 8 | 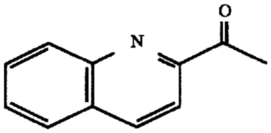 | 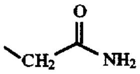 | 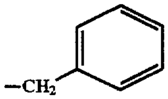 | $CH_3$ |
| 9 | 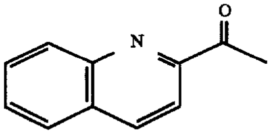 | 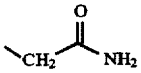 | 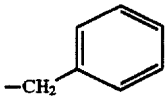 | 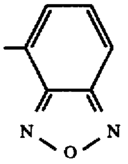 |
| 10 | 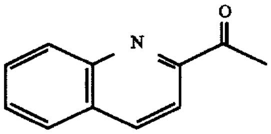 | 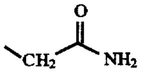 | 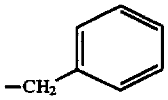 | 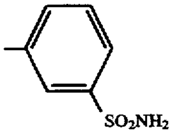 |
| 11 | 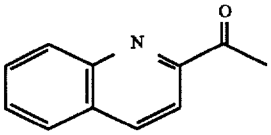 | 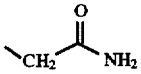 | 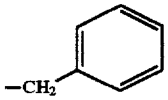 | 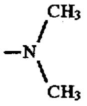 |
| 12 | 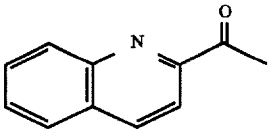 | 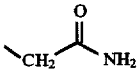 | 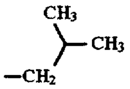 | 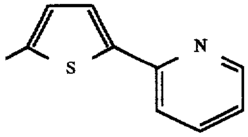 |

TABLE I-continued
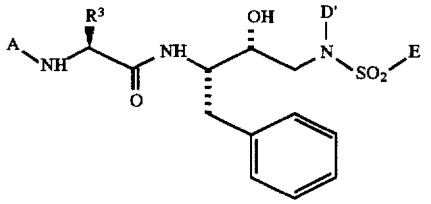
| COMPOUND | A | $R^3$ | D' | E |
|---|---|---|---|---|
| 13 | 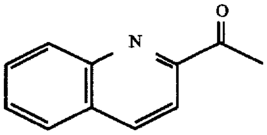 | 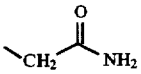 | 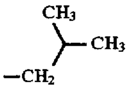 | 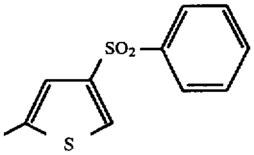 |
| 14 | 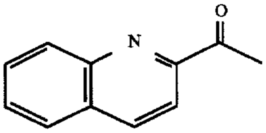 | 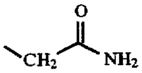 | 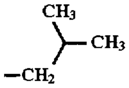 | 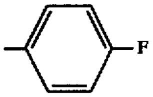 |
| 15 | 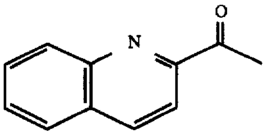 | 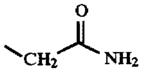 | 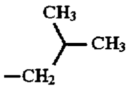 | 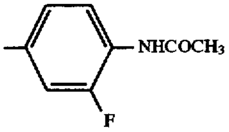 |
| 16 | 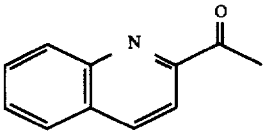 | 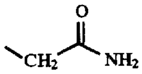 | 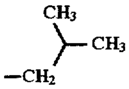 | 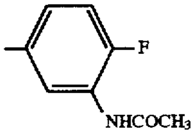 |
| 17 | 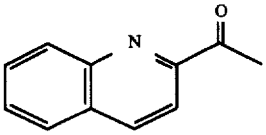 | 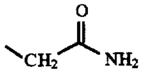 | 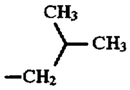 | 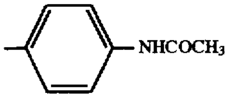 |
| 18 | 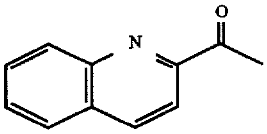 | 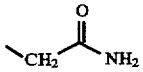 | 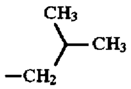 | 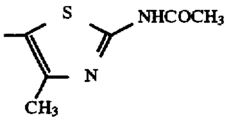 |
| 19 | 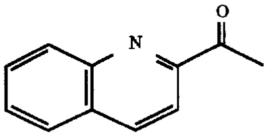 | 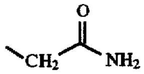 | 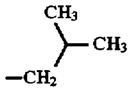 | 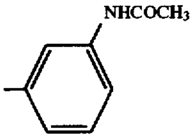 |
| 20 | 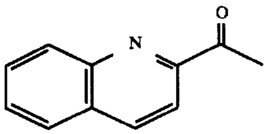 | 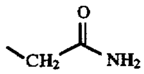 | 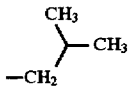 | 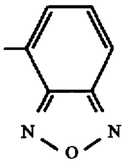 |
| 21 | 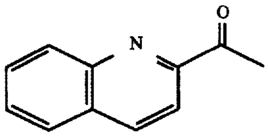 | 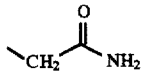 | 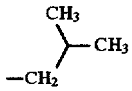 | 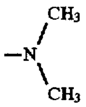 |

TABLE I-continued
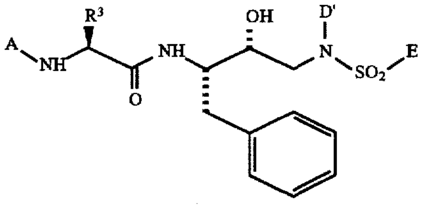
| COMPOUND | A | $R^3$ | D' | E |
|---|---|---|---|---|
| 22 | 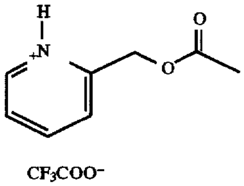 | 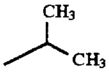 | 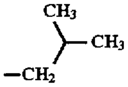 | 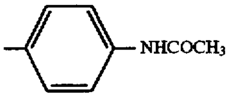 |
| 23 | 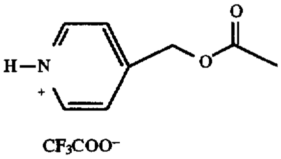 | 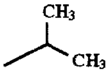 | 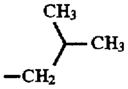 | 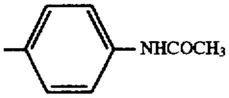 |
| 24 | 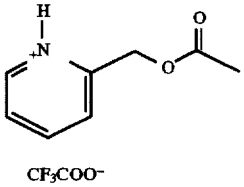 | 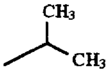 | 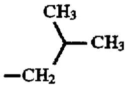 | 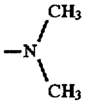 |
| 25 | 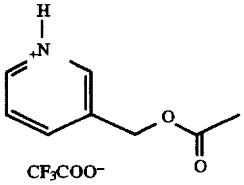 | 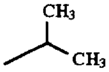 | 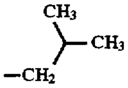 | 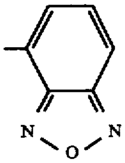 |
| 26 | 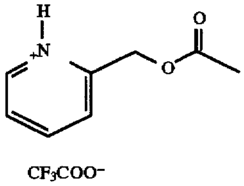 | 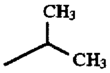 | 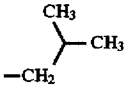 | 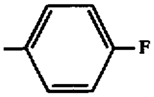 |

TABLE II
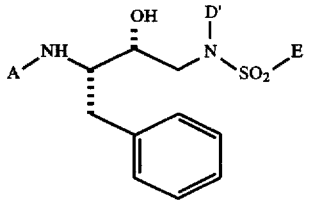
| COMPOUND | A | D' | E |
|---|---|---|---|
| 27 | 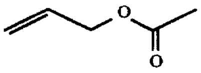 | 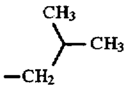 | 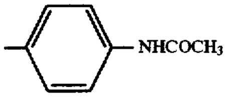 |
| 28 | 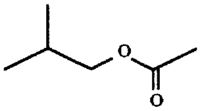 | 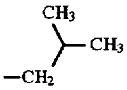 | 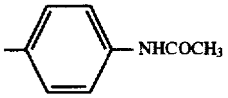 |
| 29 | 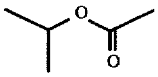 | 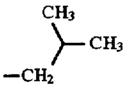 | 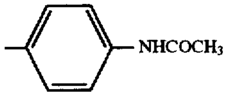 |
| 30 | 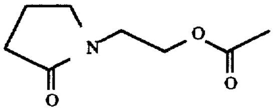 | 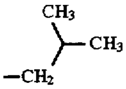 | 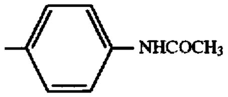 |
| 31 | 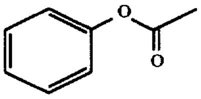 | 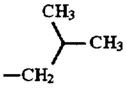 | 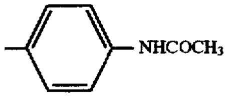 |
| 32 | 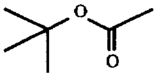 | 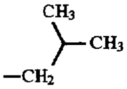 | 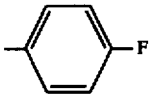 |
| 33 | 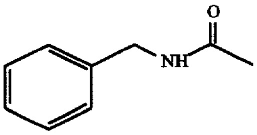 | 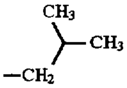 | 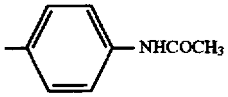 |
| 34 | 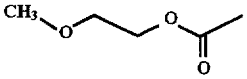 | 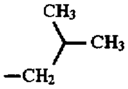 | 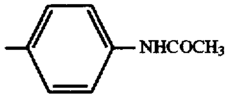 |
| 35 | 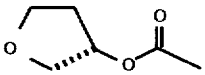 | 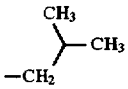 | 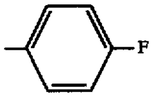 |
| 36 | 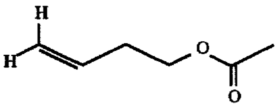 | 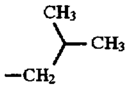 | 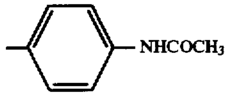 |
| 37 | 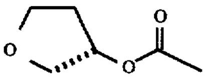 | 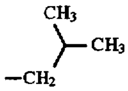 | 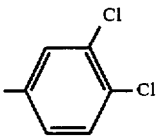 |

TABLE II-continued
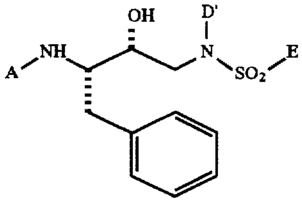
| COMPOUND | A | D' | E |
|---|---|---|---|
| 38 | 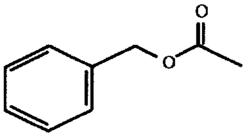 | 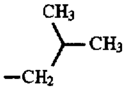 | 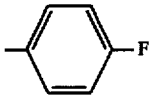 |
| 39 | 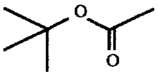 | 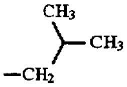 | 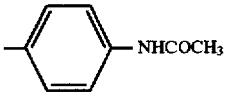 |
| 40 | 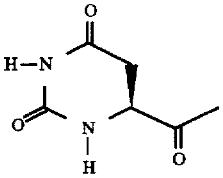 | 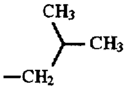 | 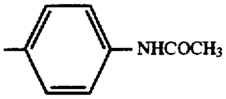 |
| 41 | 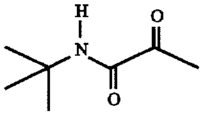 | 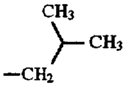 | 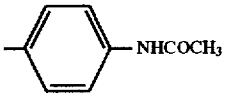 |
| 42 | 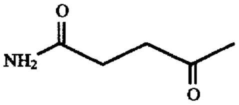 | 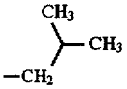 | 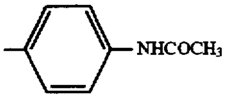 |
| 43 | 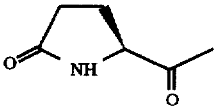 | 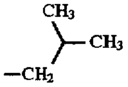 | 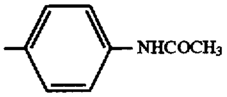 |
| 44 | 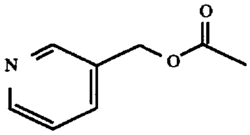 | 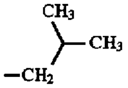 | 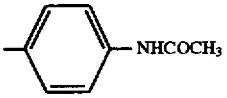 |
| 45 | 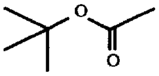 | 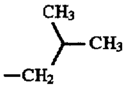 | 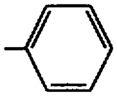 |
| 46 | 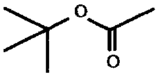 | 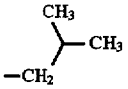 | 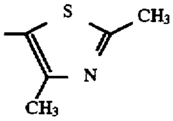 |
| 47 | 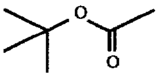 | 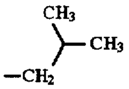 | 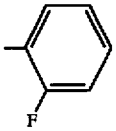 |

TABLE II-continued
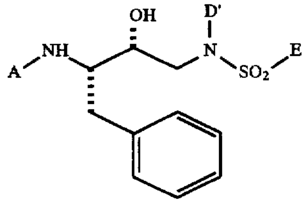
| COMPOUND | A | D' | E |
|---|---|---|---|
| 48 | 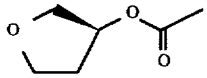 | 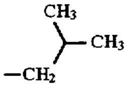 | 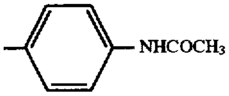 |
| 49 | 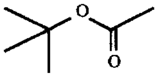 | 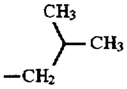 | 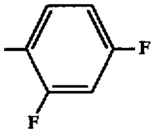 |
| 50 | 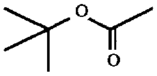 | 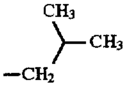 | 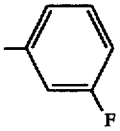 |
| 51 | 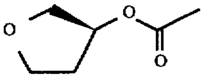 | 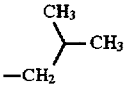 | 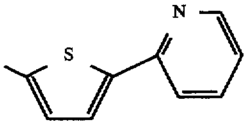 |
| 52 | 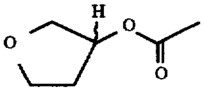 | 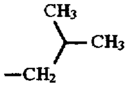 | 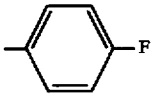 |
| 53 | 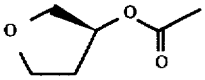 | 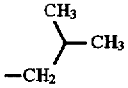 | 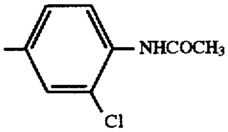 |
| 54 | 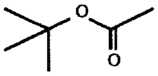 | 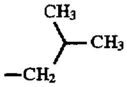 | 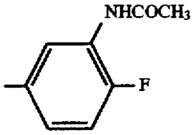 |
| 55 | 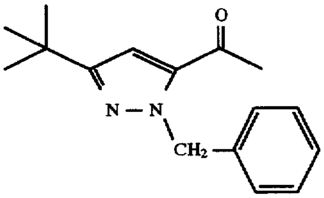 | 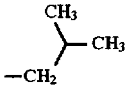 | 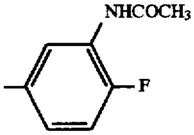 |
| 56 | 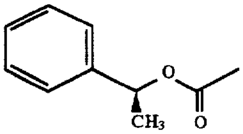 | 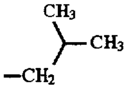 | 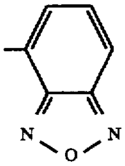 |

TABLE II-continued
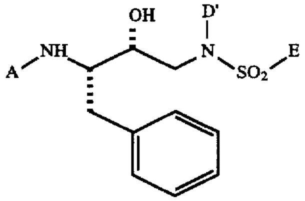
| COMPOUND | A | D' | E |
|---|---|---|---|
| 57 | 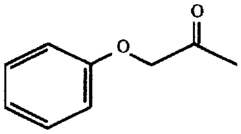 | 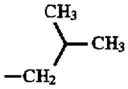 | 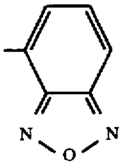 |
| 58 | 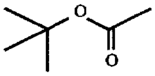 | 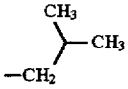 | 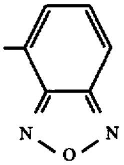 |
| 59 | 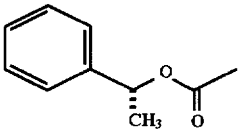 | 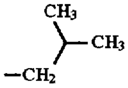 | 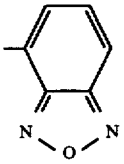 |
| 60 | 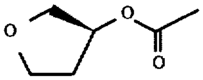 | 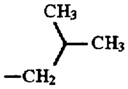 | 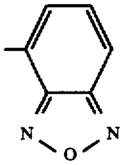 |
| 61 | 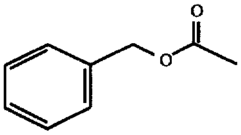 | 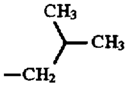 | 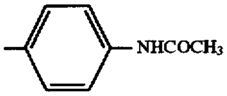 |
| 62 | 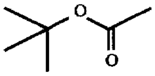 | 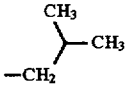 | 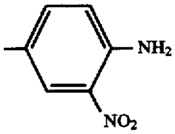 |
| 63 | 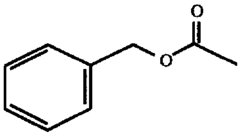 | 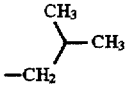 | 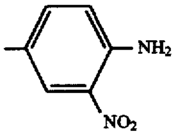 |
| 64 | 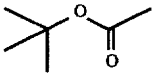 | 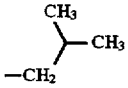 | 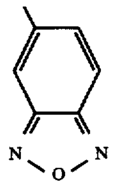 |

TABLE II-continued
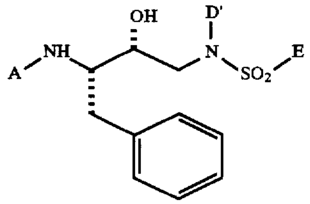
| COMPOUND | A | D' | E |
| --- | --- | --- | --- |
| 65 | 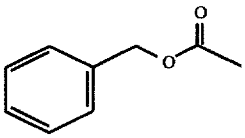 | 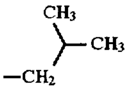 | 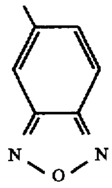 |
| 66 | 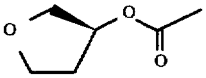 | 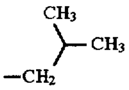 | 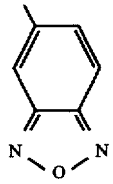 |
| 67 | 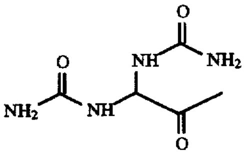 | 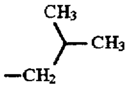 | 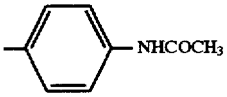 |
| 68 | 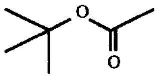 | 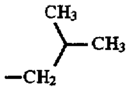 | 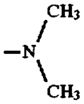 |
| 69 | 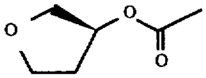 | 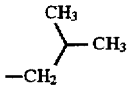 | 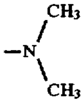 |
| 70 | 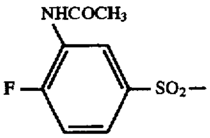 | 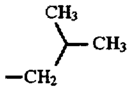 | 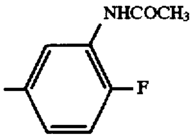 |
| 71 | 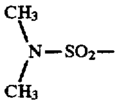 | 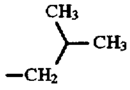 | 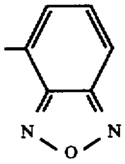 |
| 72 | 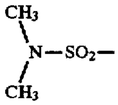 | 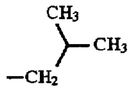 | 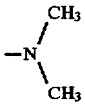 |

TABLE II-continued
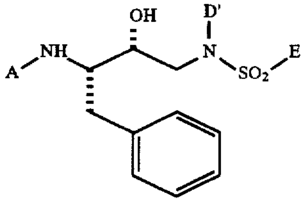
| COMPOUND | A | D' | E |
|---|---|---|---|
| 73 | 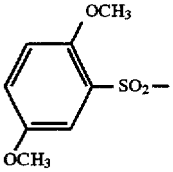 | 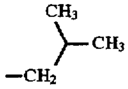 | 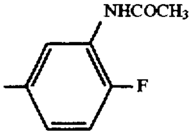 |
| 74 | 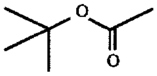 | 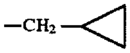 | 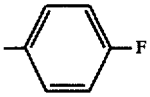 |
| 75 | 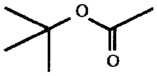 | 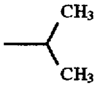 | 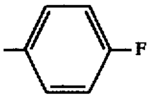 |
| 76 | 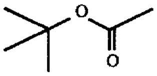 | 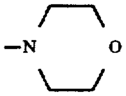 | 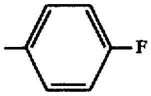 |
| 77 | 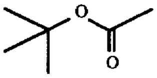 | 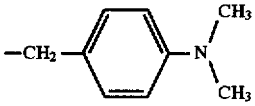 | 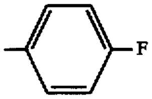 |
| 78 | 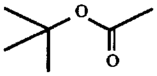 | 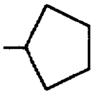 | 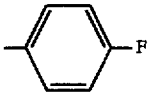 |
| 79 | 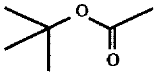 | 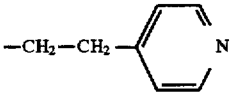 | 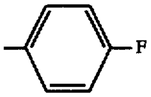 |
| 80 | 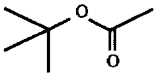 | 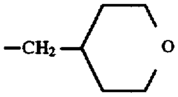 | 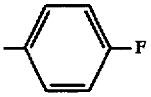 |
| 81 | 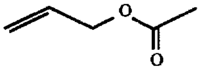 | 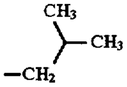 | 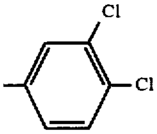 |
| 82 | 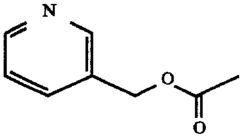 | 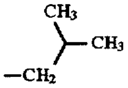 | 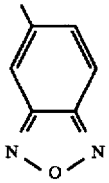 |

TABLE II-continued
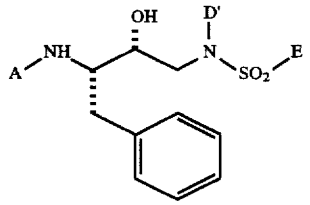
| COMPOUND | A | D' | E |
|---|---|---|---|
| 83 | 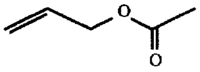 | 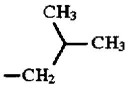 | 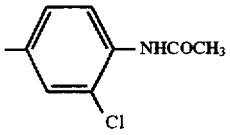 |
| 84 | 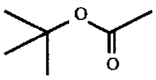 | 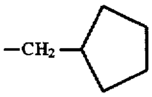 | 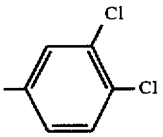 |
| 86 | 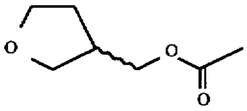 | 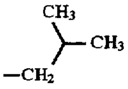 | 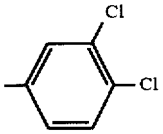 |
| 86 | 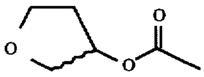 | 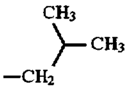 | 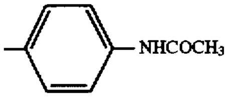 |
| 87 | 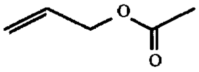 | 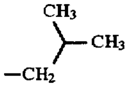 | 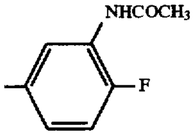 |
| 88 | 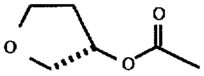 | 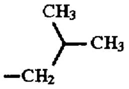 | 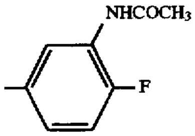 |
| 89 | 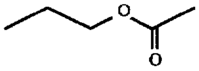 | 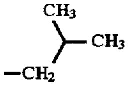 | 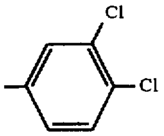 |
| 90 | 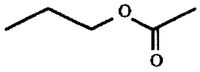 | 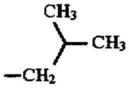 | 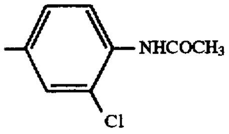 |
| 91 | 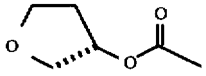 | 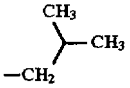 | 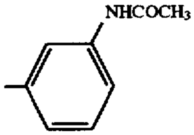 |
| 92 | 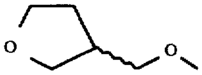 | 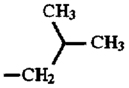 | 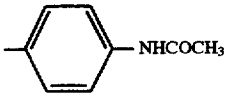 |

TABLE II-continued
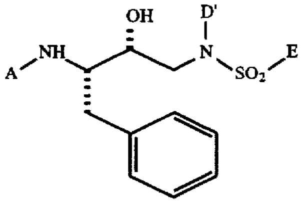
| COMPOUND | A | D' | E |
|---|---|---|---|
| 93 | 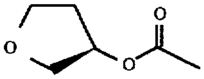 | 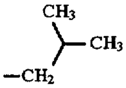 | 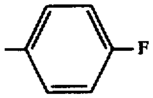 |
| 94 | 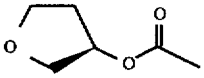 | 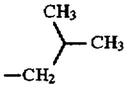 | 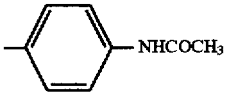 |
| 95 | 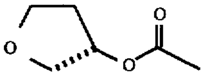 | 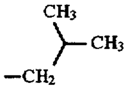 | 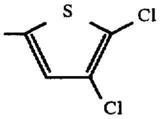 |
| 96 | 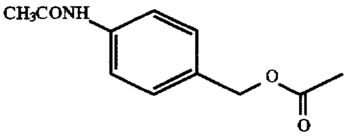 | 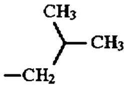 | 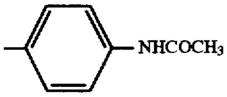 |
| 97 | 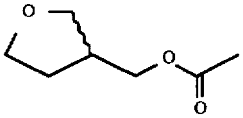 | 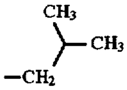 | 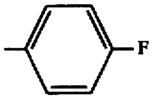 |
| 98 | 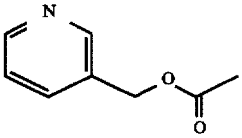 | 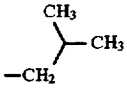 | 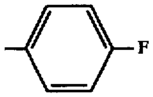 |
| 99 | 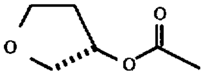 | 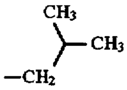 | 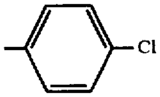 |
| 100 | 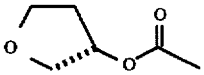 | 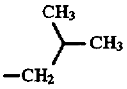 | 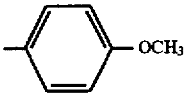 |
| 101 | 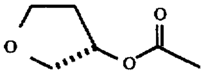 | $CH_3$ | 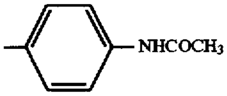 |
| 102 | 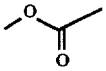 | 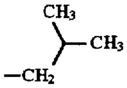 | 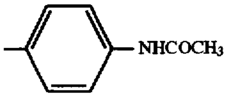 |
| 103 | 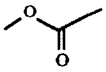 | 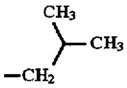 | 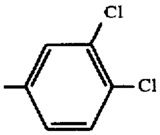 |

TABLE II-continued
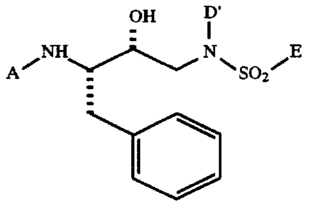
| COMPOUND | A | D' | E |
|---|---|---|---|
| 104 | 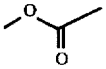 | 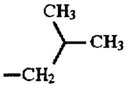 | 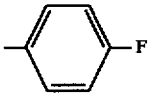 |
| 105 | 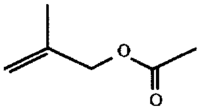 | 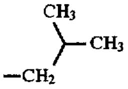 | 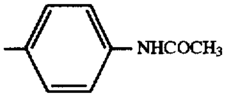 |
| 106 | 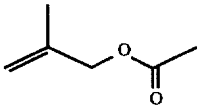 | 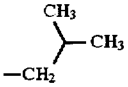 | 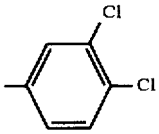 |
| 107 | 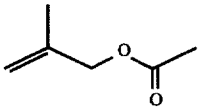 | 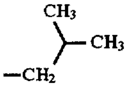 | 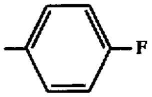 |
| 108 | 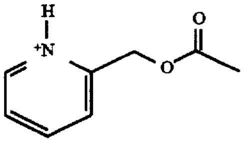 $CF_3COO^-$ | 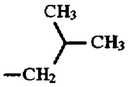 | 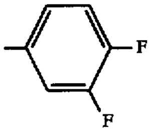 |
| 109 | 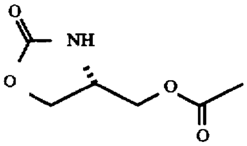 | 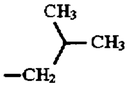 | 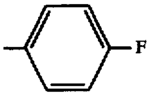 |
| 110 | 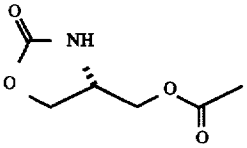 | 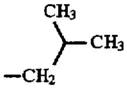 | 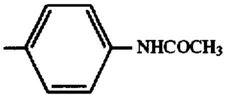 |
| 111 | 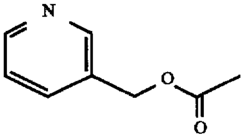 | 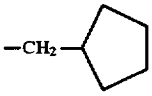 | 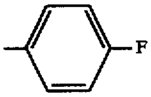 |
| 112 | 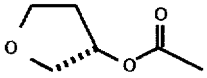 | 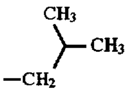 | 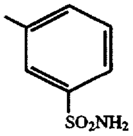 |

TABLE II-continued
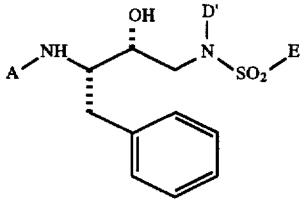
| COMPOUND | A | D' | E |
|---|---|---|---|
| 113 | 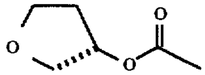 | 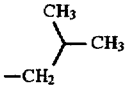 | 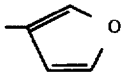 |
| 114 | 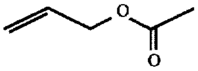 | 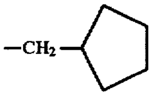 | 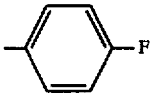 |
| 115 | 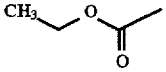 | 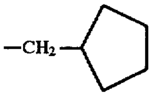 | 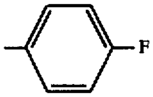 |
| 116 | 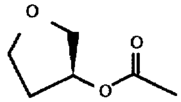 | 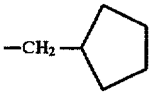 | 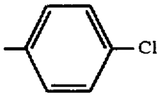 |
| 117 | 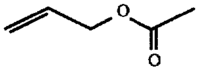 | 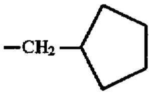 | 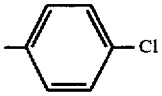 |
| 118 | 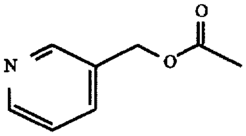 | 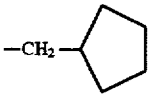 | 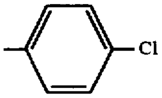 |
| 119 | 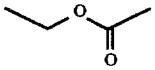 | 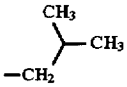 | 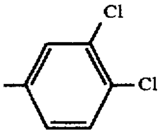 |
| 120 | 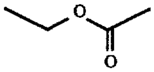 | 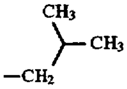 | 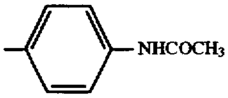 |
| 121 | 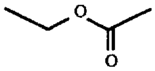 | 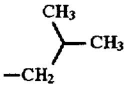 | 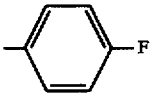 |
| 112 | 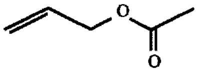 | 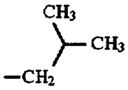 | 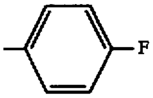 |
| 123 | 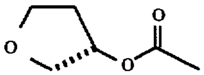 | 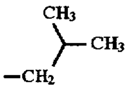 | 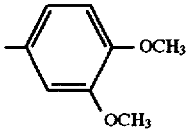 |

TABLE II-continued
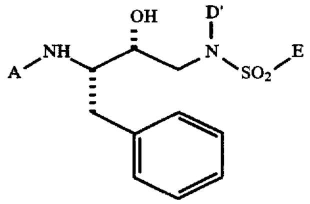
| COMPOUND | A | D' | E |
|---|---|---|---|
| 124 | 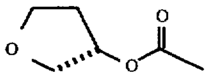 | 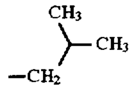 | 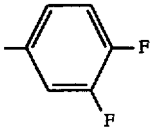 |
| 125 | 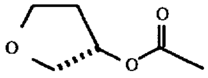 | 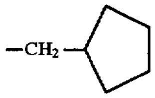 | 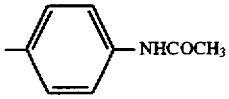 |
| 126 | 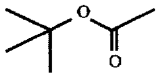 | $CH_3$ | 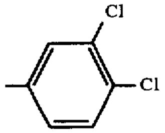 |
| 127 | 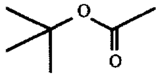 | $CH_3$ | 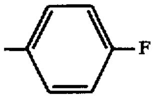 |
| 128 | 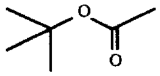 | $CH_3$ | 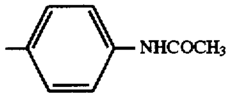 |
| 129 | 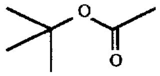 | 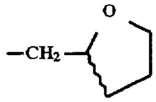 | 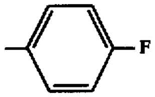 |
| 130 | 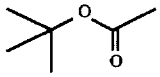 | 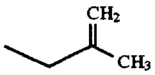 | 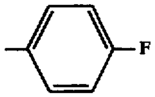 |
| 131 | 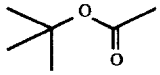 | 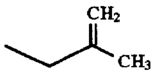 | 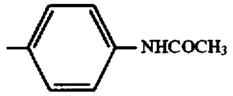 |
| 132 | 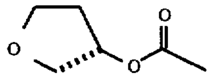 | 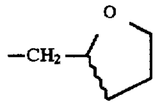 | 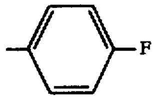 |
| 133 | 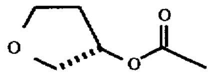 | 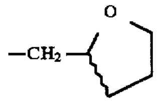 | 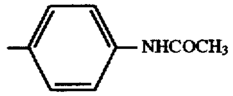 |
| 134 | 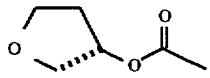 | 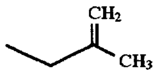 | 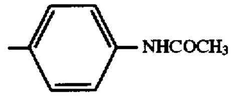 |
| 135 | 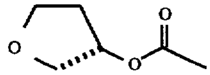 | 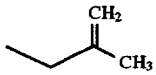 | 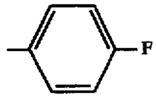 |

TABLE II-continued
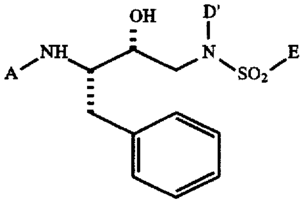
| COMPOUND | A | D' | E |
|---|---|---|---|
| 136 | 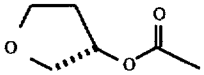 | 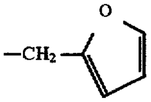 | 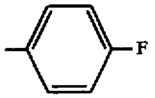 |
| 137 | 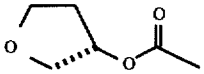 | 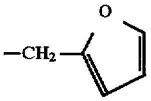 | 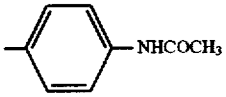 |
| 138 | 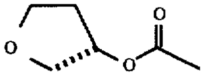 | 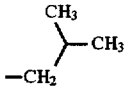 | 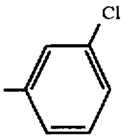 |
| 139 | 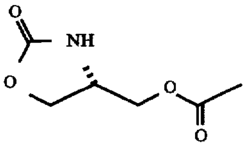 | 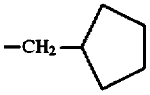 | 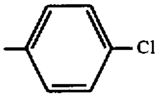 |
| 140 | 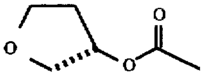 | 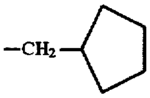 | 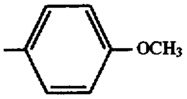 |
| 141 | 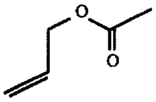 | 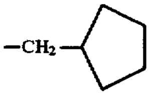 | 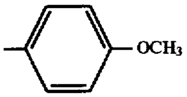 |
| 142 | 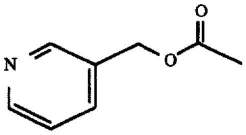 | 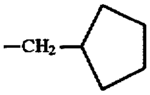 | 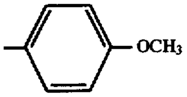 |
| 143 | 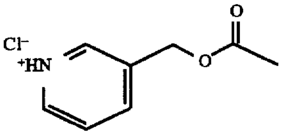 | 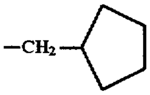 | 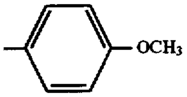 |
| 144 | 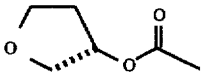 | 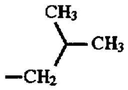 | 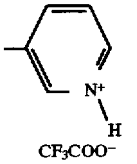 |
| 145 | 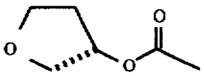 | 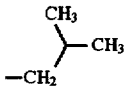 | 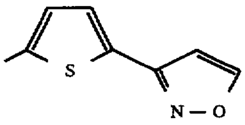 |

TABLE II-continued
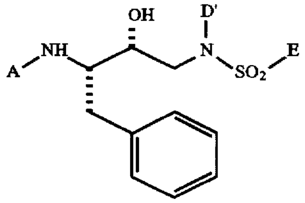
| COMPOUND | A | D' | E |
|---|---|---|---|
| 146 | 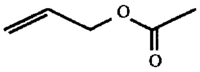 | 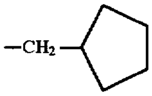 | 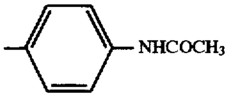 |
| 147 | 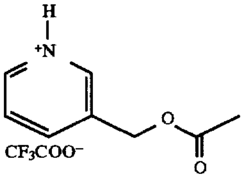 | 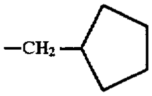 | 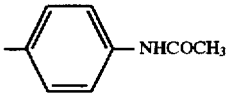 |
| 148 | 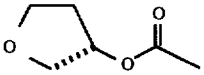 | 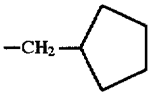 | 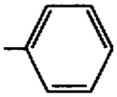 |
| 149 | 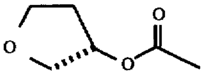 | 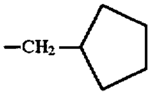 | 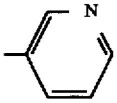 |
| 150 | 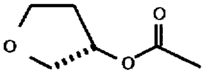 | 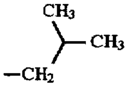 | 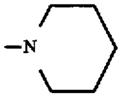 |
| 151 | 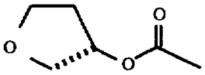 | 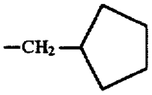 | 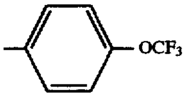 |
| 152 | 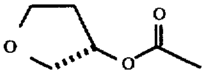 | 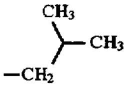 | 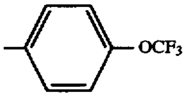 |
| 153 | 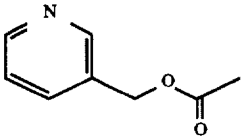 | 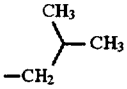 | 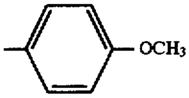 |
| 154 | 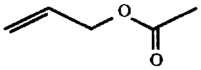 | 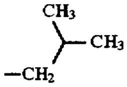 | 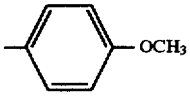 |
| 155 | 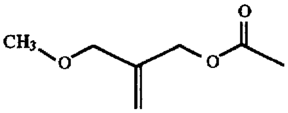 | 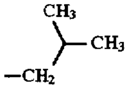 | 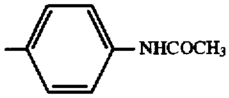 |

TABLE II-continued
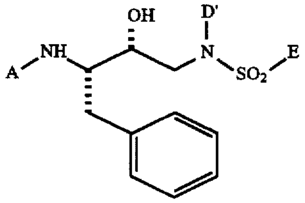
| COMPOUND | A | D' | E |
|---|---|---|---|
| 156 | 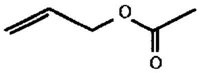 | 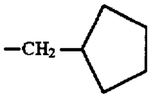 | 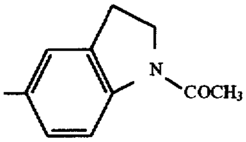 |
| 157 | 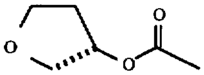 | 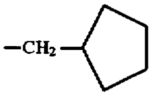 | 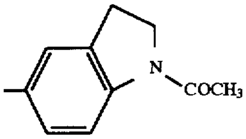 |
| 158 | 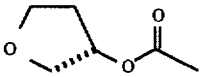 | 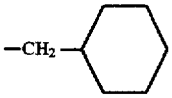 | 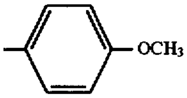 |
| 159 | 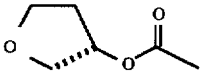 | 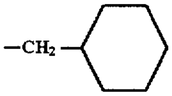 | 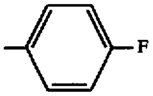 |
| 160 | 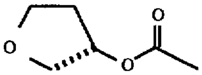 | 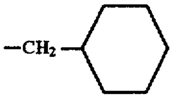 | 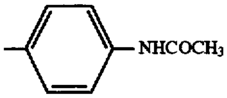 |
| 161 | 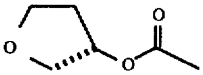 | 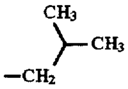 | 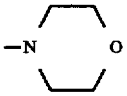 |
| 162 | 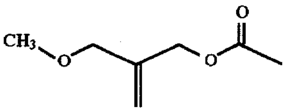 | 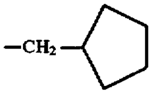 | 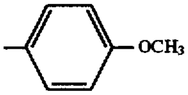 |
| 163 | 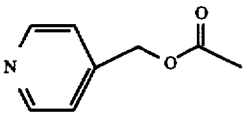 | 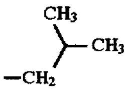 | 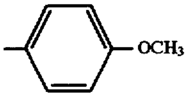 |
| 164 | 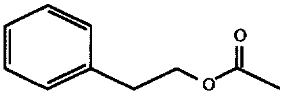 | 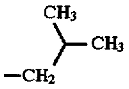 | 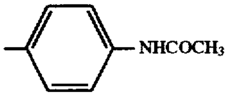 |
| 165 | 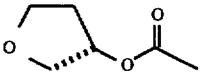 | 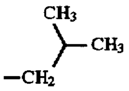 | 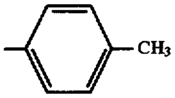 |
| 166 | 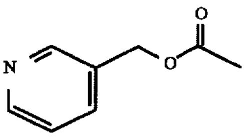 | 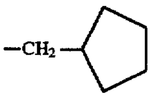 | 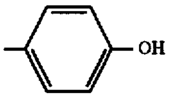 |

TABLE II-continued
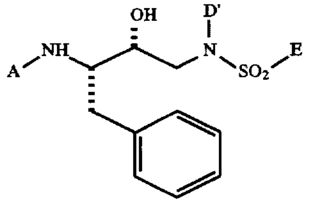
| COMPOUND | A | D' | E |
|---|---|---|---|
| 167 | 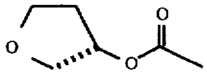 | 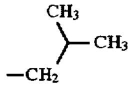 | 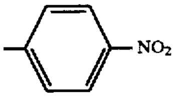 |
| 168 | 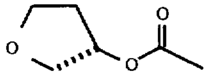 | 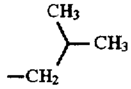 | 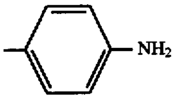 |
| 169 | 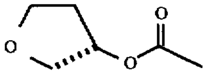 | 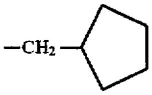 | 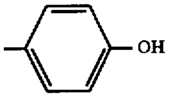 |
| 170 | 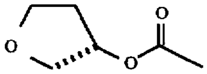 | 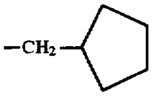 | 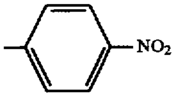 |
| 171 | 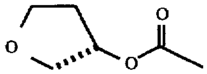 | 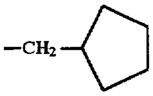 | 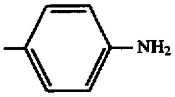 |
| 172 | 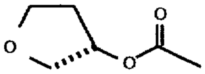 | 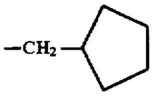 | 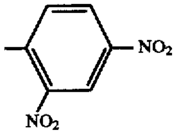 |
| 173 | 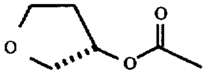 | 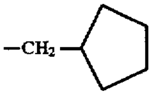 | 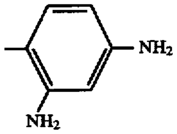 |
| 174 | 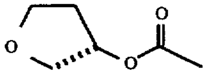 | 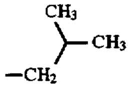 | 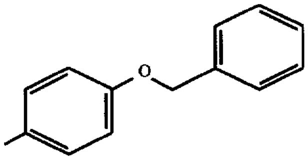 |
| 175 | 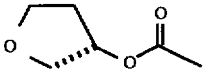 | 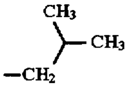 | 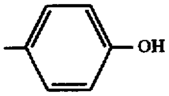 |
| 176 | 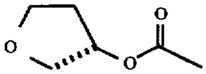 | 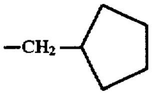 | 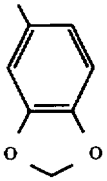 |

TABLE II-continued
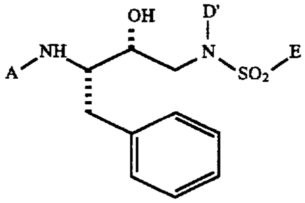
| COMPOUND | A | D' | E |
|---|---|---|---|
| 177 | 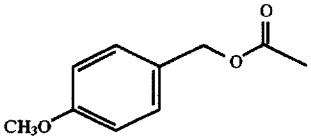 | 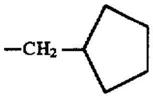 | 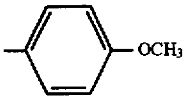 |
| 178 | 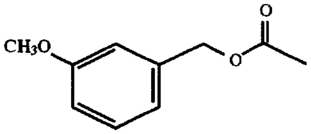 | 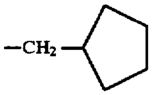 | 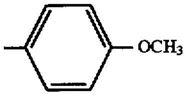 |
| 179 | 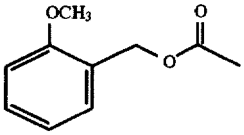 | 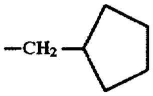 | 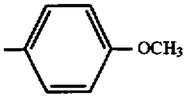 |
| 180 | 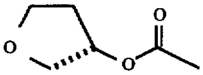 | 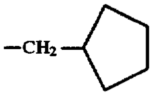 | 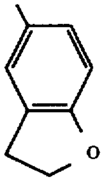 |
| 181 | 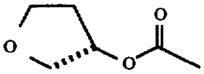 | 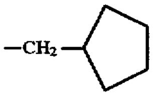 | 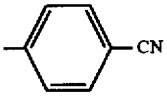 |
| 182 | 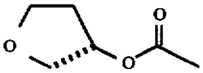 | 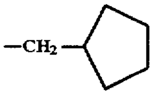 | 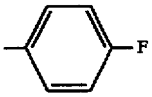 |
| 183 | 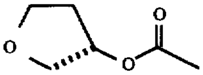 | 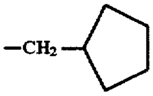 | 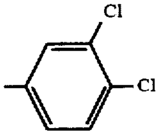 |
| 184 | 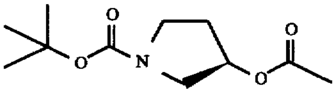 | 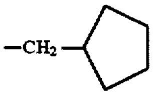 | 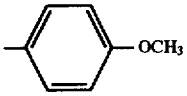 |
| 185 | 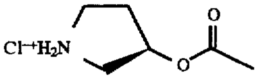 | 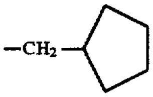 | 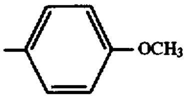 |
| 1001 | 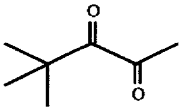 | 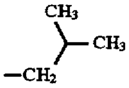 | 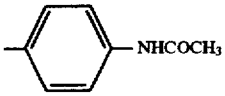 |

TABLE II-continued
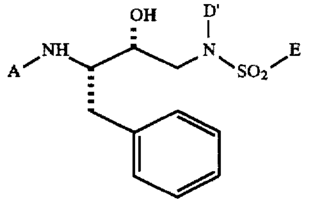
| COMPOUND | A | D' | E |
|---|---|---|---|
| 1002 | 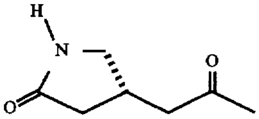 | 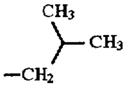 | 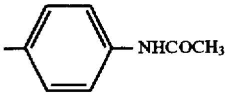 |
| 1003 | 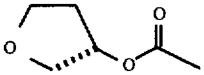 | 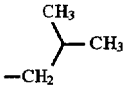 | 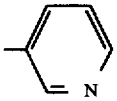 |
| 1004 | 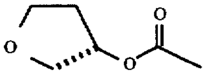 | 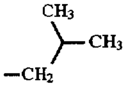 | 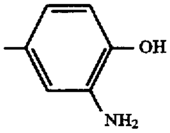 |
| 1005 | 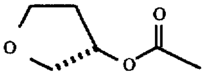 | $-CH_3$ | 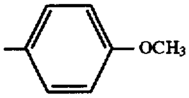 |
| 1006 | 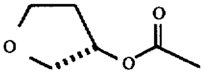 | 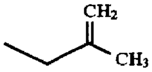 | 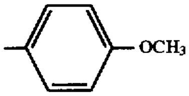 |
| 1007 | 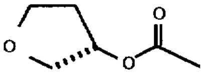 | 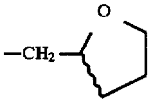 | 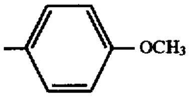 |
| 1008 | 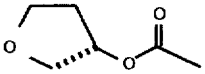 | 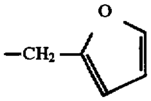 | 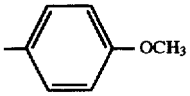 |
| 1009 | 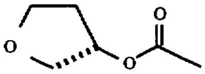 | 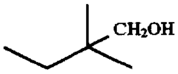 | 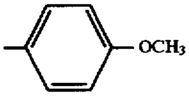 |
| 1010 | 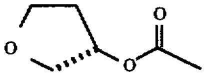 | 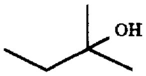 | 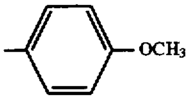 |
| 1011 | 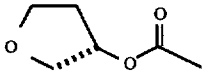 | 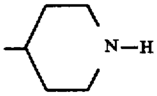 | 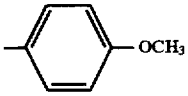 |
| 1012 | 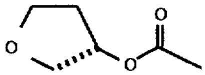 | 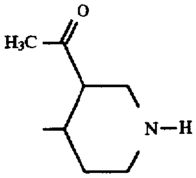 | 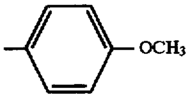 |

TABLE II-continued
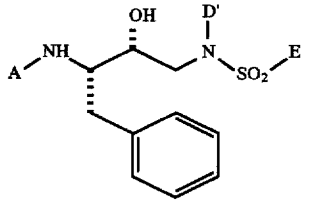
| COMPOUND | A | D' | E |
|---|---|---|---|
| 1013 | 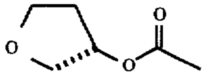 | 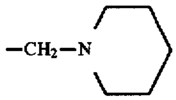 | 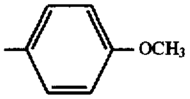 |
| 1014 | 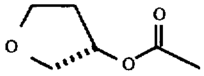 | 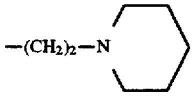 | 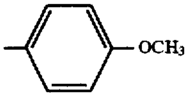 |
| 1015 | 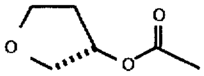 | 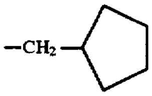 | 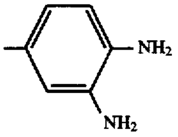 |
TABLE III
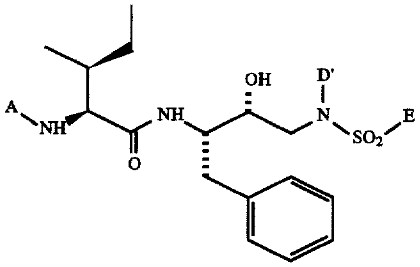
| COMPOUND | A | D' | E |
|---|---|---|---|
| 186 | 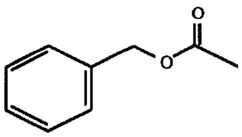 | 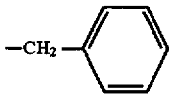 | 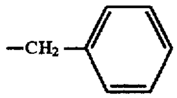 |
| 187 | 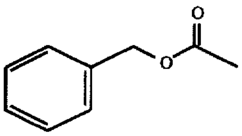 | 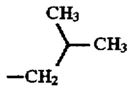 | 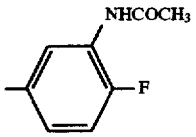 |
| 188 | 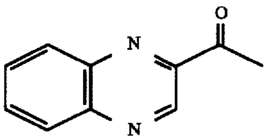 | 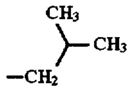 | 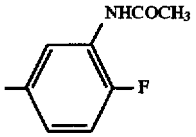 |

TABLE IV

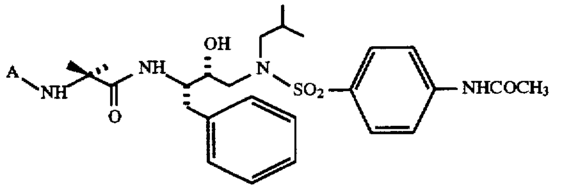

| COMPOUND | A |
|---|---|
| 189 | 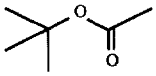 |
| 190 | 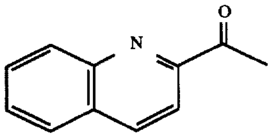 |

TABLE V

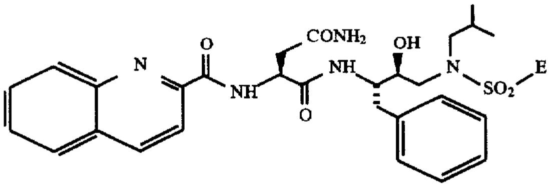

| COMPOUND | E |
|---|---|
| 191 | 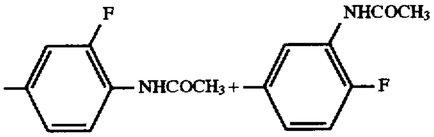 (2:1) |
| 192 | 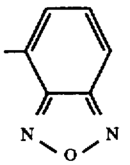 |
| 193 | 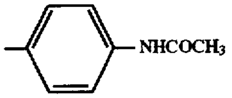 |
| 194 | 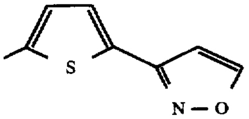 |

TABLE VI

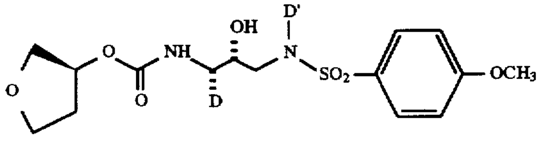

| COMPOUND | D | D' |
|---|---|---|
| 195 | 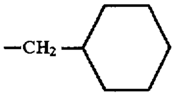 | 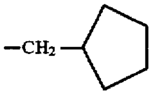 |
| 196 | 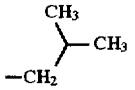 | 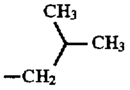 |

Preferred compounds of this invention are*:

* As can be appreciated by those of ordinary skill in the art, many different conventions are used in naming chemical compounds. Because of possible discrepencies in the art of chemical nomenclature, the structures shown in Tables I–VI herein are controlling for the definition of compounds 1–195 and 1001–1015 of this invention.

(S)-N-1-(3-((3-Acetylamino-4-fluorobenzenesulfonyl)-benzyl-amino)-(1S,2 syn)-1-benzyl-2-hydroxy-propyl)-2-((quinoline-2-carbonyl)-amino)-succinamide and (S)-N-1-(3-((4-Acetylamino-3-fluorobenzenesulfonyl)-benzyl-amino)-(1S,2 syn)-1-benzyl-2-hydroxy-propyl)-2-((quinoline-2-carbonyl)-amino)-succinamide (compounds 2);

(S)-N-1-(3-((5-Acetylamino-3-methyl-thiophene-2-sulfonyl)-benzyl-amino)-(1S,2 syn)-1-benzyl-2-hydroxypropyl)-2-((quinoline-2-carbonyl)-amino)-succinamide (compound 5);

(S)-N-1-(1-Benzyl-3-(benzyl-(5-isoxazol-3-yl-thiophene-2-sulfonyl)-amino)-(1S,2 syn)-1-benzyl-2-hydroxy-propyl)-2-((quinoline-2-carbonyl)-amino)-succinamide (compound 6);

(S)-N-1-(3-((Benzo(1,2,5)oxadiazole-4-sulfonyl)-benzyl-amino)-(1S,2 syn)-1-benzyl-2-hydroxy-propyl)-2-((quinoline-2-carbonyl)-amino)-succinamide (compound 9);

N-1-(1-(S)-Benzyl-3-(benzyl-(3-sulfamoyl-benzenesulfonyl)-amino)-2-(syn)-hydroxy-propyl)-2-((quinoline-2-carbonyl)-amino)-succinamide (compound 10);

(S)-N-1-(1-(S)-Benzyl-2-(syn)-hydroxyl-3-(isobutyl-(5-pyridin-2-yl-thiophene-2-sulfonyl)-amino)-propyl)-2-((quinoline-2-carbonyl)-amino)-succinamide (compound 12);

(S)-N-1-(3-((4-Benzenesulfonyl-thiophene-2-sulfonyl)-isobutyl-amino)-(1S,2 syn)-1-benzyl-2-hydroxy-propyl)-2-((quinoline-2-carbonyl)-amino)-succinamide (compound 13);

(S)-N-1-(1-(S)-Benzyl-3-((4-fluoro-benzenesulfonyl)-isobutyl-amino)-2-(syn)-hydroxy-propyl)-2-((quinoline-2-carbonyl)-amino)-succinamide (compound 14);

(S)-N-1-(3-((4-Acetylamino-3-fluoro-benzenesulfonyl)-isobutyl-amino)-(1S,2 syn)-1-benzyl-2-hydroxy-propyl)-2-((quinoline-2-carbonyl)-amino)-succinamide (compound 15);

(S)-N-1-(3-((3-Acetylamino-4-fluoro-benzenesulfonyl)-isobutyl-amino)-(1S,2 syn)-1-benzyl-2-hydroxy-propyl)-2-((quinoline-2-carbonyl)-amino)-succinamide (compound 16);

(S)-N-1-(1-(S)-Benzyl-3-( (4-acetylamino-benzenesulfonyl)-isobutyl-amino)-2-(syn)-hydroxy-propyl)-2-((quinoline-2-carbonyl)-amino)-succinamide (compound 17);

(S)-N-1-(3-((5-Acetylamino-3-methyl-thiophene-2-sulfonyl)-isobutyl-amino)-(1S,2 syn)-1-benzyl-2-hydroxy-propyl)-2-((quinoline-2-carbonyl)-amino)-succinamide (compound 18);

(S)-N-1-(3-((3-Acetylamino-benzenesulfonyl)-isobutyl-amino)-(1S,2 syn)-1-benzyl-2-hydroxy-propyl)-2-((quinoline-2-carbonyl)-amino)-succinamide (compound 19);

(S)-N-1-(3-((Benzo(1,2,5)oxadiazole-4-sulfonyl)-isobutyl-amino)-(1S,2 syn)-1-benzyl-2-hydroxy-propyl)-2-((quinoline-2-carbonyl)-amino)-succinamide (compound 20);

N-1-((1S-2 syn)-1-Benzyl-2-hydroxy-3-(1-isobutyl-3,3-dimethylsulfonylurea)-propyl)-2-((quinoline-2-carbonyl)-amino)-succinamide (compound 21);

N-1-(3-((4-Acetylamino-benzenesulfonyl)-isobutyl-amino)-(1S,2 syn)-1-benzyl-2-hydroxy-propyl)-2-(pyridin-2-yl-methoxycarbonyl)-succinamide (compound 22);

N-1-(3-((4-Acetylamino-benzenesulfonyl)-isobutyl-amino)-(1S,2 syn)-1-benzyl-2-hydroxy-propyl)-2-(pyridin-4-yl-methoxycarbonyl)-succinamide (compound 23);

N-1-(3-((4-Fluoro-benzenesulfonyl)-isobutyl-amino)-(1S,2 syn)-1-benzyl-2-hydroxy-propyl)-2-(pyridin-2-yl-methoxycarbonyl)-succinamide (compound 26);

4-Fluoro-N-((2 syn,3S)-2-hydroxy-4-phenyl-3-((S)-tetrahydrofuran-3-yloxycarbonylamino)-butyl)-N-isobutyl-benzenesulfonamide (compound 35);

3,4-Dichloro-N-((2 syn,3S)-2-hydroxy-4-phenyl-3-((S)-tetrahydrofuran-3-yloxycarbonylamino)-butyl)-N-isobutyl-benzenesulfonamide (compound 37);

N-(4-(((2 syn,3S)-2-Hydroxy-4-phenyl-3-(pyridin-3-yl-methoxycarbonylamino)-butyl)-isobutyl-sulfamoyl)-phenyl)-acetamide (compound 44);

2,4-Dimethyl-thiazole-5-sulfonic acid-(1,1-dimethyl-ethoxycarbonylamino)-(2 syn,3S)-2-hydroxy-4-phenyl-butyl)-isobutyl-amide (compound 46);

N-(4-(((2 syn,3S)-2-Hydroxy-4-phenyl-3-((S)-tetrahydrofuran-3-yloxycarbonylamino)-butyl)-isobutyl-sulfamoyl)-phenyl)-acetamide (compound 48);

4-Fluoro-N-((2 syn,3S)-2-hydroxy-4-phenyl-3-((R)-tetrahydrofuran-3-yloxycarbonylamino)-butyl)-N-isobutyl-benzenesulfonamide and 4-Fluoro-N-((2 syn,3S)-2-hydroxy-4-phenyl-3-((R)-tetrahydrofuran-3-yloxycarbonylamino)-butyl)-N-isobutyl-benzenesulfonamide (compounds 52);

Benzo(1,2,5)oxadiazole-5-sulfonic acid ((2 syn,3S)-2-hydroxy-4-phenyl-3-(pyridin-3-yl-methoxycarbonylamino)-butyl)-isobutylamide (compound 66);

N-(4-(((2 syn,3S)-2-Hydroxy-4-phenyl-3-((R)-tetrahydrofuran-3-yloxycarbonylamino)-butyl)-isobutyl-sulfamoyl-phenyl)-acetamide and N-(4-(((2 syn,3S)-2-Hydroxy-4-phenyl-3-((S)-tetrahydrofuran-3-yloxycarbonylamino)-butyl)-isobutyl-sulfamoyl)-phenyl)-acetamide (compounds 86);

N-(2-Fluoro-5-(((2 syn,3S)-2-hydroxy-4-phenyl-3-((S)-tetrahydrofuran-3-yloxycarbonylamino)-butyl)-isobutyl-sulfamoyl)-phenyl)-acetamide (compound 88);

N-(3-(((2 syn,3S)-2-Hydroxy-4-phenyl-3-((S)-tetrahydrofuran-3-yloxycarbonylamino)-butyl)-isobutyl-sulfamoyl)-phenyl)-acetamide (compound 91);

4-Fluoro-N-((2 syn,3S)-2-hydroxy-4-phenyl-3-((R)-tetrahydrofuran-3-yloxycarbonylamino)-butyl)-N-isobutyl-benzenesulfonamide (compound 93);

N-(4-(((syn)-2-Hydroxy-(S)-4-phenyl-3-((tetrahydro-furan-(R)-3-yl)-oxycarbonylamino)-butyl)-isobutyl-sulfamoyl)-phenyl)-acetamide (compound 94);

4-Fluoro-N-(2 syn,3S)-2-hydroxy-4-phenyl-3-((tetrahydro-furan-(R)-3-ylmethoxycarbonylamino)-butyl)-N-isobutyl-benzenesulfonamide and 4-Fluoro-N-(2 syn,3S)-2-hydroxy-4-phenyl-3-((tetrahydro-furan-(S)-3-ylmethoxycarbonylamino)-butyl)-N-isobutyl-benzenesulfonamide (compounds 97);

4-Fluoro-N-((2 syn,3S)-2-hydroxy-4-phenyl-3-(pyridin-3-yl-methoxycarbonylamino)-butyl)-N-isobutyl-benzenesulfonamide (compound 98);

4-Chloro-N-((2 syn,3S)-2-hydroxy-4-phenyl-3((S)-tetrahydrofuran-3-yloxycarbonylamino)-butyl)-isobutyl-benzenesulfonamide (compound 99);

N-((2 syn,3S)-2-Hydroxy-4-phenyl-3-((S)-tetrahydrofuran-3-yloxycarbonylamino)-butyl)-N-isobutyl-4-methoxy-benzenesulfonamide (compound 100);

4-Fluoro-N-(2-(syn)-hydroxy-3-((2-oxazolidon-(S)-4-yl)-methoxycarbonylamino)-4-(S)-phenyl-butyl)-N-isobutyl-benzenesulfonamide (compound 109);

Benzene-1,3-disulfonic acid 1-amide 3-((2 syn,3S)-2-hydroxy-4-phenyl-3-(3-(S)-tetrahydrofuran-3-yloxycarbonylamino)-butyl)-isobutyl-amide (compound 112);

Furan-3-sulfonic acid (2 syn,3S)-2-hydroxy-4-phenyl-3-((S)-tetrahydrofuran-3-yloxycarbonylamino)-butyl)-isobutyl-amide (compound 113);

N-((3-Allyloxycarbonylamino)-(2 syn,3S)-2-hydroxy-4-phenyl-butyl)-N-cyclopentylmethyl-4-fluoro-benzenesulfonamide (compound 114);

N-Cyclopentylmethyl-N-((3-ethoxycarbonylamino)-(2 syn, 3S)-2-hydroxy-4-phenyl-butyl)-4-fluoro-benzenesulfonamide (compound 115);

4-Chloro-N-cyclopentylmethyl-N-((2 syn,3S)-2-hydroxy-4-phenyl-3-((S)-tetrahydrofuran-3-yloxycarbonylamino)-butyl)-benzenesulfonamide (compound 116);

4-Chloro-N-cyclopentylmethyl-N-((2 syn,3S)-2-hydroxy-4-phenyl-3-(pyridin-3yl-methoxycarbonyl)-butyl)-benzenesulfonamide (compound 118);

N-(4-(Cyclopentylmethyl-((2 syn,3S)-2-hydroxy-4-phenyl-3-((S)-tetrahydrofuran-3-yloxycarbonylamino)-butyl)-sulfamoyl)-phenyl)-acetamide (compound 125);

3-Chloro-N-((2 syn,3S)-2-hydroxy-4-phenyl-3-((S)-tetrahydrofuran-3-yloxycarbonylamino)-butyl)-N-isobutyl-benzenesulfonamide (compound 138);

4-Chloro-N-cyclopentylmethyl-N-(2-(syn)-hydroxy-3-((2-oxazolidon-4-(S)-yl-methyl)-oxycarbonylamino)-4-phenyl-butyl)-benzenesulfonamide (compound 139);

N-cyclopentylmethyl-N-((2 syn,3S)-2-hydroxy-4-phenyl-3-((S)-tetrahydrofuran-3-yloxycarbonylamino)-butyl)-4-methoxy-benzenesulfonamide (compound 140);

N-((3-allyloxycarbonylamino)-(2 syn,3S)-2-hydroxy-4-phenyl-butyl)-N-cyclopentylmethyl-4-methoxy-benzenesulfonamide (compound 141);

N-Cyclopentylmethyl-N-((2 syn,3S)-2-hydroxy-4-phenyl-3-(3-pyridin-3-yl-methoxycarbonylamino)-butyl-4-methoxy-benzenesulfonamide (compound 142);

Pyridine-3-sulfonic acid ((2 syn,3S)-2-hydroxy-4-phenyl-3-((S)-tetrahydrofuran-3-yloxycarbonylamino)-butyl)-isobutyl-amide, trifluoroacetic acid salt (compound 144);

5-Isoxazol-3-yl-thiophene-2-sulfonic acid ((2 syn,3S)-2-hydroxy-4-phenyl-3-((S)-tetrahydrofuran-3-yloxycarbonylamino)-butyl)-isobutyl-amide (compound 145);

N-(4-((3-(Allyloxycarbonylamino)-(2 syn,3S)-2-hydroxy-4-phenyl-butyl)-cyclopentylmethylsulfamoyl)-phenyl)-acetamide (compound 146);

N-(4-(Cyclopentylmethyl-((2 syn,3S)-2-hydroxy-4-phenyl-3-(pyridin-3-yl-methoxycarbonylamino)-butyl)-sulfamoyl)-phenyl)-acetamide (compound 147);

N-Cyclopentylmethyl-N-((2 syn,3S)-2-hydroxy-4-phenyl-3-((S)-tetrahydrofuran-3-yloxycarbonylamino)-butyl)-benzenesulfonamide (compound 148);

Pyridine-3-sulfonic acid cyclopentylmethyl-((2 syn,3S)-2-hydroxy-4-phenyl-3-((S)-tetrahydrofuran-3-yloxycarbonylamino)-butyl)-amide (compound 149);

Piperidine-1-sulfonic acid ((2 syn,3S)-2-hydroxy-4-phenyl-3-((S)-tetrahydrofuran-3-yloxycarbonylamino)-butyl)-isobutyl-amide (compound 150);

N-4-((2-(syn)-Hydroxy-3-((2-methoxymethyl-allyloxycarbonylamino)-4-(S)-phenyl-butyl)-isobutyl-sulfamoyl)-phenyl)-acetamide (compound 155);

1-Acetyl-2,3-dihydro-1H-indole-6-sulfonic acid ((allyloxycarbonylamino)-(2 syn,3S)-2-hydroxy-4-phenyl-butyl)-cyclopentylmethyl-amide (compound 156);

1-Acetyl-2,3-dihydro-1H-indole-6-sulfonic acid cyclopentylmethyl-((2 syn,3S)-2-hydroxy-4-phenyl-3-((S)-tetrahydrofuran-3-yloxycarbonylamino)-butyl)-amide (compound 157);

N-Cyclohexylmethyl-N-((2 syn,3S)-2-hydroxy-4-phenyl-3-((S)-tetrahydrofuran-3-yloxycarbonylamino)-butyl)-4-methoxy-benzenesulfonamide (compound 158);

N-Cyclohexylmethyl-4-fluoro-N-((2 syn,3S)-2-hydroxy-4-phenyl-3-((S)-tetrahydrofuran-3-yloxycarbonylamino)-butyl)-benzenesulfonamide (compound 159);

N-(4-(Cyclohexylmethyl)-((2 syn,3S)-2-hydroxy-4-phenyl-3-((S)-tetrahydrofuran-3-yloxycarbonylamino)-butyl)-sulfamoyl-phenyl)-acetamide (compound 160);

N-((2 syn,3S)-2-Hydroxy-4-phenyl-3-(pyridin-4-yl-methoxycarbonylamino)-butyl)-N-isobutyl-4-methoxy-benzenesulfonamide (compound 163);

N-((2 syn,3S)-2-Hydroxy-4-phenyl-3-((syn)-tetrahydrofuran-3-yloxycarbonylamino)-butyl)-N-isobutyl-4-methyl-benzenesulfonamide (compound 165);

N-cyclopentylmethyl-4-hydroxy-N-((2 syn,3S)-2-hydroxy-4-phenyl-3-(pyridin-3-yl-methoxycarbonylamino)-butyl)-benzenesulfonamide (compound 166);

N-((2 syn,3S)-2-Hydroxy-4-phenyl-3-((S)-tetrahydrofuran-3-yloxycarbonylamino)-butyl)-N-isobutyl-4-nitro-benzenesulfonamide (compound 167);

4-Amino-N-((2 syn,3S)-2-Hydroxy-4-phenyl-3-((S)-tetrahydrofuran-3-yloxycarbonylamino)-butyl)-N-isobutyl-benzenesulfonamide (compound 168);

N-Cyclopentylmethyl-4-hydroxy-N-((2 syn,3S)-2-hydroxy-4-phenyl-3-((S)-tetrahydrofuran-3-yloxycarbonylamino)-butyl)-benzenesulfonamide (compound 169);

N-Cyclopentylmethyl-N-((2 syn,3S)-2-hydroxy-4-phenyl-3-((S)-tetrahydrofuran-3-yloxycarbonylamino)-butyl)-4-nitro-benezensulfonamide (compound 170);

4-Amino-N-cyclopentylmethyl-N-((2 syn,3S)-2-hydroxy-4-phenyl-3-((S)-tetrahydrofuran-3-yloxycarbonylamino)-butyl)-benzenesulfonamide (compound 171);

2,4-Diamino-N-cyclopentylmethyl-N-((2 syn,3S)-2-hydroxy-4-phenyl-3-((S)-tetrahydrofuran-3-yloxycarbonylamino)-butyl)-benzenesulfonamide (compound 173);

4-Hydroxy-N-(2 syn,3S)-2-hydroxy-4-phenyl-3-((S)-tetrahydrofuran-3-yloxycarbonylamino)-butyl)-N-isobutyl-benzenesulfonamide (compound 175);

N-Cyclopentylmethyl-4-fluoro-N-((2 syn,3S)-2-hydroxy-4-phenyl-3-((S)-tetrahydrofuran-3-yloxycarbonylamino)-butyl)-benzenesulfonamide (compound 182);

3,4-Dichloro-N-cyclopentylmethyl-N-((2 syn,3S)-2-hydroxy-4-phenyl-3-((S)-tetrahydrofuran-3-yloxycarbonylamino)-butyl)-benzenesulfonamide (compound 183);

Benzyloxycarbonyl-(L)-isoleucine-N-(5-((3-amino-(2 syn,3S)-2-hydroxy-4-phenyl-butyl)-isobutyl-sulfamoyl)-2-fluoro-phenyl)-acetamide (compound 187);

N-((2 syn,3S)-4-Cyclohexyl-2-hydroxy-3-((S)-tetrahydrofuran-3-yloxycarbonylamino)-butyl)-N-cyclopentylmethyl-4-methoxy-benzenesulfonamide (compound 195);

and compounds 1001 through 1015.

More preferred compounds of this invention are:

(S)-N-1-(1-(S)-Benzyl-2-(syn)-hydroxyl-3-(isobutyl-(5-pyridin-2-yl-thiophene-2-sulfonyl)-amino)-propyl)-2-((quinoline-2-carbonyl)-amino)-succinamide (compound 12);

(S)-N-1-(1-(S)-Benzyl-3-((4-fluoro-benzenesulfonyl)-isobutyl-amino)-2-(syn)-hydroxy-propyl)-2-((quinoline-2-carbonyl)-amino)-succinamide (compound 14);

(S)-N-1-(3-((4-Acetylamino-3-fluoro-benzenesulfonyl)-isobutyl-amino)-(1S,2 syn)-1-benzyl-2-hydroxy-propyl)-2-((quinoline-2-carbonyl)-amino)-succinamide (compound 15);

(S)-N-1-(3-((Benzo(1,2,5)oxadiazole-4-sulfonyl)-isobutyl-amino)-(1S,2 syn)-1-benzyl-2-hydroxy-propyl)-2-((quinoline-2-carbonyl)-amino)-succinamide (compound 20);

N-1-((1S-2 syn)-1-Benzyl-2-hydroxy-3-(1-isobutyl-3,3-dimethylsulfonylurea)-propyl)-2-((quinoline-2-carbonyl)-amino)-succinamide (compound 21);

N-(4-(((2 syn,3S)-2-Hydroxy-4-phenyl-3-((S)-tetrahydrofuran-3-yloxycarbonylamino)-butyl)-isobutyl-sulfamoyl)-phenyl)-acetamide (compound 48);

N-((2 syn,3S)-2-Hydroxy-4-phenyl-3-((S)-tetrahydrofuran-3-yloxycarbonylamino)-butyl)-N-isobutyl-4-methoxy-benzenesulfonamide (compound 100);

4-Chloro-N-cyclopentylmethyl-N-((2 syn,3S)-2-hydroxy-4-phenyl-3-((S)-tetrahydrofuran-3-yloxycarbonylamino)-butyl)-benzenesulfonamide (compound 116);

N-Cyclopentylmethyl-N-((2 syn,3S)-2-hydroxy-4-phenyl-3-((S)-tetrahydrofuran-3-yloxycarbonylamino)-butyl)-4-methoxy-benzenesulfonamide (compound 140);

N-Cyclopentylmethyl-N-((2 syn,3S)-2-hydroxy-4-phenyl-3-(3-pyridin-3-yl-methoxycarbonylamino)-butyl-4-methoxy-benzenesulfonamide (compound 142);

N-Cyclopentylmethyl-N-((2 syn,3S)-2-hydroxy-4-phenyl-3-((S)-tetrahydrofuran-3-yloxycarbonylamino)-butyl)-benzenesulfonamide (compound 148);

N-Cyclohexylmethyl-N-((2 syn,3S)-2-hydroxy-4-phenyl-3-((S)-tetrahydrofuran-3-yloxycarbonylamino)-butyl)-4-methoxy-benzenesulfonamide (compound 158);

N-(4-(Cyclohexylmethyl)-((2 syn,3S)-2-hydroxy-4-phenyl-3-((S)-tetrahydrofuran-3-yloxycarbonylamino)-butyl)-sulfamoyl-phenyl)-acetamide (compound 160);

N-cyclopentylmethyl-4-hydroxy-N-((2 syn,3S)-2-hydroxy-4-phenyl-3-(pyridin-3-yl-methoxycarbonylamino)-butyl)-benzenesulfonamide (compound 166);

4-Amino-N-((2 syn,3S)-2-Hydroxy-4-phenyl-3-((S)-tetrahydrofuran-3-yloxycarbonylamino)-butyl)-N-isobutyl-benzenesulfonamide (compound 168);

4-Amino-N-cyclopentylmethyl-N-((2 syn,3S)-2-hydroxy-4-phenyl-3-((S)-tetrahydrofuran-3-yloxycarbonylamino)-butyl)-benzenesulfonamide (compound 171);

2,4-Diamino-N-cyclopentylmethyl-N-((2 syn,3S)-2-hydroxy-4-phenyl-3-((S)-tetrahydrofuran-3-yloxycarbonylamino)-butyl)-benzenesulfonamide (compound 173);

4-Hydroxy-N-(2 syn,3S)-2-hydroxy-4-phenyl-3-((S)-tetrahydrofuran-3-yloxycarbonylamino)-butyl)-N-isobutyl-benzenesulfonamide (compound 175); and N-((2 syn,3S)-4-Cyclohexyl-2-hydroxy-3-((S)-tetrahydrofuran-3-yloxycarbonylamino)-butyl)-N-cyclopentylmethyl-4-methoxy-benzenesulfonamide (compound 195).

The sulfonamides of this invention may be synthesized using conventional techniques. Advantageously, these compounds are conveniently synthesized from readily available starting materials.

The compounds of this invention are among the most readily synthesized HIV protease inhibitors known. Previously described HIV protease inhibitors often contain four or more chiral centers, numerous peptide linkages and/or require air-sensitive reagents (such as organometallic complexes) to effect their synthesis. The relative ease with which the compounds of this invention can be synthesized represents an enormous advantage in the large scale production of these compounds.

In general, sulfonamides of formula I are conveniently obtained from α-amino acid derivatives having the general formula A—(B)$_x$—NH—CH(D)—COOH, wherein A, B, X and D are defined as above for the compounds of formula I. Such α-amino acid derivatives are often commercially available or may be conveniently prepared from commercially available α-amino acid derivatives using known techniques. See, for example, T. W. Greene and P. G. M. Wuts, "Protective Groups in Organic Synthesis", 2nd Ed., John Wiley and Sons (1991). Although this invention envisions the use of racemic mixtures of such starting materials, when x=0, a single enantiomer in the S configuration is preferred.

Using known techniques, the α-amino acid derivative of general formula A—(B)$_x$—NH—CH(D)—COOH may be readily converted to an amino ketone derivative of general formula A—(B)$_x$—NH—CH(D)—CO—$CH_2$—X, wherein X is a leaving group which suitably activates the α-carbon (i.e., makes the methylene susceptible to nucleophilic attack). Suitable leaving groups are well known in the art and include halides and sulfonates, such as methanesulfonate, trifluoromethanesulfonate or 4-toluenesulfonate X may also be a hydroxyl which is converted in situ to a leaving group (e.g. by treatment with a trialkyl- or triarylphosphine in the presence of a dialkylazodicarboxylate). Methods for the formation of such amino ketone derivatives also are well known to those of skill in the art (see, for example, S. J. Fittkau, *J. Prakt. Chem.*, 315, p. 1037 (1973)). Alternatively, certain amino ketone derivatives are commercially available (e.g., from Bachem Biosciences, Inc., Philadelphia, Pa.).

The amino ketone derivative may then be reduced to the corresponding amino alcohol, represented by the formula A—(B)$_x$—NH—CH(D)—CH(OH)—$CH_2$—X. Many techniques for reduction of amino ketone derivatives such as A—(B)$_x$—NH—CH(D)—CO—$CH_2$—X are well known to those of ordinary skill in the art (Larock, R. C. "Comprehensive Organic Transformations", pp. 527–547, VCH Publishers, Inc.© 1989 and references cited therein). A preferred reducing agent is sodium borohydride. The reduction reaction is conducted at a temperature of from about −40° C. to about 40° C. (preferably, at about 0° C. to about 20° C.), in a suitable solvent system such as, for example, aqueous or neat tetrahydrofuran or a lower alcohol, such as methanol or ethanol. Although this invention envisions both stereospecific and non-stereospecific reduction of the amino ketone derivative A—(B)$_x$—NH—CH(D)—CO—$CH_2$—X, stereoselective reduction is preferred. Stereoselective reduction may be accomplished by use of chiral reagents known in the art. In the present invention, stereoselective reduction may be conveniently achieved, for instance, under non-chelating reducing conditions, where chiral induction of the newly formed hydroxyl group is set by the stereochemistry of the D group (i.e., Felkin-Ahn addition of hydride). We particularly prefer stereoselective reductions wherein the resulting hydroxyl is syn to D. We have found that when the hydroxyl group is syn to D, the final sulfonamide product is an HIV protease inhibitor of higher potency than the anti diastereomer.

The hydroxyl group of the amino alcohol may optionally be protected by any known oxygen protecting group (such as trialkylsilyl, benzyl, or alkyloxymethyl) to yield a protected amino alcohol having the formula A—(B)$_x$—NH—CH(D)—C($OR^6$)—$CH_2$—X, wherein $R^6$ is H or any suitable hydroxy protecting group. Several useful protecting groups are described in T. W. Greene and P. G. M. Wuts, *Protective Groups in Organic Synthesis, 2d Ed.*, John Wiley and Sons (1991).

The amino alcohol may then be reacted with a nucleophilic amine compound to form an intermediate of formula III:

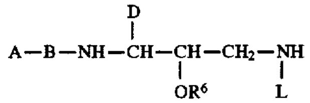

(III)

wherein D and $R^6$ are as described above, and L is either D' (as described for compounds of formula I) or hydrogen.

In a particularly advantageous synthetic scheme, simultaneous activation of the methylene and protection of the alcohol may be accomplished by forming an N-protected amino epoxide from the oxygen and its adjacent methylene to give an intermediate of formula II:

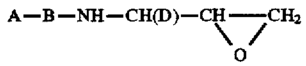

(II)

wherein A, B and D are as defined above for compounds of formula I. Suitable solvent systems for preparing the N-protected amino epoxide include ethanol, methanol, isopropanol, tetrahydrofuran, dioxane, dimethyl formamide and the like (including mixtures thereof). Suitable bases for producing the epoxide include alkali metal hydroxides, potassium t-butoxide, DBU and the like. A preferred base is potassium hydroxide.

Reaction of the N-protected amino epoxide or other suitably activated intermediates with an amine is carried out neat, i.e. in the absence of solvent, or in the presence of a polar solvent such as lower alkanols, water, dimethylformamide or dimethylsulfoxide. The reaction can be carried out conveniently between about 0° C. and 120° C., preferably between about 20° C. and 100° C. Alternatively, the reaction may be carried out in the presence of an activating agent, such as activated alumina in an inert solvent, preferably an ether, such as diethyl ether, tetrahydrofuran, dioxane, or tert-butyl methyl ether, conveniently from about room temperature to about 110° C., as described by Posner and Rogers, *J. Am Chem. Soc.*, 99, p. 8208 (1977). Other activating reagents include lower trialkylaluminum species, such as triethylaluminum, or dialkylaluminum halide species, such as diethylaluminum chloride (Overman and Flippin, *Tetrahedron Letters*, p. 195 (1981)). Reactions involving these species are conveniently carried out in inert solvents such as dichloromethane, 1,2-dichloroethane, toluene, or acetonitrile between about 0° C. and about 110° C. Further methods of displacing leaving groups, or opening epoxides with amines or their equivalents such as azides or timethylsilyl cyanide (Gassman and Guggenheim, *J. Am. Chem. Soc.* 104, p. 5849 (1982)), are known and will be apparent to those of ordinary skill in the art.

Compounds of formulae II and III, and functionality-protected derivatives thereof, are useful as intermediates for the preparation of compounds of formula I. In those cases where L represents D', compounds of formula III may be converted to compounds of formula I by reaction with sulfonyl-activated species to form sulfonamides, sulfonyl ureas, thiocarbamates and the like. Methods for preparing such sulfonyl-activated species are well within the ordinary skill of the art. Typically, sulfonyl halides are used to obtain sulfonamides. Many sulfonyl halides are commercially available; others may be easily obtained using conventional synthetic techniques (Gilbert, E. E. "Recent Developments in Preparative Sulfonation and Sulfation" Synthesis 1969: 3 (1969) and references cited therein; Hoffman, R. V. "M-Trifluoromethylbenzenesulfonyl Chloride" Org. Synth. Coll. Vol. VII, John Wiley and Sons (1990); Hartman, G. D. et. al. "4-Substituted Thiophene-and Furan-2-sulfonamides as Topical Carbonic Anhydrase Inhibitors" *J. Med. Chem.*, 35, p. 3822 (1992) and references cited therein. Sulfonyl ureas are usually obtained by the reaction of an amine with sulfuryl chloride or a suitable equivalent such as sulfuryl-bis-imidazole or sulfuryl-bis-N-methyl imidazole. Thiocarbamates are typically obtained by the reaction of an alcohol with sulfuryl chloride or a suitable equivalent such as sulfuryl-bis-imidazole or sulfuryl-bis-N-methyl imidazole.

In the case of compounds of formula III wherein L is hydrogen, conversion of the resultant primary amine to a secondary amine may be carried out by known techniques. Such techniques include reaction with an alkyl halide of alkyl sulfonate, or by reductive alkylation with an aldehyde or carboxylic acid or activated derivative thereof using, for instance, catalytic hydrogenation or sodium cyanoborohydride (Borch et al., *J. Am. Chem. Soc.*, 93, p. 2897 (1971)). Alternatively, the primary amine may be acylated followed by reduction with borane or another suitable reducing reagent, for example, as described by Cushman et al., *J. Org. Chem.*, 56, p. 4161 (1991). This technique is especially useful in compounds of formula III where B is absent and A represents a protecting group such as tert-butoxycarbonyl (Boc) or benzyloxycarbonyl (Cbz).

If variable A of a particular compound of formula I represents a removable protecting group, removal of that group followed by reaction of the resulting amine with an appropriate activated reagent will advantageously yield a different compound of formula I. For instance, reaction with an activated carboxylate, such as an acyl halide (e.g., acid fluorides, acid chlorides, and acid bromides), an activated ester such as nitrophenyl ester or 1-hydroxysuccinimide (HOSu) ester, an anhydride such as the symmetrical anhydride or isobutyl anhydride, or mixed carbonic-phosphoric or carbonic-phosphinic anhydrides, will yield the corresponding amide. Ureas may be obtained by reaction with isocyanates or amines in the presence of bis-activated carbonic acid derivatives such as phosgene or carbonyldiimdazole. Carbamates may be obtained by reaction with chlorocarbonates, with carbonates esterified with leaving groups such as 1-hydroxybenzotriazole (HOBT) or HOSu, or with alcohols in the presence of bis-activated carbonic acid derivatives such as phosgene or carbonyldiimdazole. It will be readily recognized that in order to facilitate specific reactions, the protection of one or more potentially reactive groups followed by subsequent removal of that group may be required. Such modification to the reaction schemes outlined above are within the ordinary skill of the art.

If variable B of a particular compound of formula I is absent and variable A of that compound represents a removable protecting group, removal of A, followed by reaction of the resulting amine with an amino acid or suitably N-protected derivative thereof, followed by a subsequent reaction of the free α-amine if present, as described above, will yield a further compound of formula I. The addition of amino acids and their derivatives is accomplished by well known methods of peptide synthesis. Some of these methods are generally set forth in Bodanszky and Bodanszky, "The Practice of Peptide Synthesis", Springer-Verlag, Berlin, Germany (1984) and in the "The Peptides", Gross and Meinhofer (Eds); Academic Press, 1979, Vols. I–III, which are incorporated herein by reference.

Typically, for solution phase synthesis of peptides, the α-amine of the amino acid to be coupled is protected by Boc, Cbz, allyloxycarbonyl (Alloc) or 9-fluorenylmethoxycarbonyl (Fmoc), while the free carboxyl is activated by reaction with a carbodiimide such as dicyclohexylcarbodiimide (DCC), 1-(3-dimethylaminopropyl)-3-ethylcarbodiimide hydrochloride (EDC), or diisopropylcarbodiimide (DIC), optionally in the presence of a catalyst such as HOBT, HOSu, or dimethylaminopyridine (DMAP). Other methods which proceed through the intermediacy of activated esters, acid halides, enzyme-activated amino acids and anhydrides including N-carboxy-anhydrides, symmetrical anhydrides, mixed carbonic anhydrides, carbonic-phosphinic and carbonic-phosphoric anhydrides are also suitable. After the peptide has been formed, protecting groups may be removed by methods described in the references listed above, such as by hydrogenation in the presence of a palladium, platinum or rhodium catalyst, treatment with sodium in liquid ammonia, hydrochloric, hydrofluoric, hydrobromic, formic, trifluoromethanesulfonic, or trifluoroacetic acid, secondary amines, fluoride ion, trimethylsilyl halides including bromide and iodide, or alkali.

One particularly useful synthetic scheme for producing sulfonamides of formula XV is shown below:

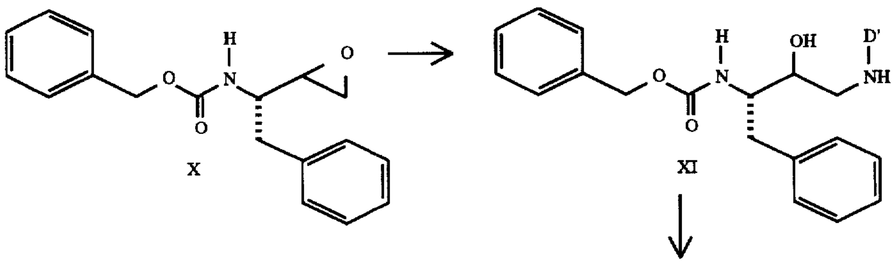

X

XI

-continued

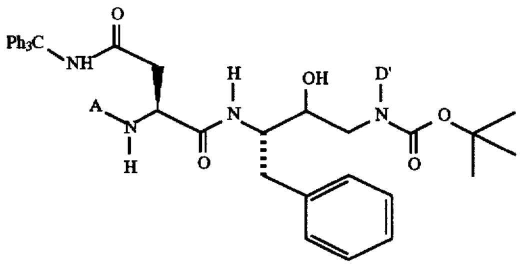

XIII

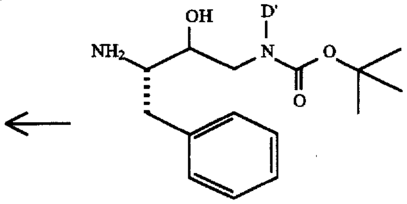

XII

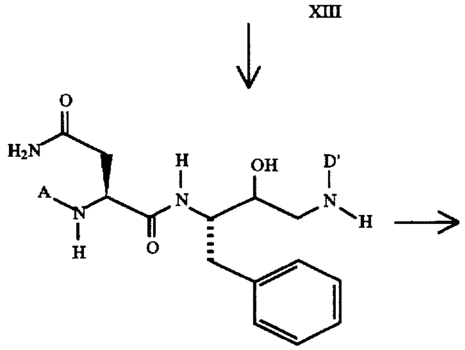

XIV

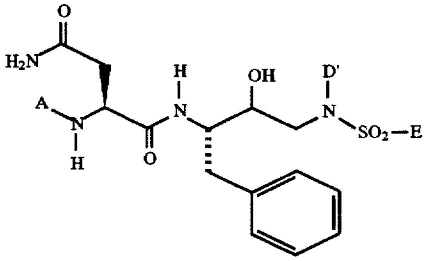

XV

Compounds of formula X may be advantageously synthesized from readily available starting materials (see D. P. Getman, *J. Med. Chem.*, 36, p. 288 (1993)). Each step of the above synthetic scheme may be carried out as generally described above.

A particularly useful synthetic scheme for producing the preferred sulfonamides of formula XXII is shown below:

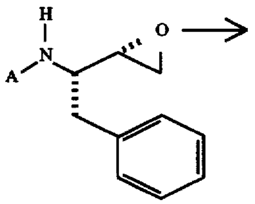

XX

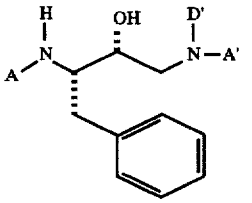

XXI

-continued

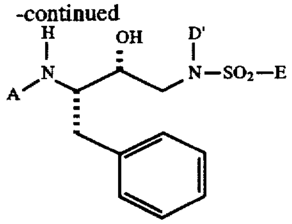

XXII

Compounds of formula XX may be advantageously synthesized from readily available starting materials (see B. E. Evans et al., *J. Org. Chem.*, 50, p. 4615 (1985)). Each step of the above synthetic scheme may be carried out as generally described above.

After converting a compound of formula XX to a compound of formula XXI, as detailed in the previous reaction scheme, the compound of formula XXI may alternatively be reacted with an amino acid or amino acid derivative, as described generally above, to yield a preferred compound of formula XXXI. A particularly useful synthetic scheme utilizing this strategy is set forth below:

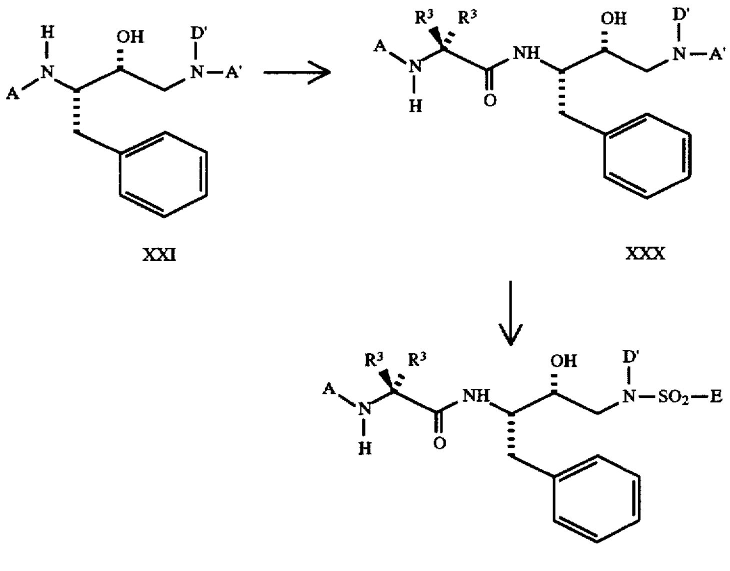

XXI

XXX

XXXI

As can be appreciated by the skilled artisan, the above synthetic schemes are not intended to comprise a comprehensive list of all means by which the compounds described and claimed in this application may be synthesized. Further methods will be evident to those of ordinary skill in the art.

The compounds of this invention may be. modified by appending appropriate functionalites to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of formula I are characterized by a superior ability to inhibit HIV protease activity and viral replication. We believe that this is due to specific steric and electronic interactions between the protease and compounds of formula I. This belief stems from our analysis of the structural basis for the activity of compounds of formula I, in view of the known crystal structures of HIV protease and bound inhibitors, such as the structure reported in Miller et al. "Structure of Complex of Synthetic HIV-1 Protease with a Substrate-Based Inhibitor at 2.3 Å Resolution", *Science*, vol. 246, pp. 1149–1152 (1989), which is incorporated herein by reference, as well as structures determined in our laboratories. According to these structures, the active site of HIV aspartyl protease is defined by a deep groove containing subpockets for accommodation of various side chains of the protease substrate—referred to as $P_1$–$P_n$ and $P_1'$–$P_n'$, according to conventional protease nomenclature. In the center of the groove, lie two aspartic acid residues (Asp25 and Asp25' according to the numbering system of Miller et al.) in a manner typical of the active site aspartates of known aspartyl proteases, which are believed to be the catalytic residues of the enzyme. The groove is covered by two $C_2$-symmetrically disposed "flaps" which also make various direct and indirect contacts with bound substrates.

We believe that the substituents A, D, D' and E of the compounds of formula I associate with HIV protease by way of hydrophobic forces in the binding pockets of the enzyme. We also believe that the sulfonamide group hydrogen binds tightly to a water molecule held by hydrogen bonds to the flaps of the protease ("the flap water molecule"; water molecule 511, according to the Miller et al. numbering system).

In view of the above discovery, an alternative embodiment of this invention relates to novel HIV protease inhibitors possessing certain structural and physicochemical features. We have discovered that compounds possessing the following novel combination of features are surprisingly effective HIV protease inhibitors:

(1) a first and a second hydrogen bond acceptor moiety, at least one of which is more highly polarizable than a carbonyl, said moieties being the same or different, and being capable of hydrogen bonding with the hydrogen atoms of the flap water molecule of an HIV aspartyl protease when the compound is bound thereto;

(2) substantially hydrophobic moieties which associate with the $P_1$ and $P_1'$ binding pockets of said HIV aspartyl protease when the compound is bound thereto;

(3) a third hydrogen bonding moiety, which may be either a hydrogen bond donor or acceptor, capable of simultaneously hydrogen bonding to Asp25 and Asp25' of said HIV aspartyl protease when the compound is bound thereto;

(4) an additional occupied volume of space of at least 100 $Å^3$ when the compound is bound to the active site of said HIV aspartyl protease, said space overlapping with the volume of space that would be filled by a native substrate of said HIV aspartyl protease or a nonhyrolyzable isostere thereof;

(5) a deformation energy of binding of the compound to said HIV aspartyl protease of not greater than 10 kcal/mole; and (6) a neutral or favorable enthalpic contribution from the sum of all electrostatic interactions between the compound and the protease when the compound is bound to said HIV aspartyl protease.

Compounds having the above-cited features can be readily identified or designed by one of ordinary skill in the art using a combination of chemical reasoning and computational methods. For example, those of ordinary skill in the art can readily identify or choose hydrogen bonding and hydrophobic moieties or groups required in features (1)–(3), while features (4)–(6) can be ascertained using well known computational methods for determination of structural (e.g. conformational) and energetic properties of molecules.

Furthermore, compounds characterized by features (1) through (6) listed above may be obtained using any conventional technique, including chemical synthesis and natural product isolation. We prefer using the synthetic schemes detailed above for compounds of formula I.

We have discovered that when an HIV protease inhibitor forms hydrogen bonds to the flap water molecule through two hydrogen bonding moieties, at least one of which is more highly polarizable than a carbonyl, the ability of those compounds to inhibit HIV protease activity is dramatically improved, as compared with conventional HIV protease inhibitors.

While not wishing to be bound by theory, we believe that the strong hydrogen bonds that form between the flap water molecule and the two hydrogen bonding moieties, at least one of which is more highly polarizable than a carbonyl, lower the overall binding energy of the inhibitor. Most HIV protease inhibitors known in the art utilize only carbonyl groups for hydrogen bonding to the flap water molecule and are, thus, inferior to those of the present invention. We believe that the increased polarization that results from the large dipole moment of the highly polarizable hydrogen bonding moiety (as compared to the dipole moment of a carbonyl moiety) creates a stronger and tighter hydrogen bond with the flap water molecule. We prefer to utilize tetravalent oxygenated sulfur, hexavalent oxygenated sulfur and pentavalent oxygenated phosphorus as the highly polarizable hydrogen bonding moiety. Tetravalent oxygenated sulfur and hexavalent oxygenated sulfur are more preferred as the highly polarizable hydrogen bonding moiety. Hexavalent oxygenated sulfur ($-SO_2-$) is most preferred.

We have found that when the highly polarizable hydrogen bonding moiety is a sulfonamide, the overall binding energy of the inhibitor is particularly low. We believe that this increased stability is due to particular conformational characteristics of the sulfonamide S—N bond. Specifically, the sulfonamide S—N bond exists in only two low-energy rotamers (see J. B. Nicholas et al., *J. Phys. Chem.*, 95, p. 9803 (1991) and R. D. Bindal et al., *J. Am. Chem. Soc.*, 112, p. 7861 (1990)). This has the effect of locking that portion of the molecule into a favorable conformation wherein one or both of the highly polarized S=O oxygens can be involved in hydrogen bonding interactions with the flap water.

The remaining five structural and physicochemical features recited above (i.e., features (2) through (6)) are generally recognized in the art to improve the ability of a compound to competitively inhibit HIV protease activity. Although there are several other features thought to increase the inhibitory property (such as binding of the inhibitor backbone to the enzyme), we have discovered that the combination of the five above-cited elements alone, together with novel element (1), typifies effective HIV protease inhibitors.

In general, the binding energy of a particular protease inhibitor is lowered when hydrophobic moieties on the inhibitor are located so as to associate with the enzyme's hydrophobic binding pockets. In the case of HIV-1 protease, the location and nature of the $P_1$ and $P_1'$ binding pockets are known to those of ordinary skill in the art (see, for example, M. Miller et al., cited above). Substantially hydrophobic side chains which fit into the well defined $P_1$ and $P_1'$ binding pockets are also known to those in the art. Preferred side chains are located within 4 Å of the enzyme when bound to HIV protease. Preferred hydrophobic side chains include those substantially similar to those of hydrophobic natural and unnatural α-amino acids, including alanine, valine, leucine, isoleucine, methionine, phenylalanine, α-amino isobutyric acid, alloisoleucine, tyrosine, and tryptophan. Insofar as a portion of this side chain is in contact with bulk solvent or protrudes out of the enzyme, it is not considered to be wholly within $P_1$ or $P_1'$ and may contain polar functionality such as a charged amine at that location.

It has also been established in the art that the presence of a hydroxyl group within hydrogen bond proximity to the two catalytic aspartic acid residues of HIV protease (Asp25 and Asp25') is an important feature of an effective HIV protease inhibitor (see, for example, R. Bone et al., "X-ray Crystal Structure of the HIV Protease Complex with L-700,417, an Inhibitor with Pseudo $C_2$ Symmetry", *J. Am. Chem. Soc.*, 113, pp. 9382–84 (1991)). It is further understood that the geometry of the Asp-binding hydrogen bonding moiety is of particular importance. Although we prefer to use a hydroxyl group at this position, any hydrogen bonding moiety that is capable of forming hydrogen bonds with the Asp residues is acceptable. Such hydrogen bonding moieties are known to those of skill in the art (e.g., phosphinic acid (D. Grobelny et al., *Biochem. Biophys. Res. Commun.*, 169, p. 1111 (1990)).

It is further understood that binding of competitive inhibitors to HIV protease is optimally accomplished by having the inhibitor traverse a volume overlapping that occupied by the native polypeptide substrate when it is bound to the active site of the enzyme. Effective HIV protease inhibitors typically have a relatively small difference in energy between their bound and free states (i.e., a small deformation energy of binding). The most preferred HIV protease inhibitors of this invention have a deformation energy of binding of not greater than 10 kcal/mole (preferably, not greater than 7 kcal/mole). It should be noted, however, that HIV protease inhibitors may interact with HIV protease in more than one conformation which is similar in overall binding energy (see K. H. M. Murthy, *J. Biol. Chem.*, 267, (1992)). In those cases, the deformation energy of binding is taken to be the difference between the energy of the free compound and the average energy of the conformations observed when the inhibitor binds to the enzyme.

Furthermore, it is understood that the most effective protease inhibitors also lack repulsive electrostatic interaction with the target protease in their bound state. Such non-complementary (e.g., electrostatic) interactions include repulsive charge-charge, dipole-dipole and charge-dipole interactions. Specifically, in the most preferred HIV protease inhibitors of this invention, the sum of all electrostatic interactions between the compound and the enzyme when the compound is bound to HIV protease makes a neutral or favorable contribution to the enthalpy of binding.

Preferred compounds characterized by the above features (1)–(6) are compounds of formula XL:

$$Z^1-Q^1-L^1-M-L^2-Q^2-Z^2 \quad (XL)$$

wherein:

$Q^1$ and $Q^2$ are independently hydrogen bond acceptor moieties capable of binding with the hydrogen atoms of the flap water molecule of an HIV aspartyl protease, with the proviso that at least one of $Q^1$ or $Q^2$ is more highly polarizable than a carbonyl;

M is a hydrogen bonding moiety, which may be either a hydrogen bond donor or acceptor, capable of simultaneously hydrogen bonding to Asp25 and Asp25' of said HIV aspartyl protease;

$L^1$ and $L^2$ are independently acyclic or cyclic linker moieties; and each of $Z^1$ and $Z^2$ may be optionally present and, if present, are independently selected from groups which occupy a volume of space overlapping with the volume of space that would be filled by the native substrate of said HIV aspartyl protease.

More preferred compounds of formula XL contain at least one group $Q^1$ or $Q^2$ comprising —$SO_2$—. Most preferrred compounds of formula XL contain at least one group $Q^1$ or $Q^2$ comprising a substituted sulfonamide.

In one embodiment of this invention, compounds of formula XL may be further constrained by "conformational locks", such as a macrocyclic ring structure. Such constraints are well known in the art of peptidomimetics and may result in compounds with strong biological activity. See, for example, Dhanoa, D. S. et al. "The Synthesis of Potent Macrocyclic Renin Inhibitors" *Tetrahedron Lett.* 33, 1725 (1992) and Flynn, G. A. et al. "An Acyl-Iminium Ion Cyclization Route to a Novel Conformationally Restricted Dipeptide Mimic: Applications to Angiotensin-Converting Enzyme Inhibition" *J. Am. Chem. Soc.* 109, 7914 (1989)).

This invention also includes novel methods for accurate identification, design, or prediction of HIV inhibitors characterized by structural and physicochemical features (1) through (6). By virtue of these methods, the skilled artisan can routinely predict and produce particularly effective HIV protease inhibitors.

We have found that the following method for identification, design or prediction of effective HIV protease inhibitors is particularly useful;

(a) selecting a candidate compound of defined chemical structure containing a first and a second hydrogen bond acceptor moiety, at least one of which is more highly polarizable than a carbonyl, said moieties being the same or different; a third hydrogen bonding moiety, which may be either a hydrogen bond donor or acceptor; and at least two substantially hydrophobic moieties;

(b) determining a low-energy conformation for binding of said compound to the active site of an HIV aspartyl protease;

(c) evaluating the capability of said first and second hydrogen bond acceptor moieties to form hydrogen bonds to the flap water molecule of said HIV aspartyl protease when said compound is bound thereto in said conformation;

(d) evaluating the capability of said substantially hydrophobic moieties to associate with the $P_1$ and $P_1'$ binding pockets of said HIV aspartyl protease when said compound is bound thereto in said conformation;

(e) evaluating the capability of said third hydrogen bonding moiety to form hydrogen bonds to Asp25 and Asp25' of said HIV aspartyl protease when said compound is bound thereto in said conformation;

(f) evaluating the overlap of the occupied volume of said compound when said compound is bound to said HIV aspartyl protease in said conformation and the occupied volume of a native substrate of HIV aspartyl protease or a nonhydrolyzable isostere thereof, when said polypeptide is bound to said HIV aspartyl protease;

(g) evaluating the deformation energy of binding of said compound to said HIV aspartyl protease;

(h) evaluating the enthalpic contribution of the sum of all electrostatic interactions between said compound and said HIV aspartyl protease when said compound is bound thereto in said conformation; and (i) accepting or rejecting said candidate compound as an HIV protease inhbitor based upon the determinations and evaluations carried out in steps (b) through (h).

Using the novel combination of steps set forth in this screening method, the skilled artisan can advantageously avoid time consuming and expensive experimentation to determine enzymatic inhibition activity of particular compounds. The method is also useful for facilitating rational design of HIV protease inhibitors and anti-HIV viral agents, including therapeutic and prophylactic agents against HIV infection. Accordingly, the present invention relates to such inhibitors and anti-viral agents produced by the screening method described above.

A variety of conventional techniques may be used to carry out each of the above evaluations. Generally, these techniques involve determining the location and binding proximity of a given moiety, the occupied volume of space of a bound compound, the deformation energy of binding of a given compound and electrostatic interaction energies. Examples of conventional techniques useful in the above evaluations include: quantum mechanics, molecular mechanics, molecular dynamics, Monte Carlo sampling, systematic searches and distance geometry methods (G. R. Marshall, *Ann. Ref. Pharmacol. Toxicol.*, 27, p. 193 (1987)). Specific computer software has been developed for use in carrying out these methods. Examples of programs designed for such uses include: Gaussian 92, revision C (M. J. Frisch, Gaussian, Inc., Pittsburgh, Pa. ©1992); AMBER, version 3.0 (U. C. Singh, University of California at San Francisco, ©1992); QUANTA/CHARMM (Molecular Simulations, Inc., Burlington, Mass. ©1992); and Insight II/Discover (Biosysm Technologies Inc., San Diego, Calif. ©1992). These programs may be implemented, for instance, using a Silicon Graphics workstation, IRIS 4D/35 or IBM RISC/6000 workstation model 550. Other hardware systems and software packages will be known and of evident applicability to those skilled in the art.

Additional analysis of the actual detailed interactions of the HIV protease-inhibitor complex can be employed to ascertain more specifically the binding associations between the enzyme and the bound inhibitor. Such analysis may be carried out, for example, by studying a solution of the complex by single- and multi-dimensional NMR techniques. Advantageously, the enzyme and/or the inhibitor may be enriched with stable isotopes such as $^{13}C$, $^{15}N$ and $^{2}H$ to more easily determine binding conformation and proximity. Techniques, such as isotope editing, may be used to enhance the resolution with which the interactions are observed.

Either as an alternative or a supplemental analysis, the HIV protease-inhibitor complex may be studied by single crystal X-ray diffraction. The process of determining the structures of protein/inhibitor complexes using the X-ray techniques described above is well known and has been used for many different complexes (see T. L. Blundel and L. N. Johnson, *Protein Crystallography*, Academic Press, (1976) and *Methods in Enzymology*, volumes 114 and 115, H. W. Wyckoff et al., eds., Academic Press (1985)). This technique can employ, for instance, a highly purified preparation of HIV protease complexed with an inhibitor of interest in a buffered solution (typically at a pH of between about 4.5 and about 8.0). The complex is allowed to crystallize in the presence of a precipitation agent (such as ammonium sulfate) under conditions which yield single crystals of the complex. Specific conditions for crystallizing HIV protease with various inhibitors have been well documented (see, for example, G. B. Dreyer et al., *Biochemistry*, 31, p. 6646 (1992)). Application of a concentrated X-ray beam to an appropriately prepared and mounted crystal (preferably, an X-ray beam from a rotating anode X-ray generator or synchrotron) will yield a diffraction pattern from the reflected X-ray beam.

Detection of the diffracted rays may be carried out by visualizing photographic paper exposed to the diffracted X-rays or alternatively, by using a multiwire area detector (such as that manufactured by Siemens Analytical X-Ray Instruments, Inc. (Madison, Wis.)) or an R-axis II image plate system from Rigaku Corporation (distributed by Molecular Structure Corporation, The Woodlands, Tex.). Other systems for generating and collecting X-ray diffraction data will be known to those of ordinary skill in the art.

Refinement of the X-ray diffraction data yields a three dimensional structure. Computer software (such as X-PLOR (Yale University, ©1992, distributed by Molecular Simulations, Inc.) has been developed to carry out this refinement.

In general, using the above techniques with an appropriately prepared crystalline complex, a structure may be refined to about 2–3 Å with an R value of about 0.25 or less. As the skilled artisan can appreciate, these values are adequate to determine the interactions between HIV protease and a given compound such that it will be clear if features (1) through (6) are present and consequently, whether that given compound is an HIV aspartyl protease inhibitor. Thus, additional inhibitors according to this invention may be designed and predicted based on a combination of crystallographic structural information and computational analysis.

For example, to predict the binding of a candidate inhibitor according to this invention, the inhibitor is examined to determine whether the molecule contains functionality which is not well represented by the existing forcefield models in CHARMM (Molecular Simulations Incorporated, Burlington, Mass.) or AMBER (Professor P. A. Kollman, UCSF). If any functionality is not well represented, we then examine all published structural information for molecules containing such functionality, and in some cases perform high-level ab initio calculations on simple molecules containing these functionalities to determine their preferred conformations and the energy differences between various conformations. More accurate parameters describing these functional groups may then be derived for the CHARMM and/or AMBER forcefields and used in subsequent calculations.

Next, the candidate inhibitor is aligned in 3-dimensional space with other, related inhibitors whose bound conformations have previously been determined by x-ray crystallography. Both Van der Walls volume and electrostatic potentials are used to direct the alignment process. The alignment is typically done with software like Quanta (Molecular Simulations) or InsightII (Biosym Technologies, San Diego, Calif.). This alignment can be done manually within this software, or more automated alignment procedures within the software (e.g. the "superimpose" option of Quanta or the "APEX" module of InsightII) may be used. The result of this alignment is a first guess of the "bound" conformation of the candidate inhibitor. This inhibitor is then docked in the active site of HIV protease, and the confomation is energy minimized with the enzyme atoms held fixed in space. These minimizations are typically done using the CHARMM or AMBER forcefields.

Because inhibitors can sometimes bind in multiple or unexpected conformations within an active site, we often then carry out further searches of the bound conformation of the enzyme-inhibitor complex. For example, a variety of Monte Carlo search techniques (e.g. as found in the Conformational Search Module of Quanta) may be used, along with high-temperature dynamics and simulated annealing. These search techniques reveal whether there are alternative, reasonable low-energy confomrations in which the inhibitor may bind to the enzyme. The effects of solvation and desolation in the formation of the various enzyme-inhibitor complexes may be estimated with programs such as DELPHI (Biosym), Polaris (Molecular Simulations) and AMSOL (Professor C. Cramer, University of Minnesota). The result of this searching is a set of one or more bound conformations for the candidate inhibitor.

For each of the low-energy conformations, waters may then be added to the active site of the enzyme and the entire system relaxed. Finally, molecular dynamics simulations may be used to study the detailed motions of the enzyme, the inhibitor, and related water molecules.

The final set of remaining low-energy conformations (typically a very small number) represents our predictions of the bound conformation of the candidate inhibitor. Each conformation includes our estimate of the dynamic flexibility of the entire system (inhibitor, enzyme, and waters).

The more advanced methodology is typically applied to the study of the first few compounds in a series, when there are the greatest uncertainties about the possible binding mode(s) in the enzyme active site. For later compounds within a series, the low energy conformers obtained from the searches on earlier compounds provide information about the possible low energy conformers of the inhibitor compounds. In addition, crystallographic information about the conformation of the bound complexes of earlier compounds within a series is often available. This prior computational and structural work advantageously facilitates the prediction of the bound conformation of candidate inhibitor molecules.

To exemplify the above screening method, we have carried out the following evaluation of compound 140 (Table II), a preferred compound of this invention, as described below.

Prediction of Binding Conformation and Energy of Compound 140 to HIV Protease

The forcefield for the benzenesulfonamide portion of compound 140 was derived from ab initio calculations and incorporated into the AMBER forcefield. The latest CHARMM forcefield parameters for this moiety were found to be adequate for energy minimization studies and are used in all Quanta/CHARMM calculations.

Figure 2:
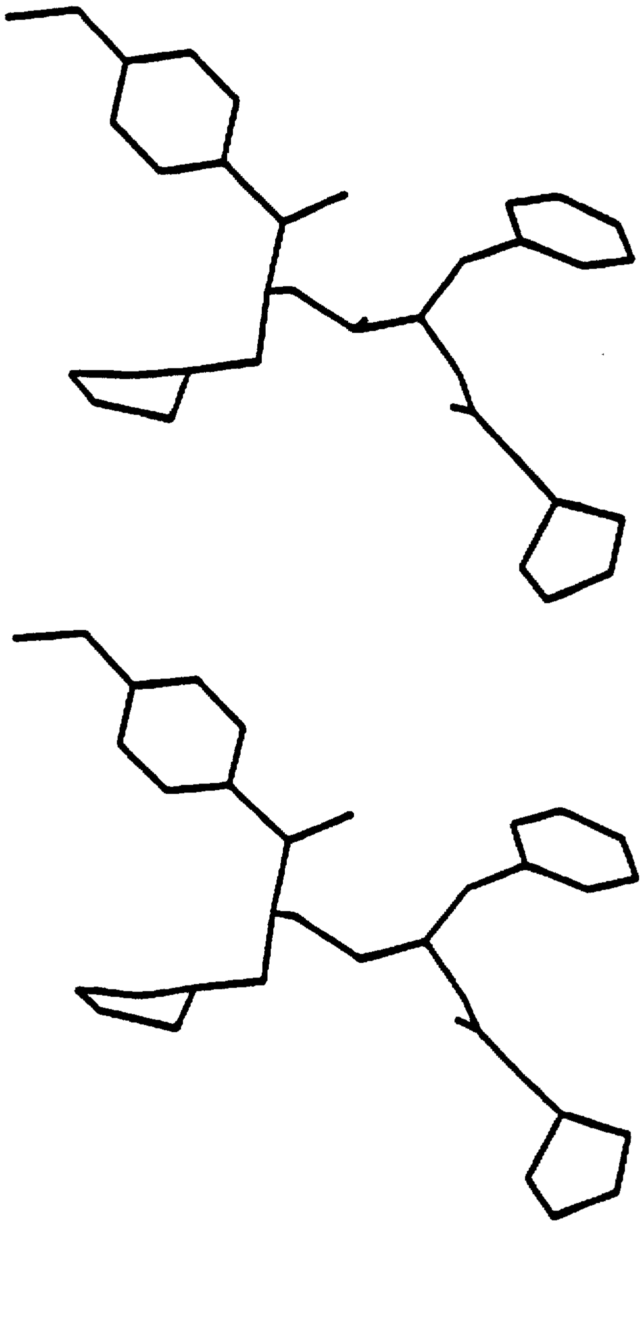
FIG. 2 depicts a stereo drawing of the actual crystal structure of Compound 140, as observed by X-ray crystallography.
Figure 3:
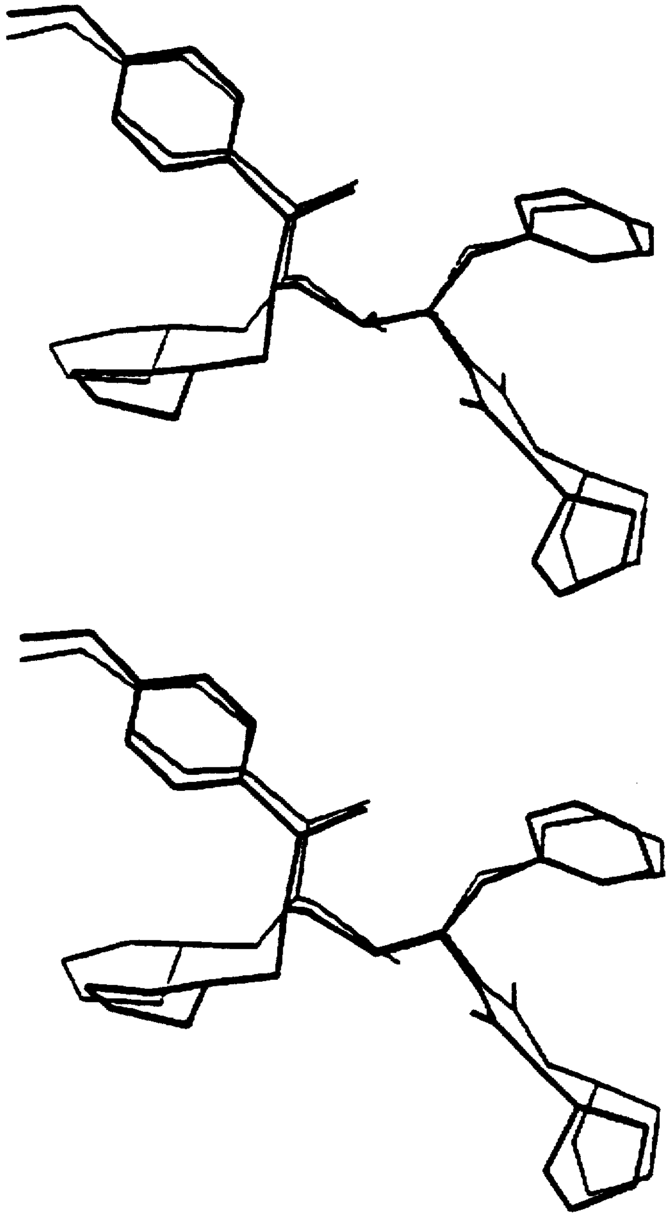
FIG. 3 depicts a stereo drawing of the correlation between the predicted (thin line) and observed (thick line) conformation of Compound 140.

The low energy conformers obtained from the conformational searches on earlier compounds in the sulfonamide series (such as compound 16) provided information about the possible low energy conformers of compound 140. These low energy conformers were aligned in 3-dimensional space with other related inhibitors whose bound conformations have previously been determined by x-ray crystallography. This alignment process was carried out manually within Quanta and, in some cases, was assisted with the "conformational search" option of Quanta. The reference crystal structure used in this alignment was the complex of HIV-1 protease with compound 16. This inhibitor structure was energy minimized in the active site of the enzyme using Quanta/CHARM. The enzyme atoms were held fixed during this minimization. only the flap water was included. Later simulations allowed the enzyme to relax and used a variety of dielectric approximations. A single low-energy conformation which was consistent with all previous conformational simulations and crystallographic data was obtained (see FIG. 1). This predicted binding conformation was later found to be essentially in agreement with the results obtained by x-ray crystallography (see FIGS. 2 and 3).

As discussed above, the novel compounds of the present invention are excellent ligands for aspartyl proteases, particularly HIV-1 and HIV-2 proteases. Accordingly, these compounds are capable of targeting and inhibiting late stage events in HIV replication, i.e., the processing of the viral polyproteins by HIV encoded proteases. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production of infectious virions, particularly from chronically infected cells. Compounds according to this invention advantageously inhibit the ability of the HIV-1 virus to infect immortalized human T cells over a period of days, as determined by an assay of extracellular p24 antigen—a specific marker of viral replication. Other anti-viral assays have confirmed the potency of these compounds.

The compounds of this invention may be employed in a conventional manner for the treatment of viruses, such as HIV and HTLV, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally-infected patient in a pharmaceutically acceptable manner and in an amount effective to lessen the severity of the viral infection.

Alternatively, the compounds of this invention may be used in vaccines and methods for protecting individuals against viral infection over an extended period of time. The compounds may be employed in such vaccines either alone or together with other compounds of this invention in a manner consistent with the conventional utilization of protease inhibitors in vaccines. For example, a compound of this invention may be combined with pharmaceutically acceptable adjuvants conventionally employed in vaccines and administered in prophylactically effective amounts to protect individuals over an extended period time against HIV infection. As such, the novel protease inhibitors of this invention can be administered as agents for treating or preventing HIV infection in a mammal.

The compounds of formula I, especially those having a molecular weight of less than about 700 g/mole, may be readily absorbed by the bloodstream of mammals upon oral administration. Compounds of formula I having a molecular weight of less than about 600 g/mole are most likely to demonstrate oral availability. This surprisingly impressive oral availability makes such compounds excellent agents for orally-administered treatment and prevention regimens against HIV infection.

The compounds of this invention may be administered to a healthy or HIV-infected patient either as a single agent or in combination with other anti-viral agents which interfere with the replication cycle of HIV. By administering the compounds of this invention with other anti-viral agents which target different events in the viral life cycle, the therapeutic effect of these compounds is potentiated. For instance, the co-administered anti-viral agent can be one which targets early events in the life cycle of the virus, such as cell entry, reverse transcription and viral DNA integration into cellular DNA. Anti-HIV agents targeting such early life cycle events include, didanosine (ddI), alcitabine (ddC), d4T, zidovudine (AZT), polysulfated polysaccharides, sT4 (soluble CD4), ganiclovir, dideoxycytidine, trisodium phosphonoformate, eflornithine, ribavirin, acyclovir, alpha interferon and trimenotrexate. Additionally, non-nucleoside inhibitors of reverse transcriptase, such as TIBO or nevirapine, may be used to potentiate the effect of the compounds of this invention, as may viral uncoating inhibitors, inhibitors of trans-activating proteins such as tat or rev, or inhibitors of the viral integrase.

Combination therapies according to this invention exert a synergistic effect in inhibiting HIV replication because each component agent of the combination acts on a different site of HIV replication. The use of such combinations also advantageously reduces the dosage of a given conventional anti-retroviral agent which would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce potential of resistance to single agent therapies, while minimizing any associated toxicity. These combinations may also increase the efficacy of the conventional agent without increasing the associated toxicity. In particular, we have discovered that these compounds act synergistically in preventing the replication of HIV in human T cells. Preferred combination therapies include the administration of a compound of this invention with AZT, ddI, ddC or d4T.

Alternatively, the compounds of this invention may also be co-administered with other HIV protease inhibitors such as Ro 31-8959 (Roche), L-735,524 (Merck), XM 323 (Du-Pont Merck) and A-80,987 (Abbott) to increase the effect of therapy or prophylaxis against various viral mutants or members of other HIV quasi species.

We prefer administering the compounds of this invention as single agents or in combination with retroviral reverse transcriptase inhibitors, such as derivatives of AZT, or other HIV aspartyl protease inhibitors. We believe that the co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The compounds of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexone and rEPO); and antibiotics (e.g., pentamidine isethiorate) to prevent or combat infection and disease associated with HIV infections, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of an aspartyl protease inhibitor of this invention and another therapeutic or prophylactic agent.

Although this invention focuses on the use of the compounds disclosed herein for preventing and treating HIV infection, the compounds of this invention can also be used as inhibitory agents for other viruses which depend on similar aspartyl proteases for obligatory events in their life cycle. These viruses include, as well as other AIDS-like diseases caused by retroviruses, such as simian immunodeficiency viruses, but are not limited to, HTLV-I and HTLV-II.

In addition, the compounds of this invention may also be used to inhibit other aspartyl proteases, and in particular, other human aspartyl proteases, including renin and aspartyl proteases that process endothelin precursors.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic. pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as *Ph. Helv* or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 50 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide or may be derivatized to bind to a stable resin as a tethered substrate for affinity chromatography applications. These and other uses which characterize commercial aspartyl protease inhibitors will be evident to those of ordinary skill in the art.

In order that this invention be more fully understood, the following examples are set forth. These examples are for the purpose of illustration only and are not to be construed as limiting the scope of the invention in any way.

General Materials and Methods

All temperatures are recorded in degrees Celsius. Thin layer chromatography (TLC) was carried out using 0.25 mm thick E. Merck silica gel 60 $F_{254}$ plates and elution with the indicated solvent system. Detection of the compounds was carried out by treating the plate with an appropriate visualizing agent, such as 10% solution of phosphomolybdic acid in ethanol or a 0.1% solution of ninhydrin in ethanol, followed by heating, and/or by exposure to UV light or iodine vapors when appropriate. Thick layer silica gel chromatography was also carried out using E. Merck 60 $F_{254}$ plates ("prep plates") of 0.5, 1.0, or 2.0 mm thickness. Following development of the plate, the band of silica containing the desired compound was isolated and eluted with an appropriate solvent. Analytical HPLC was carried out using a Water's Delta Pak, 5 μM silica, C18 reversed-phase column, 3.9 mm ID×15 cm L with a flow rate of 1.5 mL/min using the following table:

Mobile phase

A=0.1% $CF_3CO_2H$ in $H_2O$

B=0.1% $CF_3CO_2H$ in $CH_3CN$

Gradient

T=0 min., A (95%), B (5%)

T=20 min., A (0%), B (100%)

T=22.5 min., A (0%), B (100%)

Preparative HPLC was also carried out using $C_{18}$ reversed-phase media. HPLC retention times were recorded in minutes. NMR spectral data was recorded using a Bruker AMX500, equipped with either a reverse or QNP probe, at 500 MHz, and was taken in the indicated solvent.

We have measured the inhibition constants of each compound against HIV-1 protease using the method described essentially by M. W. Pennington et al., *Peptides* 1990, Gimet, E. and D. Andrew, Eds., Escom; Leiden, Netherlands (1990).

Compounds of formula I were tested for their antiviral potency in several virological assays. In the first assay, the compounds were added as a solution in dimethylsulfoxide (DMSO) to a test cell culture of CCRM-CEM cells, a strain of $CD4^+$ human T-cell lymphoma cells, previously acutely infected with $HIV_{IIIb}$ using standard protocols (see Meek, T. D. et al., "Inhibition of HIV-1 protease in infected T-lymphocytes by synthetic peptide analogues", *Nature,* 343, p. 90 (1990). Preferred compounds are those which are able to inhibit 90% of viral infectivity at a concentration of 1 μM or less. More preferred compounds are those which are able to inhibit 90% of viral infectivity at a concentration of 100 nM or less.

The effect of the compounds on inhibiting the replication of the virus was measured by determining the HIV extracellular p24 antigen concentration using a commercial enzyme immunoassay (obtained from Coulter Corporation, Hialeah, Fla.).

Depending on the cell type and the desired readout, syncytia formation, reverse-transcriptase (RT) activity, or cytopathic effect as assayed by a dye uptake method may also be used as readouts of antiviral activity. See H. Mitsuya and S. Broder, "Inhibition of the in vitro infectivity and cytopathic effect of human T-lymphotropic virus type III/lymphoadenopathy-associated virus (HTLV-III/LAV) by 2',3'-dideoxynucleosides", *Proc. Natl. Acad. Sci. USA*, vol. 83, pp. 1911–1915 (1986). The effect of compounds of formula I on clinical isolates of other HIV-1 strains was determined by obtaining low-passaged virus from HIV-infected patients and assaying the effect of the inhibitors in preventing infection of the HIV virus in freshly prepared human peripheral blood mononuclear cells (PBMCs).

Insofar as compounds of formula I are able to inhibit the replication of the HIV virus in human T-cells and furthermore, may be delivered orally to mammals, they are of evident clinical utility for the treatment of HIV infection. These tests are predictive of the compounds ability to inhibit HIV protease in vivo.

EXAMPLE 1

A. Compound XI ((syn)-OH, D'=benzyl)

184 g of Brockman Super I grade neutral alumina was slurried in sufficient diethyl ether to form a thick, stirrable suspension and was treated with 7.48 mL of benzylamine. After stirring for 5 min, 7.28 g of (1S,2S)-1-(N-benzyoxycarbonyl)-amino-2-phenylethyl-oxirane was added and the mixture stirred for 15 h. The mixture was treated with 15.28 g of di-tert-butylpyrocarbonate and 4.70 mL of diisopropylethylamine. This mixture was stirred for 3.5 h, then treated with 600 mL of methanol, allowed to stand for 3.5 h, and filtered to yield a yellow oil, which was purified by silica gel chromatography using a gradient of 0.5 to 1.5% methanol in methylene chloride to yield 3.88 g of the desired product as a white solid. Further washing the filter cake with methanol and with 3% ammonium hydroxide in methanol yielded 2.2 g of 4-benzylamino-2-N-benzyloxycarbonylamino-3-hydroxy-1-phenylbutane in several portions. Each of these portions was treated separately, as a solution in methylene chloride, with 1.1 molar equivalents each of di-tert butylpyrocarbonate and diisopropylethylamine, followed by aqueous workup with water, 10% aqueous $KHSO_4$, and brine, drying over $MgSO_4$, and concentration in vacuo. The combined products of these reactions were purified by silica gel chromatography using a gradient of 5% to 15% diethyl ether in methylene chloride. The resulting pure fractions were collected and combined with the previously purified product to yield 5.49 g of a white solid. TLC: Rf=0.56, 5% methanol/$CH_2Cl_2$; ($^1H$)-NMR ($CDCl_3$) consistent with structure.

B. Compound XII ((syn)-OH, D'=benzyl)

A solution of 5.49 g of the resultant compound of Example 1A in 40 mL of ethanol was hydrogenated under a slight positive pressure of hydrogen in the presence of 380 mg of 10% palladium on carbon for 16 h. After filtering and concentrating in vacuo, the desired product was obtained as 4.03 g of a white solid. TLC: Rf=0.21, 95:5:0.5 $CH_2Cl_2$/methanol/concentrated $NH_4OH$.

C. Compound XIII ((syn)-OH, A=benzyloxycarbonyl, D'=benzyl)

A solution of 3.02 g of the resultant compound of Example 1B in 150 mL of methylene chloride was treated with 4.35 g of $N^{\alpha}$-Cbz-$N^{\delta}$-trityl asparagine, 1.16 g of hydroxybenzotriazole hydrate, and 1.64 g of 1-(3-dimethylaminopropyl)-3-ethylcarbodiimide hydrochloride. The mixture was stirred for 16 h, then diluted with 3 volumes of diethyl ether and washed sequentially with water, saturated $NaHCO_3$ solution, 10% $KHSO_4$ solution, and brine. After drying over $MgSO_4$ and concentrating in vacuo, a yellow oil was obtained which was purified by chromatography on a Florisil column using a gradient of 0% to 25% EtOAc in $CH_2Cl_2$ as eluant to yield 8.00 g of the title compound as a white foam. TLC: Rf=0.51, 5% methanol/$CH_2Cl_2$; ($^1$H)-NMR ($CDCl_3$) consistent with structure.

D. Compound XIV ((syn)-OH, A=H, D'=benzyl)

A solution of 7.90 g of the resultant compound of Example 1C in 150 mL of ethanol was hydrogenated under a slight positive pressure of hydrogen in the presence of 550 mg of 10% palladium on carbon for 2.5 h, then ca. 50 mg more 10% palladium on carbon was added, the mixture was then filtered and concentrated in vacuo to give the desired product as 6.66 g of a white solid which was used without subsequent purification. TLC: Rf=0.26, 95:5:0.5 $CH_2Cl_2$/methanol/concentrated $NH_4OH$.

E. Compound XIV ((syn)-OH, A=quinoline-2-carbonyl, D'=benzyl)

A suspension of 1.51 g of quinaldic acid and 6.17 g of the resultant compound of Example 1D in 150 mL of acetonitrile was treated with 1.52 mL of diisopropylethylamine and 3.58 g of BOP reagent. The mixture was stirred for 14 h, then concentrated in vacuo. The gummy residue was partitioned between ether and water, and the organic layer was washed sequentially with brine, saturated $NaHCO_3$ solution, water, 10% $KHSO_4$ solution, and brine, then dried over $MgSO_4$ and concentrated in vacuo. Subsequent purification by silica gel chromatography using 0% to 8.5% solvent A in methylene chloride (where solvent A is defined as 90:10:1, methylene chloride/methanol/concentrated ammonium hydroxide) yielded 5.79 g of the title compound as a white foam, along with ca. 600 mg of slightly impure side fractions. TLC: Rf=0.41, 5% methanol/$CH_2Cl_2$; ($^1$H)-NMR ($CDCl_3$) consistent with structure.

F. Compound 1

A 58 mg portion of the resultant compound of Example 1E was treated with 1 mL of 90% aqueous TFA and allowed to stand for 17 h. The mixture was concentrated in vacuo and the residue taken up in 3 mL of $CH_2Cl_2$, treated with 100 μL of DIEA, and cooled to 0° C. To this solution was added 26 μL of benzenesulfonyl chloride, and the mixture was stirred for 18 h, warming slowly to ambient temperature. After concentration of the mixture in vacuo, the residue was purified by thick layer silica gel chromatography using 5% MeOH/$CH_2Cl_2$ as eluant followed by preparative reversed-phase $C_{18}$ HPLC using a linear gradient of 40% to 100% $CH_3CN/H_2O$ with 0.1% TFA for elution to obtain 8.3 mg of the title compound. TLC: Rf=0.50, 5% MeOH/$CH_2Cl_2$. HPLC: Rt=17.8 min. NMR (DMSO-$d_6$)δ 2.62 (dd, 1H); 2.76 9d, 2H); 2.80 (dd, 1H); 3.11, (d, 2H); 3.34 (dd, 1H); 4.59 (br s, 1H); 4.68 (br s, 1H); 3.97 (m, 1H); 4.20 (d, 1H), 4.35 (d, 1H); 4.68 (dd, 1H); 6.39 (d, 1H); 6.74 (t, 1H); 6.81 (t, 2H); 6.93 (d, 2H); 7.12–7.24 (m, 6H); 7.51 (t, 2H); 7.57 (t, 1H); 7.62 (dd, 1H); 7.77 (t, 2H), 7.96 (d, 1H); 8.09 (d, 1H); 8.16 (d, 1H); 8.31 (d, 1H); 8.53 (d, 1H).

EXAMPLE 2

Compound 2

A 150 mg portion of the resultant compound of Example 1E was dissolved in 1 mL of 90% aqueous TFA and stirred at ambient temperature overnight, then concentrated in vacuo. The crude TFA salt residue was dissolved in 7 mL of dry methylene chloride and the pH of the solution was adjusted to pH 8 with 1N NaOH. 56 mg of a mixture of 4-fluoro-3-acetamidobenzene sulfonylchloride and 3-fluoro-4-acetamidobenzene sulfonylchloride (~1:1) was added and the mixture stirred vigorously for 3 hours after which an additional 25 mg was added and the reaction allowed to continue for an additional 12 hours. The reaction was then diluted with 50 mL of ethylene chloride and the organic layer was washed sequentially with water and brine, dried over $MgSO_4$ and concentrated in vacuo. The crude residue was purified using a silica gel flash chromatography column using a gradient of 3% to 5% MeOH in methylene chloride as eluant to yield 60 mg of the title compounds. TLC: Rf=0.50, 10% MeOH/$CH_2Cl_2$; HPLC: Rt=13.93 min. NMR ($CDCl_3$): δ9.05 (s, 1H); 8.65 (d, 0.5H); 8.58 (t, 0.5H), 8.20 (dd, 0.5H), 7.85 (d, 1H) 7.75 (m, 0.5H), 7.45–7.63 (m, 1.5H), 7.14–7.25 (m, 6H), 6.78–6.95 (m, 5H), 6.70 (d, 1H), 6.41 (s, 0.5H), 6.25 (s, 0.5H), 6.18 (s, 0.5H), 6.10 (s, 0.5H), 4.88 (m, 0.5H), 4.81 (m, 0.5H), 4.37 (d, 1H), 4.35 (m, 1H), 4.21 (d, 1H), 4.00 (m, 1H), 3.46 (m, 0.5H), 3.35 (m, 0.5H), 3.27 (d, 0.5H), 3.16 (d, 0.5H), 3.14 (d, 1H), 2.45–2.75 (m, 5H); 2.16, 2.20 (2 s, 3H total).

EXAMPLE 3

Compound 3

A 23 mg portion of the resultant compound of Example 1E was treated with 1 mL of 90% aqueous TFA and allowed to stand for 15 h. The mixture was concentrated in vacuo and the residue taken upon in 2 mL of $CH_2Cl_2$, treated with 6 μL of DIEA, and cooled to 0° C. To this solution was added 23 mg of 3,5-dimethylisoxazole-4-sulfonyl chloride, and the mixture was stirred for 18 h, warming slowly to ambient temperature. After concentration of the mixture in vacuo, the residue was purified by preparative reversed-phase $C_{18}$ HPLC using a linear gradient of 35% to 100% $CH_3CN/H_2O$ with 0.1% TFA for elution to obtain 1.1 mg of the title compound. TLC: Rf=0.55, 10% MeOH/$CH_2Cl_2$. HPLC: Rt=14.5 min; ($^1$H)-NMR ($CDCl_3$) consistent with structure.

EXAMPLE 4

Compound 4

A 33 mg portion of the resultant compound of Example 1E was treated with 1 mL of 90% aqueous TFA and allowed to stand for 15 h. The mixture was concentrated in vacuo and the residue taken up in 3 mL of $CH_2Cl_2$, treated with 16 μL of DIEA, and cooled to 0° C. To this solution was added 10 μL of 3-trifluoromethylbenzene sulfonyl chloride, and the mixture was stirred for 18 h, warming slowly to ambient temperature. After concentration of the mixture in vacuo, the residue was purified by preparative reversed-phase $C_{18}$ HPLC using a linear gradient of 35% to 100% $CH_3CN/H_2O$ with 0.1% TFA for elution to obtain 1.1 mg of the title compound. TLC: Rf=0.55, 10% MeOH/$CH_2Cl_2$. HPLC: Rt=14.5 min; ($^1$H)-NMR ($CDCl_3$) consistent with structure.

EXAMPLE 5

Compound 5

A 20 mg portion of the resultant compound of Example 1E was treated with 1 mL of 90% aqueous TFA and allowed to stand for 18 h. The mixture was concentrated in vacuo and the residue taken up in 1 mL of $CH_2Cl_2$, treated with 10 μL of DIEA, and cooled to 0° C. To this solution was added 13 mg of 2-acetamido-4-methyl-5-thiazolesulfonyl chloride, and the mixture was stirred for 17 h, warming slowly to ambient temperature. After concentration of the mixture in vacuo, the residue was purified by preparative reversed-phase $C_{18}$ HPLC using a linear gradient of 35% to 100% $CH_3CN/H_2O$ with 0.1% TFA for elution to obtain 0.40 mg of the title compound. TLC: Rf=0.5, 10% $MeOH/CH_2Cl_2$. HPLC: Rt=13.8 min; ($^1$H)-NMR ($CDCl_3$) consistent with structure.

EXAMPLE 6

Compound 6

A 33 mg portion of the resultant compound of Example 1E was treated with 1 mL of 90% aqueous TFA and allowed to stand for 16 h. The mixture was concentrated in vacuo and the residue taken up in 2 mL of $CH_2Cl_2$, treated with 16 μL of DIEA, and cooled to 0° C. To this solution was added 11 mg of 5-(isoxazol-3-yl)thiophene-2-sulfonyl chloride, and the mixture was stirred for 18 h, warming slowly to ambient temperature. After concentration of the mixture in vacuo, the residue was purified by preparative reversed-phase $C_{18}$ HPLC using a linear gradient of 35% to 100% $CH_3CN/H_2O$ with 0.1% TFA for elution to obtain 1.5 mg of the title compound. TLC: Rf=0.7, 10% $MeOH/CH_2Cl_2$. HPLC: Rt=14.7 min; ($^1$H)-NMR ($CDCl_3$) consistent with structure.

EXAMPLE 7

Compound 7

A 35.5 mg portion of the resultant compound of Example 1E was treated with 1 mL of 90% aqueous TFA and allowed to stand for 18 h. The mixture was concentrated in vacuo and the residue taken up in 3 mL of $CH_2Cl_2$, treated with 16 μL of DIEA, and cooled to 0° C. To this solution was added 10 mg of 3-chlorosulfonylbenzoic acid, and the mixture was stirred for 16 h, warming slowly to ambient temperature. After concentration of the mixture in vacuo, the residue was purified by preparative reversed-phase $C_{18}$ HPLC using a linear gradient of 35% to 100% $CH_3CN/H_2O$ with 0.1% tTFA for elution to obtain 1.6 mg of the title compound. TLC: Rf=0.7, 10% $MeOH/CH_2Cl_2$. HPLC: Rt=13.6 min; ($^1$H)-NMR ($CDCl_3$) consistent with structure.

EXAMPLE 8

Compound 8

0.04 mmol of the resultant compound of Example 10A was converted to the free base by partitioning between EtOAc and sat. $NaHCO_3$. Treatment of the resulting compound with an excess of 1% HCl/MeOH and concentration in vacuo yielded the hydrochloride salt as a white solid. This compound was suspended in $CH_2Cl_2$ and treated with sufficient DIEA to bring the pH to >10 (moist pH paper). The solution was treated with 7 molar equivalents of chlorotrimethylsilane and stirred for 15 h under nitrogen, then treated with 0.06 mmol of methane sulfonyl chloride and stirred for 1 h. The resulting mixture was concentrated to a small volume, applied directly to a thick layer silica gel plate and eluted with 7% $MeOH/CH_2Cl_2$. The primary UV-quenching band was isolated and further purified by preparative reversed-phase HPLC to yield the title compound as a white solid. TLC: Rf=0.65, 10% $CH_3OH/CH_2Cl_2$, HPLC: Rt=12.3 min; ($^1$H)-NMR ($CDCl_3$) consistent with structure.

EXAMPLES 9 AND 192

A. Compound XIV ((syn, anti-OH, A=quinoline-2-carbonyl, D'=isobutyl)

A solution of 317 mg (0.425 mmol) of the resultant compounds of Example 17B, diastereomer B and 0.11 mL (0.637 mmol) of diisopropylethyl amine in 7 mL of dichloromethane was treated with 139.1 mg (0.637 mmol) of di-tert-butyl dicarbonate. After 24 hours, the mixture was diluted with dichloromethane. The mixture was washed with water, 5% $NaHCO_3$, 0.5N HCl, brine then dried over $MgSO_4$, filtered and concentrated in vacuo. The residue was purified by low pressure silica gel column chromatography using a 20% ethyl acetate/dichloromethane as eluent to yield 81.2 mg of the fast moving hydroxyl diastereomer, 65.8 mg of the slower moving hydroxyl diastereomer, and 65.8 mg of the mixed diastereomers. TLC: Rf=0.60, 0.67, 40% EtOAc/$CH_2Cl_2$; ($^1$H)-NMR ($CDCl_3$) consistent with structure.

B. Compounds 9 and 192

A solution of 35.1 mg (0.041 mmol) of the resultant mixed diastereomers (~1:1) of Example 9/192A in 0.8 mL of dichloromethane was treated with 0.8 mL of trifluoroacetic acid. After 4 hours, the mixture was concentrated in vacuo. TLC: Rf=0.11, 10% $CH_3OH/CH_2Cl_2$. To a solution of the resulting trifluoroacetic acid salt (entire yield) in 1 mL of dichloromethane was sequentialled added 0.3 mL of saturated $NaHCO_3$, a small amount of solid $NaHCO_3$ and 11.8 mg (0.054 mmol) of benzofurazan-4-sulphonyl chloride. After 3 hours, the mixture was diluted with dichloromethane. The two layers were separated and the aqueous layer was extracted once with dichloromethane. The combined organic layer was washed with brine then dried over $MgSO_4$, filtered and concentrated in vacuo. The residue was purified by preparative HPLC to yield 2.0 mg of compound 9 as a white solid: TLC: Rf=0.20, 5% $CH_3OH/CH_2Cl_2$; HPLC, RT 14.2 min. 2.7 mg of compound 192 was also obtained as a white solid, which was determined by NMR and HPLC to be contaminated with ~25% of compound 9: TLC: Rf=0.20, 5% $CH_3OH/CH_2Cl_2$; HPLC, Rt=14.2 min. ($^1$H)-NMR consistent with structure.

EXAMPLE 10

A. Compound XV ((syn)-OH, A=quinoline-2-carbonyl, D'=benzyl; TFA salt)

A 0° C. solution of 1.027 g portion of the resultant compound of Example 1E in 5 mL of $CH_2Cl_2$ was treated with 5 mL of TFA and allowed to stand for 3 h. The mixture was concentrated in vacuo to yield 0.95 g of the title compound, which was used without subsequent purification.

B. Compound 10

A solution of 30.2 mg of the resultant compound of Example 10A in 3 mL of $CH_2Cl_2$ was treated with 0.33 mL of DIEA and 31.1 mg of m-benzenedisulfonyl chloride. The mixture was stirred for 2 h, then treated with 2 mL of concentrated aqueous ammonium hydroxide. The biphasic mixture was stirred for an additional 16 h, concentrated in vacuo, and the residue partitioned between ethyl acetate and brine. The organic layer was dried over anhydrous $MgSO_4$ and concentrated in vacuo, and the residue was purified by preparative thick layer silica gel chromatography using 3% $MeOH/CH_2Cl_2$ as eluant to yield 4.5 mg of the title compound. TLC: Rf=0.5, 3% $MeOH/CH_2Cl_2$ as eluant to yield 4.5 mg of the title compound. TLC: Rf=0.5, 3% MeOH/$CH_2Cl_2$. HPLC: Rt=13.4 min; ($^1$H)-NMR ($CDCl_3$) consistent with structure.

EXAMPLE 11

Compound 11

A solution of 57.9 mg of the resultant compound of Example 10A in 5 mL of $CH_2Cl_2$ was treated with 30 μL of DIEA and 9.3 μL of dimethylsulfamoyl chloride. The mixture was stirred for 12 h, then treated with an additional 30 μL of DIEA and 9.3 μL of dimethylsulfamoyl chloride and the reaction was allowed to proceed an additional 12 hours. The mixture was then diluted with $CH_2Cl_2$ and washed with saturated $NH_4Cl$; the aqueous layer was washed with $CH_2Cl_2$, and the combined organic extracts were dried over $MgSO_4$. Filtration and concentration provided a residue which was chromatographed on a silica gel column using 2.5% MeOH/EtOAc as eluent, yielding a slightly impure product which was further purified by preparative HPLC using a linear gradient of 35% to 100% $CH_3$/CN/$H_2O$ with 0.1% TFA for elution. HPLC: Rt=13.0 minutes. NMR ($CDCL_3$): δ9.15 (d, 1H), 8.34 (d, 1H), 8.22 (d, 1H), 8.18 (d, 1H), 7.90 (d, 1H), 7.80 (t, 1H), 7.65 (t, 1H), 7.16–738 (m, 5H), 7.05 (d, 1H), 6.95 (t, 1H), 6.87 (t, 1H), 5.85 (br s, 1H), 5.62 (br s, 1H), 4.87 (M, 1H), 4.46 (s, 2H), 4.08 (m, 1H), 3.66 (m, 1H), 3.30 (m, 2H), 2.59–2.94 (m, 4H), 2.81 (s, 6H).

EXAMPLE 12

A. Compound XIV ((syn)-OH, A=quinoline-2-carbonyl, D'=benzyl; trifluoroacetate salt)

To a solution of 1.027 g (1.164 mmol) of the resultant compound of Example 1E in $CH_2Cl_2$ (5 mL) at 0° to 5° C. was added trifluoromethanesulfonic acid (5 mL). After stirring for 3 h, the reaction mixture was concentrated in vacuo to provide 0.95 g of light yellow, gummy product, containing one equivalent of triphenylmethanol, which was used without subsequent purification.

B. Compound 12

To a solution of 30.2 mg (0.038 mmol) of the resultant compound of Example 12A in $CH_2Cl_2$ (3 mL) was added diisopropylethylamine (0.33 mL, 0.189 mmol), and 2-(pyrid-2-yl)-tyiophene-5-sulfonyl chloride 13 mg, (0.249 mmol). After 14 h, the resulting mixture was diluted with ethyl acetate, washed with saturated brine, dried over magnesium sulfate, filtered and concentrated in vacuo. The residue was purified by preparative reversed-phase chromatography using a 5% to 100% $H_2O$/acetonitrile gradient as eluant to yield the title product.

EXAMPLE 13

Compound 13

To a solution of 30 mg (0.038 mmol) of the resultant compound of Example 12A in $CH_2Cl_2$ (3 mL) was added diisopropylethylamine (0.33 mL, 0.189 mmol), and 2-(3-phenylsulfonyl)thiophene sulfonyl chloride (0.113 mmol). After stirring for 2 h, the reaction mixture was made biphasic by addition of 30% ammonium hydroxide solution (2 mL). After stirring for an additional 16 h, the resultant mixture was concentrated in vacuo, reconstituted in ethyl acetate, washed with saturated brine, dried over magnesium sulfate, filtered, and re-concentrated in vacuo. Purification by thin layer preparative chromatography yielded the desired compound.

EXAMPLE 14

Compound 14

The resulting compound of Example 17B, diastereomer B (170 mg) was treated with 1 mL of 90% aqueous TFA and allowed to stand for 12 h. The mixture was concentrated in vacuo and the residue taken up in 5 mL of dry $CH_2Cl_2$. To this solution, 3 mL of saturated aqueous sodium bicarbonate and 50 mg of 4-fluorobenzenesulfonyl chloride was added and the mixture stirred for 3 h. The resulting mixture was diluted with $CH_2Cl_2$ and washed with water, dried over magnesium sulfate and filtered. After concentration of the mixture in vacuo, a portion of the residue was purified by preparative reversed-phase $C_{18}$ HPLC using a linear gradient of 35% to 100% $CH_3CN/H_2O$ with 0.1% TFA for elution to obtain 3.0 mg of the title compound. TLC: Rf=0.25, 5% $CH_3OH$ in $CH_2Cl_2$. HPLC: Rt=14.78 min; ($^1$H)-NMR ($CDCl_3$) consistent with structure.

EXAMPLE 15

Compound 15

A sample of a mixture of 4-fluoro-3-acetamidobenzenesulfonyl chloride and 3-fluoro-4-acetamidobenzenesulfonyl chloride (approx. 1:1; obtained from Maybridge Chemicals) was resolved into its respective regioisomers by silica gel chromatography using 10% isopropyl alcohol/hexane as eluent. A solution of 4-acetamido-3-fluorobenzenesulfonyl chloride (30 mg) and the resulting compound of Example 17B, diastereomer B (80 mg) in 10 mL of $CH_2Cl_2$ was reacted in the same manner as described for Example 14. After workup and purification of a portion of the product by preparative reversed-phase $C_{18}$ HPLC using a linear gradient of 35% to 100% $CH_3CN/H_2O$ with 0.1% TFA as eluent, 1.2 mg of the title compound was obtained as a white solid. TLC: Rf=0.25, 5% $CH_3OH$ in $CH_2Cl_2$. HPLC: Rt=12.91 min; ($^1$H)-NMR ($CDCl_3$) consistent with structure.

EXAMPLE 16

Compound 16

80 mg of the resulting compound of Example 17B, diastereomer B, was reacted with 45 mg of 3-acetamido-4-fluorobenzenesulfonyl chloride in the same manner as described for Example 14. After workup and purification of a portion of the product by preparative reversed-phase $C_{18}$ HPLC using a linear gradient of 35 to 100% $CH_3CN/H_2O$ with 0.1% TFA as eluent, 1.4 mg of the title compound was obtained. TLC: Rf=0.25, 5% $CH_3OH$ in $CH_2Cl_2$. HPLC: Rt=12.91 min; ($^1$H)-NMR ($CDCl_3$) consistent with structure.

EXAMPLE 17

A. (2S)-2-((1S, 2R syn, anti)-3-(2-methylpropyl)amino-1-benzyl-2-hydoxypropyl)-$N^1$-((quinoline-2-carbonyl)-amino)-$N^4$-trityl succinamide A solution of 683.1 mg (0.96 mmol) of the resultant compounds of Example 191D and 1.9 mL (19.2 mmol) of isobutylamine in 10 mL of acetonitrile in a sealed tube was heated at 90°–100° C. for 24 hours. After cooling to room temperature, the mixture was concentrated in vacuo. The residue was taken up in dichloromethane and washed with water, brine, then dried over $MgSO_4$, filtered and concentrated in vacuo to yield 783.8 mg of the mixed diastereomeric products. TLC: Rf=0.11, 10% $CH_3OH/CH_2Cl_2$; ($^1$H) -NMR ($CDCl_3$) consistent with structure.

B. Compound XIII, ((syn, anti)-OH, P=quinoline-2-carbonyl, D'=isobutyl)

A solution of 583.8 mg of the resultant compounds of Example 17A and 0.2 mL of diisopropylethylamine in 10 mL of dichloromethane was treated with 256 mg of di-tert-butyl dicarbonate. After 24 hours, the mixture was diluted with dichloromethane. The mixture was washed with water, 5% NaHCO3, 0.5N HCl, brine then dried over $MgSO_4$, filtered and concentrated in vacuo. The residue was purified by low pressure silica gel column chromatography using a 20% ethyl acetate/dichloromethane as eluent to yield 154.6 mg of the fast moving diastereomer A, later identified as having the anti configuration at the hydroxyl center; 98.8 mg of the slower moving diastereomer B, having the syn configuration at the hydroxyl center, and 204.6 mg of the mixed diastereomers A and B. TLC: Rf=0.60, 0.67, 40% EtOAc/$CH_2Cl_2$.

C. Compound 17

A solution of 64.6 mg of the resultant compounds of Example 17B, diastereomer B, in 1.5 mL of dichloromethane was treated with 1.5 mL of trifluoroacetic acid. After 4 hours, the mixture was concentrated in vacuo to yield the amine trifluoroacetate salt. TLC: Rf=0.11, 10% $CH_3OH/CH_2Cl_2$. To a solution of 17.8 mg of the resultant trifluoroacetate salt in 1 mL of dichloromethane was sequentially added 0.3 mL of saturated $NaHCO_3$, a small amount of solid $NaHCO_3$ and 10.7 mg of 4-acetamidobenzenesulphonyl chloride. After 3 hours, the mixture was diluted with dichloromethane. The two layers were separated and the aqueous layer was extracted once with dichloromethane. The combined organic layer was washed with brine then dried over $MgSO_4$, filtered and concentrated in vacuo. The residue was purified by preparative HPLC to yield 14.4 mg of the title compound as a white solid; TLC: Rf=0.54, 10% $CH_3OH/CH_2Cl_2$; HPLC, Rt=13.58 min; ($^1$H)-NMR ($CDCl_3$) consistent with structure.

EXAMPLE 18

Compound 18

To a solution of 20.8 mg (0.041 mmol) of the crude trifluoroacetate salt obtained as from Example 17B, diastereomer B, in 1 mL of dichloromethane was sequentially added 0.3 mL of saturated $NaHCO_3$, a small amount of solid $NaHCO_3$ and 13.6 mg (0.054 mmol) of 2-acetamido-4-methyl-5-thiazolesulphonyl chloride. After 3 hours, the mixture was diluted with dichloromethane. The two layers were separated and the aqueous layer was extracted once with dichloromethane. The combined organic layer was washed with brine then dried over $MgSO_4$, filtered and concentrated in vacuo. The residue was purified by preparative HPLC to yield 4.8 mg of the title compound as a white solid; TLC: Rf=0.50, 10% $CH_3OH/CH_2Cl_2$; HPLC: Rt=13.35 min; ($^1$H)-NMR ($CDCl_3$) consistent with structure.

EXAMPLE 19

A. Sodium 3-acetamidobenzenesulfonate

A solution of 118.6 mg (0.55 mmol) of 3-acetamidobenzenesulfonic acid in 0.5 mL of water was treated with 0.55 mL (0.55 mmol) of 1.0N NaOH at 0° C. After stirring at room temperature for 4 hours, the mixture was concentrated to dryness and used without subsequent purification.

B. 3-Acetamidobenzenesulfonyl chloride

The crude mixture from Example 19A was cooled to 0° C. and 0.29 g (1.38 mmol) of phosphorus pentachloride was added. The mixture of solid was stirred for 3 hours then 5 mL dichloromethane was added. After 24 hours, the slurry was filtered and concentrated in vacuo to yield 81.4 mg of solid product which was used without subsequent purification. TLC: Rf=0.50, 40% $EtOAC/CH_2Cl_2$.

C. Compound 19

A solution of 82.7 mg (0.098 mmol) of diastereomer B, obtained in Example 17B, in 2 mL of dichloromethane was treated with 2 mL of trifluoroacetic acid. After 4 hours, the mixture was concentrated in vacuo to yield the amine trifluoroacetate salt which was used without further purification; TLC: Rf=0.11, 10% $CH_3OH/CH_2Cl_2$. A solution of this salt (entire yield) in 2 mL of dichloromethane was treated sequentially with 0.5 mL of saturated $NaHCHO_3$, small amount of solid $NaHCO_3$ and a solution of 81.4 mg (0.046 mmol) of the resultant compound of Example 19B. After 3 hours, the mixture was diluted with dichloromethane. The two layers were separated and the aqueous layer was extracted once with dichloromethane. The combined organic layer was washed with brine then dried over $MgSO_4$, filtered and concentrated in vacuo. The residue was purified by preparative HPLC to yield 24.7 mg of the title compound as a white solid; TLC: Rf=0.42, 10% $CH_3OH/CH_2Cl_2$; HPLC: Rt=13.8 min; ($^1$H)-NMR ($CDCl_3$) consistent with structure.

EXAMPLE 20

Compound 20

A solution of 209.0 mg (0.24 mmol) of the resultant compound of Example 17B, diastereomer B, in 5 mL of dichloromethane was treated with 5 mL of trifluoroacetic acid. After 4 hours, the mixture was concentrated in vacuo. TLC: Rf=0.11, 10% $CH_3OH/CH_2Cl_2$. To a solution of this residue in 2 mL of dichloromethane was sequentially added 0.5 mL of saturated $NaHCO_3$, a small amount of solid $NaHCO_3$ and 70.2 mg (0.32 mmol) of benzofurazan-4-sulphonyl chloride. After 3 hours, the mixture was diluted with dichloromethane. The two layers were separated and the aqueous layer was extracted once with dichloromethane. The combined organic layer was washed with brine then dried over $MgSO_4$, filtered and concentrated in vacuo. The residue was purified by preparative HPLC to yield 108.0 mg of the title compound as a white solid; TLC: Rf=0.60, 10% $CH_3OH/CH_2Cl_2$; HPLC: Rt=14.95 min; ($^1$H)-NMR ($CDCl_3$) consistent with structure.

EXAMPLE 21

Compound 21

The resulting compound of Example 17B, diastereomer B, (228 mg, 0.27 mmol) was dissolved in 1:1 $CH_2Cl_2$/TFA (10 mL), and the reaction mixture stirred for 3.5 hours, then concentrated to dryness to afford the product trifluoroacetate salt as a yellow solid which was used in the next reaction without purification. To a solution of this residue (34.7 mg, 0.05 mmol) in $CH_2Cl_2$ (3 mL) was added Heunig's base (41 μl, 0.24 mmol) and dimethylsulfamoyl chloride (11 μl, 0.09 mmol), and the reaction was stirred for 17 hours at room temperature. The reaction mixture was then diluted with $CH_2Cl_2$ and washed with saturated $NH_4Cl$, and the organic layer was dried over $MgSO_4$. Filtration and concentration provided a residue which was chromatographed on a silica gel column using 8% $CH_3OH/CH_2Cl_2$ as eluent, yielding the desired compound which was further subject to purification by preparative HPLC. HPLC: Rt=13.8 minutes. TLC: Rf=0.40, 8% $CH_3OH/CH_2Cl_2$; ($^1$H)-NMR ($CDCl_3$) consistent with structure.

EXAMPLE 22

A. $N^\alpha$-isocyano-L-valine methyl ester

To the HCl salt of valine methyl ester (2.08 g, 12.40 mmol) in toluene (20 mL) was added a 20% solution of phosgene in toluene (32 mL, 62.00 mmol), and the solution was heated at reflux for 12 hours. The reaction was then cooled to room temperature and concentrated in vacuo to give a pale yellow liquid which was used in the subsequent reaction without purification. TLC: Rf=0.88, 50% Hexane/EtOAc; ($^1$H)-NMR ($CDCl_3$) consistent with structure.

B. $N^\alpha$-(2-pyridylmethyl)-oxycarbonyl-L-valine methyl ester

A mixture of 2-pyridylcarbinol (941 μl, 9.75 mmol) and the resulting compound of Example 22A (1.28 g, 8.12 mmol) were allowed to stir in $CH_2Cl_2$ (7 mL) for 12 hours, then the reaction was concentrated and the residue chromatographed with 50% hexane/EtOAc to afford 2.03 grams of the title compound as a colorless oil. TLC: Rf=0.26, 50% Hexane/EtOAc; ($^1$H)-NMR ($CDCl_3$) consistent with structure.

C. $N^\alpha$-(2-pyridylmethyl)-oxycarbonyl-L-valine

A solution of the resulting compound of Example 22B (634 mg, 2.38 mmol) in a 1/1 mixture of 1N HCl/THF (6 mL) containing 12N HCl (0.5 mL) was allowed to stir at room temperature over 15 hours, but much starting material was still present by TLC. Hence, more 12N HCL was added (1 mL), and the reaction stirred an additional 48 hours. The reaction was then concentrated to dryness and diluted with $CH_2Cl_2$, yielding the desired carboxylic acid as an insoluble resin which was washed with additional $CH_2Cl_2$, providing 22C which contained minor quantities of 22B. This material was used in the subsequent reaction without further purification. TLC: Rf=0.11, 8% $CH_3OH/CH_2Cl_2$; ($^1H$)-NMR ($CDCl_3$) consistent with structure.

D. Compound XXX (P=(2-pyridylmethyl)-oxycarbonyl, $R^3$=isopropyl, $R^{3'}$=H, D'=isobutyl, P'=tert-butoxycarbonyl)

To the resulting compound of Example 21B (277 mg, 0.82 mmol) in $CH_2Cl_2$ (5 mL) was added 1-(3-dimethylaminopropyl)-3-ethylcarbodiimide hydrochloride (210 mg, 1.10 mmol), the acid 22C (402 mg, 1.10 mmol), and 1-hydroxybenzotriazole hydrate (148 mg, 1.10 mmol). The reaction proceeded for 12 hours at room temperature, then was diluted with $CH_2Cl_2$ and washed successively with saturated $NH_4Cl$ and $NaHCO_3$, and the organic layer was dried over $MgSO_4$. Filtration and concentration provided a residue which was chromatographed on a silica gel column using 17% $THF/CH_2Cl_2$ as eluent, yielding 396 mg of product. TLC: Rf=0.26, 17% $THF/CH_2Cl_2$; ($^1H$)-NMR ($CDCl_3$) consistent with structure.

E. Compound 22

The resulting compound of Example 22D (396 mg, 0.69 mmol) was dissolved in 90% aqueous TFA (11 mL), and the reaction mixture stirred for 3 hours at room temperature, then was concentrated to dryness. To a solution of this residue (231 mg, 0.33 mmol) in $CH_2Cl_2$ (5 mL) was added excess solid $NaHCO_3$ (approx. 1 gram) and saturated aqueous $NaHCO_3$ (20 µl), followed by N-acetylsulfanilyl chloride (116 mg, 0.50 mmol), and the reaction proceeded for 12 hours at room temperature. The reaction mixture was then diluted with $CH_2Cl_2$ and washed with saturated $NaHCO_3$, and the organic layer was dried over $MgSO_4$. Filtration and concentration provided a residue which was chromatographed on a silica gel column using 8% $CH_3OH/CH_2Cl_2$ as eluent, yielding the desired compound which was further subject to purification by preparative HPLC (76.1 mg of 3 was obtained). HPLC: Rt=12.1 minutes. TLC: Rf=0.46, 8% $CH_3OH/CH_2Cl_2$; NMR ($CDCl_3$): 8.76 (d, 1H), 8.40 (br s, 1H), 8.26 (t, 1H), 7.72 (d, 2H), 7.67 (d, 2H), 7.58 (d, 2H), 7.37 (d, 1H), 7.25 (m, 4H), 7.16 (br d, 1H), 6.47 (d, 1H), 5.65 (d, 1H), 5.26 (d, 1H), 4.32 (m, 1H), 3.91 (t, 1H), 3.83 (m, 1H), 3.23 (d, 1H), 3.05 (m, 2H), 2.68–3.10 (m, 3H), 2.22 (m, 3H), 2.0 (m, 1H), 1.82 (m, 1H), 0.85 (d, 3H), 0.80 (d, 3H), 0.71 (d,3H), 0.65 (d, 3H).

EXAMPLE 23

Compound 23

Prepared by the same route as described for Example 22, except 4-pyridylcarbinol was utilized for reaction with the product of Example 22A. HPLC: Rt=12.0 minutes. TLC: Rf=0.50 (8% $CH_3OH/CH_2Cl_2$); ($^1H$)-NMR ($CDCl_3$) consistent with structure.

EXAMPLE 24

Compound 24

A solution of the resulting compound of the trifluoroacetic acid deprotection of Example 22D (as described in Example 22E; 215 mg, 0.31 mmol) in $CH_2Cl_2$ at room temperature was treated with diisopropylethylamine (214 µl, 1.23 mmol) and dimethylsulfamoyl chloride (40 µl, 0.37 mmol) in $CH_2Cl_2$ at room temperature in $CH_2Cl_2$ at room temperature for 12 hours. The reaction mixture was concentrated and chromatographed on a silica gel column with 5% $CH_3OH/CH_2Cl_2$ as eluent, yielding the desired compound which was further subject to purification by preparative HPLC (9.5 mg obtained). HPLC: Rt=14.4 minutes. TLC: Rf=0.88, 11% $CH_3OH/CH_2Cl_2$; ($^1H$)-NMR ($CDCl_3$) consistent with structure.

EXAMPLE 25

Compound 25

This compound was prepared by the route described for Example 22, except that 3-pyridylcarbinol was utilized for reaction with the compound produced in Example 22A, and in the reaction corresponding to 22E, the trifluoracetate-deprotected material was reacted with benzofurazan-4-sulphonyl chloride. HPLC: Rt=9.4 minutes. TLC: Rf=0.10, 11% $CH_3OH/CH_2Cl_2$; ($^1H$)-NMR ($CDCl_3$) consistent with structure.

EXAMPLE 26

Compound 26

A solution of the resulting compound from the trifluoroacetic acid deprotection of Example 22D (as described in Example 22E; 27 mg, 0.14 mmol) in $CH_2Cl_2$ was treated with excess solid $NaHCO_3$ (approx. 1 gram) and saturated aqueous $NaHCO_3$ (7 µl), then stirred vigorously at room temperature for 3 hours. The reaction mixture was decanted from the solids, concentrated, then the residue was purified directly by preparation HPLC (3.0 mg of white solid obtained). HPLC: Rt=14.7 minutes; ($^1H$)-NMR ($CDCl_3$) consistent with structure.

EXAMPLE 27

Compound 27

A solution of 33 mg of the resultant compound of Example 40A in $CH_2Cl_2$ was treated sequentially, at ambient temperature under an atmosphere of nitrogen, with 20 mg of N,N-diisopropylethylamine and 9.3 mg of allyl chloroformate. The mixture was stirred for 3 h and then concentrated in vacuo. The residue was taken up in ethyl acetate and washed with 0.5N HCl and saturated NaCl then dried over $MgSO_4$, filtered, and concentrated in vacuo. The residue was purified by preparative thin layer silica gel chromatography using a 2:1 mixture of (5:10:85 $NH_4OH/CH_3OH/CH_2Cl_2$):diethyl ether to yield 24 mg of the title compound as a white solid. TLC: Rf=0.53, 5:10:85 $NH_4OH/CH_3OH/CH_2Cl_2$. HPLC: Rt=14.53 min; ($^1H$)-NMR ($CDCl_3$) consistent with structure.

EXAMPLE 28

Compound 28

A solution of 47.5 mg of the resultant compound of Example 40A in $CH_2Cl_2$ was treated sequentially, at ambient temperature under an atmosphere of nitrogen, with 28.7 mg of N,N-diisopropylethylamine and 15.2 mg of isobutyl chloroformate. The mixture was stirred 3 h and then concentrated in vacuo. The residue was taken up in ethyl acetate and washed with 0.5N HCl and saturated NaCl then dried over $MgSO_4$, filtered, and concentrated in vacuo. The residue was purified by preparative thin layer silica gel chromatography using a 2:1 mixture of (5:10:85 $NH_4OH/CH_3OH/CH_2Cl_2$):diethyl ether to yield 45 mg of the title compound as a white solid. TLC: Rf=0.60, 5:10:85 $NH_4OH/CH_3OH/CH_2Cl_2$. HPLC: Rt=15.58 min; ($^1H$)-NMR ($CDCl_3$) consistent with structure.

EXAMPLE 29

Compound 29

A solution of 35.6 mg of the resultant compound of Example 40A in $CH_2Cl_2$ was treated sequentially, at ambient temperature under an atmosphere of nitrogen, with 21.5 mg of N,N-diisopropylethylamine and 0.083 nL of 1.0M isopropyl chloroformate. The mixture was stirred 3 h and then concentrated in vacuo. The residue was taken up in ethyl acetate and washed with 0.5N HCl and saturated NaCl then dried over $MgSO_4$, filtered, and concentrated in vacuo. The residue was purified by preparative thin layer silica gel chromatography using a 2:1 mixture of 5:10:85 $NH_4OH/CH_3OH/CH_2Cl_2$:diethyl ether to yield 33.2 mg of the title compound as a white solid. TLC: Rf=0.56, 5:10:85 $NH_4OH/CH_3OH/CH_2Cl_2$. HPLC: Rt=14.81 min; ($^1$H)-NMR ($CDCl_3$) consistent with structure.

EXAMPLE 30

A. (2-Pyrrolidinonyl-hydroxyethyl-N-hydroxysuccinimdyl carbonate

A solution of 572 mg of 1-(2-hydroxyethyl)-2-pyrrolidinone and 1.70 g of N,N'-disuccinimidyl carbonate in acetonitrile was treated, at ambient temperature under an atmosphere of nitrogen, with 1717 mg of N,N-diisopropylethylamine. The mixture was stirred for 14 h and concentrated in vacuo. The residue was taken up in ethyl acetate and washed with saturated $NaHCO_3$, saturated NaCl, then dried over $MgSO_4$, filtered, and concentrated in vacuo to yield 200 mg of a white solid. TLC: Rf=0.56, 10% isopropanol in $CH_2Cl_2$; ($^1$H)-NMR ($CDCl_3$) consistent with structure.

B. Compound 30

A solution of 68 mg of the resultant compound of Example 30A in $CH_2Cl_2$ was added, at ambient temperature under an atmosphere of nitrogen, to a solution of 32 mg of the resultant compound of Example 40A and 39 mg N,N-diisopropylethylamine in $CH_2Cl_2$. The mixture was stirred for 4 h, diluted with $CH_2Cl_2$, washed with saturated $NaHCO_3$ and saturated NaCl, then dried over $MgSO_4$, filtered, and concentrated in vacuo. The residue was subjected to preparative thin layer silica gel chromatography using a 2:1 mixture of 5:10:85 $NH_4OH/CH_3OH/CH_2Cl_2$:diethyl ether to yield 45 mg of residue. About 20 mg of this residue was purified by preparative HPLC to yield 13.5 mg of the title compound as a white solid. TLC: Rf=0.47, 5:10:85 $NH_4OH/CH_3OH/CH_2Cl_2$. HPLC: Rt=12.79 mid; ($^1$H)-NMR ($CDCl_3$) consistent with structure.

EXAMPLE 31

Compound 31

A solution of 39.7 mg of the resultant compound of Example 40A in $CH_2Cl_2$ was treated sequentially, at ambient temperature under an atmosphere of nitrogen, with 24 mg of N,N-diisopropylethylamine and 14.5 mg of phenyl chloroformate. The mixture was stirred for 3 h and then concentrated in vacuo. The residue was taken up in ethyl acetate and washed with 0.5N HCl and saturated NaCl then dried over $MgSO_4$, filtered, and concentrated in vacuo. The residue was purified by preparative thin layer silica gel chromatography using a 2:1 mixture of 5:10:85 $NH_4OH/CH_3OH/CH_2Cl_2$:diethyl ether to yield 39.7 mg of the title compound. TLC: Rf=0.53, 5:10:85 $NH_4OH/CH_3OH/CH_2Cl_2$. HPLC: Rt=15.22 min; ($^1$H)-NMR ($CDCl_3$) consistent with structure.

EXAMPLE 32

Compound 32

A solution of 391 mg of the resultant compound of Example 39A in 4:1 $CH_2Cl_2$/saturated aqueous $NaHCO_3$ was treated sequentially, at ambient temperature under an atmosphere of nitrogen, with 271 mg of 4-fluorobenzenesulfonyl chloride and 117 mg of sodium bicarbonate. The mixture was stirred for 14 h, diluted with $CH_2Cl_2$, washed with saturated NaCl then dried over $MgSO_4$, filtered, and concentrated in vacuo. The residue was purified by low pressure silica gel chromatography using 5% diethyl ether in $CH_2Cl_2$ as eluent to yield 420 mg of the title compound as a white solid. TLC: Rf=0.20, 5% diethyl ether in $CH_2Cl_2$. HPLC: Rt=17.41 min; ($^1$H)-NMR ($CDCl_3$) consistent with structure.

EXAMPLE 33

Compound 33

A solution of 30 mg of the resultant compound of Example 40A in $CH_2Cl_2$ was treated sequentially, at ambient temperature under an atmosphere of nitrogen, with 18.1 mg of N,N-diisopropylethylamine and 9.3 mg of benzyl isocyanate. The mixture was stirred 14 h and then concetrated in vacuo. The residue was taken up in ethyl acetate and washed with 0.5N HCl and saturated NaCl then dried over $MgSO_4$, filtered, and concentrated in vacuo. The residue was purified by preparative thin layer silica gel chromatography using a mixture of 5:10:85 $NH_4OH/CH_3OH/CH_2Cl_2$ to yield 30.2 mg of the title compound as a white solid. TLC: Rf=0.56, 5:10:85 $NH_4OH/CH_3OH/CH_2Cl_2$. HPLC: Rt=14.36 min; ($^1$H)-NMR ($CDCl_3$) consistent with structure.

EXAMPLE 34

Compound 34

A solution of 55 mg of the resultant compound of Example 40A in $CH_2Cl_2$ was treated sequentially, at ambient temperature under an atmosphere of nitrogen, with 33.3 mg of N,N-diisopropylethylamine and 17.8 mg of 2-methoxyethyl chloroformate. The mixture was stirred for 3 h and then concentrated in vacuo. The residue was taken up in ethyl acetate and washed with 0.5N HCl and saturated NaCl then dried over $MgSO_4$, filtered, and concentrated in vacuo. The residue was purified by preparative thin layer silica gel chromatography using a 2:1 mixture of (5:10:85 $NH_4OH/CH_3OH/CH_2Cl_2$):diethyl ether to yield 48.1 mg of the title compound as a white solid. TLC: Rf=0.56, 5:10:85 $NH_4OH/CH_3OH/CH_2Cl_2$. HPLC: Rt=13.43 min; ($^1$H)-NMR ($CDCl_3$) consistent with structure.

EXAMPLE 35

A. Compound XXI (D'=isobutyl, A'=4-fluorophenyl, hydrochloride salt)

A solution of 398 mg of the resultant compound of Example 32 in ethyl acetate was treated at −20° C. with HCl gas. The HCl was bubbled through the mixture for 20 min over which time the temperature was allowed to warm to 20° C. Nitrogen was then bubbled through the mixture for 15 min and solvent removed in vacuo to yield 347 mg of the title compound as a white solid. TLC: Rf=0.82, 5:10:85 $NH_4OH/CH_3OH/CH_2Cl_2$; ($^1$H)-NMR ($CDCl_3$) consistent with structure. ps B. Compound 35

A solution of 111 mg of the resultant compound of Example 35A in $CH_2Cl_2$ was added, at ambient temperature under an atmosphere of nitrogen, to a solution of 118 mg of the resultant compound of Example 48A and 133 mg N,N-diisopropylethylamine in $CH_2Cl_2$. The mixture was stirred for 14 h, diluted with $CH_2Cl_2$, washed with saturated $NaHCO_3$ and saturated NaCl, then dried over $MgSO_4$, filtered, and concentrated in vacuo. The residue was subjected to preparative thin layer silica gel chromatography using 5% $CH_3OH$ in $CH_2Cl_2$ to yield 98.8 mg of the title compound as a white solid. TLC: Rf=0.48, 5% $CH_3OH$ in $CH_2Cl_2$. HPLC: Rt=15.18 min; ($^1$H)-NMR ($CDCl_3$) consistent with structure.

EXAMPLE 36

Compound 36

A solution of 48 mg of the resultant compound of Example 40A in $CH_2Cl_2$ was treated sequentially, at ambient temperature under an atmosphere of nitrogen, with 29.0 mg of N,N-diisopropylethylamine and 15.1 mg of 3-butenyl chloroformate. The mixture was stirred for 3 h and then concentrated in vacuo. The residue was taken up in ethyl acetate and washed with 0.5N HCl and saturated NaCl then dried over $MgSO_4$, filtered, and concentrated in vacuo. The residue was purified by preparative thin layer silica gel chromatography using a 2:1 mixture of (5:10:85 $NH_4OH$/$CH_3OH$/$CH_2Cl_2$):diethyl ether to yield 43.8 mg of the title compound as a white solid. TLC: Rf=0.83, 5:10:85 $NH_4OH$/$CH_3OH$/$CH_2Cl_2$; Rf=0.24, 5% diethyl ether in $CH_2Cl_2$. HPLC: Rt=14.76 min; ($^1$H)-NMR ($CDCl_3$) consistent with structure.

EXAMPLE 37

Compound 37

A solution of 99 mg of the resultant compound of Example 51D in 4:1 $CH_2Cl_2$/saturated aqueous $NaHCO_3$ was treated sequentially, at ambient temperature under an atmosphere of nitrogen, with 83.2 mg of 3,4-dichlorobenzenesulfonyl chloride and 29 mg of sodium bicarbonate. The mixture was stirred for 14 h, diluted with $CH_2Cl_2$, washed with saturated NaCl then dried over $MgSO_4$, filtered, and concentrated in vacuo. The residue was subjected to operative thin layer silica gel chromatography using 5% $CH_3OH$ in $CH_2Cl_2$ to yield 107 mg of the title compound as a white solid. TLC: Rf= 0.35 (5% $CH_3OH$ in $CH_2Cl_2$). HPLC: Rt=17.27 min; ($^1$H)-NMR ($CDCl_3$) consistent with structure.

EXAMPLE 38

Compound 38

To a solution of 32 mg of the resultant compound of Example 35A in $CH_2Cl_2$ was added, at ambient temperature under an atmosphere of nitrogen, 14 mg of benzyl chloroformate and 21 mg N,N-diisopropylethylamine. The mixture was stirred for 4 h, diluted with $CH_2Cl_2$, washed with saturated $NaHCO_3$ and saturated NaCl, then dried over $MgSO_4$, filtered, and concentrated in vacuo. The residue was purified by preparative thin layer silica gel chromatography using 10% diethyl ether in $CH_2Cl_2$ as eluent to yield 33 mg of product. TLC: Rf=0.62, 10% diethyl ether in $CH_2Cl_2$. HPLC: Rt=17.27 min. ($^1$H)-NMR ($CDCl_3$) consistent with structure.

EXAMPLE 39

A. Compound XXI (D'=isobutyl, P=tert-butoxy carbonyl, P'=H)

A solution of 4.1 g of epoxide XX (P=Boc) in 30 mL of ethanol was treated with 22.4 mL of isobutylamine and heated under reflux for 1 h. The mixture was concentrated to yield the title compound as a white solid which was used without subsequent purification. NMR ($CDCl_3$): δ0.91 (d, 3H); 0.93 (d, 3H); 1.37 (s, 9H); 1.68 (br s, 2H); 2.40 (d, 2H); 2.68 (d, 2H); 2.87 (dd, 1H); 2.99 (dd, 1H); 3.46 (dd, 1H); 3.75 (br s, 1H); 3.80 (br s, 1H); 4.69 (d, 1H); 7.19–7.32 (m, 4H).

B. Compound 39

To a solution of 514.1 mg of the resultant compound of Example 39A in dichloromethane (10 mL) was added aqueous sodium bicarbonate (5 mL) and N-acetylsulfanilyl chloride (428.4 mg). After 14 h, the resulting mixture was diluted with ethyl acetate, washed with sodium bicarbonate, saturated brine, dried over magnesium sulfate, filtered and concentrated in vacuo. The residue was purified by low pressure silica gel column chromatography using 20% ethyl acetate in dichloromethane eluent to yield 714.4 mg of the title product. TLC: Rf=0.63, 60% ethyl acetate/dichloromethane, HPLC: Rt=15.3 min; ($^1$H)-NMR ($CDCl_3$) consistent with structure.

EXAMPLE 40

A. Compound XXII (D'=isobutyl, P=H, E=4-acetamidophenyl), hydrochloride salt

To a solution of 691.4 mg (1.296 mmol) of the resultant compound of Example 39B in ethyl acetate (20 mL) at −20° C. was bubbled anhydrous HCl gas for 10 min. The ice bath was removed and after an additional 15 min., the reaction mixture was sparged with nitrogen then concentrated in vacuo to provide 610 mg of title product which was used without subsequent purification.

B. Compound 40

A solution of 41.5 mg of the resultant crude compound of Example 40A in 5 mL of dichloromethane was treated sequentially, at ambient temperature under an atmosphere of nitrogen, with 18.1 mg of L-dihydroorotic acid, 0.031 mL (0.176 mmol) diisopropylethylamine, 15.5 mg (0.115 mmol) of 1-hydroxybenzotriazole hydrate, 22 mg (0.115 mmol) EDC. After 1 h, the slurry was treated with 1 mL of dimethylformamide. The mixture was stirred for 16 h and then concentrated in vacuo. The residue was taken up in ethyl acetate and washed with water and saturated brine, dried over magnesium sulfate, filtered and concentrated in vacuo. The residue was purified by thin layer preparative chromatography using (1/2/17 v/v/v/ 30% ammonium hydroxide/methanol/dichlomethane) eluent to provide 34.2 mg of the title product. TLC: Rf=0.33, 1/2/17 v/v/v/ 30% ammonium hydroxide/methanol/dichlomethane). HPLC: Rt=11.3 min; ($^1$H)-NMR ($CDCl_3$) consistent with structure.

EXAMPLE 41

Compound 41

To a solution of 42.8 mg of the resultant compound of Example 40A in 5 mL dichloromethane was added sequentially, at ambient temperature under an atmosphere of nitrogen, 17.2 mg of N-tert-butyl glyoxalic acid, 0.032 mL diisopropylethylamine, 16 mg of 1-hydroxybenzotriazole hydrate, 22.6 mg EDC. The mixture was stirred for 16 h and then concentrated in vacuo. The residue was taken up in ethyl acetate and washed with water, 0.5N hydrochloric acid, washed with sodium bicarbonate, saturated brine, dried over magnesium sulfate, filtered and concentrated in vacuo. The residue was purified by thin layer preparative chromatography using 40% ethyl acetate/dichloromethane eluent to provide 14.9 mg of the title product. TLC: Rf=0.47, 40% ethyl acetate/dichloromethane, HPLC: Rt=15.2 min; ($^1$H)-NMR ($CDCl_3$) consistent with structure.

EXAMPLE 41

Compound 42

To a solution of 43.5 mg of the resultant crude compound of Example 40A in 5 mL dichloromethane was added sequentially at ambient temperature, under an atmosphere of nitrogen, 13.0 mg of succinamic acid, 0.024 mL diisopropylethylamine, 15.0 mg of 1-hydroxybenzotriazole hydrate, and 21.3 mg EDC. The mixture was stirred for 16 h and then concentrated in vacuo. The residue was taken up in ethyl acetate and washed with sodium bicarbonate, saturated brine, dried over magnesium sulfate, filtered and concentrated in vacuo. The residue was purified by thin layer preparative chromatography using (1/2/11 v/v/v/ 30% ammonium hydroxide/methanol/dichlomethane) eluent to provide 35.3 mg of the title product. TLC: Rf=0.25, 1/2/11 v/v/v/ 30% ammonium hydroxide/methanol/dichlomethane, HPLC: Rt=11.6 min; ($^1$H)-NMR ($CDCl_3$) consistent with structure.

EXAMPLE 43

Compound 43

To a solution of 42.8 mg of the resultant compound of Example 40A in 5 mL dichloromethane was added sequentially, at ambient temperature under an atmosphere of nitrogen, with 14.1 mg of L-pyroglutamic acid, 0.024 mL diisopropylethylamine, 14.8 mg of 1-hydroxybenzotriazole hydrate, 20.9 mg EDC. The mixture was stirred for 16 h and then concentrated in vacuo. The residue was taken up in ethyl acetate and washed with water, 0.5N hydrochloric acid, washed with sodium bicarbonate, saturated brine, dried over magnesium sulfate, filtered and concentrated in vacuo. The residue was purified by thin layer preparative chromatography using (1/2/11 v/v/v/ 30% ammonium hydroxide/methanol/dichlomethane) eluent to provide 29.9 mg of the title product. TLC: Rf=0.33, 1/2/11 v/v/v/ 30% ammonium hydroxide/methanol/dichlomethane, HPLC: Rt=11.7 min; ($^1$H)-NMR ($CDCl_3$) consistent with structure.

EXAMPLE 44

A. 3-Pyridylmethyl-N-hydroxysucchinimdyl carbonate

To a solution of 181.0 mg of 3 pyidinecarbinol in 5 mL acetonitrile was added sequentially at ambient temperature under an atmosphere of nitrogen, with 0.72 mL diisopropylethylamine and 354.1 mg of N,N'-disuccinimidyl carbonate. After 4 h, the resultant mixture was concentrated in vacuo to provide a yellow solid which was used without subsequent purification.

B. Compound 44

To a solution of 58.1 mg of the resultant crude compound of Example 40A in 3 mL of dichloromethane was added sequentially, at ambient temperature under an atmosphere of nitrogen, 0.075 mL diisopropylethylamine and 46.3 mg of the resultant compound of Example 20A. The mixture was stirred for 16 h and then concentrated in vacuo. The residue was taken up in diethyl ether and extracted into 3×25 mL of 0.5N HCl. The combined aqueous extracts were adjusted to pH 8 with solid sodium bicarbonate and extracted into 3×25 mL ethyl acetate. The combined organic extracts were washed with saturated brine, dried over magnesium sulfate, filtered, and concentrated in vacuo. The residue was purified by thin layer preparative chromatography using (1/2/17/20 v/v/v/ 30% ammonium hydroxide/methanol/dichlomethane/diethyl ether) eluent to provide 10.3 mg of the title product. TLC: Rf=0.4, 1/2/17/20 v/v/v/ 30% ammonium hydroxide/methanol/dichlomethane/diethyl.ether, HPLC: Rt=11.8 min; ($^1$H)-NMR ($CDCl_3$) consistent with structure.

EXAMPLE 45

Compound 45

To a solution of 28.3 mg of the resultant compound of Example 39A in 4 mL of dichloromethane was added 1 mL saturated aqueous sodium bicarbonate solution, 9.2 mg sodium bicarbonate, and 0.013 mL of benzenesulfonyl chloride. After 14 h, the resulting mixture was diluted with ethyl acetate, washed with saturated brine, dried over magnesium sulfate, filtered and concentrated in vacuo. The residue was purified by thin layer preparative chromatography using 10% diethyl ether/dichloromethane eluent to provide 19.3 mg of the title product. TLC: Rf=0.84, 25% diethyl ether/dichlormethane, HPLC: Rt=17.2 min; ($^1$H)-NMR ($CDCl_3$) consistent with structure.

EXAMPLE 46

Compound 46

To a solution of 47.0 mg (0.140 mmol) of the resultant compound of Example 39A in 4 mL of dichloromethane was added 1 mL saturated aqueous sodium bicarbonate solution, 17.6 mg of solid sodium bicarbonate, and 41.4 mg of 2,4 dimethylthiazole-5-sulfonyl chloride. After 14 h, the resulting mixture was diluted with ethyl acetate, washed with saturated brine, dried over magnesium sulfate, filtered and concentrated in vacuo. The residue was purified by thin layer preparative chromatography using 25% ethyl acetate/dichloromethane eluent to provide 34.6 mg of the title product. TLC: Rf=0.44, 25% diethyl ether/dichloromethane, HPLC: Rt=16.4 min; ($^1$H)-NMR ($CDCl_3$) consistent with structure.

EXAMPLE 47

Compound 47

To a solution of 50.7 mg of the resultant compound of Example 39A in 4 mL of dichloromethane was added 1 mL saturated aqueous sodium bicarbonate solution, 15.2 mg of solid sodium bicarbonate, and 2-fluorobenzenesulfonyl chloride 35.2 mg. After 14 h, the resulting mixture was diluted with ethyl acetate, washed with saturated brine, dried over magnesium sulfate, filtered and concentrated in vacuo. The residue was purified by thin layer preparative chromatography using 10% diethyl ether/dichloromethane eluent to provide 40.5 mg of the title product. TLC: Rf=0.44, 25% diethyl ether/dichloromethane, HPLC: Rt=17.2 min; ($^1$H)-NMR ($CDCl_3$) consistent with structure.

EXAMPLE 48

A. N-succinimidyl-(S)-3-tetrahydrofuryl carbonate

To a solution of 12.5 mL of 1.93M phosgene in toluene at 0°–5° C. was added 1.3 g of (S)-(+)-3-hydroxytetrahydrofuran. After stirring for 2 h, the reaction mixture was sparged with nitrogen and then concentrated to dryness in vacuo to provide 1.486 g of crude chloroformate. This material was taken up in 10 mL of acetonitrile and treated sequentially at ambient temperature under an atmosphere of nitrogen with 1.17 g of N-hydroxysuccinimide and 1.41 mL of triethylamine. After stirring for 14 h, the reaction mixture was concentrated in vacuo to provide 3.44 g of the title product as a white solid.

B. Compound 48

To a solution of 87.2 mg of the resultant compound of Example 40A in 5 mL of dichloromethane was added sequentially, at ambient temperature under an atmosphere of nitrogen, 0.113 mL diisopropylethylamine and 68 mg of the resultant compound of Example 48A. The mixture was stirred for 16 h and then concentrated in vacuo. The residue was taken up in ethyl acetate and washed with water, 0.5N HCl, saturated sodium bicarbonate, saturated brine, dried over magnesium sulfate, filtered, and concentrated in vacuo. The residue was purified by silica gel chromatography using (3/6/20/65 v/v/v/v/ 30% ammonium hydroxide/methanol/diethyl ether/dichlomethane) eluent followed by crystallization from a mixture of dichloromethane, diethyl ether, and hexanes to provide 58 mg of the title product. TLC: Rf=0.17, 75% ethyl acetate/dichloromethane, HPLC: Rt=13.1 min.; ($^1$H)-NMR ($CDCl_3$) consistent with structure.

EXAMPLE 49

Compound 49

Following the procedure described in Example 83, a solution of the resultant compound of Example 39A in $CH_2Cl_2$ is reacted with 2,4-difluorobenzenesulfonyl chloride in the presence of water and $NaHCO_3$. Following dilution with additional $CH_2Cl_2$ and aqueous workup, the resultant product is dried over $MgSO_4$ filtered, and concentrated in vacuo. The residue is then purified by silica gel chromatography using an appropriate solvent system to yield the title product.

EXAMPLE 50

Compound 50

A solution of 30 mg of the resulting compound of Example 58 and 9 µL of dimethysulfamoyl chloride in 10 mL of $CH_2Cl_2$ was reacted in the same manner as described for Example 14. After workup and purification by preparative reversed-phase $C_{18}$ HPLC using a linear gradient of 35% to 100% $CH_3CN/H_2O$ with 0.1% TFA as eluent, 6.5 mg of the title compound was obtained. TLC: Rf=0.2, 3% $CH_3OH$ in $CH_2Cl_2$. HPLC: Rt=15.96 min; ($^1H$)-NMR ($CDCl_3$) consistent with structure.

EXAMPLE 51

A. Compound XXI (A=tert-butoxycarbonyl, D'=isobutyl, A'=benzyloxycarbonyl)

To a solution of the resultant compound of Example 39A (2.5 g, 7.43 mmol) in $CH_2Cl_2$ (50 mL) was added triethylamine (2.1 mL, 14.9 mmol) followed by addition of benzyl chloroformate (1.2 mL, 8.1 mmol). The mixture was allowed to stir at ambient temperature for 6 h. The solution was diluted with 1 L of $CH_2Cl_2$ and washed with water. The organics were dried over anhydrous $MgSO_4$, concentrated under reduced pressure, then purified via silica gel chromatography. Gradient solvent system: $CH_2Cl_2$ followed by 3:97 methanol/$CH_2Cl_2$. The title compound (2.97 g, was obtained as a colorless oil. TLC: Rf=0.14, 3:97 methanol/$CH_2Cl_2$; ($^1H$)-NMR ($CDCl_3$) consistent with structure.

B. Compound XXI (A=H, D'=isobutyl, A'=benzyloxycarbonyl, hydrochloride salt)

To a solution of 1.5 g (3.187 mmol) of the resultant compound of Example 51A in ethyl acetate (25 mL) at −20° C. was bubbled anhydrous HCl gas for 10 min. The ice bath was removed and after an additional 15 min. the reaction is mixture was sparged with nitrogen, then concentrated in vacuo to provide 1.29 g of title product as a white solid which was used directly for ensuing reaction. TLC: Rf=0.14, 10% methanol/$CH_2Cl_2$.

C. Compound XXI (A=(S)-3-tetrahydrofuryloxycarbonyl, D'=isobutyl, A'=benzyloxycarbonyl)

To a solution of 1.077 g of the resultant crude compound of Example 51B (2.647 mmol) in acetonitrile (10 mL) was added sequentially at ambient temperature under an atmosphere of nitrogen, 1.61 mL (9.263 mmol) of diisopropylethylamine and 910 mg (3.97 mmol) of the resultant compound of Example 48A. After stirring for 3 h, an additional 223 mg (0.973 mmol) of the resultant compound of Example 48A was added. The mixture was stirred for 16 h and then concentrated in vacuo. The residue was taken up in ethyl acetate and washed with water, 0.5N HCl, saturated sodium bicarbonate, saturated brine, dried over magnesium sulfate, filtered, and concentrated in vacuo. The residue was purified by low pressure silica gel column chromatography using a gradient 10% to 25% ethyl acetate in $CH_2Cl_2$ eluent to yield 1.025 g of the title product as a white solid. TLC: Rf=0.10, 10% ethyl acetate/$CH_2Cl_2$; ($^1H$)-NMR ($CDCl_3$) consistent with structure.

D. Compound XXI (A=(S)-3-tetrahydrofuryloxycarbonyl, D'=isobutyl, A'=H)

A solution of 872 mg (1.799 mmol) of the resultant compounds of Example 51C in (10 mL) of ethyl alcohol was added, at ambient temperature under a nitrogen atmosphere, to a slurry of 87 mg (10% by weight) of 10% palladium on carbon in (5 mL) ethyl alcohol and hydrogenated for 16 h under a slight positive pressure of hydrogen. The mixture was filtered and concentrated in vacuo to yield 553.2 mg of the title product as a colorless glass which was used directly for ensuing reaction. TLC: Rf=0.46, 10% methanol/$CH_2Cl_2$.

E. Compound 51

To a solution of 72.7 mg (0.207 mmol) of the resultant compound of Example 51D in $CH_2Cl_2$ (4 mL) was added aqueous sodium bicarbonate (1 mL), solid sodium bicarbonate 22.6 mg (0.27 mmol), and 2-(pyrid-2-yl)-thiophene-5-sulfonyl chloride 64.6 mg, (0.249 mmol). After 14 h, the resulting mixture was diluted with ethyl acetate, washed with saturated brine, dried over magnesium sulfate, filtered and concentrated in vacuo. The residue was purified by thin layer preparative chromatography using 15 to 30% ethyl acetate/$CH_2Cl_2$ eluent to provide 53 mg of the title product as a white solid. TLC; RF=0.25, 25% ethyl acetate/$CH_2Cl_2$, HPLC: Rt=15.3 min; ($^1H$)-NMR ($CDCl_3$) consistent with structure.

EXAMPLE 52

A. N-hydroxysuccinimidyl-(RS)-3-hydroxyltetrahydrofuryl carbonate

The title compound was prepared as described in Example 48A starting with 1.0 g of (RS)-3-hydroxy-tetrahydrofuran and yielding 2.33 g of a white solid.

B. Compound 52

To a solution of 105 mg of the resultant compound of Example 35A in $CH_2Cl_2$ was added, at ambient temperature under an atmosphere of nitrogen, 112 mg of the resultant compound of Example 52A and 126 mg N,N-diisopropylethylamine. The mixture was stirred for 4 h, diluted with $CH_2Cl_2$, washed and saturated $NaHCO_3$ and saturated NaCl, then dried over $MgSO_4$, filtered, and concentrated in vacuo. The residue was purified by low pressure silica gel chromatography using 5% $CH_3OH$ in $CH_2Cl_2$ as eluent to yield 101.4 mg of product. TLC: Rf=0.52, 5% $CH_3OH$ in $CH_2Cl_2$. HPLC: Rt=15.05 min. ($^1H$)-NMR ($CDCl_3$) consistent with structure.

EXAMPLE 53

Compound 53

To a solution of 72.3 mg (0.19 mmol) of the resultant compound of Example 51D in $CH_2Cl_2$ (4 mL) was added aqueous sodium bicarbonate (1 mL), solid sodium bicarbonate 19.2 mg (0.228 mmol), and 4-acetamido-3-chlorobenzene sulfonyl chloride 61.1 mg, (0.228 mmol). After 14 h, the resulting mixture was diluted with EtOAc, washed with saturated brine, dried over magnesium sulfate, filtered and concentrated in vacuo. The residue was purified by low pressure silica gel column chromatography using 20% to 45% EtOAc/$CH_2Cl_2$ eluent to provide 49.1 mg of the title product. TLC: RF=0.29, 50% EtOAc/$CH_2Cl_2$. HPLC: Rt=13.9 min; ($^1H$)-NMR ($CDCl_3$) consistent with structure.

EXAMPLE 54

Compound 54

A solution of 260 mg of the resulting Compound of 39A and 45 mg of 3-acetamido-4-fluorobenzenesulfonyl chloride in 10 mL of $CH_2Cl_2$ was reacted in the same manner as described for Example 14. After workup and purification by preparative reversed-phase $C_{18}$ HPLC using a linear gradient of 35% to 100% $CH_3CN/H_2O$ with 0.1% TFA as eluent, 1.4 mg of the title compound was obtained. TLC: Rf=0.25, 5% $CH_3OH$ in $CH_2Cl_2$. HPLC: Rt=15.63 min; ($^1H$)-NMR ($CDCl_3$) consistent with structure.

EXAMPLE 55

Compound 55

35.0 mg of the resulting compound of Example 54 was treated with 1 mL of 90% aqueous TFA and allowed to stand for 12 h. The mixture was concentrated in vacuo and the residue taken up in 10 mL of dry $CH_2Cl_2$, treated with 34 µL of DIEA (0.23 mmoles) and 20 mg of 1-benzyl-3-tert-butyl- 1H-pyrazole-5-carbonyl chloride. The mixture was stirred for 1.5 h, then diluted with in $CH_2Cl_2$, and washed with 1N HCl. After drying over $MgSO_4$ and concentrating in vacuo, a portion of the mixture was purified by preparative reversed-phase $C_{18}$ HPLC using a linear gradient of 35% to 100% $CH_3CN/H_2O$ with 0.1% TFA for elution to obtain 1.1 mg of the title compound. TLC: Rf=0.8, 5% $CH_3OH$ in $CH_2Cl_2$. HPLC: Rt=18.25 min; ($^1$H)-NMR ($CDCl_3$) consistent with structure.

EXAMPLE 56

A. S(−)-1-phenylethyl-N-hydroxysuccinimdyl carbonate

The title compound was prepared from 9.5 μL of S(−)-1-phenylethanol and 30 m of N,N-disuccinimidyl carbonate as described in Example 44A. The resulting material was used without subsequent purification; ($^1$H)-NMR ($CDCl_3$) consistent with structure.

B. Compound 56

45.0 mg Of the resulting compound of Example 58 was treated with 1 mL of 90% aqueous TFA and allowed to stand for 12 h. The mixture was concentrated in vacuo and the residue taken up in 15 mL of dry $CH_2Cl_2$, treated with the above mixed anhydride and 65 μL of triethylamine. The mixture was stirred for 14 h then diluted with ethyl acetate and washed with saturated sodium bicarbonate solution and saturated brine, dried over magnesium sulfate, filtered and concentrated in vacuo. A portion of the mixture was purified by preparative reversed-phase $C_{18}$ HPLC using a linear gradient of mixture was purified by preparative reversed-phase $C_{18}$ HPLC using a linear gradient of 35% of 100% $CH_3CN/H_2O$ with 0.1% TFA for elution to obtain 1.1 mg of the title compound. TLC: Rf=0.5, 3% $CH_3OH$ in $CH_2Cl_2$ HPLC: Rt=17.44 min; ($^1$H)-NMR ($CDCl_3$) consistent with structure.

EXAMPLE 57

Compound 57

30 mg of the resultant compound of Example 58 was treated with 1 mL of 90% aqueous TFA and allowed to stand for 12 h. The mixture was concentrated in vacuo and the residue taken up in 25 mL of dry $CH_2Cl_2$, washed and saturated sodium bicarbonate solution, dried over magnesium sulfate, filtered and concentrated in vacuo. A solution of 14 mg of the resultant free amine in 10 mL of $CH_2Cl_2$ was treated with 6 μL of phenoxyacetyl chloride and 12 μL of triethylamine. The mixture was stirred under an inert atmosphere for 1 h, then diluted in $CH_2Cl_2$ and washed with 1N HCl. After drying over $MgSO_4$ and concentrating in vacuo. A portion of the mixture was purified by preparative reversed-phase $C_{18}$ HPLC using a linear gradient of 35% to 100% $CH_3CN/H_2O$ with 0.1% TFA as eluant to obtain 16.5 mg of the title compound. TLC: Rf=0.25, 3% MeOH in $CH_2Cl_2$. HPLC: Rt=16.6 min; ($^1$H)-NMR ($CDCl_3$) consistent with structure.

EXAMPLE 58

Compound 58

A solution of 500 mg of the resulting compound of Example 39A and 370 mg of benzofurazan-4-sulfonyl chloride in 10 mL of $CH_2Cl_2$ was reacted in the same manner as described for Example 14. After workup, the title compound was obtained by crystallization from hot ethanol. Further purification of this material by preparative reversed-phase $C_{18}$ HPLC using a linear gradient of 35% to 100% $CH_3CN/H_2O$ with 0.1% TFA as eluent gave 2.0 mg of the title compound. TLC: Rf=0.35, 3% $CH_3OH$ in $CH_2Cl_2$. HPLC: Rt=17.00 min; ($^1$H)-NMR ($CDCl_3$) consistent with structure.

EXAMPLE 59

A. R(+)-1-phenylethyl-N-hydroxysuccinimdyl carbonate

The title compound was prepared from R(+)-1-phenylethanol as described in Example 56A to yield a white solid. The resulting material was used directly for subsequent reaction; ($^1$H)-NMR ($CDCl_3$) consistent with structure.

B. Compound 59

A 36 mg portion of the resultant compound of Example 58 and 0.21 μmol of the resulting compound of 59A were reacted in the manner described in example 56B. After workup and purification by preparative reversed-phase $C_{18}$ HPLC using a linear gradient of 35% to 100% $CH_3CN/H_2O$ with 0.1% TFA as eluant, 1.0 mg of the title compound was obtained as a white solid. TLC: Rf=0.45, 3% MeOH in $CH_2Cl_2$. HPLC: Rt=17.34 min; ($^1$H)-NMR ($CDCl_3$) consistent with structure.

EXAMPLE 60

Compound 60

To a solution of 70 mg of the resultant compound of Example 51D in 10 mL of $CH_2Cl_2$ was added 3 mL of saturated aqueous sodium bicarbonate solution, 50 mg of sodium bicarbonate, and 53 mg of benzofurazan-4-sulfonyl chloride. The mixture was stirred vigorously for 4 h, then the resulting mixture was diluted with $CH_2Cl_2$, washed with saturated brine, dried over magnesium sulfate and filtered. After concentration of the mixture in vacuo, the residue was purified by thick layer silica gel chromatography using 5% MeOH/$CH_2Cl_2$ as eluant to obtain 80 mg of the title compound as a white solid. TLC: Rf=0.80, 5% MeOH in $CH_2Cl_2$. HPLC: Rt=14.96 min; ($^1$H)-NMR ($CDCl_3$) consistent with structure.

EXAMPLE 61

Compound 61

To a solution of 35.5 mg (0.076 mmol) of the resultant compound of Example 16 in 1 mL of dichloromethane was sequentially added 27.6 μL (0.159 mmol) of diisopropylethyl amine and 12 μL (0.083 mmol) of benzyl chloroformate. After 1 hour, the mixture was concentrated in vacuo. The residue was purified by preparative thin layer chromatography with 50% ethyl acetate/dichloromethane as an eluent to yield 38.7 mg of the title compound as a white solid; TLC: Rf=0.63, 50% ethyl acetate/dichlormethane; HPLC: Rt=15.45 min; ($^1$H)-NMR ($CDCl_3$) consistent with structure.

EXAMPLE 62

A. Benzofurazan-4-sulfonic acid

To a solution of 252.0 mg (1.05 mmol) of o-nitroaniline-m-sulfonic acid sodium salt in 1 mL of water was added 0.52 mL of 2.0N HCl. After ½ h, 0.68 mL (1.05 mmol) of tetrabutylammonium hydroxide (40% in water) was added. After 2 hours, the mixture was concentrated in vacuo. A solution of the residue in 7 mL of acetic acid was treated with 488.5 mg (1.10 mmol) of lead tertraacetate. After 24 hours, the precipitate was filtered and washed with small amount of acetic acid. The solid was further dried in vacuo to yield 267.9 mg of product. TLC: Rf=0.09, 10% $CH_3OH$/$CH_2Cl_2$.

B. Benzofurazan-4-sulfonyl chloride

To a solution of 137.0 mg (0.522 mmol) of triphenylphosphine in 0.5 mL of dichloromethane was slowly added 47 μL (0.594 mmol) of sulfuric chloride at 0° C. The ice-water bath was removed and the crude resultant compound of Example 62A in 0.5 mL of dichloromethane was added slowly. After 3 hours, the mixture was treated with 30 mL of 50% ether/hexane. The supernatant was decanted into a dry flask and concentrated in vacuo. The residue was purified by filtering through a plug of silica gel with 25% ethyl acetate as an eluent to yield 23 mg of product. TLC: Rf=0.6, 10% $CH_3OH/CH_2Cl_2$; ($^1H$)-NMR ($CDCl_3$) consistent with structure.

C. Compound 62

To a solution of 55.7 mg (0.166 mmol) of the resultant compound of Example 39A in 1 mL of dichloromethane was sequentially added 0.5 mL of saturated $NaHCO_3$, a small amount of solid $NaHCO_3$ and the resultant compound of Example 62B. After 3 hours, the mixture was diluted with dichloromethane. The two layers were separated and the aqueous layer was extracted once with dichloromethane. The combined organic layer was washed with brine then dried over $MgSO_4$, filtered and concentrated in vacuo. The residue was purified by preparative HPLC to yield 5.3 mg of the title compound as a white solid; TLC: Rf=0.40, 50% ethyl acetate/dichloromethane; HPLC Rt=16.5 min; ($^1H$)-NMR ($CDCl_3$) consistent with structure.

EXAMPLE 63

A.

A solution of 3.0 mg (0.0058 mmol) of the resultant title compound of Example 62 in 2 mL ethyl acetate was treated with HCl gas (moderate stream) for 3 minutes. The mixture was concentrated in vacuo to yield the crude amine hydrochloride salt. TLC: Rf=0.20, 10% $CH_3OH/CH_2Cl_2$.

B. Compound 63

To a solution of the crude resultant compound of Example 63A in 1 mL of dichloromethane was sequentially added 2.1 uL (0.0121 mmol) of diisopropyl ethyl amine and 0.9 uL (0.0064 mmol) of benzyl chloroformate. After 1 hour, the mixture was concentrated in vacuo. The residue was purified by preparative thin layer chromatography with 90% dichloromethane/methanol as an eluent to yield 2.6 mg of the title compound as a white solid; TLC: Rf=0.34, 50% ethyl acetate/dichloromethane; HPLC, Rt=17.1 min; ($^1H$)-NMR ($CDCl_3$) consistent with structure.

EXAMPLE 64

A. 5-(Dimethylamino)thioxomethoxy)-benzofurazan

To a solution of 500 mg (3.67 mmol) of 5-hydroxybezofurazan in 10 mL of DMF was added 140 mg (4.59 mmol) of NaH in small portions. The resulting mixture was stirred at room temperature until no more gas evolved. The flask was then immersed in a cold water bath and 540 mg (4.41 mmol) of dimethylthiocarbamoyl chloride (from Aldrich) was added. After 5 minutes, the water bath was removed the mixture was heated to 80° C. for 1 hour. After being cooled to room temperature, the mixture was poured into 20 mL of 0.5N NaOH three times and water three times. The solid was dried in vacuum to yield 580 mg of product that was used in the next reaction without further purification; TLC: Rf=0.20, 20% ethyl acetate/hexane; ($^1H$)-NMR ($CDCl_3$) consistent with structure.

B. 5-((Dimethylamino)carbonyl)thio)-benzofurazan

The crude product, 510 mg (2.28 mmol), from Example 64A was heated to 190° C. in a sealed tube. After 5 hours, it was cooled to room temperature and ethyl acetate was added. The solution was filtered through a plug of a silica and concentrated in vacuo to yield 360 mg of product which was again used in the next reaction without further purification. TLC: Rf=0.20, 20% ethyl acetate/hexane.

C. 5-Mercaptobenzofurazan

To a solution of 357.4 mg (1.60 mmol) of the resultant compound of Example 64B in 2 mL of methanol was added 7 mL of 6N NaOH. The mixture was heated to 90° C. for 2 hours. The mixture was poured into 100 mL ice and acidified with concentrated HCl. The slurry was filtered and rinsed three times with water. The residue was dried in vacuo to yield 145.6 mg of product; TLC: Rf=0.70, 20 ethyl acetate/hexane; ($^1H$)-NMR ($CDCl_3$) consistent with structure.

D. Benzofurazan-5-sulfonyl chloride

Chlorine gas was bubbled through a solution of 39.9 mg (0.26 mmol) of the resultant compound of Example 64C in a mixture of 1 mL of ethyl acetate and 0.5 mL of water for 3 minutes. The mixture was then washed repeatedly with brine until no more precipitate formed. The organic layer was dried over $MgSO_4$, filtered and concentrated to yield 30 mg of the product (52%). TLC: Rf=0.22, 20% ethyl acetate/hexane.

E. Compound 64

A solution of the resultant compounds of Examples 52D and 39A (total yields) in a mixture of 1 mL of dichloromethane, 0.3 mL of saturated $NaHCO_3$ and a small amount of solid $NaHCO_3$ was stirred at room temperature for 2 hours. The solution was diluted with 30 mL of dichloromethane and the two layers were separated. The aqueous layer was extracted once with dichloromethane chloride. The combined organic layer was washed with brine, dried over $MgSO_4$ and concentrated. The residue was purified by preparative thin layer chromatography with 90% dichloromethane/ether as an eluent to yield 30 mg of the title product as a white solid; TLC: Rf=0.46, 10% $Et_2O/CH_2Cl_2$, HPLC Rt=17.6 min; ($^1H$)-NMR ($CDCl_3$): δ8.45 (s), 1H; 7.96(d), 1H; 7.65 (d), 1H; 7.25(m), 5H; 4.65(d), 1H; 3.85 (m), 1H; 3.78(m), 1H; 3.30(d), 2H; 3.10(m), 2H; 2.90(m), 2H: 1.90(m), 1H; 1.40(s), 9H; 0.90 (d), 6H.

EXAMPLE 65

Compound 65

A solution of 13.1 mg (0.025 mmol) of the resultant compound of Example 64E in 1.5 mL of ethyl acetate was treated with gaseous HCl (moderate stream) at 0° C. for 3 minutes. The solvent was removed to yield a solid residue which was used in the next reaction without further purification; TLC: Rf=0.52, 10% $CH_3OH/CH_2Cl_2$. A solution of this hydrochloride salt (entire yield) in 1 mL of dichloromethane was treated sequentially with 9.2 μL (0.053 mmol) of diisopropyl ethyl amine and 4.0 μL (0.028 mmol) of benzyl chloroformate. After 3 hours, the mixture was concentrated and purified by preparative thin layer chromatography with 90% dichloromethane/ether as an eluent to yield 11.7 mg of the title compound as a white solid; TLC: Rf=0.65, 10% $Et_2O/CH_2Cl_2$; HPLC Rt=17.6 min; ($^1H$)-NMR ($CDCl_3$: δ8.45(s), 1H; 7.96(d), 1H; 7.65(d), 1H; 7.25(m), 10H; 5.00,(m), 2H; 4.85(d), 1H; 3.86(m), 2H; 3.60(bs), 1H; 3.25(m), 12H; 3.05(d), 2H; 2.96(m), 1H: 2.98(m), 1H; 1.88(m), 1H; 0.90(dd), 6H.

EXAMPLE 66

Compound 66

A solution of 100 mg (0.46 mmol) of the resultant compound of Example 64D and 101 mg (0.286 mmol) of the resultant compound of Example 48A in a mixture of 2 mL of dichloromethane, 0.5 mL of saturated $NaHCO_3$ and small amount of solid $NaHCO_3$ was stirred at room temperature for 2 hours. The solution was diluted with 50 mL of dichloromethane and the two layers were separated. The aqueous layer was extracted once with dichloromethane. The combined organic layer was washed with brine, dried over $MgSO_4$ and concentrated. The residue was purified by preparative thin layer chromatography with 20% ethyl acetate/hexane as an eluent to yield 82 mg of the title product as a slightly impure pale yellow solid. The material was further purified by preparative HPLC with a linear gradient solvent system of 35% to 80% of acetonitrile/water (0.1% TFA) over 80 min. Upon removal the solvents 50 mg of white solid was obtained. TLC: Rf=0.46, 10% $Et_2O/CH_2Cl_2$; HPLC, Rt=17.6 min; ($^1H$)-NMR ($CDCl_3$): δ8.45 (s), 1H; 7.96 (d), 1H; 7.65 (d), 1H; 7.25 (m), 5H; 5.15 (m), 1H; 4.85 (d), 1H; 3.82 (m) 4H; 3.68 (d), 1H; 3.20(m), 2H, 3.05 (d), 2H; 2.96 (m), 1H; 2.88 (m), 1H; 2.14(m), 1H; 1.92(m), 2H; 1.50(bs), 1H; 0.90(dd), 6H.

EXAMPLE 67

Compound 67

Following the procedure described in Example 40B, a solution of the resultant compound of Example 40A in $CH_2Cl_2$ is treated with bis-((carboxamido)-amino)-acetic acid, diisopropylethylamine, HOBt, and EDC in a 1:1:1:1:1 molar ratio. the mixture is stirred for 16 h at ambient temperature while protected from moisture, then diluted with additional $CH_2Cl_2$ and washed sequentially with $H_2O$, saturated $NaHCO_3$ solution and brine, then dried over $MgSO_4$ and concentrated in vacuo. The residue is purified by silica gel chromatography using an appropriate eluant to yield the title product.

EXAMPLE 68

Compound 68

This compound was prepared by the route described in Example 26, except that the reacting amine used was the resulting compound of Example 39A (146 mg, 0.43 mmol) and the acylating agent was 4-fluorophenyl sulphonyl chloride (27 mg, 0.14 mmol). After chromatographic purification on a silica gel column using 8% $CH_3OH/CH_2Cl_2$ as eluent, 92.8 mg of the title compound was obtained. HPLC: Rt=15.9 minutes. TLC: Rf=0.54, 8% $MeOH/CH_2Cl_2$ ($^1H$)-NMR ($CDCl_3$) consistent with structure.

EXAMPLE 69

A

The resulting compound of Example 68 (72.1 mg, 0.167 mmol) was dissolved in 90% aqueous TFA (3.3 mL), and the reaction mixture stirred for 3 hours at room temperature, then was concentrated to dryness. TLC: Rf=0.29, 8% $MeOH/CH_2Cl_2$.

B. Compound 69

To a solution of the resulting compound of Example 69A (41.7 mg, 0.09 mmol) in $CH_2Cl_2$ (2 mL) was added diisopropylethtylamine (47 μl, 0.27 mmol) and the resulting compound of Example 48A (33 mg, 0.15 mmol), and the reaction proceeded for 14 hours at room temperature. The reaction mixture was then concentrated, and the residue was chromatographed on a silica gel column using 8% $THF/CH_2Cl_2$ was eluent, yielding the desired compound which was further subjected to purification by preparative HPLC, yielding 7.8 mg of a white solid. HPLC: Rt=13.5 minutes. TLC: Rf=0.36, 8% $THF/CH_2Cl_2$; ($^1H$)-NMR ($CDCl_3$) consistent with structure.

EXAMPLE 70

Compound 70

A solution of 30 mg of the resulting compound of Example 54 and 17.6 mg of 3-acetamido-4-fluorobenzenesulfonyl chloride in 10 mL of $CH_2Cl_2$ was reacted in the same manner as described for Example 14. After workup and purification by preparative reversed-phase $C_{18}$ HPLC using a linear gradient of 35% to 100% $CH_3CN/H_2O$ with 0.1% TFA as eluent, 2.0 mg of the title compound was obtained. TLC: Rf=0.5, 10% $CH_3OH$ in $CH_2Cl_2$. HPLC: Rt=13.74 min; ($^1H$)-NMR ($CDCl_3$) consistent with structure.

EXAMPLE 71

Compound 71

A 30 mg portion of the resultant compound of Example 58 was deprotected with trifluoroacetic acid and the resulting compound reacted with 9 μL of dimethysulfamoyl chloride in 10 mL of $CH_2Cl_2$ was reacted in the manner described in Example 14. After workup and purification by preparative reversed-phase $C_{18}$ HPLC using a linear gradient of 35% to 100% $CH_3CN/H_2O$ with 0.1% TFA as eluant, 6.5 mg of the title compound was obtained. TLC: Rf=0.2, 3% MeOH in $CH_2Cl_2$. HPLC: Rt=15.96 min; ($^1H$)-NMR ($CDCl_3$) consistent with structure.

EXAMPLE 72

Compound 72

A solution of the resulting compound from the trifluoroacetic acid deprotection of Example 69A (31 mg, 0.07 mmol) in $CH_2Cl_2$ (2 mL) was added diisopropylethylamine (47 μl, 0.27 mmol) and dimethylsulfamoyl chloride (22 μl, 0.20 mmol), and the reaction proceeded for 16 hours at room temperature. The reaction mixture was then concentrated, and the residue was chromatographed on a thick layer silica gel plate (1.0 mm) using 5% $THF/CH_2Cl_2$ as eluent, yielding the desired compound which was further subjected to purification by preparative HPLC to yield 7.8 mg of a white solid. HPLC: Rt=14.8 minutes. TLC: Rf=0.44, 5% $THF/CH_2Cl_2$.

EXAMPLE 73

Compound 73

A 43 mg portion of the resultant compound of Example 54 was treated with 1 mL of 90% aqueous TFA and allowed to stand for 12 h. The mixture was concentrated in vacuo and the residue taken up in 5 mL of $CH_2Cl_2$. To this solution, 3 mL saturated aqueous sodium bicarbonate and 25 mg of 2,5-dimethoxybenzenesulfonyl chloride was added, and the mixture was stirred for 12 h, warming slowly to ambient temperature. After concentration of the mixture in vacuo, the residue was purified by thick layer silica gel chromatography using 3% $MeOH/CH_2Cl_2$ as eluant followed by preparative reversed-phase $C_{18}$ HPLC using a linear gradient of 35% to 100% $CH_3CN/H_2O$ with 0.1% TFA as eluant to obtain 5.5 mg of the title compound. TLC: Rf=0.20, 3% $MeOH/CH_2Cl_2$. HPLC: Rt=15.15 min; ($^1H$)-NMR ($CDCl_3$) consistent with structure.

EXAMPLE 74

A. Compound XXI (A=tert-butoxycarbonyl, D'=cyclopropylmethyl, A'=H)

To a solution of compound XX (A=tert-butoxycarbonyl) (0.8 g, 2.67 mmol) in ethanol (30 mL) was added a solution of KOH (0.18 g, 3.2 mmol) in ethanol (20 mL) and the mixture stirred for 45 min at room temperature. In a separate flask, a solution of cyclopropylmethyl-amine hydrochloride (1.44 g, 13.3 mmol) in ethanol (20 mL) was added KOH (0.75 g, 13.3 mmol). The mixture was stirred 30 min at room temperature. The solutions were combined and heated at 85° C. for 3 h. The solution was concentrated under reduced pressure and the residue slurried in diethyl ether and filtered. The ethereal layer was concentrated to give 0.32 g of a white solid; ($^1H$)-NMR ($CDCl_3$) consistent with structure.

B. Compound 74

To a solution of the resulting compound of Example 74A (0.1 g, 0.30 mmol) in $CH_2Cl_2$ (20 mL) was added a saturated solution of sodium bicarbonate, followed by addition of solid sodium bicarbonate (30 mg, 0.36 mmol), then 4-fluorobenzenesulfonyl chloride (0.07 g, 0.36 mmol). The mixture was allowed to stir at room temperature for 4 h. The organics were extracted into 250 mL $CH_2Cl_2$, dried over anhydrous $MgSO_4$, concentrated under reduced pressure then purified via medium pressure liquid chromatography using a gradient system of $CH_2Cl_2$ followed by 0.5:99.5 methanol/$CH_2Cl_2$ followed by 1:99 methanol/$CH_2Cl_2$. The title compound was obtained as 35 mg of a colorless foam. HPLC: Rt=16.8 min. TLC: Rf=0.32, 3:97 methanol/$CH_2Cl_2$; ($^1$H)-NMR ($CDCl_3$) consistent with structure.

EXAMPLE 75

A. Compound XXI (A=tert-butoxycarbonyl, D'=isopropyl, A'=H)

To a solution of Compound XX (A=tert-butoxycarbonyl) (1.67 mmol) in ethanol (10 mL) was treated with isopropylamine (10 mL). The solution was heated to 85° C. for 72 h. The solution was filtered then concentrated under reduced pressure to give 0.56 g of the title compound which was used without subsequent purification. ($^1$H)-NMR ($CDCl_3$) consistent with structure.

B. Compound 75

To a solution of the resultant compound of Example 75A (0.2 g, 0.65 mmol) in $CH_2Cl_2$ (10 mL) was added a saturated solution of sodium bicarbonate (3 mL), followed by addition of solid sodium bicarbonate (0.11 g, 1.31 mmol), then p-fluorobenzenesulfonyl chloride (0.25 g, 1.28 mmol). The mixture was stirred overnight at ambient temperature. The organics were extracted into 100 mL $CH_2Cl_2$, dried over anhydrous $MgSO_4$, concentrated under reduced pressure then purified via medium pressure silica gel chromatography using a gradient system of $CH_2Cl_2$ followed by 1:99 methanol/$CH_2Cl_2$. The title compound was obtained as a colorless foam 200 mg. TLC: Rf=0.22, 3:97 methanol/$CH_2Cl_2$, HPLC: Rt=16.48 min; ($^1$H)-NMR ($CDCl_3$) consistent with structure.

EXAMPLE 76

A. Compound XXI (A=tert-butoxycarbonyl, D'=morpholinyl, A'=H)

To a solution of compound XX (A=Boc) in ethanol is added 3 molar equivalents of N-amino morpholine. The mixture is heated under reflux for 12 h, cooled, and the mixture concentrated in vacuo. The residue is purified by preparative reversed-phase chromatography using a linear gradient of 5% to 100% acetonitrile/$H_2O$ as eluant to yield the title compound.

B. Compound 76

Following the procedure described in Example 81, a solution of the resultant compound of Example 76A in $CH_2Cl_2$ is reacted with 4-fluorobenzenesulfonyl chloride in the presence of water and $NaHCO_3$. Following dilution with additional $CH_2Cl_2$ and aqueous workup, the resultant product is dried over $MgSO_4$, filtered, and concentrated in vacuo. The residue is then purified by silica gel chromatography using an appropriate solvent system to yield the title product.

EXAMPLE 77

A. Compound XXI (A=tert-butoxycarbonyl, D'=4-(N,N-dimethylamino)-benzyl, A'=H)

To a solution of compound XX (A=Boc) in ethanol is added 3 molar equivalents of 4-aminomethyl-(N,N-dimethyl)-aniline. The mixture is heated under reflux for 12 h, cooled, and the mixture concentrated in vacuo. The residue is purified by silica gel chromatography using an appropriate solvent system as eluant to yield the title product.

B. Compound 77

Following the procedure described in Example 81, a solution of the resultant compound of Example 77A in $CH_2Cl_2$ is reacted with 4-fluorobenzenesulfonyl chloride in the presence of water and $NaHCO_3$. Following dilution with additional $CH_2Cl_2$ and aqueous workup, the resultant product is dried over $MgSO_4$, filtered, and concentrated in vacuo. The residue is then purified by silica gel chromatography using an appropriate solvent system to yield the title product.

EXAMPLE 78

A. Compound XXI (A=tert-butoxycarbonyl, D'=cyclopentyl, A'=H)

To a solution of compound XX (A=Boc) in ethanol is added 10 molar equivalents of cyclopentylamine. The mixture is heated under reflux for 12 h, cooled, and the mixture concentrated in vacuo. The residue is used without subsequent purification.

B. Compound 78

Following the procedure described in Example 81, a solution of the resultant compound of Example 78A in $CH_2Cl_2$ is reacted with 4-fluorobenzenesulfonyl chloride in the presence of water and $NaHCO_3$. Following dilution with additional $CH_2Cl_2$ and aqueous workup, the resultant product is dried over $MgsO_4$, filtered, and concentrated in vacuo. The residue is then purified by silica gel chromatography using an appropriate solvent system to yield the title product.

EXAMPLE 79

A. Compound XXI (A=tert-butoxycarbonyl, D'=2-(4-pyridyl)ethyl, A'=H)

To a solution of compound XX (A=Boc) in ethanol is added 3 molar equivalents of 4-aminoethylpyridine. The mixture is heated under reflux for 12 h, cooled, and the mixture concentrated in vacuo. The residue is purified by preparative reversed-phase chromatography using a linear gradient of 5% to 100% acetonitrile/$H_2O$ as eluant to yield the title product.

B. Compound 79

Following the procedure described in Example 81, a solution of the resultant compound of Example 79A in $CH_2Cl_2$ is reacted with 4-fluorobenzenesulfonyl chloride in the presence of water and $NaHCO_3$. Following dilution with additional $CH_2Cl_2$ and aqueous workup, the resultant product is dried over $MgSO_4$, filtered, and concentrated in vacuo. The residue is then purified by silica gel chromatography using an appropriate solvent system to yield the title product.

EXAMPLE 80

A. 4-Cyanotetrahydro-4H-pyran

Following essentially the procedure of Yoneda, R. "Cyanophosphate: An Efficient intermediate for Conversion of Carbonyl compounds to Nitriles," *Tetrahedron Lett.*, 30, 3681 (1989), a solution of tetrahydro-4H-pyran-one (9.9 g, 97.8 mmol) in dry THF (50 mL) is reacted with lithium cyanide (9.7 g, 294 mmol) and diethylcyanophosphonate (24 g, 146 mmol). The mixture is stirred for 24 h at ambient temperature. The reaction is quenched by the addition of 100 mL $H_2O$. The product is extracted into 1.5 L of diethyl ether, dried over anhydrous $MgSO_4$ then concentrated under reduced pressure. The residue is dissolved in dry THF (30 mL) and tert-butyl alcohol (7.25 g, 97.8 mmol). This solution is added slowly to 75 mL of a 1M solution of $SmI_2$. The mixture is stirred for 15 h at ambient temperature. The reaction is quenched by addition of 100 mL of saturated aqueous $NH_4Cl$. The resulting mixture is extracted with diethyl ether and the organic layers dried over anhydrous $MgSO_4$ and concentrated under reduced pressure. Purification by silica gel chromatography gives the title compound.

B. 4-(aminomethyl)tetrahydro-4H-pyran

To a solution of the compound of the Example 80A (10 g, 89.9 mmol) in absolute ethanol (200 mL) is added Raney Nickel (2.0 g, 50% slurry in water). The mixture is stirred for 24 hours at ambient temperature under 40 psig of hydrogen. The solution is filtered through celite and the solution concentrated under reduced pressure. The residue is taken up in ether (2L) washed with brine, dried in anh. $MgSO_4$, then concentrated under reduced pressure to give the title compound.

C. (1S,2R)-N-(1-Benzyl-3-(N-(4-(aminomethyl)tetrahydro-4H-pyran))-2-hydroxypropyl)-tert butoxycarbonylamine To a solution of the compound of Example 80B (5 g, 48.5 mmol) in absolute ethanol (20 mL) is added the compound XX (A=Boc) (2.55 g, 9.7 mmol). The mixture is stirred for 24 hours at ambient temperature. The solution is concentrated under reduced pressure and the crude product is puffed via column chromatography to give the title compound.

D. Compound XXII (A=Boc, D'=(4-tetrahydro-4H-pyranyl) methyl, A'=H)

To a solution of compound XX (A=Boc) in ethanol is added 3 molar equivalents of the resulting compound of Example 80C. The mixture is heated under reflux for 12 h, cooled, and the mixture concentrated in vacuo. The residue is purified by preparative reversed-phase chromotography using a linear gradient of 5% to 100% acetonitrile/$H_2O$ as eluant to yield the title compound.

To a solution of compound XX(A=Boc) in ethanol is added 3 molar equivalents of N-amino morpholine. The mixture is heated under reflux for 12 h, cooled, and the mixture concentrated in vacuo. The residue is purified by preparative reversed-phase chromatography using a linear gradient of 5% to 100% acetonitrile/$H_2O$ as eluant to yield the title compound.

E. Compound 80

Following the procedure described in Example 81, a solution of the resultant compound of Example 80D in $CH_2Cl_2$ is reacted with 4-fluorobenzenesulfonyl chloride in the presence of water and $NaHCO_3$. Following dilution with additional $CH_2Cl_2$ and aqueous workup, the resultant product is dried over $MgSO_4$, filtered, and concentrated in vacuo. The residue is then purified by silica gel chromatography to yield the title product.

EXAMPLE 81

A. Compound XXII (P=tert-butoxycarbonyl, D'=isobutyl, E=3,4-dichlorophenyl)

A solution of 316 mg of the resultant compound of Example 39A in 4:1 $CH_2Cl_2$/saturated aqueous $NaHCO_3$ was treated sequentially, at ambient temperature under an atmosphere of nitrogen, with 276 mg of 3,4-dichorobenzenesulfonyl chloride and 95 mg of sodium bicarbonate. The mixture was stirred for 14 h, diluted with $CH_2Cl_2$, washed with saturated NaCl then dried over $MgSO_4$, filtered, and concentrated in vacuo. The residue was purified by low pressure silica gel chromatography using 5% diethyl ether/$CH_2Cl_2$ as eluent to yield 490 mg of product. TLC: Rf=0.26, 5% diethyl ether in $CH_2Cl_2$. HPLC: Rt=18.92 min. ($^1H$)-NMR ($CDCl_3$) consistent with structure.

B. Compound XXII (P=H, D'=isobutyl, E=3,4-dichlorophenyl, hydrochloride salt)

A solution of 467 mg of the resultant compound of Example 81A in ethyl acetate was treated at −20° C. with HCl gas. The HCl was bubbled through the mixture for 20 min over which time the temperature was allowed to warm to 20° C. Nitrogen was then bubbled through the mixture for 15 min and solvent removed in vacuo to yield 412 mg of product as a white solid which was used without subsequent purification.

C. Compound 81

A solution of 91 mg of the resultant compound of Example 81B in $CH_2Cl_2$ was treated sequentially, at ambient temperature under an atmosphere of nitrogen, with 25 mg of allyl chloroformate and 52 mg N,N-diisopropylethylamine. The mixture was stirred for 4 h and then concentrated in vacuo. The residue was taken up in ethyl acetate and washed with 0.5N HCl and saturated NaCl then dried over $MgSO_4$, filtered, and concentrated in vacuo to yield 89 mg of the title product as a white solid. TLC: Rf=0.53, 5% diethyl ether in $CH_2Cl_2$. HPLC: Rt=17.95 min. ($^1H$)-NMR ($CDCl_3$) consistent with structure.

EXAMPLE 82

A. (3-Pyridyl)-methyl-4-nitrophenyl-carbonate

To a solution of 3.65 g of bis-(nitrophenyl) carbonate in 25 mL of $CH_2Cl_2$ at 0° C. was added sequentially 0.97 mL of 3-pyridyl carbinol and 1.3 mL of 4-methyl morphine. After stirring at room temperature for 24 hours, the resultant mixture was diluted with 100 mL of $CH_2Cl_2$, washed with saturated sodium bicarbonate, water and brine, dried over magnesium sulfate, filtered and concentrated in vacuo. The residue was purified by filtration through a plug of silica gel, using 0–40% EtOAc/$CH_2Cl_2$ as eluent to provide 1.68 g of the title product. TLC: Rf=0.19, 50% EtOAc/hexane.

B. Compound XXII (P=tert-butoxycarbonyl, D'=isobutyl, E=3,4-benzofurazan)

To a solution of 498.6 mg of the resultant compound of Example 39A in 10 mL of $CH_2Cl_2$ was added sequentially, 2 mL of saturated sodium bicarbonate, a small amount of solid sodium bicarbonate and 518.4 mg of the resultant compound of Example 64D. After stirring at room temperature for 3 hours, the resultant mixture was diluted with 60 mL of $CH_2Cl_2$, washed with saturated sodium bicarbonate and brine, dried over magnesium sulfate, filtered and concentrated in vacuo. The residue was purified by silica gel chromatography using 5% diethyl ether/hexane as eluent to yield 300 mg of white solid. TLC: Rf=0.80, 50% EtOAc/hexane.

C. Compound XXII (P=H, D'=isobutyl; E=3,4-benzofurazan, hydrochloride salt.)

A solution of 60.3 mg of the resultant compound of Example 82B in 3 mL of EtOAc at −20° C. was treated with anhydrous HCl gas for 5 min. The ice bath was removed and after an additional 10 min. The reaction mixture was sparged with nitrogen then concentrated in vacuum and the resulting white solid used without subsequent purification for subsequent reaction.

D. Compound 82

To a solution of the resultant compound of Example 82C (entire yield) in 2 mL of $CH_2Cl_2$ was added sequentially, 45 μL of diisopropylethylamine and 35.1 mg of the resultant compound of Example 82A. The mixture was stirred for 24 hours and then concentrated in vacuo. The residue was purified by preparative thin layer chromatography using 60% ether/$CH_2Cl_2$ as eluent followed by preparative reversed-phase $C_{18}$ HPLC using a linear gradient of 40% to 100% $CH_3CN/H_2O$ with 0.1% TFA as eluant. The resultant TFA salt of the title compound was washed with saturated sodium bicarbonate to yield 6.5 mg of the title compound. TLC: Rf=0.15, 20% EtOAc/$CH_2Cl_2$. HPLC: Rt=13.52 min. ($^1H$)-NMR ($CDCl_3$) consistent with structure.

EXAMPLE 83

A. Compound XXII (A=tert-butoxycaronyl, D'=isobutyl, E=4-acetamido-3-chlorophenyl)

A solution of 339 mg of the resultant compound of Example 39A in 4:1 $CH_2Cl_2$/saturated aqueous $NaHCO_3$ was treated sequentially, at ambient temperature under an atmosphere of nitrogen, with 324 mg of 4-acetamido-3-chlorobenzenesulfonyl chloride and 102 mg of sodium bicarbonate. The mixture was stirred for 14 h, diluted with $CH_2Cl_2$, washed with saturated NaCl then dried over $MgSO_4$, filtered, and concentrated in vacuo. The residue was purified by low pressure silica gel chromatography using 20% diethyl ether in $CH_2Cl_2$ as eluent to yield 498 mg of product. TLC: Rf=0.27 (20% diethyl ether in $CH_2Cl_2$). HPLC: Rt=16.20 min. ($^1$H)-NMR ($CDCl_3$) consistent with structure.

B. Compound XXII (A=H, D'=isobutyl, E=4-acetamido-3-chlorophenyl, hydrochloride salt)

A solution of 474 mg of the resultant compound of Example 83A in ethyl acetate was treated at −20° C. with HCl gas. The HCl was bubbled through the mixture for 20 min over which time the temperature was allowed to warm to 20° C. Nitrogen was then bubbled through the mixture for 15 min and the solvent was removed in vacuo to yield 421 mg of product as a white solid which was used without subsequent purification.

C. Compound 83

A solution of 92 mg of the resultant compound of Example 83B in $CH_2Cl_2$ was treated sequentially, at ambient temperature under an atmosphere of nitrogen, with 24 mg of allyl chloroformate and 52 mg N,N-diisopropylethylamine. The mixture was stirred for 4 h and then concentrated in vacuo. The residue was taken up in ethyl acetate and washed with 0.5N HCl and saturated NaCl, then dried over $MgSO_4$, filtered, and concentrated in vacuo to yield 106 mg of the title product as a white solid. TLC: Rf=0.38 (20% diethyl ether in $CH_2Cl_2$). HPLC: Rt=15.28 min. ($^1$H)-NMR ($CDCl_3$) consistent with structure.

EXAMPLE 84

Compound XXII (P=tert-butoxycarbonyl, D'=isobutyl, E=3,4-dichlorophenyl)

To a solution of the resultant compound of Example 51D (220 mg, 0.61 mmol) in $CH_2Cl_2$ (10 mL) was added the 3,4-dichlorobenzenesulfonyl chloride (300 mg, 1.22 mmol) followed by the addition of a saturated solution of sodium bicarbonate (3 mL) followed by addition of 0.1 g of solid sodium bicarbonate. The mixture was stirred at ambient temperature overnight. The solution was diluted with 100 mL $CH_2Cl_2$, the organics separated, dried over anhydrous, $MgSO_4$, and the organics concentrated under reduced pressure to obtain 0.17 g of crude product. The crude product was purified via medium pressure liquid chromatography using $CH_2Cl_2$ followed by 0.5:99.5 methanol/$CH_2Cl_2$ followed by a 1:99 methanol/$CH_2Cl_2$ solution as the solvent system to give 103 mg of the title compound as a white solid. TLC: Rf=0.56 (3:97 methanol/$CH_2Cl_2$), HPLC: Rt=19.78 min, ($^1$H)-NMR ($CDCl_3$) consistent with structure.

EXAMPLE 85

A. (3-Tetrahydrofuryl)-methyl-4-nitrophenylcarbonate

To a solution of 1.21 g of p-nitrophenyl chloroformate in 20 mL of $CH_2Cl_2$ 0° C. was added sequentially, 0.51 g of tetrahydro-3-furanmethanol and 0.66 mL of 4-methyl morpholine. After stirring at room temperature for 2 hours. The mixture was stirred for 2 hours and concentrated in vacuo. The residue was purified by filtering through a plug of silica gel, using 0–50% EtOAc/$CH_2Cl_2$ as eluent to provide 1.17 g of the title product as a pale yellow solid. TLC: Rf=0.20, 50% EtOAc/hexane.

B. Compound 85

To a solution of 70 mg of the resultant compound of Example 81B in 1 mL of THF was added sequentially, 56 μL of diisopropylethylamine and a solution of 46.6 mg of the resultant compound of Example 85A in 1 mL of THF. The mixture was stirred for 24 hours and then concentrated in vacuo. The residue was diluted with 60 mL of $CH_2Cl_2$, washed with 5% sodium bicarbonate and brine, dried over magnesium sulfate, filtered and concentrated in vacuo to yield 120 mg of crude product. The residue was purified by preparative thin layer chromatography using 20% EtOAc/$CH_2Cl_2$ as eluent to yield 82 mg of the title compound. TLC: Rf=0.4, 20% EtOAc/$CH_2Cl_2$. HPLC: Rt=17.08 min. ($^1$H)-NMR ($CDCl_3$) consistent with structure.

EXAMPLE 86

Compound 86

A solution of 42 mg of the resultant compound of Example 40A in $CH_2Cl_2$ was treated sequentially, at ambient temperature under an atmosphere of nitrogen, with 41 mg of the product of Example 52A and 46 mg N,N-diisopropylethylamine. The mixture was stirred 14 h, diluted with $CH_2Cl_2$, washed with saturated $NaHCO_3$ and saturated NaCl, then dried over $MgSO_4$, filtered, and concentrated in vacuo. The residue was purified by preparative thin layer silica gel chromatography using ethyl acetate as eluent to yield 43 mg of product. TLC: Rf=0.44 (20% ethyl acetate). HPLC: Rt=13.14 min. ($^1$H)-NMR ($CDCl_3$) consistent with structure.

EXAMPLE 87

A. Compound XXII (P=H, D'=isobutyl, E=4-acetamido, 3-fluoro)

A solution of 25 mg of the resultant compound of Example 54 in EtOAc (10 mL) at 0° C. was treated with anhydrous hydrogen chloride gas for 10 min., and allowed to stand for 12 h while warming to ambient temperature. The resultant mixture was then concentrated in vacuo to yield compound as a white solid which was used without subsequent purification for ensuing reaction.

B. Compound 87

A 0.045 mmol portion of the resultant compound of Example 87A was taken up in 5 mL of $CH_2Cl_2$. To this solution, 40 μL of diisopropylethylamine and 6 μL of allyl chloroformate were added at 0° C. and the mixture was stirred for 12 h, while warming slowly to ambient temperature. The resulting mixture was diluted with $CH_2Cl_2$, washed with saturated brine, dried over magnesium sulfate and filtered. After concentrated in vacuo, the residue was purified by preparative reversed-phase $C_{18}$ HPLC using a linear gradient of 35% to 100% $CH_3CN/H_2O$ with 0.1% TFA as eluant to obtain 11.6 mg of the title compound. TLC: Rf=0.20, 5% MeOH/$CH_2Cl_2$. HPLC: Rt=14.6 min; ($^1$H)-NMR ($CDCl_3$) consistent with structure.

EXAMPLE 88

Compound 88

A 0.033 mmol portion of the resultant compound of Example 87A was taken up in 5 mL of $CH_2Cl_2$. To this solution, 26 μL of triethylamine and 12 mg of the resultant compound of Example 48A were added and stirred for 12 h. The resulting mixture was diluted with $CH_2Cl_2$, washed with saturated sodium bicarbonate solution and saturated brine, dried over magnesium sulfate and filtered. After concentration of the mixture in vacuo, the residue was purified by thick layer silica gel chromatography using 5% MeOH/$CH_2Cl_2$ as eluant followed by preparative reversed-phase $C_{18}$ HPLC using a linear gradient of 35% to 100% $CH_3CN/H_2O$ with 0.1% TFA as eluant to obtain 7.5 mg of the title compound. TLC: Rf=0.30, 5% MeOH/$CH_2Cl_2$. HPLC: Rt=13.38 min; ($^1$H)-NMR ($CDCl_3$) consistent with structure.

EXAMPLE 89

Compound 89

A solution of 28 mg of the resultant compound of Example 81B in $CH_2Cl_2$ was treated sequentially, at ambient temperature under an atmosphere of nitrogen, with 8 mg of n-propyl chloroformate and 17 mg N,N-diisopropylethylamine. The mixture was stirred for 3 h and then concentrated in vacuo. The residue was taken up in ethyl acetate and washed with 0.5N HCl and saturated NaCl then dried over $MgSO_4$, filtered, and concentrated in vacuo to yield 31 mg of the title product as a white solid. TLC: Rf=0.35 (5% diethyl ether in $CH_2Cl_2$). HPLC: Rt=18.12 min. ($^1H$)-NMR ($CDCl_3$) consistent with structure.

EXAMPLE 90

Compound 90

A solution of 28 mg of the resultant compound of Example 83B in $CH_2Cl_2$ was treated sequentially, at ambient temperature under an atmosphere of nitrogen, with 7 mg of n-propyl chloroformate and 15 mg N,N-diisopropylethylamine. The mixture was stirred for 3 h and then concentrated in vacuo. The residue was taken up in ethyl acetate and washed with 0.5N HCl and saturated NaCl then dried over $MgSO_4$, filtered, and concentrated in vacuo to yield 30 mg of the title product as a white solid. TLC: Rf=0.47 (20% diethyl ether in $CH_2Cl_2$). HPLC: Rt=15.41 min. ($^1H$)-NMR ($CDCl_3$) consistent with structure.

EXAMPLE 91

A. 3-Acetamidobenzene sulfonic acid

A solution of 1.48 g of 3-aminobenzene sulfonic acid in 1:1 tetrahydrofuran/water was treated at 0° C. with 1.43 g of sodium bicarbonate. After 5 min, 1.30 g of acetic anhydride was added dropwise and the reaction allowed to warm to ambient temperature under an atmosphere of nitrogen over 14 h. The reaction mixture was passed through a column of Amberlyst 15 ion exchange resin, eluted with water, and concentrated in vacuo to yield an oil which upon treatment with benzene and azeotropic removal of water in vacuo yielded 1.8 g of the title product as a white crystalline solid. ($^1H$)-NMR ($CDCl_3$) consistent with structure.

B. 3-Acetamidobenzene sulfonic acid, sodium salt

The resultant compound of Example 91A in water was treated at 0° C. with 8.5 mL of 1N sodium hydroxide. The mixture was stirred for 3 h and concentrated in vacuo to yield an oil which upon treatment with benzene and azeotropic removal of water in vacuo yielded the title product as a tan solid which was used directly in the next reaction.

C. 3-Acetamidobenzenesulfonyl chloride

The resultant compound of Example 91B in $CH_2Cl_2$ was treated at 0° C. with 4.5 g of phosphorous pentachloride under an atmosphere of nitrogen. The mixture was stirred 14 h, extracted with $CH_2Cl_2$, and concentrated in vacuo to yield 1.7 g of the title product as a brown oil. TLC: Rf=0.21 (1:1 toluene/diethyl ether). ($^1H$)-NMR ($CDCl_3$) consistent with structure.

D. Compound XXII (A=tert-butoxycarbonyl, D'=isobutyl, E=3-acetamidophenyl)

A solution of 280 mg of the resultant compound of Example 39A in 4:1 $CH_2Cl_2$/saturated aqueous $NaHCO_3$ was treated sequentially, at ambient temperature under an atmosphere of nitrogen, with 252 mg of the resultant compound of Example 91C and 105 mg of sodium bicarbonate. The mixture was stirred for 60 h, diluted with $CH_2Cl_2$, washed with saturated NaCl then dried over $MgSO_4$, filtered and concentrated in vacuo. The residue was purifed by low pressure silica gel chromatography using 20% diethyl ether in $CH_2Cl_2$ as eluent to yield 156 mg of the title product. TLC: Rf=0.14 (20% diethyl ether in $CH_2Cl_2$was). HPLC: Rt=15.39 min. ($^1H$)-NMR ($CDCl_3$) consistent with structure.

E. Compound XXII (A=H, D'=isobutyl, E=3-acetamidophenyl, hydrochloride salt)

A solution of 123 mg of the resultant compound of Example 91D in ethyl acetate was treated at −20° C. with HCl gas. The HCl was bubbled through the mixture for 20 min, over which time the temperature was allowed to warm to 20° C. Nitrogen was then bubbled through the mixture for 15 min and solvent removed in vacuo to yield 118 mg of the title product as a white solid which was used directly in subsequent reactions.

F. Compound 91

A solution of 49 mg of the resultant compound of Example 91E in $CH_2Cl_2$ was added, at ambient temperature under an atmosphere of nitrogen, to a solution of 48 mg of the resultant compound of Example 48A and 54 mg N,N-diisopropylethylamine in $CH_2Cl_2$. The mixture was stirred for 14 h, diluted with $CH_2Cl_2$, washed with saturated $NaHCO_3$ and saturated NaCl, then dried over $MgSO_4$, filtered and concentrated in vacuo. The residue was subjected to preparative thin layer silica gel chromatography using 5% $CH_3OH$ in $CH_2Cl_2$ to yield 42 mg of product. TLC: Rf=0.32 (5% $CH_3OH$ in $CH_2Cl_2$). HPLC: Rt=13.27 min. ($^1H$)-NMR ($CDCl_3$) consistent with structure.

EXAMPLE 92

Compound 92

To a solution of 63.5 mg of the resultant compound of Example 17B, diastereomer B in 1 mL of THF was added sequentially, 52 μL of diisopropylethylamine and a solution of 43.3 mg of the resultant compound of Example 85A in 1 mL of THF. The mixture was stirred for 24 hours and then concentrated in vacuo. The residue was diluted with 60 mL of $CH_2Cl_2$, washed with 5% sodium bicarbonate and brine, dried over magnesium sulfate, filtered and concentrated in vacuo to yield 70.7 mg of crude product. The residue was purified by preparative reversed-phase $C_{18}$ HPLC using a linear gradient of 30% to 100% $CH_3CN/H_2O$ with 0.1% TFA as eluant to obtain 43.9 mg of the title compound. TLC: Rf=0.29, 100% EtOAc. HPLC: Rt=13.24 min; ($^1H$) NMR ($CDCl_3$) consistent with structure.

EXAMPLE 93

A. N-hydroxysuccinimidyl-(R)-3-hydroxytetrahydrofuryl carbonate

The title compound was prepared as described in Example 48A starting with 81 mg of (R)-3-hydroxytetrahydrofuran to yield 56 mg of the title product as a white solid. ($^1H$)-NMR ($CDCl_3$) consistent with structure.

B. Compound 93

To a solution of 43 mg of the resultant compound of Example 35A in $CH_2Cl_2$ was added, at ambient temperature under an atmosphere of nitrogen, 27 mg of the resultant compound of Example 93A and 39 mg N,N-diisopropylethylamine. The mixture was stirred for 14 h, diluted with $CH_2Cl_2$, washed with saturated $NaHCO_3$ and saturated NaCl, then dried over $MgSO_4$, filtered, and concentrated in vacuo. The residue was purified by preparative thin layer silica gel chromatography using 2% $CH_3OH$ in $CH_2Cl_2$ as eluent to yield 45 mg of the title product as a white solid. TLC: Rf=0.52 (5% $CH_3OH$ $CH_2Cl_2$). HPLC: Rt=14.94 min. ($^1H$)-NMR ($CDCl_3$) consistent with structure.

EXAMPLE 94

Compound 94

A solution of 47 mg of the resultant compound of Example 40A in $CH_2Cl_2$ was treated sequentially, at ambient temperature under an atmosphere of nitrogen, with 28 mg of the product of Example 93A and 39 mg N,N-diisopropylethylamine. The mixture was stirred for 14 h, diluted with $CH_2Cl_2$, washed with saturated $NaHCO_3$ and saturated NaCl, then dried over $MgSO_4$, filtered, and concentrated in vacuo. The residue was purified by preparative thin layer silica gel chromatography using 5% methanol in $CH_2Cl_2$ as eluent to yield 40 mg of the title product as a white solid. TLC: Rf=0.38 (ethyl acetate). HPLC: Rt=13.09 min. ($^1$H)-NMR ($CDCl_3$) consistent with structure.

EXAMPLE 95

Compound 95

To a solution of 72.0 mg (0.189 mmol) of the resultant compound of Example 51D in $CH_2Cl_2$ (4 mL) was added aqueous sodium bicarbonate (1 mL), solid sodium bicarbonate 19.1 mg (0.227 mmol), and 2,3-dichlorothiophenesulfonyl chloride 57.1 mg, (0.227 mmol). After 14 h, the resulting mixture was diluted with EtOAc, washed with saturated brine, dried over magnesium sulfate, filtered and concentrated in vacuo. The residue was purified by low pressure silica gel column chromatography using 5 to 12% $EtOAc/CH_2Cl_2$ eluent to provide 49.1 mg of the title product. TLC: Rf=0.62 25% $EtOAc/CH_2Cl_2$, HPLC: Rt=17.3 min; ($^1$H)-NMR ($CDCl_3$) consistent with structure.

EXAMPLE 96

A. (4-Acetamido)-phenylmethyl-4-nitrophenylcarbonate

To a solution of 242.8 mg of p-nitrophenyl chloroformate in 5 mL of acetonitrile at 0° C. was added sequentially, 165.2 mg of 4-acetamidobenzyl alcohol and 0.13 mL of 4-methyl morpholine. The mixture was stirred for 24 hours and concentrated in vacuo. The residue was taken up in $CH_2Cl_2$ and washed with 5% sodium bicarbonate and brine, dried over magnesium sulfate, filtered and concentrated in vacuo to yield 320 mg of the title compound. TLC: Rf=0.23, 50% EtOAc/hexane.

B. Compound 96

To solution of the resultant compound of Example 40A in 1 mL of THF was added sequentially, 56 µL of diisopropylethylamine and 63 mg of the resultant compound of Example 96A. The mixture was stirred for 24 hours and then concentrated in vacuo. The residue was purified by preparative thin layer chromatography using 10% methanol/$CH_2Cl_2$ as eluent followed by preparative reversed-phase $C_{18}$ HPLC using a linear gradient of 30% to 100% $CH_3CN/H_2O$ with 0.1% TFA as eluant to yield 50.2 mg of the title compound. TLC: Rf=0.43, 10% methanol/$CH_2Cl_2$. HPLC: Rt=13.54 min. ($^1$H)-NMR ($CDCl_3$) consistent with structure.

EXAMPLE 97

Compound 97

To solution of 60 mg of the resultant compound of Example 35A in 1 mL of THF was added sequentially, 54 µL of diisopropylethylamine and a solution of 48.9 mg of the resultant compound of Example 85A in 1 mL THF. The mixture was stirred for 24 hours and then concentrated in vacuo. The residue was diluted with 60 mL of $CH_2Cl_2$, washed with 5% sodium bicarbonate and brine, dried over magnesium sulfate, filtered and concentrated in vacuo. The residue was purified by preparative thin layer chromatography using 20% $EtOAc/CH_2Cl_2$ as eluent to yield 46.9 mg of the title compound. TLC: Rf=0.31, 20% $EtOAc/CH_2Cl_2$. HPLC: Rt=15.18 min. ($^1$H)-NMR ($CDCl_3$) consistent with structure.

EXAMPLE 98

Compound 98

To a solution of 61.0 mg of the resultant compound of Example 35A in 1 mL of THF was added sequentially, 49 µL of diisopropylethylamine and a solution of 44 mg of the resultant compound of Example 82A in 1 mL THF. The mixture was stirred for 24 hours and then concentrated in vacuo. The residue was purified by preparative thin layer chromatography using 5% methanol/$CH_2Cl_2$ as eluent to yield 61.0 mg of a white solid. TLC: Rf=0.19, 5 methanol/$CH_2Cl_2$. HPLC: Rt=13.28 min; 13.28 min. ($^1$H)-NMR ($CDCl_3$) consistent with structure.

EXAMPLE 99

Compound 99

A solution of 75 mg of the resultant compound of Example 51D and 45 mg of 4-chlorobenzenesulfonyl chloride were reacted in the manner described in Example 60. After workup and purification by preparative reversed-phase $C_{18}$ HPLC using a linear gradient of 35% to 100% $CH_3CN/H_2O$ with 0.1% TFA as eluant, 24.6 mg of the title compound was obtained. TLC: Rf=0.3, 4% MeOH/$CH_2Cl_2$. HPLC: Rt=15.87 min; ($^1$H)-NMR ($CDCl_3$) consistent with structure.

EXAMPLE 100

Compound 100

A solution of 40 mg of the resultant compound of Example 51D and 45 mg of 4-methoxybenzenesulfonyl chloride were reacted in the manner described in Example 60. After workup and purification by preparative reversed-phase $C_{18}$ HPLC using a linear gradient of 35% to 100% $CH_3CN/H_2O$ with 0.1% TFA as eluant, 21.4 mg of the title compound was obtained as a white solid. TLC: Rf=0.2, 4% MeOH/$CH_2Cl_2$. HPLC: Rt=14.85 min; ($^1$H)-NMR ($CDCl_3$) consistent with structure.

EXAMPLE 101

Compound 101

This compound was prepared from the resultant compound of Example 128 by treatment with hydrogen chloride gas and subsequent reaction with the resultant compound of Example 48A in the manner described in Example 132. After workup and purification by preparative reversed-phase $C_{18}$ HPLC using a linear gradient of 35% to 100% $CH_3CN/H_2O$ with 0.1% TFA as eluant on a portion of the crude mixture, 4.2 mg of the title compound was obtained as a white solid. TLC: Rf=0.2, 4% MeOH/$CH_2Cl_2$. HPLC: Rt=11.53 min; ($^1$H)-NMR ($CDCl_3$) consistent with structure.

EXAMPLE 102

Compound 102

A solution of 36 mg of the resultant compound of Example 40A in $CH_2Cl_2$ was treated sequentially, at ambient temperature under an atmosphere of nitrogen, with 8 mg of methyl chloroformate and 22 mg N,N-diisopropylethylamine. The mixture was stirred for 3 h and then concentrated in vacuo. The residue was taken up in ethyl acetate and washed with 0.5N HCl and saturated NaCl then dried over $MgSO_4$, filtered, and concentrated in vacuo. The residue was purified by low pressure silica gel chromatography using 30% diethyl ether in $CH_2Cl_2$ as eluent to provide 27 mg of the title product as a white solid. TLC: Rf=0.10 (30% diethyl ether in $CH_2Cl_2$). HPLC: Rt=13.49 min. ($^1$H)-NMR ($CDCl_3$) consistent with structure.

EXAMPLE 103

Compound 103

A solution of 29 mg of the resultant compound of Example 81B in $CH_2Cl_2$ was treated sequentially, at ambient temperature under an atmosphere of nitrogen, with 6 mg of methyl chloroformate and 17 mg N,N-diisopropylethylamine. The mixture was stirred for 3 h and then concentrated in vacuo. The residue was taken up in ethyl acetate and washed with 0.5N HCl and saturated NaCl then dried over $MgSO_4$, filtered, and concentrated in vacuo. The residue was purified by low pressure silica gel chromatography using 5% diethyl ether/$CH_2Cl_2$ as eluent to provide 29 mg of the title product as a white solid. TLC: Rf=0.24 (5% diethyl ether in $CH_2Cl_2$). HPLC: Rt=17.07 min. ($^1$H)-NMR ($CDCl_3$) consistent with structure.

EXAMPLE 104

Compound 104

A solution of 31 mg of the resultant compound of Example 35A in $CH_2Cl_2$ was treated sequentially, at ambient temperature under an atmosphere of nitrogen, with 8 mg of methyl chloroformate and 21 mg N,N-diisopropylethylamine. The mixture was stirred for 3 h and then concentrated in vacuo. The residue was taken up in ethyl acetate and washed with 0.5N HCl and saturated NaCl then dried over $MgSO_4$, filtered, and concentrated in vacuo. The residue was purified by low pressure silica gel chromatography using 5% diethyl ether/$CH_2Cl_2$ as eluent to provide 24 mg of the title product as a white solid. TLC: Rf=0.23 (5% diethyl ether in $CH_2Cl_2$). HPLC: Rt=15.41 min. ($^1$H)-NMR ($CDCl_3$) consistent with structure.

EXAMPLE 105

A. N-hydroxysuccinimidyl methallyl carbonate

To a solution of 2.9 mL of 1.93M phosgene in toluene at −10° C. was added 857 mg of methallyl alcohol. The mixture was stirred for 2 h at −10° C. to produce a 1.9M solution of the title compound which was used directly in subsequent reactions.

B. Compound 105

A solution of 39 mg of the resultant compound of Example 40A in $CH_2Cl_2$ was treated sequentially, at ambient temperature under an atmosphere of nitrogen, with 0.05 mL of the resultant compound of Example 105A and 24 mg N,N-diisopropylethylamine. The mixture was stirred for 3 h and then concentrated in vacuo. The residue was taken up in ethyl acetate and washed with 0.5N HCl and saturated NaCl then dried over $MgSO_4$, filtered, and concentrated in vacuo. The residue was purified by preparative thin layer silica gel chromatography using ethyl acetate as eluent to yield 18 mg of the title product as a white solid. TLC: Rf=0.67 (ethyl acetate). HPLC: Rt=14.97 min. ($^1$H)-NMR ($CDCl_3$) consistent with structure.

EXAMPLE 106

Compound 106

A solution of 31 mg of the resultant compound of Example 81B in $CH_2Cl_2$ was treated sequentially, at ambient temperature under an atmosphere of nitrogen, with 0.04 mL of the resultant compound of Example 105A and 18 mg N,N-diisopropylethylamine. The mixture was stirred for 3 h and then concentrated in vacuo. The residue was taken up in ethyl acetate and washed with 0.5N HCl and saturated NaCl then dried over $MgSO_4$, filtered, and concentrated in vacuo. The residue was purified by low pressure silica gel chromatography using 5% diethyl ether/$CH_2Cl_2$ as eluent to provide 19 mg of the title product as a white solid. TLC: Rf=0.34 (5% diethyl ether/$CH_2Cl_2$). HPLC: Rt=18.24 min. ($^1$H)-NMR ($CDCl_3$) consistent with structure.

EXAMPLE 107

Compound 107

A solution of 28 mg of the resultant compound of Example 35A in $CH_2Cl_2$ was treated sequentially, at ambient temperature under an atmosphere of nitrogen, with 0.05 mL of the resultant compound of Example 105A and 19 mg N,N-diisopropylethylamine. The mixture was stirred for 3 h and then concentrated in vacuo. The residue was taken up in ethyl acetate and washed with 0.5N HCl and saturated NaCl then dried over $MgSO_4$, filtered, and concentrated in vacuo. The residue was purified by low pressure silica gel chromatography using 5% diethyl ether in $CH_2Cl_2$ as eluent to provide 18 mg of the title product as a white solid. TLC: Rf=0.25 (5% diethyl ether in $CH_2Cl_2$). HPLC: Rt=16.68 min. ($^1$H)-NMR ($CDCl_3$) consistent with structure.

EXAMPLE 108

Compound 108

To a solution of 62.5 mg of 124B in 1 mL of THF was added sequentially 56 μL of diisopropylethylamine and a solution of 49.6 mg of the resultant compound of Example 82A in 1 mL THF. The mixture was stirred for 24 hours and then concentrated in vacuo. The residue was purified by preparative thin layer chromatography using 50% EtOAc/$CH_2Cl_2$ as eluent followed by preparative reversed-phase $C_{18}$ HPLC using a linear gradient of 30% to 100% $CH_3CN$/$H_2O$ with 0.1% TFA as eluant on a portion of the crude mixture, 4.2 mg of the title compound was obtained as a white solid. TLC: Rf=0.16, 10% methanol/$CH_2Cl_2$. HPLC: Rt=13.67 min. ($^1$H) NMR ($CDCl_3$) consistent with structure.

EXAMPLE 109

A. (S)-4-Methoxycarbonyl-oxazlidin-2-one

To a solution of 4.88 g of serine methyl ester hydrochloride in 25 mL of water was added 6.94 g of potassium carbonate. The mixture was cooled to 0° C. and 19.5 mL of phosgene was added dropwise. After stirring at 0° C. for 3 hours, water was removed to yield a white solid was washed with copious of $CH_2Cl_2$. The organic solution was then dried over magnesium sulfate, filtered and concentrated to yield 3.26 g of the title product as a clear oil. ($^1$H) NMR ($D_2O$): δ=3.82 (s, 3H), 4.43 (dd, 1H), 4.53 (dd, 1h), 4.67 (t, 1H), 6.29 (s, 1H).

B. (S)-4-Hydroxymethyl-oxazlidin-2-one

To a solution of 3.26 g of the resultant compound of Example 109A in 20 mL of ethanol at 0° C. was added 0.85 g of sodium borohydride in small portions. The ice bath was removed and after additional 3 hours, 20 mL of 2.0N hydrogen chloride was added to the mixture, which was then concentrated to yield an oil. The residue was extracted with EtOAc and the organic solution was dried over magnesium sulfate, filtered and concentrated to yield 2.50 g of the title compound. ($^1$H) NMR ($CDCl_3$) δ=2.48 (s, 1H), 3.69 (dd, 1H), 4.08 (m, 1H), 4.31 (t, 1H), 4.57 (t, 1H).

C. 4-Nitrophenyl-((S)-4-oxazlidin-2-onyl)-methyl carbonate

To a solution of 1.04 g of p-nitrophenyl chloroformate in 20 mL of $CH_2Cl_2$ at 0° C. was added sequentially, 0.5 g of the resultant compound of Example 109B and 0.6 mL of 4-methyl morpholine. The mixture was stirred for 2 hours at ambient temperature and then concentrated in vacuo. The residue was purified by low pressure silica gel column chromatography using 20% EtOAc in $CH_2Cl_2$ eluent to yield 0.57 g of the title compound. TLC: Rf=0.10, 50% EtOAc/hexane.

D. Compound 109

To a solution of 60 mg of the resultant compound of Example 35A in 1 mL of THF was added sequentially, 56 μL of diisopropylethylamine and a solution of 51.1 mg of the resultant compound of Example 109C in 1 mL acetonitrile. The mixture was stirred for 24 hours and then concentrated in vacuo. The residue was purified by preparative thin layer chromatography using 5% methanol/$CH_2Cl_2$ as eluent to yield 60.4 mg of the title compound. TLC: Rf=0.38, 5% methanol/$CH_2Cl_2$. HPLC: Rt=14.11 min. ($^1H$) NMR ($CDCl_3$) consistent with structure.

EXAMPLE 110

Compound 110

To a solution of 60 mg of the resultant compound of Example 40A in 1 mL of acetonitrile was added sequentially, 51 μL of diisopropylethylamine and a solution of 46.8 mg of the resultant compound of Example 109C in 1 mL acetonitrile. The mixture was stirred for 48 hours and then concentrated in vacuo. The residue was purified by preparative thin layer chromatography using 10% methanol/$CH_2Cl_2$ eluent followed by preparative reversed-phase $C_{18}$ HPLC using a linear gradient of 30% to 100% $CH_3CN/H_2O$ with 0.1% TFA as eluant to yield 16 mg of the title compound. TLC: Rf=0.28, 50% EtOAc/$CH_2Cl_2$. HPLC: Rt=12.47 min. ($^1H$) NMR ($CDCl_3$) consistent with structure.

EXAMPLE 111

A solution of 0.067 mmol of the resultant compound of Example 114D in 5 mL of tetrahydrofuran was added 20 μL of diisopropylethylamine followed dropwise by a solution of the resultant compound of Example 82A in 5 mL of tetrahydrofuran during one hour. The mixture was stirred 16 h and then concentrated in vacuo. The crude residue was purified by thick layer silica gel chromatography using 5% MeOH/$CH_2Cl_2$ as eluant to obtain 21.8 mg of the title compound. TLC: Rf=0.45, 5% MeOH/$CH_2Cl_2$; ($^1H$)-NMR ($CDCl_3$) consistent with structure.

EXAMPLE 112

A. Compound XXII (A=tert-butoxycarbonyl, D'=isobutyl, E=3-sulfonamidophenyl)

To a solution of 96.6 mg (0.287 mmol) of the resultant compound of Example 39A in $CH_2Cl_2$ (4 mL) was added aqueous sodium bicarbonate (1 mL), solid sodium bicarbonate 36.2 mg (0.431 mmol), and m-benzene disulfonylchloride 86.9 mg, (1.08 mmol). After stirring for 1 h, 30% ammonium hydroxide (10 mL) was added. After 14 h the resulting mixture was diluted with $CH_2Cl_2$, washed with saturated brine, dried over magnesium sulfate, filtered and concentrated in vacuo. The residue was purified by flash chromatography using 0% to 10% methanol/$CH_2Cl_2$ eluent to provide 49.3 mg of the title product. ($^1H$)-NMR ($CDCl_3$) consistent with structure.

B. Compound XXII (A=H, D'=isobutyl, E=3-sulfonamidophenyl, hydrochloride salt)

A solution of 49.3 mg (0.089 mmol) of the resultant compound of Example 112A in EtOAc (10 mL) at −20° C. was treated with anhydrous HCl gas for 10 min. The ice bath was removed and after an additional 15 min., the reaction mixture was sparged with nitrogen then concentrated in vacuo to provide 53.1 mg of title product as the HCl salt. ($^1H$)-NMR ($CDCl_3$) consistent with structure.

C. Compound 112

To a solution of 53.1 mg of the resultant compound of Example 112B (0.089 mmol) in $CH_2Cl_2$ (3 mL) was treated sequentially at ambient temperature under an atmosphere of nitrogen, with 0.031 mL (0.177 mmol) diisopropylethylamine and 24.3 mg (0.106 mmol) of the resultant compound of Example 48A. The mixture was stirred 16 h and then concentrated in vacuo. The residue was taken up in $CH_2Cl_2$ and washed with saturated brine, dried over magnesium sulfate, filtered, and concentrated in vacuo. The residue was purified by low pressure silica gel column chromatography using a gradient 5% to 20% EtOAc in $CH_2Cl_2$ as eluent to yield 10.8 mg of the title product. TLC: RF=0.4 25% EtOAc in $CH_2Cl_2$. HPLC: Rt=13.3 min; ($^1H$) NMR ($CDCl_3$) consistent with structure.

EXAMPLE 113

A. 3-Furansulfonyl chloride

In flame dried glassware under a nitrogen atmosphere to a solution of 428 mg (2.909 mmol) of 3 bromofuran in anhydrous tetrahydrofuran at −78° C. was added 2.0 mL n-butyl lithium (3.2 mmol at 1.6 molar in hexane). After 45 minutes the resultant solution was added via cannula to a 20° C. solution of sulfuryl chloride in diethyl ether (5 mL plus a 2 mL rinse). After 1 h, the reaction was quenched with 0.5N hydrochloric acid and extraced into diethyl ether. The ethereal extracts were washed with saturated brine, dried over magnesium sulfate, filtered and concentrated in vacuo to provide 158 mg of the title product. ($^1H$) NMR ($CDCl_3$) consistent with structure.

B. Compound XXII (A=tert-butoxycarbonyl, D'=isobutyl, E=3-furyl)

To a solution of 289.7 mg (0.861 mmol) of the resultant compound of Example 39A in $CH_2Cl_2$ (8 mL) was added aqueous sodium bicarbonate (2 mL), solid sodium bicarbonate 108 mg (1.292 mmol), and the resultant product from Example 113A 157.8 mg, (1.08 mmol). After stirring for 1 h 30% ammonium hydroxide (10 mL) was added. After 14 h, the resulting mixture was diluted with $CH_2Cl_2$, washed with saturated brine, dried over magnesium sulfate, filtered and concentrated in vacuo. The residue was purified by flash chromatography using 1% to 15% EtOAc/$CH_2Cl_2$.

C. Compound XXII (A=H, D'=isobutyl, E=3-furyl, hydrochloride salt)

A solution of 217.3 mg (0.581 mmol) of the resultant compound of Example 113B in EtOAc (15 mL) at −20° C. was treated with anhydrous HCl gas for 10 min. The ice bath was removed and after an additional 15 min. the reaction mixture was sparged with nitrogen then concentrated in vacuo to provide 228 mg of title product as the HCl salt. TLC: Rf=0.52 10% methanol/$CH_2Cl_2$.

D. Compound 113

To a solution of 65.3 mg of the resultant compound of Example 113C (0.162 mmol) in $CH_2Cl_2$ (3 mL) was treated sequentially at ambient temperature under an atmosphere of nitrogen, with 0.056 mL (0.324 mmol) diisopropylethylamine and 44.6 mg (0.194 mmol) of the resultant compound of Example 48A. The mixture was stirred 16 h and then concentrated in vacuo. The residue was taken up in $CH_2Cl_2$ and washed with saturated brine, dried over magnesium sulfate, filtered, and concentrated in vacuo. The residue was purified by low pressure silica gel column chromatography using a gradient 3% to 20% EtOAc in $CH_2Cl_2$ eluent to yield 10.8 mg of the title product. TLC: Rf=0.6, 25% EtOAc/$CH_2Cl_2$. HPLC: Rt=13.9% min; ($^1H$) NMR ($CDCl_3$) consistent with structure.

EXAMPLE 114

A. Aminomethylcyclopentane

To a solution of $LiAlH_4$ (38 g, 1.0 mole) in diethyl ether (2 L) was added cyclopentanecarbonitrile (73.2 g, 0.77 mol) as a solution in 250 mL ether. The solution was stirred overnight at ambient temperature and then quenched by addition of the organics to 3 L of a saturated potassium, sodium tartrate solution. The amine was extracted into 3 L of ether, dried over anhydrous $K_2CO_3$ then concentrated by distillation to approximately 400 mL total volume. The crude product was purified via distillation to give 58.2 g of the title compound as a colorless oil. ($^1H$)-NMR ($CDCl_3$) consistent with structure.

B. Compound XXI (P=tert-butoxycarbonyl, D'=cyclopentylmethyl, P'=H)

To the resultant compound of Example 114A (20 g, 0.2 mol) was added compound XX (P=Boc) (5.84 g) and the mixture was stirred for 24 h at ambient temperature. The solution was concentrated by distillation under reduced pressure. The residue was triturated with hexane and the solid collected by suction filtration and washed with hexane to give 7.08 g of a white solid which was used without further purification. TLC: Rf=0.59 (1:10:90 concentrated $NH_4OH$/methanol/$CH_2Cl_2$). ($^1H$)-NMR ($CDCl_3$) consistent with structure.

C. Compound XXII (P=tert-butoxycarbonyl, D'=cyclopentylmethyl, E=4-fluorophenyl)

To a solution of the resultant compound of Example 114B (200 mg, 0.55 mmol) in $CH_2Cl_2$ (10 mL) was added 4-fluorobenzenesulfonyl chloride (210 mg, 1.1 mmol) followed by the addition of a saturated solution of sodium bicarbonate (3 mL) followed by addition of solid sodium bicarbonate (0.1 g, 1.2 mmol). The mixture was allowed to stir at ambient temperature overnight. The solution was diluted with 100 mL $CH_2Cl_2$, the organics separated, dried over anhydrous $MgSO_4$, and the organics concentrated under reduced pressure to obtain 0.33 g of crude product. This material was purified via medium pressure liquid chromatography using $CH_2Cl_2$, followed by 0.5:99.5 methanol/$CH_2Cl_2$, followed by a 1:99 methanol/$CH_2Cl_2$ solution as the solvent system to give 120 mg (42% yield) of the title compound as a white solid. TLC: Rf=0.48 (3:97 methanol/$CH_2Cl_2$); HPLC: Rt=18.22 min, ($^1H$)-NMR ($CDCl_3$) consistent with structure.

D. Compound XXII (P=H, D'=cyclopentylmethyl, E=4-fluorophenyl, hydrochloride salt)

A solution of 266 mg of the resultant compound of Example 114C in ethyl acetate was treated at −20° C. with HCl gas for 20 min, during which time the temperature was allowed to warm to 20° C. Nitrogen was then bubbled through the mixture for 15 min and the solvent removed in vacuo to yield 224 mg of white solid which was used directly for ensuing reaction.

E. Compound 114

A solution of 31 mg of the resultant compound of Example 114D in $CH_2Cl_2$ was treated sequentially, at ambient temperature, under an atmosphere of nitrogen, with 9 mg of allyl chloroformate and 19 mg N,N-diisopropylethylamine. The mixture was stirred for 3 h and then concentrated in vacuo. The residue was taken up in ethyl acetate and washed in 0.5N HCl and saturated NaCl then dried over $MgSO_4$, filtered, and concentrated in vacuo to yield 34 mg of the title product as a white solid. TLC: Rf=0.34 (5% diethyl ether in $CH_2Cl_2$). HPLC: Rt=17.21 min. ($^1H$)-NMR ($CDCl_3$) consistent with structure.

EXAMPLE 115

Compound 115

A solution of 31 mg of the resultant compound of Example 114B in $CH_2Cl_2$ was treated sequentially, at ambient temperature under an atmosphere of nitrogen, with 8 mg of ethyl chloroformate and 19 mg N,N-diisopropylethylamine. The mixture was stirred for 3 h and then concentrated in vacuo. The residue was taken up in ethyl acetate and washed with 0.5N HCl and saturated NaCl then dried over $MgSO_4$, filtered, and concentrated in vacuo to yield 35 mg of the title product as a white solid. TLC: Rf=0.32 (5% diethyl ether/$CH_2Cl_2$). HPLC: Rt=16.86 min. ($^1H$)-NMR ($CDCl_3$) consistent with structure.

EXAMPLE 116

A. Compound XXII (A=tert-butoxycarbonyl, D'=cyclopentylmethyl, E=4-chlorophenyl)

The resultant compound of Example 114B (252 mg) was reacted with 4-chlorobenzenesulfonyl chloride (175 mg) in the manner described in Example 166A. Workup and purification by silica gel chromatography using EtOAc/$CH_2Cl_2$ as eluant yielded the product as a white solid; ($^1H$) NMR ($CDCl_3$) consistent with structure.

B. Compound XXII (A=H, D'=cyclopentylmethyl, E=4-chlorophenyl, hydrochloride salt)

A solution of 320 mg of the resultant compound of Example 116A in 20 mL of EtOAc was treated with anhydrous HCl gas for 5 min. The reaction mixture was sparged with nitrogen then concentrated in vacuo to yield a white solid which was used directly for subsequent reaction.

C. Compound 116

To a solution of 63.4 mg of the resultant compound of Example 116B in 1 mL of THF was added sequentially 54 μL of diisopropylethylamine and a solution of 39.9 mg of the resultant compound of Example 48A in 1 mL THF. The mixture was stirred for 24 hours and then concentrated in vacuo. The residue was purified by low pressure silica gel column chromatography using 20% EtOAc in $CH_2Cl_2$ eluent to yield 0.62 g of the title compound. TLC: Rf=0.71, 40% EtOAc/$CH_2Cl_2$. HPLC: Rt=16.88 min. ($^1H$) NMR ($CDCl_3$) consistent with structure.

EXAMPLE 117

Compound 117

A solution of 66.1 mg of the resultant compound of Example 116B in 1 mL of THF was treated sequentially with 56 μL of diisopropylethylamine and 19.3 μL of allyl chloroformate. The mixture was stirred for 4 hours and concentrated in vacuo. The residue was taken into 50 mL of EtOAc and washed with 1.0N HCl, saturated sodium bicarbonate, brine, dried over magnesium sulfate, filtered and concentrated. The residue was purified by low pressure silica gel column chromatography using 20% EtOAc in hexane eluent to yield 69.7 mg of the title compound. TLC: Rf=0.20, 20% EtOAc/hexane. HPLC: Rt=17.83 min. ($^1H$) NMR ($CDCl_3$) consistent with structure.

EXAMPLE 118

Compound 118

To a solution of 65.3 mg of the resultant compound of Example 116B in 1 mL of THF was added sequentially 55 μL of diisopropylethylamine and a solution of 49.2 mg of the resultant compound of Example 82A in 1 mL THF. The mixture was stirred for 24 hours and concentrated in vacuo. The residue was purified by low pressure silica gel column chromatography using 40% EtOAc in $CH_2Cl_2$ as eluent followed by preparative reversed-phase $C_{18}$ HPLC using a linear gradient of 40% to 80% $CH_3CN/H_2O$ for elution to yield 70.7 mg of the title compound. TLC: Rf=0.27, 40% EtOAc/$CH_2Cl_2$. HPLC: Rt=14.85 min. ($^1H$) NMR ($CDCl_3$) consistent with structure.

EXAMPLE 119

Compound 119

A solution of 26 mg of the resultant compound of Example 81B in $CH_2Cl_2$ was treated sequentially, at ambient temperature under an atmosphere of nitrogen, with 6 mg of ethyl chloroformate and 15 mg N,N-diisopropylethylamine.

The mixture was stirred for 3 h and then concentrated in vacuo. The residue was taken up in ethyl acetage and washed with 0.5N HCl and saturated NaCl then dried over $MgSO_4$, filtered, and concentrated in vacuo. The residue was purified by low pressure silica gel chromatography using 5% diethyl ether/$CH_2Cl_2$ as eluent to provide 26 mg of the title product as a white solid. TLC: Rf=0.19 (5% diethyl ether in $CH_2Cl_2$). HPLC: Rt=17.50 min. ($^1$H)-NMR ($CDCl_3$) consistent with structure.

EXAMPLE 120

Compound 120

A solution of 30 mg of the resultant compound of Example 40A in $CH_2Cl_2$ was treated sequentially, at ambient temperature under an atmosphere of nitrogen, with 8 mg of ethyl chloroformate and 18 mg N,N-diisopropylethylamine. The mixture was stirred for 3 h and then concentrated in vacuo. The residue was taken up in ethyl acetage and washed with 0.5N HCl and saturated NaCl then dried over $MgSO_4$, filtered, and concentrated in vacuo. The residue was purified by preparative thin layer silica gel chromatography using ethyl acetate as eluent to yield 25 mg of the title product as a white solid. TLC: Rf=0.60 (ethyl acetate). HPLC: Rt=13.86 min. ($^1$H)-NMR ($CDCl_3$) consistent with structure.

EXAMPLE 121

Compound 121

A solution of 26 mg of the resultant compound of Example 35A in $CH_2Cl_2$ was treated sequentially, at ambient temperature under an atmosphere of nitrogen, with 7 mg of ethyl chloroformate and 17 mg N,N-diisopropylethylamine. The mixture was stirred for 3 h and then concentrated in vacuo. The residue was taken up in ethyl acetate and washed with 0.5N HCl and saturated NaCl then dried over $MgSO_4$, filtered, and concentrated in vacuo. The residue was purified by low pressure silica gel chromatography using 5% diethyl ether/$CH_2Cl_2$ as eluent to provide 22 mg of the title product as a white solid. TLC: Rf=0.14 (5% diethyl ether/$CH_2Cl_2$). HPLC: Rt=15.95 min. ($^1$H)-NMR ($CDCl_3$) consistent with structure.

EXAMPLE 122

Compound 122

A solution of 27 mg of the resultant compound of Example 35A in $CH_2Cl_2$ was treated sequentially, at ambient temperature under an atmosphere of nitrogen, with 8 mg of allyl chloroformate and 18 mg N,N-diisopropylethylamine. The mixture was stirred for 3 h and then concentrated in vacuo. The residue was taken up in ethyl acetate and washed with 0.5N HCl and saturated NaCl then dried over $MgSO_4$, filtered, and concentrated in vacuo. The residue was purified by low pressure silica gel chromatography using 5% diethyl ether in $CH_2Cl_2$ as eluent to provide 23 mg of the title product as a white solid. TLC: Rf=0.33, 5% diethyl ether in $CH_2Cl_2$. HPLC: Rt=16.28 min. ($^1$H)-NMR ($CDCl_3$) consistent with structure.

EXAMPLE 123

A. Compound XXII (A=tert-butoxycarbonyl, D'=isobutyl, E=3,4-dimethoxyphenyl)

To a solution of 401 mg (1.192 mmol) of the resultant compound of Example 39A in $CH_2Cl_2$ (12 mL) was added aqueous sodium bicarbonate (3 mL), solid sodium bicarbonate 130 mg (1.549 mmol), and 3, 4-dimethoxybenzenesulfonyl chloride 33.8 mg, (1.43 mmol). After 14 h, the resulting mixture was diluted with EtOAc, washed with saturated brine, dried over magnesium sulfate, filtered and concentrated in vacuo. The residue was purified by flash chromatography using 5% to 25% EtOAc/$CH_2Cl_2$ eluent to provide 440.1 mg of the title product. TLC: Rf=0.72, 20% EtOAc/$CH_2Cl_2$.

B. Compound XXII (A=H, D'=isobutyl, E=3,4-dimethoxyphenyl, hydrochloride salt)

A solution of 440 mg (0.820 mmol) of the resultant compound of Example 123A in EtOAc (15 mL) at −20° C. was treated with anhydrous HCl gas for 10 min. The ice bath was removed and after an additional 15 min. the reaction mixture was sparged with nitrogen then concentrated in vacuo to provide 610 mg of title product as the HCl salt. TLC: Rf=0.44, 10% methanol/$CH_2Cl_2$.

C. Compound 123

A solution of 38.9 mg of the resultant compound of Example 123B (0.170 mmol) in $CH_2Cl_2$ (3 mL) was treated sequentially at ambient temperature under an atmosphere of nitrogen with 0.049 mL (0.283 mmol) diisopropylethylamine and 66.9 mg (169.6 mmol) of the resultant compound of Example 48A. The mixture was stirred for 16 h and then concentrated in vacuo. The residue was taken up in $CH_2Cl_2$ and washed with saturated brine, dried over magnesium sulfate, filtered, and concentrated in vacuo. The residue was purified by low pressure silica gel column chromatography using a gradient 10% to 25% diethyl ether in $CH_2Cl_2$ cluent to yield 57.6 mg of the title product. TLC: Rf=0.39, 25% diethyl ether/$CH_2Cl_2$. HPLC: Rt=14.3 min; ($^1$H) NMR ($CDCl_3$) consistent with structure.

EXAMPLE 124

A. Compound XXII (A=tert-butoxycarbonyl, D'=isobutyl, E=3,4 difluorophenyl)

To a solution of 332.7 mg (0.989 mmol) of the resultant compound of Example 39A in $CH_2Cl_2$ (12 mL) was added aqueous sodium bicarbonate (3 mL), solid sodium bicarbonate 125 mg (1.483 mmol), and 3,4 difluorobenzensulfonyl chloride 231 mg. (1.088 mmol). After 14 h, the resulting mixture was diluted with $CH_2Cl_2$, washed with saturated brine, dried over magnesium sulfate, filtered and concentrated in vacuo. The residue was purified by flash chromatography using 5% to 25% diethyl ether/$CH_2Cl_2$ eluent to provide 313.6 mg of the title product. ($^1$H)-NMR ($CDCl_3$) consistent with structure.

B. Compound XXII (A=H, D'=isobutyl, E=3,4 difluorophenyl, hydrochloride salt)

A solution of 312.6 mg (0.610 mmol) of the resultant compound of Example 124A in EtOAc (15 mL) at −20° C. was treated with anhydrous HCl gas for 10 min. The ice bath was removed and after an additional 15 min., the reaction mixture was sparged with nitrogen then concentrated in vacuo to provide 280 mg of title product as a white solid. TLC: Rf=0.46, 10% methanol/$CH_2Cl_2$.

C. Compound 124

To a solution of 64.7 mg of the resultant compound of Example 124B (0.144 mmol) in $CH_2Cl_2$ (3 mL) was treated sequentially at ambient temperature under an atmosphere of nitrogen, with 0.050 mL (0.288 mmol) diisopropylethylamine and 39.6 mg (172.9 mmol)of the resultant compound of Example 48A. The mixture was stirred for 16 h and then concentrated in vacuo. The residue was taken up in $CH_2Cl_2$ and washed with saturated brine, dried over magnesium sulfate, filtered, and concentrated in vacuo. The residue was purified by low pressure silica gel column chromatography using a gradient 5% to 20% diethyl ether in $CH_2Cl_2$ eluent to yield 44 mg of the title product. TLC: RF=0.54 25% diethyl ether/$CH_2Cl_2$. HPLC: Rt=15.4 min. ($^1$H) NMR ($CDCl_3$) consistent with structure.

EXAMPLE 125

Compound 125

This compound was prepared from the resultant compound of Example 146B in the manner described in Example 88. After workup and purification by preparative reversed-phase $C_{18}$ HPLC using a liner gradient of 35% to 100% $CH_3CN/H_2O$ with 0.1% TFA as eluant, 10.5 mg of the title compound was obtained as a white solid. TLC: Rf=0.4, 4% $MeOH/CH_2Cl_2$. HPLC: Rt=14.06 min; ($^1H$)-NMR ($CDCl_3$) consistent with structure.

EXAMPLE 126

A. Compound XXI (P=tert-butoxycarbonyl, D'=methyl, P'=H)

To a solution compound XX (1.7 mmol) in ethanol (20 mL) was added methylamine gas, at ambient temperature, for 30 min. The solution was stirred overnight, then concentrated under reduced pressure to give 0.47 g of the title compound which was used without subsequent purification. TLC: Rf=0.19, 1:10:90 $NH_4OH$/methanol/$CH_2Cl_2$, ($^1H$)-NMR ($CDCl_3$) consistent with structure.

B. Compound 126

To a solution of the product of Example 126A (0.15 g, 0.51 mmol) in $CH_2Cl_2$ (10 mL) was added a saturated solution of sodium bicarbonate (3 mL), followed by addition of solid sodium bicarbonate (90 mg, 1.1 mmol), followed by addition of 3,4-dichlorobenzenesulfonyl chloride (0.25 g, 1.0 mmol). The mixture was stirred at ambient temperature overnight. The organics were extracted into 100 mL $CH_2Cl_2$, dried over anhydrous, $MgSO_4$, concentrated under reduced pressure then purified via medium pressure silica gel chromatography using a gradient system of $CH_2Cl_2$ followed by 5:95 ether/$CH_2Cl_2$. The title compound was obtained as a colorless foam 210 mg. TLC: Rf=0.42 (3:97 methanol/$CH_2Cl_2$), HPLC: Rt=17.2 min; ($^1H$)-NMR ($CDCl_3$) consistent with structure.

EXAMPLE 127

Compound 127

To a solution of the product of Example 126A (0.15 g, 0.51 mmol) in $CH_2Cl_2$ (10 mL) was added a saturated solution of sodium bicarbonate (3 mL), followed by addition of solid sodium bicarbonate (100 mg, 1.0 mmol), followed by addition of 4-fluorobenzenesulfonyl chloride (0.20 g, 1.0 mmol). The mixture was stirred at ambient temperature overnight. The organics were extracted into 100 mL $CH_2Cl_2$, dried over anhydrous, $MgSO_4$, concentrated under reduced pressure then purified via medium pressure silica gel chromatography using a gradient system of $CH_2Cl_2$ followed by 5:95 ether/$CH_2Cl_2$. The title compound was obtained as a white solid 104 mg. TLC: Rf=0.36, 3:97 methanol/$CH_2Cl_2$, HPLC: Rt=15.86 min; ($^1H$)-NMR ($CDCl_3$) consistent with structure.

EXAMPLE 128

Compound 128

To a solution of the product of Example 126A (0.15 g, 0.51 mmol) in $CH_2Cl_2$ (6 mL) was added a saturated solution of sodium bicarbonate (3 mL), followed by addition of solid sodium bicarbonate (90 mg, 1.0 mmol), followed by addition of acetamidobenzenesulfonyl chloride (0.24 g, 1.02 mmol). The mixture was stirred at ambient temperature overnight. The organics were extracted into 100 mL $CH_2Cl_2$, dried over anhydrous, $MgSO_4$, concentrated under reduced pressure then purified via medium pressure silica gel chromatography using a gradient system of $CH_2Cl_2$ followed by 5:95 EtOAc/$CH_2Cl_2$, followed by 10:90 EtOAc/$CH_2Cl_2$. The title compound was obtained as 244 mg of white solid. TLC: Rf=0.13, 3:97 methanol/$CH_2Cl_2$, HPLC: Rt=13.47 min; ($^1H$)-NMR ($CDCl_3$) consistent with structure.

EXAMPLE 129

A. Compound XXI (P=tert-butoxycarbonyl, D'=(2-tetrahydrofuryl)-methyl, P'=H)

To a solution compound XX (3.3 mmol) in ethanol (30 mL) was added tetrahydrofurfurylamine (1.03 mL, 10 mmol). The mixture was warmed to 85° C. and stirred overnight. The solution was filtered and the solution concentrated under reduced pressure to give 1.29 g of the title compound which was used without subsequent purification. TLC: Rf=0.52, 1:10:90 $NH_4OH$/methanol/$CH_2Cl_2$ B. Compound 129

To a solution of the resultant compound of Example 129A (200 mg, 0.55 mmol) in $CH_2Cl_2$ (6 mL) was added 4-fluorobenzenesulfonyl chloride (320 mg, 1.6 mmol) followed a saturated solution of sodium bicarbonate (3 mL) and solid sodium bicarbonate (0.1 g, 1.2 mmol). The mixture was stirred at ambient temperature overnight. The solution was diluted with 100 mL $CH_2Cl_2$, the organics separated, dried over anhydrous $MgSO_4$, and the organics concentrated under reduced pressure. The crude product was purified via medium pressure liquid chromatography using a gradient solvent system of $CH_2Cl_2$ followed by 5:95 ether/$CH_2Cl_2$ followed by a 10:90 ether/$CH_2Cl_2$ solution to give 130 mg of the title compound as a white solid. TLC: Rf=0.35, 3:97 methanol/$CH_2Cl_2$, HPLC: Rt=16.37 min, ($^1H$)-NMR ($CDCl_3$) consistent with structure.

EXAMPLE 130

A. Compound XXI (P=tert-butoxycarbonyl, D'=(isobutenyl, P'=H))

To a solution compound XX (P=tert-butoxycarbonyl) (2.5 mmol) in ethanol (30 mL) was added a solution 2-methylallylamine hydrochloride (1.34 g, 12.5 mmol) and KOH (0.70 g, 12.5 mmol) in ethanol (20 mL). The mixture stirred 30 min at ambient temperature. The solutions were combined and heated to 85° C. for 24 h. The solution was filtered and concentrated under reduced pressure to give 0.82 g of the title compound which was used without subsequent purification. TLC: Rf=0.45, 1:10:90 concentrated $NH_4OH$/methanol/$CH_2$ $Cl_2$.

B. Compound 130

To a solution of the product of Example 130A (0.20 g, 0.60 mmol) in $CH_2Cl_2$ (6 mL) was added a saturated solution of sodium bicarbonate (3 mL), followed by solid sodium bicarbonate (0.1 g, 1.2 mmol) and then p-fluorobenzenesulfonyl chloride (0.35 g, 1.78 mmol). The mixture was stirred at ambient temperature for 24 h. The organics were extracted into 100 mL $CH_2Cl_2$, dried over anhydrous $MgSO_4$, concentrated under reduced pressure then purified via medium pressure silica gel chromatography using a gradient system of $CH_2Cl_2$, followed by 1:99 methanol/$CH_2Cl_2$. The title compound was obtained as a white solid 180 mg. TLC: Rf=0.35, 3:97 methanol/$CH_2Cl_2$, HPLC: Rt=16.82 min; ($^1H$)-NMR ($CDCl_3$) consistent with structure.

EXAMPLE 131

Compound 131

To a solution of the resultant compound of Example 130A (200 mg, 0.60 mmol) in $CH_2Cl_2$ (6 mL) was added 4-acetamidobenzenesulfonyl chloride (410 mg, 1.76 mmol), followed by a saturated solution of sodium bicarbonate (3 mL) and solid sodium bicarbonate (0.1 g, 1.2 mmol). The mixture was stirred at ambient temperature overnight. The solution was diluted with 100 mL $CH_2Cl_2$, the organics separated, dried over anhydrous $MgSO_4$, and the organics concentrated under reduced pressure. The crude product was purified via medium pressure liquid chromatography using a gradient solvent system of $CH_2Cl_2$, followed by 30:70 EtOAc/$CH_2Cl_2$ solution to give 140 mg of the title compound as a white solid. TLC: Rf=0.19, 3:97 methanol/$CH_2Cl_2$ HPLC: Rt=15.06 min, ($^1$H)-NMR ($CDCl_3$) consistent with structure.

EXAMPLE 132

A. Compound XXII (A=H, D'=(2-tetrahydrofuryl)methyl, E=4-fluorophenyl, hydrochloride salt)

To a solution of the resultant compound of Example 129B (30 mg, 0.057 mmol) in EtOAc (3 mL) was added 30% w/w HCl in EtOAc (1 mL). The mixture was stirred overnight at ambient temperature. The solution was concentrated under reduced pressure to give 16 mg of the title compound as a white solid which was used without subsequent purification. TLC: Rf=0.60 (1:10:90 $NH_4OH$/methanol/$CH_2Cl_2$).

B. Compound 132

To a solution of the resultant compound of Example 132A (16 mg) in $CH_2Cl_2$ (5 mL) was added triethylamine (0.1 mL, 0.72 mmol) followed by the compound of Example 48A (20 mg, 0.09 mmol). The mixture was stirred at ambient temperature for 24 hours. The solution was concentrated under reduced pressure and the crude product purified via medium pressure colum chromatography using 20:80 EtOAc/$CH_2Cl_2$ as the solvent system to give 7.4 mg. Rf=0.37 (3:97 methanol/$CH_2Cl_2$), HPLC: Rt=14.19 min, ($^1$H)-NMR ($CDCl_3$) consistent with structure.

EXAMPLE 133

A. Compound XXII (A=tert-butoxycarbonyl, D'=(2-tetrahydrofuryl)-methyl, E=4-acetamidophenyl)

To a solution of the resultant compound of Example 129A (200 mg, 0.55 mmol) in $CH_2Cl_2$ (6 mL) was added 4-acetamidobenzenesulfonyl chloride (380 mg, 1.6 mmol) followed by a saturated solution of sodium bicarbonate (3 mL) and solid sodium bicarbonate (0.1 g, 1.2 mmol). the mixture was stirred at ambient temperature overnight. The solution was diluted with 100 mL $CH_2Cl_2$, the organics separated, dried over anhydrous. $MgSO_4$, and the organics concentrated under reduced pressure. The crude product was purified via medium pressure liquid chromatography using a gradient solvent system of $CH_2Cl_2$, followed by 10:90 EtOAc/$CH_2Cl_2$, followed by a 30:70 EtOAc/$CH_2Cl_2$ solution to give 120 mg of the title compound as a white solid. TLC: Rf=0.13, 3:97 methanol/$CH_2Cl_2$ ($^1$H)-NMR ($CDCl_3$) consistent with structure.

B. Compound XXII (A=H, D'=(2-tetrahydrofuryl)methyl, E=4-acetamidophenyl, hydrochloride salt)

To a solution of the resultant compound of Example 133A (120 mg 0.22 mmol) in EtOAc (5 mL) was added 30% w/w HCl in EtOAc (2 mL). The mixture was stirred overnight at ambient temperature. The solution was concentrated under reduced pressure to give the title compound which was used without subsequent purification. TLC: Rf=0.50, 1:10:90 $NH_4OH$/methanol/$CH_2Cl_2$.

C. Compound 133

To a solution of the resultant compound of Example 133B in $CH_2Cl_2$ (5 mL) was added triethylamine (0.2 mL, 1.4 mmol) followed by the compound of Example 48A (73 mg, 0.32 mmol). The mixture was stirred at ambient temperature for 24 hours. The solution was concentrated under reduced pressure and the crude product purified via medium pressure column chromatography using a gradient solvent system of $CH_2Cl_2$, followed by 1:99 methanol/$CH_2Cl_2$, followed by 3:97 methanol/$CH_2Cl_2$ as the solvent system to give 87.8 mg. Rf=0.09, 3:97 methanol/$CH_2Cl_2$, HPLC: Rt=12.53 min, ($_1$H)-NMR ($CDCl_3$) consistent with structure.

EXAMPLE 134

A. Compound XXII (A=H, D'=isobutenyl, E=4-acetamidophenyl, hydrochloride salt)

To a solution of the resultant compound of Example 131 (40 mg 0.075 mmol) in EtOAc (5 mL) was added 30% w/w HCl in EtOAc (2 mL). The mixture was stirred overnight at ambient temperature. The solution was concentrated under reduced pressure to give the title compound, which was used without subsequent purification. TLC: Rf=0.38, 1:10:90 $NH_4OH$/methanol/$CH_2Cl_2$.

B. Compound 134

To a solution of the resultant compound of Example 134A in $CH_2Cl_2$ (5 mL) was added triethylamine (0.1 mL, 0.72 mmol), followed by the compound of Example 48A (26 mg, 0.11 mmol). The mixture was stirred at ambient temperature for 24 hours. The solution was concentrated under reduced pressure and the crude product purified via medium pressure column chromatography using a gradient solvent system of $CH_2Cl_2$, followed by 1:99 methanol/$CH_2Cl_2$, followed by 3:97 methanol/$CH_2Cl_2$ as the solvent system to give 10.1 mg of the title compound. Rf=0.11 (3:97 methanol/$CH_2Cl_2$), HPLC: Rt=12.86 min, ($_1$H)-NMR ($CDCl_3$) consistent with structure.

EXAMPLE 135

A. Compound XXI (A=H, D'=(isobutenyl, E=4-fluoropheynl, hydrochloride salt)

To a solution of the resultant compound of Example 130B (50 mg, 0.10 mmol) in EtOAc (5 mL) was added 30% w/w HCl in EtOAc (1 mL). The mixture was stirred overnight at ambient temperature. The solution was concentrated under reduced pressure to give the title compound which was used without subsequent purification. TLC: Rf=0.48, 1:10:90 $NH_4OH$/methanol/$CH_2Cl_2$.

B. Compound 135

To a solution of the resultant compound of Example 135A in $CH_2Cl_2$ (5 mL) was added triethylamine (0.1 mL, 0.72 mmol), followed by the compound of Example 48A (35 mg, 0.15 mmol). The mixture was stirred at ambient temperature for 24 hours. The solution was concentrated under reduced pressure and the crude product purified via medium pressure column chromatography using a gradient solvent system of $CH_2Cl_2$ followed by 20:80 EtOAc/$CH_2Cl_2$ as the solvent system to give 12 mg. Rf=0.34, 3:97 methanol/$CH_2Cl_2$, HPLC: Rt=14.64 min, ($^1$H)-NMR ($CDCl_3$) consistent with structure.

EXAMPLE 136

A. Compound XXI (A=tert-butoxycarbonyl, D'=2-furfuryl, A'=H)

To a solution compound XX (2.5 mmol) in ethanol (30 mL) was added furfurylamine (0.67 mL, 7.5 mmol) and the mixture was heated to 85° C. for 24 h. The solution was filtered and concentrated under reduced pressure to give 0.80 g of the title compound which was used without subsequent purification. TLC: Rf=0.38, 1:10:90 concentrated $NH_4OH$/methanol/$CH_2Cl_2$.

B. Compound XXII (A=tert-butoxycarbonyl, D'=2-furyl, E=4-fluorophenyl)

To a solution of the product of Example 136A (0.20 g, 0.60 mmol) in $CH_2Cl_2$ (6 mL) was added a saturated solution of sodium bicarbonate (3 mL), followed by addition of solid sodium bicarbonate (0.1 g, 1.2 mmol), then p-fluorobenzenesulfonyl chloride (0.32 g, 1.6 mmol). The mixture was stirred at ambient temperature for 24 h. The organics were extracted into 100 mL $CH_2Cl_2$, dried over anhydrous $MgSO_4$, concentrated under reduced pressure, then purified via medium pressure silica gel chromatography using a gradient system of $CH_2Cl_2$, followed by 1:99 methanol/$CH_2Cl_2$. The title compound was obtained as a white solid (86.1 mg). TLC: Rf=0.17, 3:97 methanol/$CH_2Cl_2$, HPLC: Rt=16.5 min; ($_1$H)-NMR ($CDCl_3$) consistent with structure.

C. Compound XXII (A=H, D'=2-furyl, E=4-fluorophenyl, hydrochloride salt)

To a solution of the resultant compound of Example 136B (16 mg, 0.031 mmol) in EtOAc (3 mL) was added 30% w/w HCl in EtOAc (1 mL). The mixture was stirred overnight at ambient temperature. The solution was concentrated under reduced pressure to give the title compound, which was used without subsequent purification. TLC: Rf=0.48, 1:10:90 $NH_4OH$/methanol/$CH_2Cl_2$.

D. Compound 136

To a solution of the resultant compound of Example 136C in $CH_2Cl_2$ (5 mL) was added triethylamine (0.1 mL, 0.72 mmol), followed by the resultant compound of Example 48A (11 mg, 0.05 mmol). The mixture was stirred at ambient temperature for 24 hours. The solution was concentrated under reduced pressure and the crude product purified via medium pressure column chromatography using a gradient solvent system of $CH_2Cl_2$ followed by 20:80 EtOAc/$CH_2Cl_2$ as the solvent system to give 4.9 mg. TLC: Rf=0.28, (3:97 methanol/$CH_2Cl_2$, HPLC: Rt=14.57 min, ($_1$H)-NMR ($CDCl_3$) consistent with structure.

EXAMPLE 137

A. Compound XXII (A=tert-butoxycarbonyl, D'=2-furyl, E=4-acetamidophenyl)

To a solution of the resultant compound of Example 136B (200 mg, 0.55 mmol) in $CH_2Cl_2$ (6 mL) was added 4-acetamidobenzenesulfonyl chloride (390 mg, 1.7 mmol) followed by saturated solution of sodium bicarbonate (3 mL) and solid sodium bicarbonate (0.1 g, 1.2 mmol). The mixture was stirred at ambient temperature overnight. The solution was diluted with 100 mL $CH_2Cl_2$, the organics separated, dried over anhydrous. $MgSO_4$, and the organics concentrated under reduced pressure. The crude product was purified via medium pressure liquid chromatography using a gradient solvent system of $CH_2Cl_2$, followed by 10:90 EtOAc/$CH_2Cl_2$, followed by a 30:70 EtOAc/$CH_2Cl_2$ solution to give 100 mg of the title compound as a white solid. TLC: Rf=0.19, 3:97 methanol/$CH_2Cl_2$, ($^1$H)-NMR ($CDCl_3$) consistent with structure.

B. Compound XXII (A=H, D'=2-furyl, E=4-acetamidophenyl, hydrochloride salt)

To a solution of the resultant compound of Example 137A (30 mg, 0.054 mmol) in EtOAc (3 mL) was added 30% w/w HCl in EtOAc (1 mL). The mixture was stirred overnight at ambient temperature. The solution was concentrated under reduced pressure to give the title compound which was used without subsequent purification. TLC: Rf=0.37 (1:10:90 $NH_4OH$/methanol/$CH_2Cl_2$).

C. Compound 137

To a solution of the resultant compound of Example 137a in $CH_2Cl_2$ (5 mL) was added triethylamine (0.1 mL, 0.72 mmol) followed by the compound of Example 48A (19 mg, 0.083 mmol). The mixture was stirred at ambient temperature for 24 hours. The solution was concentrated under reduced pressure and the crude product purified via medium pressure column chromatography using a gradient solvent system of $CH_2Cl_2$, followed by 1:99 methanol/$CH_2Cl_2$, followed by 3:97 methanol/$CH_2Cl_2$ as the solvent system to give 8.5 mg of the title compound. TLC: Rf=0.11 (3:97 methanol/$CH_2Cl_2$), HPLC: Rt=12.69 min; ($_1$H)-NMR ($CDCl_3$) consistent with structure.

EXAMPLE 138

Compound 138

A solution of 75 mg of the resultant compound of Example 51D and 45 mg of 3-chlorobenzenesulfonyl chloride were reacted in the manner described in Example 60. After workup and purification by preparative reversed-phase $C_{18}$ HPLC using a linear gradient of 35% to 100% $CH_3CN$/$H_2O$ with 0.1% TFA as eluant, 29.7 mg of the title compound was obtained. TLC: Rf=0.3, 4% MeOH/$CH_2Cl_2$, HPLC: Rt=15.83 min; ($^1$H)-NMR ($CDCl_3$) consistent with structure.

EXAMPLE 139

Compound 139

To a solution of 67.9 mg of the resultant compound of Example 116B in 1 mL of THF was added sequentially, 57 μL of diisopropylethylamine and a solution of 52.6 mg of the resultant compound of Example 109C in 1 mL THF. The mixture was stirred for 24 hours and concentrated in vacuo. The residue was purified by preparative thick layer silica gel chromatography using 7% methanol in $CH_2Cl_2$ eluent to yield 70.0 mg of the title compound. TLC: Rf=0.30, 5% methanol/$CH_2Cl_2$. HPLC: Rt=15.78 min; ($^1$H) NMR ($CDCl_3$) consistent with structure.

EXAMPLE 140

A. 3(S)-amino-2(syn)-hydroxy-4-phenyl-1-chlorobutane formate salt

To a slurry of 16.33 g of 10% palladium on carbon (25% by weight) in methanol and tetrahydrofuran (400 mL, 1:1) was added, under $N_2$, 65.35 g of 3(S)-N-(-benzyloxycarbonyl) -amino-1-chloro-2(syn)-hydroxy-4-phenylbutane (195.77 mmol) as a solution in methanol and tetrahydrofuran (1.2 L). To this slurry was added 540 mL of formic acid. After 15 h, the reaction mixture was filtered through diatomaceous earth and concentrated to dryness. The resultant oil was slurried in toluene and evaporated, then triturated sequentially with diethyl ether and $CH_2Cl_2$ to provide 47.64 g of product as a granular tan solid. TLC: Rf=0.17, 5% acetic acid/ethyl acetate.

B. 3(S)-N-(3(S)-tetrahydrofuryloxycarbonyl)-amino-1-chloro-2(syn)-hydroxy-4-phenylbutane To a solution of the resultant compound of Example 140A (1.97 g, 7.95 mmol) in $CH_2Cl_2$ (20 mL) was added a saturated solution of sodium bicarbonate (5 mL), followed by solid sodium bicarbonate (1.33 g, 17.9 mmol), and the resultant compound of Example 48A (2.0 g, 8.7 mmol). The mixture was stirred at ambient temperature overnight. The solution was diluted with 200 mL $CH_2Cl_2$, the organics separated, dried over anhydrous $MgSO_4$, and concentrated under reduced pressure. The residue was recrystallized from ethyl acetate/hexane to give 1.01 g of the title compound as a white solid. TLC: Rf=0.35, 3:97 methanol/$CH_2Cl_2$. ($^1$H)-NMR ($CDCl_3$) consistent with structure.

C. Compound XX (A=3(s)-tetrahydrofuryloxycarbonyl).

To a solution of the resultant compound of Example 140B (1.0 g, 3.2 mmol) in absolute ethanol (15 mL) was added solid KOH (0.21 g, 3.8 mmol). The mixture was stirred at ambient temperature for 1.0 h. The solution was filtered through a pad of Celite then concentrated under reduced pressure. The residue was taken up in ether (100 mL), washed with brine, dried over $MgSO_4$, the concentrated under reduced pressure to give 0.88 g of the title compound as a white solid. TLC: Rf=0.49 (3:97 methanol/$CH_2Cl_2$), ($^1$H)-NMR ($CDCl_3$) consistent with structure.

D. Compound XXI (A=(S)-3-tetrahydrofuryloxycarbonyl, D'=cyclopentylmethyl, A'=H)

The resultant compound of Example 140C (0.88 g, 3.2 mol) was added to the resultant compound of Example 114A (5.0 g, 50.4 mmol) and stirred for 24 h at ambient temperature. The solution was concentrated by distillation under reduced pressure. The residue was triturated with hexane and the solid collected by suction filtration and washed with hexane to give 0.93 g of the title compound. TLC: Rf=0.44, 1:10:90 concentrated $NH_4OH$/methanol/$CH_2Cl_2$; ($^1H$)-NMR ($CDCl_3$) consistent with structure.

E. Compound 140

To a solution of the resultant compound of Example 140D (0.93 g, 2.47 mmol) in $CH_2Cl_2$ (20 mL) was added a saturated solution of sodium bicarbonate (5 mL) followed by addition of solid sodium bicarbonate (0.42 g, 4.94 mmol) and 4-methoxybenzenesulfonyl chloride (0.61 g, 2.96 mmol). the mixture was stirred at ambient temperature for 4 hours. The solution was diluted with 200 mL $CH_2Cl_2$, the organics separated, dried over anhydrous $MgSO_4$, and the organics concentrated under reduced pressure. The crude product was purified via medium pressure liquid chromatography using $CH_2Cl_2$ followed by 1:99 methanol/$CH_2Cl_2$ solution as the eluent system to give 1.28 g of the title compound as a white solid. TLC: Rf=0.26, 3:97 methanol/$CH_2Cl_2$, HPLC: Rt=15.66 min, ($^1H$)-NMR ($CDCl_3$) consistent with structure.

EXAMPLE 141

A. Compound XXII (A=H, D'=cyclopentylmethyl, E=4-methoxyphenyl, hydrochloride salt)

A solution of 71.3 mg of the resultant compound of Example 166A in EtOAc (25 mL) at 0° C. was treated with anhydrous HCl gas for 10 min., and allowed to stand for 12 h while warming to ambient temperature, then concentrated under reduced pressure and the resulting white solid used without purification for subsequent reaction.

B. Compound 141

The resultant compound of Example 141A (0.134 mmol) was reacted with allyl chloroformate in the manner described in Example 87B. After concentration of the mixture in vacuo and workup, the residue was purified by thick layer silica gel chromatography using 5% MeOH/$CH_2Cl_2$ as eluant followed by preparative reversed-phase $C_{18}$ HPLC using a linear gradient of 35% to 100% $CH_3CN/H_2O$ with 0.1% TFA as eluant to obtain 21.6 mg of the title compound. TLC: Rf=0.45, 5% MeOH/$CH_2Cl_2$. HPLC: Rt=16.96 min.

EXAMPLE 142

Compound 142

To a solution of 4.0 g of the resultant compound of Example 141A in 45 mL of THF was added sequentially, 1.96 mL of diisopropylethylamine and a solution of 2.68 g of the resultant compound of Example 82A in 45 mL THF. The mixture was stirred for 24 hours and concentrated in vacuo. The residue was taken up in $CH_2Cl_2$, washed with saturated sodium bicarbonate and brine, dried over magnesium sulfate, filtered and concentrated in vacuo. The residue was purified by low pressure silica gel column chromatography using 20% to 40% EtOAc in hexane eluent to yield 3.69 g of the title compound. TLC: Rf=0.41, 50% EtOAc/$CH_2Cl_2$.

EXAMPLE 143

Compound 143

A solution of 3.69 g of the resultant compound of Example 142 in 100 mL of ethyl ether was treated with anhydrous HCl gas for 10 min. The reaction mixture was sparged with nitrogen then filtered. The solid was taken up in methanol and concentrated to yield 3.71 g of the title compound. TLC: Rf=0.62, 90/10/1 $CH_2Cl_2$/MeOH/AcOH, HPLC: Rt=13.87 min. ($^1H$)-NMR ($CDCl_3$) consistent with structure.

EXAMPLE 145

A. Compound XXII (A=tert-butoxycarbonyl, D'=isobutyl, E=2-(5-isoxazoy-3-yl)-thiophene)

To a solution of 342.5 mg (1.02 mmol) of the resultant compound of Example 39A in $CH_2Cl_2$ (8 mL) was added aqueous sodium bicarbonate (2 mL), solid sodium bicarbonate 257 mg (3.1 mmol), and 5-(isoxazol-3-yl) thiophenesulfonyl chloride 254.2 mg, (1.02 mmol). After 14 h, the resulting mixture was diluted with $CH_2Cl_2$, washed with saturated brine, dried over magnesium sulfate, filtered and concentrated in vacuo. The residue was purified by flash chromatography using 5% to 25% EtOAc/$CH_2Cl_2$ eluent and recrystallized from ether $CH_2Cl_2$ to provide 228.6 mg of the title product. ($^1H$)-NMR ($CDCl_3$) consistent with structure.

B. Compound XXII (A-H, D'=isobutyl, E=2-(5-isoxazoy-3-ly)-thiopene, hydrochloride salt)

A solution of 228.6 mg (0.416 mmol) of the resultant compound of Example 145A in EtOAc (15 mL) at −20° C. was treated with anhydrous HCl gas for 10 min. The ice bath was removed and after an additional 15 min, the reaction mixture was sparged with nitrogen then concentrated in vacuo to provide 223.6 mg of title product as the HCl salt. TLC: Rf=0.48, 10% methanol/$CH_2Cl_2$.

C. Compound 145

A solution of 78.5 mg of the resultant compound of Example 145B (0.162 mmol) in $CH_2Cl_2$ (3 mL) was treated sequentially at ambient temperature under an atmosphere of nitrogen with 0.07 mL (0.408 mmol) diisopropylethylamine and 55.6 mg (0.243 mmol) of the resultant compound of Example 48A. The mixture was stirred 16 h and then concentrated in vacuo. The residue was taken up in $CH_2Cl_2$ and washed with saturated brine, dried over magnesium sulfate, filtered, and concentrated in vacuo. The residue was purified by preparative HPLC to yield 48.7 mg of the title product. TLC: Rf=0.36, 25% EtAOc/$CH_2Cl_2$. HPLC: Rt=15.2 min; ($^1H$)-NMR ($CDCl_3$) consistent with structure.

EXAMPLE 146

A. Compound XXI (P=tert-butoxycarbonyl, D'=cyclopentylmethyl, E=4-acetamidophenyl)

To a solution of the resultant compound of Example 114B (300 mg, 0.83 mmol) in $CH_2Cl_2$ (15 mL) was added 4-acetamidobenzenesulfonyl chloride (580 mg, 2.48 mmol) followed by the addition of a saturated solution of sodium bicarbonate (4 mL) and solid sodium bicarbonate (0.14 g, 1.67 mmol). The mixture was stirred at ambient temperature overnight. The solution was diluted with 150 mL $CH_2Cl_2$, the organics separated, dried over anhydrous. $MgSO_4$, and the organics concentrated under reduced pressure. The crude product was purified via medium pressure liquid chromatography using a gradient solvent system of $CH_2Cl_2$, followed by 5:95 EtOAc/$CH_2Cl_2$, followed by 10:90 EtOAc/$CH_2Cl_2$ solution to give 310 mg of the title compound as a white solid. TLC: Rf=0.10, 3:97 methanol/$CH_2Cl_2$, HPLC: Rt=15.96 min, ($^1H$)-NMR ($CDCl_3$) consistent with structure.

B. Compound XXII (P=H, D'=cyclopentylmethyl, E=4-acetamidophenyl, hydrochloride salt)

To a solution of the resultant compound of Example 146A (210 mg, 0.38 mmol) was added 30% w/w HCl in EtOAc (15 mL). The mixture was stirred for 1 hour at ambient temperature. The solution was concentrated under reduced pressure to give 180 mg of the title compound which was used without subsequent purification. TLC: Rf=0.14, 1:10:90 $NH_4OH$/methanol/$CH_2Cl_2$.

C. Compound XXII (P=allyloxycarbonyl, D'=cyclopentylmethyl, E=4-acetamidophenyl)

To a solution of the resultant compound of Example 146B (100 mg, 0.20 mmol) in $CH_2Cl_2$ (10 mL) was added triethylamine (0.1 mL, 0.72 mmol), followed by allylchloroformate (0.04 mL, 0.3 mmol). The mixture was stirred at ambient temperature for 24 hours. The solution was diluted with 150 mL $CH_2Cl_2$, washed with water, dried over anhydrous $MgSO_4$, and the organics concentrated under reduced pressure. The crude product was purified via medium pressure column chromatography using a gradient solvent system of $CH_2Cl_2$, followed by 1:99 methanol/$CH_2Cl_2$, followed by 3:97 methanol/$CH_2Cl_2$ as the solvent system to give 103 mg. Rf=0.22, 3:97 methanol/$CH_2Cl_2$, HPLC: Rt=15.29 min, ($^1$H)-NMR ($CDCl_3$) consistent with structure.

EXAMPLE 147

Compound 147

To a solution of the resultant compound of Example 146B (80 mg, 0.16 mmol) in $CH_2Cl_2$(5 mL) was added triethylamine (0.07 mL, 0.48 mmol), followed by slow addition over 3 hours of the resultant compound of Example 82A (53 mg, 0.19 mmol) as a solution in $CH_2Cl_2$ (3 mL). The mixture was stirred at ambient temperature for 24 hours. The solution was diluted with 100 mL $CH_2Cl_2$ washed with water, dried over anhydrous $MgSO_4$, and the organics concentrated under reduced pressure. The crude product was purified via medium pressure column chromatography using a gradient solvent system of $CH_2Cl_2$, followed by 1:99 methanol/$CH_2Cl_2$, followed by 2:98 methanol/$CH_2Cl_2$ as the solvent system to give 71.7 mg of the title compound. Rf=0.06, 3:97 methanol/$CH_2Cl_2$, HPLC: Rt=12.61 min, ($^1$H)-NMR ($CDCl_3$) consistent with structure.

EXAMPLE 148

A. Compound XXII (A=tert-butoxycarbonyl, D'=cyclopentylmethyl, E=phenyl)

A solution of 297 mg of the resultant compound of Example 114B in 4:1 $CH_2Cl_2$/saturated aqueous $NaHCO_3$ was treated sequentially, at ambient temperature under an atmosphere of nitrogen, with 217 mg of benzenesulfonyl chloride and 103 mg of sodium bicarbonate. The mixture was stirred for 6 h, diluted with $CH_2Cl_2$, washed with saturated NaCl then dried over $MgSO_4$, filtered, and concentrated in vacuo to yield 426 mg of the title product as a white solid. TLC: Rf=0.32, 5% diethyl ether/$CH_2Cl_2$. ($^1$H) -NMR ($CDCl_3$) consistent with structure.

B. Compound XXII (A=H, D'=cyclopentylmethyl, E=phenyl, hydrochloride salt)

A solution of 400 mg of the resultant compound of Example 148A in ethyl acetate was treated at −20° C. with HCl gas for 20 min, during which time the temperature was allowed to warm to 20° C. Nitrogen was then bubbled through the mixture for 15 min and solvent removed in vacuo to yield 349 mg of white solid which was used directly for the ensuing reaction.

C. Compound 148

A solution of 40 mg of the resultant compound of Example 148B in $CH_2Cl_2$ was added, at ambient temperature under an atmosphere of nitrogen, to a solution of 31 mg of the resultant compound of Example 48A and 35 mg N,N-diisopropylethylamine in $CH_2Cl_2$. The mixture was stirred for 14 h, diluted with $CH_2Cl_2$, washed with saturated $NaHCO_3$ and saturated NaCl, then dried over $MgSO_4$, filtered, and concentrated in vacuo. The residue was purified by low pressure silica gel chromatography using 20% diethyl ether/$CH_2Cl_2$ as eluent to provide 45 mg of the title product as a white solid. TLC: Rf=0.46, 20% diethyl ether/$CH_2Cl_2$. HPLC: Rt=15.78 min. ($^1$H)-NMR ($CDCl_3$) consistent with structure.

EXAMPLE 149

A. Compound XXII (A=tert-butoxycarbonyl, D'=cyclopentymethyl, E=3-pyridyl)

To a solution of 153 mg (0.422 mmol) of the resultant compound of Example 114B in $CH_2Cl_2$ (4 mL) was added aqueous sodium bicarbonate (1 mL), solid sodium bicarbonate 141.7 mg (1.69 mmol), and the resultant compound of Example 144A 156.1 mg, (0.879 mmol). After 14 h, the resulting mixture was diluted with $CH_2Cl_2$, washed with saturated brine, dried over magnesium sulfate, filtered and concentrated in vacuo. The residue was purified by flash chromatography using 20% to 40% EtOAc/$CH_2Cl_2$ eluent to provide 64.7 mg of the title product. TLC; Rf=0.24, 20% EtOAc/$CH_2Cl_2$.

B. Compound XXII (A=tert-butoxycarbonyl, D'=cyclopentylmethyl, E=3-pyridyl, hydrochloride salt)

A solution of 273.1 mg (0.572 mmol) of the resultant compound of Example 149A in EtOAc (15 mL) at −20° C. was treated with anhydrous HCl gas for 10 min. The ice bath was removed and after an additional 15 min., the reaction mixture was sparged with nitrogen then concentrated in vacuo. To a solution of the resulting residue in $CH_2Cl_2$ (3 mL) was added, sequentially at ambient temperature under an atmosphere of nitrogen, with 0.076 mL (0.437 mmol) diisopropylethylamine and 34.3 mg (0.150 mmol) of the resultant compound of Example 48A. The mixture was stirred for 16 h and then concentrated in vacuo. The residue was taken up in $CH_2Cl_2$ and washed with saturated brine, dried over magnesium sulfate, filtered, and concentrated in vacuo. The residue was purified by low pressure silica gel column chromatography using a gradient 20% to 50% EtOAc in $CH_2Cl_2$ eluent to yield 11.3 mg of the title product. TLC; Rf=0.15 40% EtOAc/$CH_2Cl_2$. HPLC: Rt=13.7 min; ($^1$H) NMR ($CDCl_3$) consistent with structure.

EXAMPLE 150

A. 1-Piperidinesulfonyl chloride

A solution of 4 g of sulfuryl chloride in acetronitrile was treated dropwise with 861 mg of piperidine at ambient temperature under an atmosphere of nitrogen. After complete addition, the mixture was refluxed for 18 h, cooled to room temperature and concentrated in vacuo to yield the title product as a red oil. TLC: Rf=0.86, $CH_2Cl_2$. ($^1$H)-NMR ($CDCl_3$) consistent with structure.

B. Compound XXII (A=tert-butoxycarbonyl, D'=isobutyl, E=piperidinyl)

A solution of 73 mg of the resultant compound of Example 39A in $CH_2Cl_2$ was treated sequentially, at ambient temperature under an atmosphere of nitrogen, with 121 mg of the resultant compound of Example 150A and 84 mg of N,N-diisopropylethylamine. The mixture was stirred for 14 h, diluted with $CH_2Cl_2$, washed with saturated NaCl then dried over $MgSO_4$, filtered, and concentrated in vacuo. The residue was purified by low pressure silica gel chromatography using 5% diethyl ether/$CH_2Cl_2$ as eluent to provide 70 mg of the title product as a white solid. TLC: Rf=0.21 (5% diethyl ether in $CH_2Cl_2$). HPLC: Rt=17.40 min. ($^1$H)-NMR ($CDCl_3$) consistent with structure.

C. Compound XXII (A=H, D'=isobutyl, E=piperidinyl, hydrochloride salt)

A solution of 70 mg of the resultant compound of Example 150B in ethyl acetate was treated at −20° C. with HCl gas for 20 min during which time the temperature was allowed to warm to 20° C. Nitrogen was then bubbled through the mixture for 15 min and solvent removed in vacuo to yield a viscous oil which was used directly for the ensuing reaction.

D. Compound 150

A solution of the resultant compound of Example 150C in $CH_2Cl_2$ was added, at ambient temperature under an atmosphere of nitrogen, to a solution of 50 mg of the resultant compound of Example 48A and 56 mg N,N-diisopropylethylamine in $CH_2Cl_2$. the mixture was stirred for 14 h, diluted with $CH_2Cl_2$, washed with saturated $NaHCO_3$ and saturated NaCl, then dried over $MgSO_4$, filtered, and concentrated in vacuo. The residue was purified by low pressure silica gel chromatography using 20% diethyl ether/$CH_2Cl_2$ as eluent to provide 16 mg of the title product as a white solid. TLC: Rf=0.45, (0% diethyl ether/$CH_2Cl_2$. HPLC: Rt=15.00 min. ($^1$H)-NMR ($CDCl_3$) consistent with structure.

EXAMPLE 151

A. Compound XXII (A tert butoxycarbonyl, D'=cyclopentylmethyl, E=4-trifluormethoxyphenyl)

A solution of 71 mg of the resultant compound of Example 114B in 4:1 $CH_2Cl_2$/saturated aqueous $NaHCO_3$ was treated sequentially, at ambient temperature under an atmosphere of nitrogen, with 76 mg of 4-trifluoromethoxybenzensulfonyl chloride and 25 mg of sodium bicarbonate. The mixture was stirred, 14 h, diluted with $CH_2Cl_2$, washed with saturated NaCl then dried over $MgSO_4$, filtered, and concentrated in vacuo. The residue was purified by low pressure silica gel chromatography using 5% diethyl ether/$CH_2Cl_2$ as eluent to provide 92 mg of the title product as a white solid. TLC: Rf=0.34, 5% diethyl ether/$CH_2Cl_2$. ($^1$H)-NMR ($CDCl_3$) consistent with structure.

B. Compound XXII (A=H, D'=cyclopentylmethyl, E=4-trifluormethoxyphenyl, hydrochloride salt)

A solution of 92 mg of the resultant compound of Example 151A in ethyl acetate was treated at −20° C. with HCl gas for 20 min, during which time the temperature was allowed to warm to 20° C. Nitrogen was then bubbled through the mixture for 15 min and solvent removed in vacuo to yield 83 mg of white solid which was used directly for the ensuing reaction.

C. Compound 151

A solution of 22 mg of the resultant compound of Example 151B in $CH_2Cl_2$ was added, at ambient temperature under an atmosphere of nitrogen, to a solution of 15 mg of the resultant compound of Example 48A and 16 mg N,N-diisopropylethylamine in $CH_2Cl_2$. The mixture was stirred for 60 h, diluted with $CH_2Cl_2$, washed with saturated $NaHCO_3$ and saturated NaCl, then dried over $MgSO_4$, filtered, and concentrated in vacuo. The residue was purified by low pressure silica gel chromatography using 20% diethyl ether/$CH_2Cl_2$ as eluent to provide 23 mg of the title product as a white solid. TLC: Rf=0.44, 20% diethyl ether/$CH_2Cl_2$. HPLC: Rt=16.99 min. ($^1$H)-NMR ($CDCl_3$) consistent with structure.

EXAMPLE 152

A. Compound XXII (A=tert-butoxycarbonyl, D'=isobutyl, E=4-trifluormethoxyphenyl)

A solution of 97 mg of the resultant compound of Example 39A in 4:1 $CH_2Cl_2$/saturated aqueous $NaHCO_3$ was treated sequentially, at ambient temperature under an atmosphere of nitrogen, with 113 mg of 4-trifluoromethoxybenzenesulfonyl chloride and 36 mg of sodium bicarbonate. The mixture was stirred for 14 h, diluted with $CH_2Cl_2$, washed with saturated NaCl then dried over $MgSO_4$, filtered, and concentrated in vacuo. The residue was purified by low pressure silica gel chromatography using 5% diethyl ether/$CH_2Cl_2$ as eluent to provide 120 mg of the title product as a white solid. TLC: Rf=0.34, 5% diethyl ether/$CH_2Cl_2$. HPLC: Rt=18.54 min. ($^1$H)-NMR ($CDCl_3$) consistent with structure.

B. Compound XXII (A=H, D'=isobutyl, E=4-trifluormethoxyphenyl, hydrochloride salt)

A solution of 100 mg of the resultant compound of Example 152A in ethyl acetate was treated at −20° C. with HCl gas for 20 min, during which time the temperature was allowed to warm to 20° C. Nitrogen was then bubbled through the mixture for 15 min and solvent removed in vacuo to yield 89 mg of white solid which was used directly for ensuing reaction.

C. Compound 152

A solution of 41 mg of the resultant compound of Example 152B in $CH_2Cl_2$ was added, at ambient temperature under the atmosphere of nigrogen, to a solution of 28 mg of the resultant compound of Example 48A and 32 mg N,N-diisopropylethylamine in $CH_2Cl_2$. The mixture was stirred 14 h, diluted with $CH_2Cl_2$, washed with saturated $NaHCO_3$ and saturated NaCl, then dried over $MgSO_4$, filtered, and concentrated in vacuo. The residue was purified by low pressure silica gel chromathography using 5% diethyl ether/$CH_2Cl_2$ as eluent to provide 30 mg of the title product as white solid. TLC: Rf–0.08 (5% diethyl ether/$CH_2Cl_2$). HPLC: Rt=16.52 min. ($^1$H)-NMR ($CDCl_3$) consistent with structure.

EXAMPLE 153

A. Compound XXII (A=tert-butoxycarbonyl, D'=isobutyl, E=4-methoxyphenyl)

To a solution of the resultant compound of Example 39A (600 mg, 1.77 mmol) in $CH_2Cl_2$ (10 mL) was added 4-methoxybenzenesulfonyl chloride (0.55 g, 2.66 mmol) followed by the addition of a saturated solution of sodium bicarbonate (3 mL) and 0.30 g of solid sodium bicarbonate. The mixture was stirred at ambient temperature overnight. The solution was diluted with 200 mL $CH_2Cl_2$, the organics were separated, dried over anhydrous $MgSO_4$, and the organics concentrated under reduced pressure. The crude product was purified via medium pressure liquid chromatography using a gradient solvent system of $CH_2Cl_2$ followed by 5:95 ether/$CH_2Cl_2$ solution to give 630 mg of the title compound as a white solid. TLC: Rf=0.48, 3:97 methanol/$CH_2Cl_2$. ($^1$H)-NMR ($CDCl_3$) consistent with structure.

B. Compound XXII (A=H, D'=isobutyl, E=4-methoxyphenyl, hydrochloride salt)

To a solution of the resultant compound of Example 153A (0.63 g, 1.24 mmol) in EtAc (5 mL) was added 30% w/w HCl in EtOAc (5 mL.) The mixture was stirred for 6 hours ambient temperature. The solution was concentrated under reduced pressure to give 0.59 g of a white solid which was used directly for subsequent reaction. TLC Rf=0.12, 3:97 methanol/$CH_2Cl_2$.

C. Compound XXII (A=(3-pyridyl)-methyloxycarbonyl, D'=isobutyl, E=4-methoxyphenyl)

To a solution of the resultant compound of Example 153B (100 mg, 0.23 mmol) in $CH_2Cl_2$ (5 mL) was added triethylamine (0.1 mL, 0.72 mmol) followed by slow addition over 3 hours of the resultant compound of Example 82A (75 mg, 0.27 mmol) as a solution in $CH_2Cl_2$ (5 mL). The mixture was stirred at ambient temperature for 24 hours. The organics was concentrated under reduced pressure and the crude product was purified via medium pressure column chromatography using a gradient solvent system of $CH_2Cl_2$, followed by 1:99 methanol/$CH_2Cl_2$, followed by 3:97 methanol/$CH_2Cl_2$ as the solvent system to give 49.3 mg of the title compound. Rf=0.33, 3:97 methanol/$CH_2Cl_2$. HPLC: Rt=13.18 min, ($^1$H)-NMR ($CDCl_3$) consistent with structure.

EXAMPLE 154

Compound 154

To a solution of the resultant compound of Example 153B (100 mg, 0.20 mmol) in $CH_2Cl_2$ (5 mL) was added triethylamine (0.25 mL, 1.8 mmol) followed by allylchloroformate (0.1 mL, 0.94 mmol). The mixture was stirred at ambient temperature for 24 hours. The solution was concentrated under reduced pressure and the crude product purified via medium pressure column chromatography using a gradient solvent system of $CH_2Cl_2$, followed by 1:99 methanol/$CH_2Cl_2$ as the solvent system to give 94 mg of the title compound. Rf=0.71, 3:97 methanol/$CH_2Cl_2$. HPLC: Rt=16.12 min, ($^1$H)-NMR ($CDCl_3$) consistent with structure.

EXAMPLE 155

A. N-hydroxysuccinimidyl-1-methoxypropane-3-carbonate

A solution of 355 mg of 2-methylene-1,3-propanediol in acetonitrile (30 mL) was added sequentially, at ambient temperature, 65 mg of sodium hydride and 0.25 mL iodomethane. The mixture was stirred for 12 h and concentrated in vacuo. The residue was then taken up in 15 mL of acetonitrile and treated sequentially, at ambient temperature under an atmosphere of nitrogen, with 1.3 g of N,N-disuccinimidyl carbonate and 1.6 mL of triethylamine. After stirring for 14 h, the reaction mixture was concentrated in vacuo and the residue was diluted $CH_2Cl_2$, washed with saturated sodium bicarbonate solution and saturated brine, dried over magnesium sulfate, filtered and concentrated in vacuo. The residue was purified by silica gel chromatography with EtOAc as eluant to give 95 mg of the title compound. ($^1$H)-NMR ($CDCl_3$) consistent with structure.

B. Compound 155

A solution of 0.056 mmol of the resultant compound of Example 40A was reacted with the resultant compound of Example 155A in the manner described in Example 132. After concentration of the mixture in vacuo and workup, the residue was purified by thick layer silica gel chromatography using 7% MeOH/$CH_2Cl_2$ as eluant followed by preparative reversed-phase $C_{18}$ HPLC using a linear gradient of 35% to 100% $CH_3CN/H_2O$ with 0.1% TFA as eluant to obtain 3.7 mg of the title compound. TLC: Rf=0.45, 7% MeOH/$CH_2Cl_2$. HPLC: Rt=13.78 min.

EXAMPLE 156

A. 1-acetylindoline-5-sulfonyl chloride

A 1.02 g portion of 1-acetylindoline was treated with 2 mL of chlorosulfonic acid at 0° C. The mixture was heated at 60° C. for 2 h, then treated with crushed ice, filtered and dried to give 1.3 g of the title compound which was used directly for subsequent reaction. TLC: Rf=0.18, 50% EtOAc/hexane. ($^1$H)-NMR ($CDCl_3$) consistent with structure.

B. Compound XXII (P=tert-butoxycarbonyl, D'=cyclopentylmethyl, E=5-(N-acetyl)-indoline)

To a solution of 60 mg of the resultant compound of Example 114B in 15 mL of $CH_2Cl_2$ was added (5 mL) saturated aqueous sodium bicarbonate solution, 50.0 mg sodium bicarbonate, and 60 mg of the resultant compound of Example 156A. After 4 h, the resulting mixture was diluted with $CH_2Cl_2$, washed with saturated brine, dried over magnesium sulfate and filtered. The mixture was then concentrated in vacuo to give the desired product which was used directly for subsequent reastion. ($^1$H)-NMR ($CDCl_3$) consistent with structure.

C. Compound 156

A solution of 37 mg of the resultant compound of Example 156B in EtOAc (15 mL) at 0° C. was treated with anhydrous hydrogen chloride gas for 10 min., and allowed to stand for 12 h while warming to ambient temperature. This crude material was then reacted with allyl chloroformate in the manner described in Example 87B. After concentration of the mixture in vacuo and workup, the residue was purified by thick layer silica gel chromatography using 70% MeOH/$CH_2Cl_2$ as eluant followed by preparative reversed-phase $C_{18}$ HPLC using a linear gradient of 35% to 100% $CH_3CN/H_2O$ with 0.1% TFA as eluant to obtain 10.5 mg of the title compound. TLC: Rf=0.75, 10% MeOH/$CH_2Cl_2$. HPLC: Rt=15.78 min; ($^1$H)-NMR ($CDCL_3$) consistent with structure.

EXAMPLE 157

Compound 157

A solution of 37 mg of the resultant compound of Example 156B in EtOAc (15 mL) at 0° C. was treated with anhydrous hydrogen chloride gas for 10 min., and allowed to stand for 12 h while warming to ambient temperature. This crude material was then reacted with the resultant compound of Example 48A in the manner described in Example 88. After concentration of the mixture in vacuo, the residue was purified by preparative reversed-phase $C_{18}$ HPLC using a linear gradient of 35 to 100% $CH_3CN/H_2O$ with 0.1% TFA as eluant to obtain 17.9 mg of the title compound. TLC: Rf=0.6, 10% MeOH/$CH_2Cl_2$. HPLC: Rt=14.68 min; ($^1$H)-NMR ($CDCL_3$) consistent with structure.

EXAMPLE 158

A. Compound XXII (A=tert-butoxycarbonyl, D'=cyclohexylmethyl, E=H)

To a solution of compound XX (A=Boc) (5.0 mmol) in ethanol (20 mL) was added cyclohexylmethylamine (3.25 mL, 2.83 mmol) and the mixture was stirred for 3 hours at ambient temperature. The solution was filtered and concentrated under reduced pressure to give 1.49 g of a white solid which was used directly for subsequent reaction. TLC: Rf=0.14, 3:97 methanol/$CH_2Cl_2$. ($^1$H)-NMR ($CDCl_3$) consistent with structure.

B. Compound XXII (A=tert-butoxycarbonyl, D'=cyclohexylmethyl, E=4-methoxyphenyl)

To a solution of the resultant compound of Example 158A (400 mg, 1.06 mmol) in $CH_2Cl_2$ (10 mL) was added 4-methoxybenzenesulfonyl chloride (0.66 g, 3.1 mmol) followed by addition of a saturated solution of sodium bicarbonate (3 mL) and 0.18 g of solid sodium bicarbonate. The mixture was stirred at ambient temperature overnight. The solution was diluted with 200 mL $CH_2Cl_2$, the organics separated, dried over anhydrous $MgSO_4$, and the organics concentrated under reduced pressure. The crude product was purified via medium pressure liquid chromatography using $CH_2Cl_2$, followed by 1:99 methanol/$CH_2Cl_2$ as the solvent system to give 340 mg of the title compound as a white solid. TLC: Rf=0.39, 3:97 methanol/$CH_2Cl_2$, ($^1$H)-NMR ($CDCL_3$) consistent with structure.

C. Compound XXI (A=H, D'=cyclohexylmethyl, E=4-methoxyphenyl, hydrochloride salt)

To a solution of the resultant compound of Example 158B (0.34 g, 0.62 mmol) in EtOAc (10 mL) was added 30% w/w HCl in EtOAc (5 mL). The mixture was stirred for 3 hours at ambient temperature. The solution was concentrated under reduced pressure to give 0.3 g of a white solid which was used directly for subsequent reaction. TLC: Rf=0.12, 3:97 methanol/$CH_2Cl_2$.

D. Compound 158

To a solution of the resultant compound of Example 158C (100 mg, 0.21 mmol) in $CH_2Cl_2$ (8 mL) was added triethylamine (0.2 mL, 1.44 mmol) followed by the resultant compound of Example 48A (71 mg, 0.31 mmol). The mixture was stirred at ambient temperature for 6 hours. The solution was diluted with $CH_2Cl_2$, (200 mL) washed with a saturated solution of sodium bicarbonate (30 mL), the organics separated, dried over anhydrous $MgSO_4$ and concentrated under reduced pressure and the crude product purified via medium pressure column chromatography using a gradient solvent system of $CH_2Cl_2$ followed by 10:90 EtOAc/$CH_2Cl_2$ as the solvent system to give 84.9 mg of the title compound. TLC: Rf=0.48, 3:97 methanol/$CH_2Cl_2$, HPLC: Rt=16.35 min; ($^1$H)-NMR ($CDCl_3$) consistent with structure.

EXAMPLE 159

A. Compound XXII (A=tert-butoxycarbonyl, D'=cyclohexylmethyl, E=4-fluorophenyl)

To a solution of the resultant compound of Example 158A (400 mg, 1.06 mmol) in $CH_2Cl_2$ (10 mL) was added 4-fluorobenzenesulfonyl chloride (0.62 g, 3.2 mmol) followed by addition of a saturated solution of sodium bicarbonate (3 mL) and 0.18 g of solid sodium bicarbonate. The mixture was stirred at ambient temperature overnight. The solution was diluted with 200 mL $CH_2Cl_2$, the organics separated, dried over anhydrous $MgSO_4$, and the organics concentrated under reduced pressure. The crude product was purified via medium pressure liquid chromatography using $CH_2Cl_2$ followed by 1:99 methanol/$CH_2Cl_2$ solution as the solvent system to give 280 mg of a white solid. TLC: Rf=0.47, 3:97 methanol/$CH_2Cl_2$, ($^1$H)-NMR ($CDCl_3$) consistent with structure.

B. Compound XXII (A=H, D'=cyclohexylmethyl, E=4-fluorophenyl, hydrochloride salt)

To a solution of the resultant compound of Example 159A (0.28 g, 0.52 mmol) was added 30% w/w HCl in EtOAc (10 mL). The mixture was stirred for 3 hours at ambient temperature. The solution was concentrated under reduced pressure to give 0.23 g of a white solid which was used directly for subsequent reaction. TLC: Rf=0.13, (3:97 methanol/$CH_2Cl_2$, ($^1$H)-NMR (CDCL$_3$) consistent with structure.

C. Compound 159

To a solution of the resultant compound of Example 159C (100 mg, 0.21 mmol) in $CH_2Cl_2$ (8 mL) was added triethylamine (0.2 mL, 1.44 mmol) followed by the resultant compound of Example 48A (73 mg, 0.32 mmol). The mixture was stirred at ambient temperature for 6 hours. The solution was diluted with $CH_2Cl_2$, (200 mL) washed with saturated solution of sodium bicarbonate (30 mL), dried over anhydrous $MgSO_4$, the organics concentrated under reduced pressure and the crude product purified via medium pressure column chromatography using a gradient solvent system of $CH_2Cl_2$, followed by 10:90 EtOAc/$CH_2Cl_2$ as the solvent system to give 54 mg of the title compound. TLC: Rf=0.46, 3:97 methanol/$CH_2Cl_2$, HPLC: Rt=16.48 min; ($^1$H)-NMR (CDCL$_3$) consistent with structure.

EXAMPLE 160

A. Compound XXII (A=tert-butoxycarbonyl, D'=cyclohexylmethyl, E=4-acetamidophenyl)

To a solution of the resultant compound of Example 158A (400 mg, 1.06 mmol) in $CH_2Cl_2$ (10 mL) was added 4-acetamidobenzenesulfonyl chloride (0.75 g, 3.2 mmol) followed by addition of a saturated solution of sodium bicarbonate (3 mL) and 0.18 g of solid sodium bicarbonate. The mixture was stirred at ambient temperature overnight. The solution was diluted with 200 mL $CH_2Cl_2$, the organics separated, dried over anhydrous $MgSO_4$, and the organics concentrated under reduced pressure. The crude product was purified via medium pressure liquid chromatography using $CH_2Cl_2$, followed by 1:99 methanol/$CH_2Cl_2$ and 2:98 methanol/$CH_2Cl_2$ as the solvent system to give 290 mg of the title compound as a white solid. TLC: Rf=0.14, 3:97 methanol/$CH_2Cl_2$, ($^1$H)-NMR ($CDCl_3$) consistent with structure.

B. Compound XXII (A=H, D'=cyclohexylmethyl, E=4-acetamidophenyl, hydrochloride salt)

To the resultant compound of Example 160A (0.29 g, 0.51 mmol) was added 30% w/w HCl in EtOAc (10 mL). The mixture was stirred for 3 hours at ambient temperature. The solution was concentrated under reduced pressure to give 0.28 g of a white solid which was used directly for subsequent reaction. TLC: Rf=0.10, 3:97 methanol/$CH_2Cl_2$.

C. Compound 160

To a solution of the resultant compound of Example 160B (100 mg, 0.20 mmol) in $CH_2Cl_2$ (8 mL) was added triethylamine (0.2 mL, 1.44 mmol) followed by the resultant compound of Example 48A (67 mg, 0.30 mmol). The mixture was stirred at ambient temperature for 6 hours. The solution was diluted with $CH_2Cl_2$, (200 mL) washed with saturated solution of sodium bicarbonate (30 mL), dried over anhydrous $MgSO_4$, the organics concentrated under reduced pressure and the crude product purified via medium pressure column chromatography using a gradient solvent system of $CH_2Cl_2$, followed by 10:90 EtOAc/$CH_2Cl_2$, followed by 20:80 EtOAc/$CH_2Cl_2$ as the solvent system to give 56.8 mg of a white solid. TLC: Rf=0.17, 3:97 methanol/$CH_2Cl_2$, HPLC: Rt=14.65 min; ($^1$H)-NMR ($CDCl_3$) consistent with structure.

EXAMPLE 161

A. 4-Morpholinesulfonyl chloride

A solution of 4.6 g of sulfuryl chloride in acetonitrile was treated dropwise with 996 mg of morpholine at ambient temperature under an atmosphere of nitrogen. After complete addition, the mixture was refluxed for 16 h, cooled to room temperature, and concentrated in vacuo to yield the title product as a red oil. TLC: Rf= 0.65 $CH_2Cl_2$. ($^1$H)-NMR ($CDCl_3$) consistent with structure.

B. Compound XXII (A-tert-butoxycarbonyl, D'=isobutyl, E=morpholinyl)

A solution of 98 mg of the resultant compound of Example 39A in 4:1 $CH_2Cl_2$/saturated aqueous $NaHCO_3$ was treated sequentially, at ambient temperature under an atmosphere of nitrogen, with 270 mg of the resultant compound of Example 161A and 122 mg of sodium bicarbonate. The mixture was stirred for 14 h, diluted with $CH_2Cl_2$, dried over $MgSO_4$, filtered, and concentrated in vacuo. The residue was purified by low pressure silica gel chromatography using $CH_2Cl_2$ as eluent followed by preparative HPLC to provide 22 mg of the title product as an oily solid. TLC: Rf=0.46, 20% diethyl ether/$CH_2Cl_2$. HPLC: Rt=15.50 min. ($^1$H)-NMR ($CDCl_3$) consistent with structure.

C. Compound XXII (A=H, D'=isobutyl, E=morpholinyl, hydrochloride salt)

A solution of 22 mg of the resultant compound of Example 161B in ethyl acetate was treated at −20° C. Nitrogen was then bubbled through the mixture for 15 min and solvent removed in vacuo to yield an oily semi-solid mass which was used directly for the ensuing reaction.

D. Compound 161

A solution of the resultant compound of Example 161C in $CH_2Cl_2$ was added, at ambient temperature under an atmosphere of nitrogen, to a solution of 16 mg of the resultant compound of Example 48A and 18 mg N,N-diisopropylethylamine in $CH_2Cl_2$. The mixture was stirred for 14 h, diluted with $CH_2Cl_2$, washed and saturated with $NaHCO_3$ and saturated NaCl, then dried over $MgSO_4$, filtered, and concentrated in vacuo. The residue was purified by preparative HPLC to provide 21 mg of the title product as an oily solid. TLC: Rf=0.22, 20% diethyl ether/$CH_2Cl_2$. HPLC: Rt=13.01 min. ($^1$H)-NMR ($CDCl_3$) consistent with structure.

EXAMPLE 162

Compound 162

A solution of 30 mg of the resultant compound of Example 166A was deprotected with hydrogen chloride gas and the resultant compound was reacted with the resultant compound of Example 155A in the manner described in Example 155B. After concentration of the mixture in vacuo and workup, the residue was purified by thick layer silica gel chromatography using 5% MeOH/$CH_2Cl_2$ as eluant, followed by preparative reversed-phase $C_{18}$ HPLC using a linear gradient of 35% to 100% $CH_3CN/H_2O$) with 0.1% TFA as eluant to obtain 6.2 mg of the title compound. TLC: Rf=0.65, 5% MeOH/$CH_2Cl_2$. HPLC: Rt=15.93 min ($^1$H)-NMR ($CDCl_3$) consistent with structure.

EXAMPLE 163

Compound 163

A 120.3 mg portion of the resultant compound of Example 153B was reacted with the resultant compound of Example 82A as described in Example 82B. After workup and concentration in vacuo, the residue was purified by low pressure silica gel column chromatography using 50% EtOAc in $CH_2Cl_2$ eluent, followed by preparative reversed-phase $C_{18}$ HPLC using a linear gradient of 40% to 100% acetonitrile/water for elution to obtain 44.3 mg of the title compound. TLC: Rf=0.18, 50% EtOAc/$CH_2Cl_2$. HPLC: Rt=13.13 min; ($^1$H) NMR ($CDCl_3$) consistent with structure.

EXAMPLE 164

A. N-hydroxysuccinimidyl-(2-phenyl)ethyl carbonate

A solution of 306 mg of phenethyl alcohol and 535 mg of N,N'-disuccinimidyl carbonate in acetonitrile was treated, at ambient temperature under an atmosphere of nitrogen, with 810 mg of N,N-diisopropylethylamine. The mixture was stirred for 60 h and concentrated in vacuo. The residue was taken up in ethyl acetate and washed with saturated $NaHCO_3$, saturated NaCl, then dried over $MgSO_4$, filtered, and concentrated in vacuo to yield the title product as a yellow oil. TLC: Rf=0.40 (5% methanol in $CH_2Cl_2$). ($^1$H)-NMR ($CDCl_3$) consistent with structure.

B. Compound 164

A solution of 81 mg of the resultant compound of Example 164A in $CH_2Cl_2$ was added, at ambient temperature under an atmosphere of nitrogen, to a solution of 41 mg of the resultant compound of example 40a and 45 mg N,N-diisopropylethylamine in $CH_2Cl_2$. The mixture was stirred for 4 h, diluted with $CH_2Cl_2$, washed with saturated $NaHCO_3$ and saturated NaCl, then dried over $MgSO_4$, filtered, and concentrated in vacuo. The residue was subjected to preparative HPLC to yield 18 mg of the title product. TLC: Rf=0.83 (5:10:85 $NH_4H/CH_3OH/CH_2Cl_2$). HPLC: Rt=15.78 min. ($^1$H)-NMR ($CDCl_3$) consistent with structure.

EXAMPLE 165

Compound 165

A solution of 36 mg of the resultant compound of Example 51D in 4:1 $CH_2Cl_2$/saturated aqueous $NaHCO_3$ was treated sequentially, at ambient temperature under an atmosphere of nitrogen, with 20 mg of p-toluenesulfonyl chloride and 18 mg of sodium bicarbonate. The mixture was stirred for 3 h, diluted with $CH_2Cl_2$, washed with saturated NaCl then dried over $MgSO_4$, filtered, and concentrated in vacuo. The residue was purified by low pressure silica gel chromatography using 5 diethyl ether/$CH_2Cl_2$ as eluent to provide 38 mg of the title product as a white solid. TLC: Rf=0.15, 5% diethyl ether/$CH_2Cl_2$. HPLC: Rt=15.27 min. ($^1$H)-NMR ($CDCl_3$) consistent with structure.

EXAMPLE 166

A. Compound XXII (P=tert-butoxycarbonyl, D'=cyclopentylmethyl, E=4-methoxyphenyl)

To a solution of the resultant compound of Example 114B (1.8 g, 4.96 mmol) in $CH_2Cl_2$ (10 mL) was added 4-methoxylbenzensulfonyl chloride (2.10 g, 9.93 mmol), followed by addition of a saturated solution of sodium bicarbonate (3 mL) and 0.83 g of solid sodium bicarbonate. The mixture was stirred at ambient temperature for 24 hours. The solution was diluted with 200 mL $CH_2Cl_2$, the organics were separated, dried over anhydrous $MgSO_4$, and concentrated under reduced pressure. The crude product was purified via medium pressure liquid chromatography using $CH_2Cl_2$, followed by 1:99 methanol/$CH_2Cl_2$ followed by 2:98 methanol/$CH_2Cl_2$ as the solvent system to give 1.49 g of the title compound as a white solid. TLC: Rf=0.37, 3:97 methanol/$CH_2Cl_2$; ($^1$H)-NMR ($CDCl_3$) consistent with structure.

B. Compound XXII (P=H, D'=cyclopentylmethyl, E=4-hydroxyphenyl)

A solution of the resultant compound of Example 166A (1.11 g, 2.08 mmol) in $CH_2Cl_2$ (20 mL) was added to a solution of boron tribromide in $CH_2Cl_2$ (1.0M, 10.4 mL). The mixture was stirred at ambient temperature for 24 hours. The solution was poured onto 40 mL of a saturated solution of sodium bicarbonate. The aqueous layer was extracted with 250 mL $CH_2Cl_2$ followed by extraction with 250 mL EtOAc. The combined organics were dried over anhydrous $MgSO_4$, concentrated under reduced pressure and the crude product purified via medium pressure column chromatography using a gradient solvent system of $CH_2Cl_2$, followed by 1:99 methanol/$CH_2Cl_2$, followed by 9:98 methanol/$CH_2Cl_2$, followed by a 1:5:95 concentrated $NH_4OH$/methanol/$CH_2Cl_2$ solution as the solvent system to give 0.38 g of the title compound. TLC: Rf=0.18, 3:97 methanol/$CH_2Cl_2$, ($^1$H)-NMR ($CDCl_3$) consistent with structure.

C. Compound 166

To a solution of the resultant compound of Example 166B (300 mg, 0.69 mmol) in $CH_2Cl_2$ (5 mL) was added triethylamine (0.12 mL, 8.6 mmol), followed by slow addition over 3 hours of the resultant compound of Example 82A (0.21 g, 0.77 mmol) as a solution in $CH_2Cl_2$ (5 mL). The mixture was stirred at ambient temperature for 24 hours. The solution was diluted with 250 mL $CH_2Cl_2$, washed with water, dried over anhydrous $MgSO_4$, and the organics concentrated under reduced pressure. The crude product was purified via medium pressure column chromatography using a gradient solvent system of $CH_2Cl_2$ followed by 1:99 methanol/$CH_2Cl_2$, followed by 2:98 methanol/$CH_2Cl_2$ as the solvent system to give 110 mg of a white solid. TLC: Rf=0.14 (3:97 methanol/$CH_2Cl_2$), HPLC: Rt=12.69 min, ($^1$H)-NMR ($CDCl_3$) consistent with structure.

EXAMPLE 167

Compound 167

A solution of 102 mg of the resultant compound of Example 51D in 4:1 $CH_2Cl_2$/saturated aqueous $NaHCO_3$ was treated sequentially, at ambient temperature under an atmosphere of nitrogen, with 65 mg of p-nitrobenzenesulfonyl chloride and 51 mg of sodium bicarbonate. The mixture was stirred for 14 h, diluted with $CH_2Cl_2$, washed with saturated NaCl, then dried over $MgSO_4$, filtered, and concentrated in vacuo. The residue was purified by low pressure silica gel chromatography using 20% diethyl ether/$CH_2Cl_2$ as eluent to provide 124 mg of the title product as a white solid. TLC: Rf=0.36, 20% diethyl ether/$CH_2Cl_2$. HPLC: Rt=15.15 min. ($^1$H)-NMR ($CDCl_3$) consistent with structure.

EXAMPLE 168

Compound 168

A solution of 124 mg of the resultant compound of Example 167 in ethyl acetate was treated, at ambient temperature, with 13 mg of 10% palladium on carbon. The mixture was stirred for 14 h under an atmosphere of hydrogen, filtered through a pad of Celite filter agent, and concentrated in vacuo. The residue was subjected to preparative HPLC to yield 82 mg of the title product as a white solid. TLC: Rf=0.10, 20% ether/$CH_2Cl_2$. HPLC: Rt=13.16 min. ($^1$H)-NMR ($CDCl_3$) consistent with structure.

EXAMPLE 169

Compound 169

To a solution of the resultant compound of Example 166B (80 mg, 0.18 mmol) in $CH_2Cl_2$ (15 mL) was added a saturated solution of sodium bicarbonate (5 mL) followed by the addition of the resultant compound of Example 48A (55 mg, 0.24 mmol). The mixture was stirred at ambient temperature for 5 hours. The solution was diluted with 200 mL $CH_2Cl_2$, the organics separated, dried over anhydrous $MgSO_4$, and concentrated under reduced pressure. The crude product was purified via medium pressure liquid chromatography using $CH_2Cl_2$, followed by 1:99 methanol/$CH_2Cl_2$ as the solvent system to give 56 mg of the title compound as a white solid. TLC: Rf=0.24, 3:97 methanol/$CH_2Cl_2$, HPLC: Rt=14.29 min. ($^1$H)-NMR ($CDCl_3$) consistent with structure.

EXAMPLE 170

A. Compound XXII (A=tert-butoxycarbonyl, D'=cyclopentylmethyl, E=4,nitrophenyl)

To a solution of the resultant compound of Example 114B (250 mg, 0.69 mmol) in $CH_2Cl_2$ (15 mL) was added a saturated solution of sodium bicarbonate (5 mL) followed by solid sodium bicarbonate (0.12 g, 1.37 mmol) and 4-nitrobenzensulfonyl chloride (200 mg, 0.9 mmol). The mixture was stirred at ambient temperature for 24 hours. The solution was diluted with 200 mL $CH_2Cl_2$, the organics separated, dried over anhydrous $MgSO_4$, and concentrated under reduced pressure. The crude product was purified via medium pressure liquid chromatography using a gradient solvent system of $CH_2Cl_2$ followed by 1:99 methanol/$CH_2Cl_2$ to give 360 mg of the title compound as an orange solid. TLC: Rf=0.45, 3:97 methanol/$CH_2Cl_2$. ($^1$H)-NMR ($CDCl_3$) consistent with structure.

B. Compound XXII (A=H, D'=cyclopentylmethyl, E-4-nitrophenyl, hydrochloride salt)

To the resultant compound of Example 170A (360 mg, 0.66 mmol) was added 10% w/w HCl in EtOAc (15 mL). The mixture was stirred for 3 hours at ambient temperature. The solution was concentrated under reduced pressure to give 310 mg of the title compound as an orange solid which was used directly for subsequent reaction. TLC: Rf=0.70, 1:10:90 $NH_4OH$/methanol/$CH_2Cl_2$.

C. Compound 170

To a solution of the resultant compound of Example 170B (310 mg, 0.64 mmol) in $CH_2Cl_2$ (15 mL) was added a saturated solution of sodium bicarbonate (5 mL) followed by the addition of solid sodium bicarbonate (0.11 g, 1.3 mmol) and the resultant compound of Example 48A (0.18 g, 0.77 mmol). The mixture was stirred at ambient temperature for 24 hours. The solution was diluted with 150 mL $CH_2Cl_2$, the organics separated, dried over anhydrous $MgSO_4$, and concentrated under reduced pressure. The crude product was purified via medium pressure liquid chromatography using $CH_2Cl_2$, followed by 1:99 methanol/$CH_2Cl_2$ as the solvent system to give 0.32 g of the title compound as a white solid. TLC: Rf=0.28, 3:97 methanol/$CH_2Cl_2$, HPLC: Rt=16.06 min, ($^1$H)-NMR ($CDCl_3$) consistent with structure.

EXAMPLE 171

Compound 171

A solution of the resultant compound of Example 170C (0.19 g, 0.34 mmol) in EtOAc (10 mL) was treated at ambient temperature with 50 mg of 10% palladium on carbon and hydrogenated for 72 hours under a slight positive pressure of hydrogen. The mixture was filtered and concentrated in vacuo and the crude product purified via medium pressure liquid chromatography using $CH_2Cl_2$, followed by 1:99 methanol/$CH_2Cl_2$, followed by 3:97 methanol/$CH_2Cl_2$, followed by 10:90 methanol/$CH_2Cl_2$ as the solvent system to give 97 mg of the title compound as a white solid. TLC: Rf=0.25, 3:97 methanol/$CH_2Cl_2$, HPLC: Rt=14.28 min, ($^1$H)-NMR ($CDCl_3$) consistent with structure.

EXAMPLE 172

A. Compound XXII (A=tert-butoxycarbonyl, D'=cyclopentylmethyl, E=2,4-dinitrophenyl)

To a solution of the resultant compound of Example 114B (500 mg, 1.38 mmol) in $CH_2Cl_2$ (15 mL) was added a saturated solution of sodium bicarbonate (5 mL) followed by solid sodium bicarbonate (0.23 g, 2.76 mmol) and 2,4-dinitrobenzenesulfonyl chloride (440 mg, 1.65 mmol). The mixture was stirred at ambient temperature for 2 hours. The solution was diluted with 200 mL $CH_2Cl_2$, the organics separated, dried over anhydrous $MgSO_4$, and concentrated under reduced pressure. The crude product was purified via medium pressure liquid chromatography using a gradient solvent system of $CH_2Cl_2$, followed by 1:99 methanol/$CH_2Cl_2$ to give 700 mg of the title compound as a brown solid. TLC: Rf=0.48, 3:97 methanol/$CH_2Cl_2$, ($^1$H)-NMR ($CDCl_3$), consistent with structure.

B. Compound XXII (A=H, D'=cyclopentylmethyl, E-2,4-dinitrophenyl, hydrochloride salt)

To a the resultant compound of Example 172A (700 mg, 1.18 mmol) was added 10% w/w HCl in EtOAc (20 mL). The mixture was stirred for 3 hours at ambient temperature. The solution was concentrated under reduced pressure to give 590 mg of the title compound as a brown solid which was used without subsequent purification. TLC: Rf=0.55, 1:10:90 $NH_4OH$/methanol/$CH_2Cl_2$.

C. Compound 172

To a solution of the resultant compound of 172B (590 mg, 1.11 mmol) in $CH_2Cl_2$ (15 mL) was added a saturated solution of sodium bicarbonate (5 mL), followed by solid sodium bicarbonate (0.19 g, 2.2 mmol) and the resultant compound of Example 48A (0.31 g, 1.3 mmol). The mixture was stirred at ambient temperature for 24 hours. The solution was diluted with 150 mL $CH_2Cl_2$, the organics separated, dried over anhydrous $MgSO_4$, and the organics concentrated under reduced pressure. The crude product was purified via medium pressure liquid chromatography using a $CH_3OH/CH_2Cl_2$ gradient as eluant, to yield the product as 0.59 g of a white solid. HPLC: Rt=16.36 min, ($^1H$)-NMR ($CDCl_3$) consistent with structure.

EXAMPLE 173

Compound 173

A solution of the resultant compound of Example 172C (0.20 g, 0.33 mmol) in EtOAc (10 mL) was treated under ambient temperature with 50 mg of 10% palladium on carbon and hydrogenated for 72 hours under a slight positive pressure of hydrogen. The mixture was filtered and concentrated in vacuo and the crude product purified via medium pressure liquid chromatography using $CH_2Cl_2$, followed by 1:99 methanol/$CH_2Cl_2$, 3:97 methanol/$CH_2Cl_2$, and 10:90 methanol/$CH_2Cl_2$ as the solvent system to give 120.2 mg of the title compound as a light brown solid. TLC: Rf=0.17, 3:97 methanol/$CH_2Cl_2$, HPLC: Rt=13.47 min, ($^1H$)-NMR ($CDCl_3$) consistent with structure.

EXAMPLE 174

A. 4-Benzyloxybenzenesulfonyl chloride

To 0.87 g of dimethylformamide, at 0° C. under an atmosphere of nitrogen, was added 1.61 g of sulfuryl chloride. The mixture was stirred for 15 min and treated with 2.00 g of benzyl phenyl ether. The mixture was then heated at 100° C. for 1.5 h, cooled to about 40° C., poured onto ice, extracted with $CH_2Cl_2$, dried over $MgSO_4$, filtered, and concentrated in vacuo. The residue was purified by low pressure silica gel chromatography using 10% ethyl acetate in hexane as eluent to provide 0.78 g of the title product as a white solid. TLC: Rf=0.46, 10% ethyl acetate in hexane. ($^1H$)-NMR ($CDCl_3$) consistent with structure.

B. Compound 174

A solution of 30 mg of the resultant compound of Example 51D in 4:1 $CH_2Cl_2$/saturated aqueous $NaHCO_3$ was treated sequentially, at ambient temperature under an atmosphere of nitrogen, with 24 mg of the resultant compound of Example 174A and 18 mg of sodium bicarbonate. The mixture was stirred for 14 h, diluted with $CH_2Cl_2$, washed with saturated NaCl then dried over $MgSO_4$, filtered, and concentrated in vacuo. The residue was purified by low pressure silica gel chromatography using 20% diethyl ether/$CH_2Cl_2$ as the eluent to provide 14 mg of the title product as a white solid. TLC: Rf=0.43, 20% diethyl ether/$CH_2Cl_2$. HPLC: Rt=17.01 min. ($^1H$)-NMR ($CDCl_3$) consistent with structure.

EXAMPLE 175

Compound 175

A solution of 11 mg of the resultant compound Example 174B in ethyl acetate was treated at ambient temperature, with 2 mg of 10% palladium on carbon. The mixture was stirred for 14 h under an atmosphere of hydrogen, filtered through a pad of Celite filter agent, filtered, and concentrated in vacuo. The residue was purified by low pressure silica gel chromatography using 10% methanol in $CH_2Cl_2$ as the eluent to provide 9 mg of the title product as a white solid. TLC: Rf=0.38, 10% methanol in $CH_2Cl_2$. HPLC: Rt=13.37 min. ($^1H$)-NMR ($CDCl_3$) consistent with structure.

EXAMPLE 176

A. 1,3-Benzodioxole-5-sulfonyl chloride

To 3.50 g of dimethylformamide, at 0° C. under an atmosphere of nitrogen, was added 6.47 g of sulfuryl chloride. The mixture was stirred 15 min and treated with 5.32 g of 1,3-benxodioxole. The mixture was then heated at 120° C. for 45 min, cooled to about 40° C., poured onto ice, extracted with $CH_2Cl_2$, dried over $MgSO_4$, filtered, and concentrated in vacuo. The residue was purified by low pressure silica gel chromatography using 40% $CH_2Cl_2$ in hexane as eluent to provide 2.70 g of the title product as a yellow solid. TLC: Rf=0.37, 40% $CH_2Cl_2$ in hexane. ($^1H$) -NMR ($CDCl_3$) consistent with structure. ps B. Compound XXII (A=tert-butoxy, D'=isobutyl, E=3,4-benzodioxole)

A solution of 49 mg of the resultant compound of Example 39A in 4:1 $CH_2Cl_2$/saturated aqueous $NaHCO_3$ was treated sequentially, at ambient temperature under an atmosphere of nitrogen, with 45 mg of the resultant compound of Example 176A and 28 mg of sodium bicarbonate. The mixture was stirred for 14 h, diluted with $CH_2Cl_2$, washed with saturated NaCl then dried over $MgSO_4$, filtered, and concentrated in vacuo. The residue was purified by low pressure silica gel chromatography using 20% diethyl ether/$CH_2Cl_2$ as the eluent to provide 71 mg of the title product as a waxy solid. TLC: Rf=0.65, 20% diethyl ether/$CH_2Cl_2$. ($^1H$)-NMR ($CDCl_3$) consistent with structure.

C. Compound XXII (A=H, D'=isobutyl, E=3,4-benzodioxole, hydrochloride salt)

A solution of 71 mg of the resultant compound of Example 176B in ethyl acetate was treated at −20 ° C. with HCl gas. The HCl was bubbled through the mixture for 20 min over which time the temperature was allowed to warm to 20° C. Nitrogen was then bubbled through the mixture for 15 min and solvent removed in vacuo to yield 66 mg of the title product as a white solid which was used directly in subsequent reactions.

D. Compound 176

A solution of 18 mg of the resultant compound of Example 176C in $CH_2Cl_2$ was added, at ambient temperature under an atmosphere of nitrogen, to a solution of 13 mg of the resultant compound of Example 48A and 14 mg N,N-diisopropylethylamine in $CH_2Cl_2$. The mixture was stirred for 16 h, diluted with $CH_2Cl_2$, washed with saturated $NaHCO_3$ and saturated NaCl, then dried over $MgSO_4$, filtered, and concentrated in vacuo. The residue was purified by low pressure silica gel chromatography using 5% diethyl ether/$CH_2Cl_2$ as the eluent to provide 9 mg of the title product as a white solid. TLC: Rf=0.14, 5% diethyl ether/ $CH_2Cl_2$. HPLC: Rt=15.52 min; ($^1H$)-NMR ($CDCl_3$) consistent with structure.

EXAMPLE 177

A. (4-Methoxyphenyl)-methyl-4-nitrophenyl carbonate

To a solution of 1.50 g of p-nitrophenyl chloroformate in 30 mL of $CH_2Cl_2$ at 0° C. was added sequentially, 0.77 mL of 4-methoxybenzyl alcohol and 0.82 mL of 4-methyl morpholine. After stirring for a half hour at ambient temperature, the resulting mixture was diluted with $CH_2Cl_2$, washed with water, brine, dried over magnesium sulfate, filtered and concentrated in vacuo to yield a pale yellow solid which was triturated with $CH_2Cl_2$/hexane and filtered to yield 1.51 g of the title compound. TLC: Rf=0.40, 20% EtOAc/hexane.

B. Compound 177

To a solution of 96.7 mg of the resultant compound of Example 141A in 2 mL of $CH_2Cl_2$ was added sequentially, 90 μL of diisopropylethylamine and 81.3 mg of the resultant compound of Example 178A. After stirring for 24 hours, the mixture was diluted with $CH_2Cl_2$, washed with water and brine, dried over magnesium sulfate, filtered and concentrated in vacuo. The residue was purified by preparative thin layer chromatography using 5% methanol in $CH_2Cl_2$ eluent to yield 104.8 mg of the title compound. TLC: Rf=0.4, 20% EtOAc/hexane, HPLC: Rt=17.66 min, ($^1H$)NMR ($CDCl_3$) consistent with structure.

EXAMPLE 178

A. (3-Methoxyphenyl)-methyl-4-nitrophenyl carbonate

Prepared by the same route as described for Example 177A, except 3-methoxybenzyl alcohol was utilized for reaction with p-nitrophenyl chloroformate to yield the title compound as a pale yellow solid. TLC: Rf=0.40, 20% EtOAc/hexane.

B. Compound 178

To a solution of 97.8 mg of the resultant compound of Example 141A in 2 mL of $CH_2Cl_2$ was added sequentially, 91 μL of disopropylethylamine and 82.2 mg of the resultant compound of Example 178A. After stirring for 24 hours, the mixture was diluted with $CH_2Cl_2$, washed with water and brine, dried over magnesium sulfate, filtered and concentrated in vacuo. The residue was purified by preparative thin layer chromatography using 5% methanol in $CH_2Cl_2$ eluent to yield 25.7 mg of the title compound. TLC: Rf=0.4, 20% EtOAc/hexane, HPLC: Rt=17.75 min. ($^1$H)NMR ($CDCl_3$) consistent with structure.

EXAMPLE 179

A. (2-Methoxyphenyl)-methyl-4-nitrophenyl carbonate

Prepared by the same route as described for Example 177A, except 2-methoxybenzyl alcohol was utilized for reaction with p-nitrophenyl chloroformate to yield the title compound as a pale yellow solid. TLC: Rf=0.40, 20% EtOAc/hexane.

B. Compound 179

To a solution of 97.8 mg of the resultant compound of Example 141A in 2 mL of $CH_2Cl_2$ was added sequentially, 99 μL of diisoprophylethylamine and 89.2 mg of the resultant compound of Example 179A. After stirring for 24 hours the mixture was diluted with $CH_2Cl_2$, washed with water and brine, dried over magnesium sulfate, filtered and concentrated in vacuo. The residue was purified by preparative thin layer chromatography using 5% methanol in $CH_2Cl_2$ eluent to yield 107.0 mg of the title compound. TLC: Rf=0.4, 20% EtOAc/hexane, HPLC: Rt=17.58 min. ($^1$H) NMR ($CDCl_3$) consistent with structure.

EXAMPLE 180

A. 2,3-Dihydrobenzofuran-5-sulfonyl chloride

To 3.35 g of dimethylformamide, at 0° C. under an atmosphere of nitrogen, added 6.18 g of sulfuryl chloride. The mixture was stirred 15 min and treated with 4.69 g of 2,3-dihydrobenzofuran. The mixture was then heated at 100° C. for 1.5 h, cooled to about 40° C., poured onto ice, extracted with $CH_2Cl_2$, dried over $MgSO_4$, filtered, and concentrated in vacuo. The residue was taken up in ethyl acetate, cooled to 5° C. for 16 h, and the resultant pink crystals collected by vacuum filtration to provide 6.12 g of the title product. TLC: Rf=0.41, 10% ethyl acetate in hexane. ($^1$H)-NMR ($CDCl_3$) consistent with structure.

B. Compound 180

A solution of 32 mg of the resultant compound of Example 140D in 4:1 $CH_2Cl_2$/saturated aqueous $NaHCO_3$ was treated sequentially, at ambient temperature under an atmosphere of nitrogen, with 22 mg of the resultant compound of Example 180A and 18 mg of sodium bicarbonate. The mixture was stirred 14 h, diluted with $CH_2Cl_2$, washed with saturated NaCl then dried over $MgSO_4$, filtered, and concentrated in vacuo. The residue was purified by low pressure silica gel chromatography using 20% diethyl ether/$CH_2Cl_2$ as eluent to provide 20 mg of the title product as a white solid. TLC: Rf=0.52, 20% diethyl ether/$CH_2Cl_2$. HPLC: Rt=15.49 min ($^1$H)-NMR ($CDCl_3$) consistent with structure.

EXAMPLE 181

Compound 181

A solution of the resultant compound of Example 140D (150 mg, 0.4 mmol) in $CH_2Cl_2$ (10 mL) was added a saturated solution of sodium bicarbonate (5 mL) followed by solid sodium bicarbonate (0.1 g, 1.2 mmol) and 4-cyanobenzensulfonyl chloride (0.1 g, 0.48 mmol). The mixture was stirred at ambient temperature for 4 hours. The solution was diluted with 200 mL $CH_2Cl_2$, the organics separated, dried over anhydrous $MgSO_4$, and the organics concentrated under reduced pressure. The crude product was purified via medium pressure liquid chromatography using $CH_2Cl_2$, followed by 1:99 methanol/$CH_2Cl_2$ solution as the solvent system to give 0.19 g (86% yield) of the title compound as a white solid. TLC: Rf=0.40, 3:97 methanol/$CH_2Cl_2$. HPLC: Rt=15.02 min. ($^1$H)-NMR ($CDCl_3$) consistent with structure.

EXAMPLE 182

Compound 182

This compound was prepared from the resultant compound of Example 114D and the resultant compound of Example 48A in the same manner described in Example 88. After workup and purification by preparative reversed-phase $C_{18}$ HPLC using a linear gradient of 35% to 100% $CH_3CN$/$H_2O$ with 0.1% TFA as eluant, 32.8 mg of the title compound was obtained. TLC: Rf=0.25, 4% MeOH/$CH_2Cl_2$. HPLC: Rt=16.06 min; ($^1$H)NMR ($CDCl_3$) consistent with structure.

EXAMPLE 183

Compound 183

This compound was prepared from the resultant compound of Example 84 by treatment with hydrogen chloride gas and subsequent reaction with the resultant compound of Example 48A in the manner described in Example 132. After workup and purification by crystallization from EtOAc, 33.0 mg of the title compound was obtained as a white solid. TLC: Rf=0.25, 4% MeOH/$CH_2Cl_2$. HPLC: Rt=17.71 min; ($^1$H)-NMR ($CDCL_3$) consistent with structure.

EXAMPLE 184

A. (N-tert-butoxycarbonyl)-(R)-3-pyrrolidinyl-N-hydroxysuccinimidyl carbonate

To a solution of 1.0 g of (R)-3-hydroxypyrrolidine in tetrahydrofuran (50 mL) was added sequentially, at ambient temperature, 3.75 g of di-tert-butyl dicarboante and 1 mL of 2N sodium hydroxide. The mixture was stirred for 1 hour, filtered and concentrated in vacuo. The resultant compound was reacted with N,N-disuccinimidyl carbonate in the manner described in Example 155A. Workup and purification by thick layer silica gel chromatography using an EtOAc eluent yielded the title compound as a white solid; ($^1$H)-NMR ($CDCl_3$) consistent with structure.

B. Compound 184

A solution of 350 mg of the resultant compound of Example 166A was deprotected with hydrogen chloride gas and the resultant compound was reacted with the resultant compound of Example 184A in the manner described in Example 88. After concentration of the mixture in vacuo and workup, the residue was purified by thick layer silica gel chromatography using 7% MeOH/$CH_2Cl_2$ as eluant, to obtain 120 mg of the title compound. TLC: Rf=0.45, 5% MeOH/$CH_2Cl_2$. HPLC: Rt=16.97 min; ($^1$H)-NMR ($CDCl_3$) consistent with structure.

EXAMPLE 185

Compound 185

A solution of 120 mg of the resultant compound of Example 184B in EtOAc (25 mL) at 0° C. was treated with anhydrous hydrogen chloride gas for 10 min., and allowed to stand for 12 h while warming to ambient temperature. Concentration in vacuo yielded 110 mg of the title compound. TLC: Rf=0.35, 10% MeOH/89% $CH_2Cl_2$/1% $NH_4OH$. HPLC: Rt=13.72 min; ($^1H$)-NMR ($CDCl_3$) consistent with structure.

EXAMPLE 186

A. Compound XXX ((syn, anti)-OH, A=carbobenzyloxy, $R^3$=(s)-sec-butyl, $R^{3'}$=H, D'-benzyl, A'=tert-butoxycarbonyl)

A solution of 1.37 g of the resultant compound of Example 1B in 150 mL of methylene chloride was treated with 1.03 g of Cbz-Ile, 523 mg of HOBT.$H_2O$, and 742 mg of EDC. The mixture was stirred for 18 h, then diluted with 3 volumes of diethyl ether and washed sequentially with water, saturated $NaHCO_3$ solution, 10% $KHSO_4$ solution, and brine. After drying over $MgSO_4$ and concentrating in vacuo, the residue was purified by chromatography on a silica gel column using a gradient of 1% to 1.5% MeOH in $CH_2Cl_2$ as eluant to yield 2.10 g of the title compound as a white foam. TLC: Rf=0.51, 5% methanol/$CH_2Cl_2$.

B. Compound XXX ((syn, anti)-OH, A=carbobenzyloxy, $R^3$=(S)-sec-butyl, $R^{3'}$=H, D'=benzyl, A'=H), hydrochloride salt A solution of 650 mg of the resultant compound of Example 12A in 12 mL of ethyl acetate was cooled in an ice/water bath and treated with a slow stream of HCl gas for approximately 6 min with vigorous stirring. The mixture was capped and stirred for an additional 10 min, then purged with a stream of nitrogen for 15 minutes and concentrated in vacuo to yield a white solid which was used without subsequent purification. TLC: Rf=0.18, 95:5:0.5 $CH_2Cl_2$/methanol/concentrated $NH_4OH$.

C. Compound 186

A solution of 20 mg of the resultant compound of Example 186B in 0.8 mL of methylene chloride was cooled in ice/methanol (approximately 15° C.), then treated with 13.8 μL of DIEA followed by 7.6 mg of α-toluene sulfonyl chloride. The mixture was stirred for 15 h, warming slowly to ambient temperature. The mixture was concentrated to a small volume, applied to a 0.5 mm thick prep plate and eluted with 3.5% MeOH/$CH_2Cl_2$. The band containing the desired diastereomer was isolated and eluted with 8% MeOH/$CH_2Cl_2$ to yield 4.8 mg of the title compound. TLC: Rf=0.42, 15% diethyl ether/$CH_2Cl_2$. HPLC: Rt=17.81 min. NMR ($CDCl_3$): 0.78 (dd, 6H) 0.84 (m, 1H) 1.07, (m, 1H) 1.76–1.86 (m, 2H) 2.72 (m, 2H); 3.14 (s, 2H); 3.49 (dd, 1H); 3.87 (dd, 1H); 3.58 (m, 1H); 4.01 (d, 1H); 4.14, (d, 1H); 4.26, (d, 1H); 4.35, (d, 1H); 4.90, (m, 1H); 5.08, (s, 2H); 5.97, (d, 1H), 7.08, (d, 2H); 7.17, (t, 1H); 7.20–7.40, (m, 17H).

EXAMPLE 187

Compound 187

100 mg of the resulting compound 54A was treated with 1 mL of 90% aqueous TFA and allowed to stand for 12 h. The mixture was concentrated in vacuo and the residue taken up in 10 mL of dry $CH_2Cl_2$, treated with 65 mg of N-Cbz-L-isoleucine (0.235 mmol), 50 μL of DIEA (0.27 mmoles), 30 mg of HOBt (0.22 mmoles), and 42 mg of 1-(3-dimethylaminopropyl)-3-ethylcarbodiimide hydrochloride (0.22 mmoles). The mixture was stirred for 3 h, then diluted with in $CH_2Cl_2$ and washed sequentially with water, saturated $NaHCO_3$ solution, and brine. After drying over $MgSO_4$ and concentrating in vacuo, the mixture was purified by chromatography on a silica gel column using 5% $CH_3OH$ in $CH_2OH$ in $CH_2Cl_2$ as eluent to yield the title compound, a portion which was purified by preparative reversed-phase $C_{18}$ HPLC using a linear gradient of 35% to 100% $CH_3CN$/$H_2O$ with 0.1% TFA for elution to obtain 36.0 mg 99.0% pure compound. TLC: Rf=0.25, 5% $CH_3OH$ in $CH_2Cl_2$. HPLC: Rt=16.45 min; ($^1H$)-NMR ($CDCl_3$) consistent with structure.

EXAMPLE 188

Compound 188

A solution of 51 mg of the resulting compound of Example 187A in 15 mL of methanol was hydrogenated under a slight positive pressure of hydrogen in the presence of 10 mg of 10% $Pd(OH)_2$ for 14 h. After filtering and concentrating in vacuo, the crude mixture was taken up into 10 mL $CH_2Cl_2$ and treated with 0.203 mL of DIEA and 19.0 mg of 2-quinoxaloyl chloride. The mixture was stirred for 6 h, then diluted with $CH_2Cl_2$ and washed with water. After drying over $MgSO_4$ and concentrating in vacuo, a portion of the mixture was purified by preparative reversed-phase $C_{18}$ HPLC using a linear gradient of 35% to 100% $CH_3CN$/$H_2O$ with 0.1% TFA for elution to obtain 2.1 mg of the title compound. TLC: Rf=0.25, 6% $Ch_3CN$/$H_2O$ with 0.1% TFA for elution to obtain 2.1 mg of the title compound. TLC: Rf=0.25, 6% $CH_3OH$ in $CH_2Cl_2$. HPLC: Rt=16.21 min; ($^1H$)-NMR ($CDCl_3$) consistent with structure.

EXAMPLE 189

A. Compound XXII (D'=isobutyl, A=H, E=4-acetamidophenyl, trifluoroacetate salt)

To a solution of 89.3 mg. (0.167 mmol) of the resultant compound of Example 39B in $CH_2Cl_2$ (1 mL) at 0° to 5° C. was added trifluoromethanesulfonic acid (1 mL). After stirring for 0.5 h the resultant mixture was concentrated in vacuo and the resulting yellow gum used without subsequent purification.

B. Compound 189

A solution of the resultant compound of Example 189A (0.167 mmol) in $CH_2Cl_2$ was treated sequentially, at ambient temperature under an atmosphere of nitrogen, with 44.2 mg (0.217 mmol) of N-Boc-α-aminoisobutyric acid, 0.044 mL (0.251 mmol) diisopropylethylamine, 27.1 mg (0.201 mmol) of 1-hydroxybenzotriazole hydrate, 38.5 mg (0.201 mmol) 1-(3-dimethylaminopropyl)-3-ethylcarbodiimide hydrochloride. The mixture was stirred for 16 h and then concentrated in vacuo. The residue was taken up in ethyl acetate and washed with water, 0.5N hydrochloric acid, washed with sodium bicarbonate, saturated brine, dried over magnesium sulfate, filtered and concentrated in vacuo. The residue was purified by low pressure silica gel column chromatography using a 10% to 35% gradient of ethyl acetate/$CH_2Cl_2$ eluent to yield 69.3 mg of the title product as a white solid. TLC: Rf=0.46, 60% ethyl acetate/$CH_2Cl_2$, HPLC: Rt=15.0 min; ($^1H$)-NMR ($CDCl_3$) consistent with structure.

EXAMPLE 190

A. Compound XXXI (A=H, $R^3$=methyl, $R^{3'}$=methyl, D'=isobutyl, E=4-acetamidophenyl, hydrochloride salt)

To a solution of 60.1 mg of the resultant compound of Example 189B in $CH_2Cl_2$ (1 mL) at 0° to 5° C. was added trifluoromethanesulfonic acid (1 mL). After stirring for 0.75 h, the resultant mixture was concentrated in vacuo and the resulting white solid used directly for subsequent reaction.

B. Compound 190

To a solution of 37 mg (0.059 mmol) of the resultant compound of Example 190A in $CH_2Cl_2$ (3 mL) was added sequentially, at ambient temperature under an atmosphere of nitrogen, with 15.4 mg (0.089 mmol) of 1-hydroxybenzotriazole hydrate, and 17.8 mg (0.089 mmol) EDC. The mixture was stirred for 16 h and then concentrated in vacuo. The residue was taken up in EtOAc and washed with saturated brine, dried over magnesium sulfate, filtered and concentrated in vacuo. The residue was purified by thin layer silica gel column chromatography using 50% of EtOAc in $CH_2Cl_2$ as eluent to yield 32.5 mg of the title product. TLC: Rf=0.35, 50% EtOAc/$CH_2Cl_2$, HPLC: Rt=15.65 min; ($^1$H)-NMR ($CDCl_3$) consistent with structure.

EXAMPLE 191

A. (2S,3RS)-S-Amino-1-chloro-2-hydroxy-4-phenylbutane)

A solution of 2.24 g (6.71 mmol) of (1S,2RS)-N-(1-benzyl-3-chloro-2-hydroxypropyl)benzyloxycarbonylamine in 5 mL of methanol was added, at ambient temperature under a nitrogen atmosphere, to a slurry of 0.22 g (10% by weight) of 10% palladium on carbon in 60 mL methanol and hydrogenerated for 24 h, under a slight positive pressure of hydrogen. The mixture was filtered and concentrated in vacuo to yield 1.34 g of the mixed diastereomeric products. TLC: Rf=0.33, 10% $CH_3OH/CH_2Cl_2$.

B. (2S)-2-Benzyloxycarbonylamino-N$^1$-((1S,2RS)-1-benzyl-3-chloro-2-hydroxypropyl)-N$^4$-trityl succinamide A solution of 1.34 g (6.71 mmol) of the resultant compounds of Example 191A in 60 mL of dichloromethane was treated sequentially, at ambient temperature under an atmosphere of nitrogen, with 3.58 g (7.05 mmol) of Cbz-N$^δ$-trityl-asparagine, 0.95 g (7.05 mmol) of 1-hydroxybenzotriazole hydrate, 1.35 g (7.05 mmol) of EDC. The mixture was stirred for 24 hours and then concentrated in vacuo. The residue was taken up in ethyl acetate and washed with water, saturated $NaHCO_3$, saturated NaCl; dried over $MgSO_4$; filtered and concentrated in vacuo. The residue was purified by low pressure silica gel column chromatography using 10% ethyl acetate/dichloromethane as eluent to yield 3.08 g total of the mixed diastereomeric products. TLC: Rf=0.75, 0.83, 40% EtOAc/$CH_2Cl_2$; ($^1$H)-NMR ($CDCl_3$) consistent with structure.

C. (2S)-2-Amino-N$^1$-((1S,2RS)-1-benzyl-3-chloro-2-hydroxypropyl)-N$^4$-trityl succinamide A solution of 2.80 g (4.06 mmol) of the resultant compounds of Example 191B in 5 mL of methanol was added, at ambient temperature under a nitrogen atmosphere, to a slurry of 0.28 g (10% by weight) of 10% palladium on carbon in 100 mL methanol and hydrogenated for 24 h under a slight positive pressure of hydrogen. The mixture was filtered and concentrated in vacuo to yield 2.26 g of the mixed distereomeric products. TLC: Rf=0.42, 10% $CH_3OH/CH_2Cl_2$.

D. (2S)-2-((1S,2RS)-1-Benzyl-3-chloro-2-hydroxypropyl)-N$^1$-((quinoline-2-carbonyl)-amino)-N$^4$-trityl succinamide A solution of 2.26 g (4.06 mmol) of the resultant compounds of Example 191C in 60 mL of dichloromethane was treated sequentially, at ambient temperature under an atmosphere of nitrogen, with 0.74 g (4.27 mmol) of quinaldic acid, 0.58 g (4.27 mmol) of 1-hydroxybenzotriazole hydrate, and 0.82 g (4.27 mmol) of EDC. After 24 hours, 30 mL of dichloromethane was added. The mixture was washed with water, 5% $NaHCO_3$ solution, saturated NaCl, dried over $MgSO_4$, filtered and concentrated in vacuo. The residue was dissolved in 50% ethyl acetate/hexane and filtered through a plug of silica gel. Removal of the solvents yielded 2.30 g of the mixed diastereomeric products. TLC: Rf=0.53, 0.58, 40% EtOAc/$CH_2Cl_2$; ($^1$H)-NMR ($CDCl_3$) consistent with structure.

E. (2S)-2-((1S,2RS)-1-Benzyl-2-hydroxy-3-iodopropyl)N$^1$-((quinoline-2-carbonyl)-amino)-N$^4$-trityl succinamide A solution of 1.05 g (1.48 mmol) of the resultant compounds of Example 191D and 0.36 g (2.37 mmol) of sodium iodide in 15 mL of methyl ethyl ketone was heated to reflux for 24 hours. The mixture was cooled to room temperature and then concentrated in vacuo. The residue was taken up in dichloromethane and washed with water, saturated NaCl, dried over $MgSO_4$, filtered and concentrated in vacuo to yield 1.3 g of the mixed diastereomeric products. TLC: Rf=0.58, 0.65, 40% EtOAc/$CH_2Cl_2$; ($^1$H)-NMR ($CDCl_3$) consistent with structure.

F. (2S)-2-((1S,2 syn, anti)-3-(2-methylpropyl)amino-1-benzyl-2-hydroxypropyl)-N$^1$-((quinoline-2-carbonyl)-amino)-N$^4$-trityl succinamide A solution of 207.6 mg (0.26 mmol) of the resultant compounds of Example 191E and 0.5 mL (5.17 mmol) of isobutylamine in 9 mL of acetonitrile in a sealed tube was heated to reflux for 24 hours. After cooling to room temperature, the mixture was concentrated in vacuo. The residue was taken up in dichloromethane and washed with water, saturated NaCl, dried over $MgSO_4$, filtered and concentrated in vacuo to yield 209.2 mg of the mixed diastereomeric products. TLC: Rf=0.11, 10% $CH_3OH/CH_2Cl_2$; ($^1$H)-NMR ($CDCl_3$) consistent with structure.

G. Compound XIV ((syn, anti)-OH, P=quinoline-2-carbonyl, D'=isobutyl)

A solution of 192.9 mg (0.26 mmol) of the resultant compounds of Example 191F and 0.07 mL (0.388 mmol) of diisopropylethylamine in 5 mL of dichloromethane was treated with 112.9 mg (0.517 mmol) of di-tert-butyldicarbonate. After 24 hours, the mixture was diluted with dichloromethane. The mixture washed with water, 5% $NaHCO_3$, 0.5N HCl, saturated NaCl, dried over $MgSO_4$, filtered and concentrated in vacuo. The residue was purified by low pressure silica gel column chromatography using 40% ethyl acetate/dichloromethane as eluent to yield 147.3 mg of the mixed diastereomeric products. TLC: Rf=0.60, 0.67, 40% EtOAc/$CH_2Cl_2$; ($^1$H)-NMR ($CDCl_3$) consistent with structure.

H. Compounds 191

A solution of 147.3 mg (0.174 mmol) of the resultant compounds of Example 191G in 2 mL of dichloromethane was treated with 2 mL of trifluoroacetic acid. After 4 hours, the mixture was concentrated in vacuo. TLC: Rf=0.11, 10% $CH_3OH/CH_2Cl_2$. To a solution of the resultant compound in 2 mL of dichloromethane was sequentially added 0.5 mL of saturated $NaHCO_3$, small amount of solid $NaHCO_3$ and 67 mg (0.226 mmol) of a mixture of 4-acetamido-3-fluorobenzenesulphonyl chloride and 3-acetamido-4-fluorobenzenesulphonyl chloride. After 3 hours, the mixture was diluted with dichloromethane. The two layers were separated and the aqueous layer was extracted once with dichloromethane. The combined organic layer was washed with saturated NaCl then dried over $MgSO_4$, filtered and concentrated in vacuo. The residue was purified by low pressure silica gel column chromatography using 2% methanol/dichloromethane was eluent to yield 64 mg of the mixed diastereomers and regioisomers which were further purified with preparative HPLC to yield 18.9 mg of the mixed regioisomers comprising compounds 191 as a white solid. TLC: Rf=0.14, 5% $CH_3OH/CH_2Cl_2$; HPLC, Rt=13.36 min; ($^1$H)-NMR ($CDCl_3$) consistent with structure.

EXAMPLE 193

Compound 193

A solution of 81.2 mg (0.096 mmol) of the resultant lower Rf diastereomer of Example 9/192A in 3 mL of dichloromethane was treated with 3 mL of trifluoroacetic acid. After 4 hours, the mixture was concentrated in vacuo. TLC: Rf=0.11, 10% $CH_3OH/CH_2Cl_2$. To a solution of 20.6 mg (0.0431 mmol) of the resultant residue in 1 mL of dichloromethane was sequentially added 0.3 mL of saturated $NaHCO_3$, small amount of solid $NaHCO_3$ and 12.4 mg (0.053 mmol) of 4-acetamidobenzenesulphonyl chloride. After 3 hours, the mixture was diluted with dichloromethane. The two layers were separated and the aqueous layer was extracted once with dichloromethane. The combined organic layer was washed with brine then dried over $MgSO_4$, filtered and concentrated in vacuo. The residue was purified by preparative HPLC to yield 8.3 mg of the title compound as a white solid; TLC: Rf=0.10, 5% $CH_3OH/CH_2Cl_2$; HPLC, Rt=12.7 min; ($^1$H)-NMR ($CDCl_3$) consistent with structure.

EXAMPLE 194

Compound 194

To a solution of 13.0 mg (0.026 mmol) of the trifluoroacetic acid deprotection product described in Example 193 in 1 mL of dichloromethane was sequentially added 0.3 mL of saturated $NaHCO_3$, small amount of solid $NaHCO_3$ and 8.4 mg (0.033 mmol) of 5-(isoxazol-3-yl)thiophene-2-sulphonyl chloride. After 3 hours, the mixture was diluted with dichloromethane. The two layers were separated and the aqueous layer was extracted once with dichloromethane. The combined organic layer was washed with brine then dried over $MgSO_4$, filtered and concentrated in vacuo. The residue was purified by preparative HPLC to yield 5.1 mg of the title product as a white solid; TLC: Rf=0.27, 5% $CH_3OH/CH_2Cl_2$; HPLC, Rt=14.4 min; ($^1$H)-NMR ($CDCl_3$) consistent with structure.

EXAMPLE 195

A. Compound XXII(A=(S)-3-tetrahydrofuryl, D'=cyclopentylmethyl, A'=tert-butoxycarbonyl)

To a solution of 264 mg of the resultant compound of Example 140D in 10 mL of $CH_2Cl_2$ was added 0.14 mL of disopropylethylamine and 175 mg of di-tert butylpyrocarbonate. After stirring for 4 hours, the mixture was diluted with 50 mL of $CH_2Cl_2$, washed with 0.5N of HCl and brine, dried over magnesium sulfate, filtered and concentrated in vacuo to yield 364 mg of the title compound as a white solid which was used without subsequent purification. TLC: Rf=0.58, 40% $EtOAc/CH_2Cl_2$.

B

A solution of 334 mg of the resultant compound of Example 195A in 5 mL of ethanol was hydrogenated under 30 psi of hydrogen in the presence of 80 mg of platinum (IV) oxide for 24 hours. The mixture was filtered and concentrated. The residue was purified by a low pressure silica gel column chromatography using 20% EtOAc in $CH_2Cl_2$ eluent to yield 268 mg of the title compound. TLC: Rf=0.55, 40% $EtOAc/CH_2Cl_2$. ($^1$H)-NMR ($CDCl_3$) consistent with structure.

C

A solution of 268 mg of the resultant compound of Example 195B in 10 mL of EtOAc was treated with anhydrous HCl gas for 5 min. The reaction mixture was sparged with nitrogen then concentrated in vacuo and the resulting white solid used without subsequent purification for subsequent reaction.

D. Compound 195

To a solution of 233 mg of the crude resultant compound of Example 195C in 10 mL of $CH_2Cl_2$ was added 2 mL of saturated aqueous sodium bicarbonate and 149 mg of 4-methyloxybenzene sulfonyl chloride. After 3 hours, the resulting mixture was diluted with $CH_2Cl_2$, washed with sodium bicarbonate, brine, dried over magnesium sulfate, filtered and concentrated in vacuo. The residue was purified by low pressure silica gel column chromatography using 0% to 20% $EtOAc/CH_2Cl_2$ to yield 225 mg of the title compound as a white solid. TLC: Rf=0.40, 20% $EtOAc/CH_2Cl_2$; HPLC: Rt=15.65 min.: ($^1$H)NMR ($CDCl_3$) consistent with structure.

EXAMPLE 196

A. (1S,2S)-N-(1-Isobutyl-3-chloro-2-hydroxypropyl) benzyloxycarbonylamine

To a solution of N-Cbz-leucine chloromethyl ketone (2.0 g) in 20 mL of methanol was added, at 0° C., 1.0 g of sodium borohydride and the mixture was stirred at ambient temperature for 24 h. The solution was concentrated under reduced pressure and the residue partitioned between 20 mL of saturated aqueous $NH_4Cl$ and 500 ml of diethyl ether. The organic fraction was separated, dried over $MgSO_4$ and concentrated in vacuo and the residue purified by silica gel chromatography to yield 1.8 g of white solid.

B. (1S)-1-1(S)(Carbobenzyloxy)amino-2-isobutyloxirane

To a solution of the resultant compound of Example 196A (300 mg) in absolute ethanol was added 67 mg of powdered KOH. The mixture was stirred for 3 h at ambient temperature, filtered through diatomaceous earth, and concentrated in vacuo. The residue was dissolved in diethyl ether, dried over $MgSO_4$, and concentrated to yield 230 mg of colorless oil, which was used directly for subsequent reaction.

C. (2R,3S)-N$^3$-Carbobenzyloxy-N$^1$-isobutyl-1,3-diamino-2-hydroxy-5-methylhexane A 230 mg portion of the resultant compound of example 196B was suspended in 5 mL of isobutylamine and the mixture stirred overnight at ambient temperature. The mixture was concentrated in vacuo to yield the title product as 179 mg of a white solid, which was used directly for subsequent reaction.

D. Compound I (A=tert-butoxycarbonyl, x=0,D=isobutyl, E=4-methoxyphenyl, (s)-hydroxy)

Following the procedure described in Example 81, a solution of the resultant compound of example 196C (170 mg) in $CH_2Cl_2$ was reacted with 4-methoxybenzenxulfoyl chloride (150 mg) in the presence of aqueous $NaHCO_3$. Workup and silica gel chromatography yielded 90 mg of product as a white solid.

E. Compound I (A=H, x=0, D=isobutyl, E=4-methoxyphenyl, (S)-hydroxy)

A solution of the resultant compound of Example 196D (90 mg) in ethanol was treated with 50 mg of 10% palladium on carbon and the mixture stirred under an atmosphere of hydrogen. After completion of reaction, the mixture was filtered and concentrated in vacuo to yield 60 mg of the title compound which was used directly for subsequent reaction.

F. Compound 196

Reaction of the resultant compound of Example 196E (60 mg) in $CH_2Cl_2$ was reacted with the resultant product of example 48A (150 mg) as described earlier yielded, following aqueous workup, drying over $MgSO_4$, filtering, and concentration in vacuo, a residue which was purified by silica gel chromatography using methanol/$CH_2CL_2$ as eluant to yield the title product as 40 mg of white solid. [$^1$h]-NMR ($CDCl_3$) consistent with structure.

EXAMPLE 197

We measured the inhibition constants of the compounds listed in Table VII against HIV-1 protease using the above-cited method of Pennington et al.

We also measured the anti-viral potency of the compounds in CCRM-CEM cells by the above-cited method of Meek et al. In the Tables below, $K_i$ and $IC_{90}$ values are expressed in nM.

In Table VIII, the following classifications have been employed:

A: inhibits HIV replication at concentration of 100 nM or less.

B: inhibits HIV replication at concentration of between 101 and 1,000 nM.

C: inhibits HIV replication at a concentration of between 1,001 and 10,000 nM.

D: inhibits HIV replication at a concentration of between 10,001 and 40,000 nM.

ND: not tested.

TABLE VII

| Compound | $K_i$value | Compound | $K_i$value | Compound | $K_i$value |
|---|---|---|---|---|---|
| 1 | 4.0 | 55 | 430 | 109 | 6.0 |
| 2 | 2.0 | 56 | 60 | 110 | 28 |
| 3 | 32 | 57 | 200 | | |
| 4 | 19 | 58 | 34 | 111 | 0.3 |
| 5 | 2.0 | 59 | 206 | 112 | 4.0 |
| 6 | 3.0 | 60 | 4.0 | 113 | 3.0 |
| 7 | 8.0 | | | 114 | 0.35 |
| 8 | 850 | 61 | 4.0 | 115 | 0.5 |
| 9 | 4.0 | 62 | 72 | 116 | <0.1 |
| 10 | 4.0 | 63 | 7.0 | 117 | 0.26 |
| | | 64 | 3.0 | 118 | <0.1 |
| 11 | 34 | 65 | 0.7 | 119 | 1.8 |
| 12 | 0.1 | 66 | 0.4 | 120 | 11 |
| 13 | 0.2 | 67 | 7,400 | | |
| 14 | 0.1 | 68 | 120 | 121 | 2.0 |
| 15 | <0.1 | 69 | 42 | 122 | 1.2 |
| 16 | <0.1 | 70 | 25 | 123 | 10 |
| 17 | <0.1 | | | 124 | 1.1 |
| 18 | <0.1 | 71 | 470 | 125 | 0.3 |
| 19 | <0.1 | 72 | 4000 | 126 | 310 |
| 20 | 0.1 | 73 | 140 | 127 | 650 |
| | | 74 | 11 | 128 | >5000 |
| 21 | 0.7 | 75 | 290 | 129 | 19 |
| 22 | 1.0 | 76 | ND | 130 | 14 |
| 23 | 1.5 | 77 | ND | | |
| 24 | 32,500 | 78 | ND | 131 | 60 |
| 25 | 3,000 | 79 | ND | 132 | 6.0 |
| 26 | 0.1 | 80 | ND | 133 | 24 |
| 27 | 8.0 | | | 134 | 8.4 |
| 28 | 17 | 81 | 2.3 | 135 | 2.7 |
| 29 | 17 | 82 | 1.5 | 136 | 18 |
| 30 | 61 | 83 | ND | 137 | 26 |
| | | 84 | 1.4 | 138 | 1.4 |
| 31 | ND | 85 | 4.0 | 139 | 1.2 |
| 32 | 2.5 | 86 | 5.0 | 140 | <0.1 |
| 33 | 80 | 87 | 10 | | |
| 34 | 17 | 88 | 1.4 | 141 | 0.1 |
| 35 | 4.0 | 89 | 2.0 | 142 | <0.1 |
| 36 | 19 | 90 | 93 | 143 | <0.1 |
| 37 | 0.1 | | | 144 | 8.0 |
| 38 | 1.5 | 91 | 2.5 | 145 | 1.4 |
| 39 | 17 | 92 | 20 | 146 | 2.0 |
| 40 | 1,100 | 93 | 0.8 | 147 | 1.6 |
| | | 94 | 1.7 | 148 | 0.2 |
| 41 | 220 | 95 | 1.3 | 149 | 1.7 |
| 42 | 46 | 96 | 8.0 | 150 | 6.0 |
| 43 | 4,200 | 97 | 2.5 | | |
| 44 | 5.0 | 98 | 0.5 | 151 | 0.8 |
| 45 | 6.0 | 99 | 0.24 | 152 | 2.5 |
| 46 | 154 | 100 | 0.16 | 153 | 0.2 |
| 47 | 4.0 | | | 154 | 0.5 |
| 48 | 1.4 | 101 | 250 | 155 | 1.7 |
| 49 | 9.0 | 102 | 33 | 156 | 2.8 |
| 50 | 11 | 103 | 4.5 | 157 | 0.7 |
| | | 104 | 5.5 | 158 | <0.1 |

TABLE VII-continued

| Compound | $K_i$value | Compound | $K_i$value | Compound | $K_i$value |
|---|---|---|---|---|---|
| 51 | ND | 105 | 7.5 | 159 | 0.2 |
| 52 | 0.4 | 106 | 1.4 | 160 | 1.0 |
| 53 | 27 | 107 | 1.4 | | |
| 54 | 22 | 108 | 2.0 | 161 | 20 |
| 162 | 0.5 | | | | |
| 163 | 0.5 | | | | |
| 164 | 130 | | | | |
| 165 | 0.4 | | | | |
| 166 | <0.1 | | | | |
| 167 | 0.45 | | | | |
| 168 | 0.6 | | | | |
| 169 | <0.1 | | | | |
| 170 | 0.2 | | | | |
| 171 | 0.2 | | | | |
| 172 | 21 | | | | |
| 173 | 0.6 | | | | |
| 174 | 10 | | | | |
| 175 | 0.1 | | | | |
| 176 | <0.1 | | | | |
| 177 | <0.1 | | | | |
| 178 | 0.1 | | | | |
| 179 | 0.4 | | | | |
| 180 | <0.1 | | | | |
| 181 | 0.3 | | | | |
| 182 | 0.2 | | | | |
| 183 | 0.1 | | | | |
| 184 | 5.0 | | | | |
| 185 | 3.5 | | | | |
| 186 | 140 | | | | |
| 187 | 0.3 | | | | |
| 188 | 11.5 | | | | |
| 189 | 5,500 | | | | |
| 190 | ND | | | | |
| 191 | 33 | | | | |
| 192 | 67 | | | | |
| 193 | 400 | | | | |
| 194 | 350 | | | | |
| 195 | 0.2 | | | | |
| 196 | ND | | | | |
| 1001 | 220 | | | | |
| 1002 | 28 | | | | |
| 1003 | 8 | | | | |
| 1004 | 0.2 | | | | |
| 1005 | 250 | | | | |
| 1006 | 8 | | | | |
| 1007 | 42 | | | | |
| 1008 | 20 | | | | |
| 1009 | 20 | | | | |
| 1010 | 4 | | | | |
| 1011 | 1500 | | | | |
| 1012 | 11 | | | | |
| 1013 | 1500 | | | | |
| 1014 | 9300 | | | | |
| 1015 | 19 | | | | |

TABLE VIII

| Compound | $IC_{90}$ Range | Compound | $IC_{90}$ Range |
|---|---|---|---|
| 1 | C | 55 | ND |
| 2 | B | 56 | ND |
| 3 | C | 57 | ND |
| 4 | C | 58 | ND |
| 5 | B | 59 | ND |
| 6 | B | 60 | C |
| 7 | D | | |
| 8 | ND | 61 | C |
| 9 | B | 62 | ND |
| 10 | B | 63 | C |
| 11 | ND | 64 | C |
| 12 | A | 65 | C |
| 13 | A | 66 | B |
| 14 | A | 67 | ND |

TABLE VIII-continued

| Compound | $IC_{90}$ Range | Compound | $IC_{90}$ Range |
|---|---|---|---|
| 15 | A | 68 | ND |
| 16 | B | 69 | ND |
| 17 | B | 70 | ND |
| 18 | B | | |
| 19 | B | 71 | ND |
| 20 | A | 72 | ND |
| 21 | A | 73 | ND |
| 22 | B | 74 | ND |
| 23 | B | 75 | ND |
| 24 | ND | 76 | ND |
| 25 | ND | 77 | ND |
| 26 | B | 78 | ND |
| 27 | C | 79 | ND |
| 28 | ND | 80 | ND |
| 29 | C | | |
| 30 | ND | 81 | C |
| 31 | ND | 82 | C |
| 32 | C | 83 | ND |
| 33 | ND | 84 | C |
| 34 | ND | 85 | C |
| 35 | B | 86 | B |
| 36 | ND | 87 | C |
| 37 | B | 88 | B |
| 38 | C | 89 | C |
| 39 | C | 90 | ND |
| 40 | ND | | |
| | | 91 | B |
| 41 | ND | 92 | ND |
| 42 | ND | 93 | B |
| 43 | ND | 94 | B |
| 44 | B | 95 | C |
| 45 | C | 96 | ND |
| 46 | ND | 97 | B |
| 47 | C | 98 | B |
| 48 | B | 99 | B |
| 49 | C | 100 | A |
| 50 | C | | |
| | | 101 | ND |
| 51 | C | 102 | ND |
| 52 | B | 103 | C |
| 53 | ND | 104 | C |
| 54 | C | 105 | ND |
| | | 106 | C |
| | | 107 | C |
| | | 108 | C |
| 109 | B | 163 | B |
| 110 | ND | 164 | ND |
| | | 165 | B |
| 111 | C | 166 | A |
| 112 | B | 167 | B |
| 113 | B | 168 | A |
| 114 | B | 169 | A |
| 115 | B | 170 | B |
| 116 | A | | |
| 117 | C | 171 | A |
| 118 | B | 172 | ND |
| 119 | C | 173 | A |
| 120 | ND | 174 | ND |
| | | 175 | A |
| 121 | C | 176 | ND |
| 122 | C | 177 | ND |
| 123 | ND | 178 | ND |
| 124 | D | 179 | ND |
| 125 | B | 180 | ND |
| 126 | ND | | |
| 127 | ND | 181 | ND |
| 128 | ND | 182 | B |
| 129 | ND | 183 | B |
| 130 | ND | 184 | ND |
| | | 185 | ND |
| 131 | ND | 186 | ND |
| 132 | ND | 187 | B |
| 133 | ND | 188 | C |
| 134 | ND | 189 | ND |
| 135 | C | 190 | ND |
| 136 | ND | | |
| 137 | ND | 191 | C |

TABLE VIII-continued

| Compound | $IC_{90}$ Range | Compound | $IC_{90}$ Range |
|---|---|---|---|
| 138 | B | 192 | C |
| 139 | B | 193 | ND |
| 140 | A | 194 | ND |
| | | 195 | A |
| 141 | B | 196 | ND |
| 142 | A | 1001 | ND |
| 143 | A | 1002 | ND |
| 144 | B | 1003 | B |
| 145 | B | 1004 | A |
| 146 | B | 1005 | ND |
| 147 | B | 1006 | ND |
| 148 | A | 1007 | ND |
| 149 | B | 1008 | ND |
| 150 | B | 1009 | ND |
| | | 1010 | ND |
| 151 | C | 1011 | ND |
| 152 | ND | 1012 | ND |
| 153 | ND | 1013 | ND |
| 154 | ND | 1014 | ND |
| 155 | B | 1015 | A |
| 156 | B | | |
| 157 | B | | |
| 158 | A | | |
| 159 | B | | |
| 160 | A | | |
| 161 | ND | | |
| 162 | C | | |

As demonstrated in Tables VII and VIII, all of the compounds tested displayed inhibitory and anti-viral activity. Moreover, several of these compounds exhibited activity levels far greater than those of known HIV protease inhibitors.

While we have described a number of embodiments of this invention, it is apparent that our basic constructions may be altered to provide other embodiments which utilize the products and processes of this invention. Therefore, it will be appreciated that the scope of this invention is to be defined by the appended claims, rather than by the specific embodiments which have been presented by way of example.

We claim:

1. A compound of formula I:

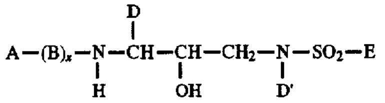

(I)

wherein:

A is selected from the group consisting of H; Ht; $-R^1-$Ht; $-R^1-C_1-C_6$ alkyl, which is optionally substituted with one to two groups independently selected from the group consisting of hydroxy, $C_1-C_4$ alkoxy, Ht, —O—Ht, $-NR^2-CO-N(R^2)(R^2)$ and $-CO-N(R^2)(R^2)$; and $-R^1-C_2-C_6$ alkenyl, which is optionally substituted with one to two groups independently selected from the group consisting of hydroxy, $C_1-C_4$ alkoxy, Ht, —O—Ht, $-NR^2-CO-N(R^2)(R^2)$ and $-CO-N(R^2)(R^2)$;

each $R^1$ is independently selected from the group consisting of —C(O)—, $S(O)_2$—, —C(O)—C(O)—, —O—C(O)—, $-O-S(O)_2$, $-NR^2-S(O)_2-$, $-NR^2-C(O)-$ and $-NR^2-C(O)-C(O)-$;

each Ht is independently selected from the group consisting of $C_3-C_7$ cycloalkyl; $C_5-C_7$ cycloalkenyl; $C_6-C_{10}$ aryl; and 5-7 membered saturated or unsaturated heterocycle, containing one or more heteroatoms selected from N and O, with the proviso that said heterocycle may not be a pyridyl group and wherein said heterocycle is optionally benzofused; and wherein any member of said Ht is optionally substituted with one to two substituents independently selected from the group consisting of oxo, —$OR^2$, —$R^2$, —$N(R^2)(R^2)$, —$R^2$—OH, —CN, —$CO_2R^2$, —C(O)—$N(R^2)(R^2)$, —$S(O)_2$—$N(R^2)(R^2)$, —$N(R^2)$—C(O)—$R_2$, —C(O)—$R^2$, —$S(O)_n$—$R^2$, —$OCF_3$, —$S(O)_n$—$R^7$, methylenedioxy, —$N(R^2)$—$S(O)_2(R^2)$, halo, —$CF_3$, —$NO_2$, $R^7$ and —O—$R^7$;

each $R^2$ is independently selected from the group consisting of H and $C_1$–$C_3$ alkyl optionally substituted with $R^7$;

B, when present, is —$N(R^2)$—$C(R^3)(R^3)$—C(O)—;

x is 0 or 1;

each $R^3$ is independently selected from the group consisting of H, Ht, $C_1$–$C_6$ alkyl, $C_2$–$C_6$ alkenyl, $C_3$–$C_6$ cycloalkyl and $C_5$–$C_6$ cycloalkenyl, wherein any member of said $R^3$, except H, is optionally substituted with one to two substituents independently selected from the group consisting of —$OR^2$, —C(O)—NH—$R^2$, —$S(O)_n$—$N(R^2)(R^2)$, Het, —CN, —$SR^2$, —$CO_2R^2$, and $NR^2$—C(O)—$R^2$;

each n is independently 1 or 2;

D and D' are independently selected from the group consisting of $R^7$; $C_1$–$C_4$ alkyl substituted with $C_3$–$C_6$ cycloalkyl, —O—$R^7$ or $R^7$, and optionally substituted with one additional substituent selected from $C_3$–$C_6$ cycloalkyl, —O—$R^7$, $R^7$, $OR^2$ or —$R^3$; $C_2$–$C_4$ alkenyl substituted with $C_3$–$C_6$ cycloalkyl, —O—$R^7$ or $R^7$, and optionally substituted with one additional substituent selected from $C_3$–$C_6$ cycloalkyl, —O—$R^7$, $R^7$, $OR^2$ or —$R^3$; $C_3$–$C_6$ cycloalkyl, which is optionally substituted with or fused with $R^7$; and $C_5$–$C_6$ cycloalkenyl, which is optionally substituted with or fused with $R^7$;

each $R^7$ is independently selected from the group consisting of phenyl and 3–6 membered carbocyclic ring, wherein said carbocyclic ring may be saturated or unsaturated and wherein $R^7$ is optionally substituted with one to two groups independently selected from the group consisting of oxo, —$OR^2$, —$R^2$, —$N(R^2)(R^2)$, —$N(R^2)$—C(O)—$R^2$, —$R^2$—OH, —CN, —$CO_2R^2$, —C(O)—$N(R^2)(R^2)$, halo and —$CF_3$;

E is a 5-membered heterocyclic ring containing one S and optionally containing N as an additional heteroatom, wherein said heterocyclic ring is optionally substituted with one to two groups independently selected from the group consisting of —$CH_3$, $R^4$ and Ht; and each $R^4$ is independently selected from the group consisting of —$OR^2$, —C(O)—$NHR^2$, —$S(O)_2$—$NHR^2$, halo, —$NR^2$—C(O)—$R^2$ and —CN.

2. The compound according to claim 1, wherein said compound has the structure of formula XXII:

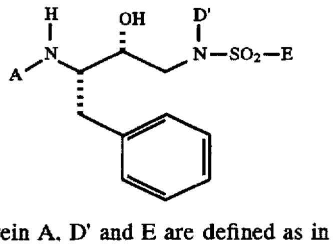

(XXII)

wherein A, D' and E are defined as in claim 1.

3. The compound according to claim 1, wherein said compound has the structure of formula XXIII:

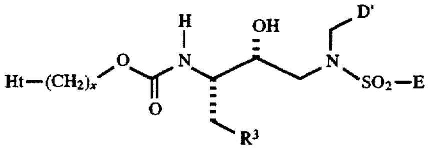

(XXIII)

wherein x, Ht, $R^3$, D' and E are defined as in claim 1.

4. The compound according to claim 1, wherein:

A is selected from the group consisting of H; —$R^1$—Ht; —$R^1$—$C_1$–$C_6$ alkyl, which is optionally substituted with one to two groups independently selected from the group consisting of hydroxy, $C_1$–$C_4$ alkoxy, Ht and —O—Ht; and —$R^1$—$C_2$–$C_6$ alkenyl, which is optionally substituted with one to two groups independently selected from the group consisting of hydroxy, $C_1$–$C_4$ alkoxy, Ht and —O—Ht;

each $R^1$ is independently selected from the group consisting of —C(O)—, —$S(O)_2$—, —C(O)—C(O)—, —O—CO—, —O—$S(O)_2$— and —$NR^2$—$S(O)_2$—;

each Ht is independently selected from the group consisting of $C_3$–$C_7$ cycloalkyl; $C_5$–$C_7$ cycloalkenyl; $C_6$–$C_{10}$ aryl; and 5–7 membered saturated or unsaturated heterocycle, containing one or more heteroatoms selected from N and O, with the proviso that said heterocycle may not be a pyridyl group and wherein said heterocycle is optionally benzofused; and wherein any member of said Ht is optionally substituted with one to two substituents independently selected from the group consisting of oxo, —$OR^2$, —$R^2$, —$N(R^2)_2$, —$R^2$—OH, —CN, —$CO_2R^2$, —C(O)—$N(R^2)_2$ and —$S(O)_2$—$N(R^2)_2$;

B, when presents is —NH—$CH(R^3)$—C(O)—;

x is 0 or 1;

each $R^3$ is independently selected from the group consisting of Ht, $C_1$–$C_6$ alkyl, $C_2$–$C_6$ alkenyl, $C_3$–$C_6$ cycloalkyl and $C_5$–$C_6$ cycloalkenyl, wherein any member of said $R^3$ is optionally substituted with one to two substituents independently selected from the group consisting of —$OR^2$, —C(O)—NH—$R^2$, —$S(O)_n$—$N(R^2)_2$, Ht and —CN;

n is 1 or 2; and

D and D' are independently selected from the group consisting of $R^7$; $C_1$–$C_4$ alkyl substituted with $C_3$–$C_6$ cycloalkyl, —O—$R^7$ or $R^7$; $C_2$–$C_4$ alkenyl substituted with $C_3$–$C_6$ cycloalkyl, —O—$R^7$ or $R^7$, and optionally substituted with one additional substituent selected from $C_3$–$C_6$ cycloalkyl, —O—$R^7$, $R^7$, $OR^2$ or —$R^3$; $C_3$–$C_6$ cycloalkyl, which is optionally substituted with or fused with $R^7$; and $C_5$–$C_6$ cycloalkenyl, which is optionally substituted with or fused with $R^7$; with the proviso that when D is attached to N, D may not be methyl or $C_2$ alkenyl.

5. The compound according to claim 2 or 3, wherein:

A is $R^1$—Ht; and

D' is selected from the group consisting of $C_1$–$C_3$ alkyl and $C_3$ alkenyl, wherein said alkyl or alkenyl is substituted with one to two groups independently selected from the group consisting of $C_3$–$C_6$ cycloalkyl, —O—$R^7$ and $R^7$, and optionally substituted with one additional —$OR^2$.

6. The compound according to claim 3, wherein:

$R^3$ is selected from the group consisting of $C_1$–$C_6$ alkyl, $C_2$–$C_6$ alkenyl, $C_5$–$C_6$ cycloalkyl, $C_5$–$C_6$ cycloalkenyl and Ht, wherein Ht is a 5–6 membered saturated or unsaturated heterocycle, and wherein any member of said $R^3$ is optionally substituted with one to two substituents independently selected from the group consisting of —$OR^2$, —C(O)—NH—$R^2$, —$S(O)_nN(R^2)(R^2)_2$, Ht, —CN, —$SR^2$, —$C(O)_2R^2$, and $NR^2$—C(O)—$R^2$; and D' is selected from the group consisting of $C_1$–$C_3$ alkyl and $C_3$ alkenyl, wherein said alkyl or alkenyl is substituted with one to two groups independently selected from the group consisting of $C_3$–$C_6$ cycloalkyl, —O—$R^7$ and $R^7$, and optionally substituted with one additional —$OR^2$.

7. A compound selected from the group consisting of:

4-Fluoro-N-((2 syn,3S)-2-hydroxy-4-phenyl-3-((S)-tetrahydrofuran-3-yloxycarbonylamino)-butyl)-N-isobutyl-benzenesulfonamide (compound 35);

3,4-Dichloro-N-((2 syn,3S)-2-hydroxy-4-phenyl-3-((S)-tetrahydrofuran-3-yloxycarbonylamino)-butyl)-N-isobutyl-benzenesulfonamide (compound 37);

N-(4-(((2 syn,3S)-2-Hydroxy-4-phenyl-3-(pyridin-3-yl-methoxycarbonylamino)-butyl)-isobutyl-sulfamoyl)-phenyl)acetamide (compound 44);

2,4-Dimethyl-thiazole-5-sulfonic acid-(1,1-dimethyl-ethoxycarbonylamino)-(2 syn,3S)-2-hydroxy-4-phenyl-butyl)-isobutyl-amide (compound 46);

N-(4-(((2 syn,3S)-2-Hydroxy-4-phenyl-3-((S)-tetrahydrofuran-3-yloxycarbonylamino)-butyl)-isobutyl-sulfamoyl)-phenyl)-acetamide (compound 48);

4-Fluoro-N-((2 syn,3S)-2-hydroxy-4-phenyl-3-((R)-tetrahydrofuran-3-yloxycarbonylamino)-butyl)-N-isobutyl-benzenesulfonamide and 4-Fluoro-N-((2 syn,3S)-2-hydroxy-4-phenyl-3-((R)-tetrahydrofuran-3-yloxycarbonylamino)-butyl)-N-isobutyl-benzenesulfonamide (compounds 52);

Benzo(1,2,5)oxadiazole-5-sulfonic acid ((2 syn,3S)-2-hydroxy-4-phenyl-3-(pyridin-3-yl-methoxycarbonylamino)-butyl)-isobutylamide (compound 66);

N-(4-(((2 syn,3S)-2-Hydroxy-4-phenyl-3-((R)-tetrahydrofuran-3-yloxycarbonylamino)-butyl)-isobutyl-sulfamoyl-phenyl)-acetamide and N-(4-(((2 syn,3S)-2-Hydroxy-4-phenyl-3-((S)-tetrahydrofuran-3-yloxycarbonylamino)-butyl)-isobutyl-sulfamoyl)-phenyl)-acetamide (compounds 86);

N-(2-Fluoro-5-(((2 syn,3S)-2-hydroxy-4-phenyl-3-((S)-tetrahydrofuran-3-yloxycarbonylamino)-butyl)-isobutyl-sulfamoyl)-phenyl)-acetamide (compound 88);

N-(3-(((2 syn,3S)-2-Hydroxy-4-phenyl-3-((S)-tetrahydrofuran-3-yloxycarbonylamino)-butyl)-isobutyl-sulfamoyl)-phenyl)-acetamide (compound 91);

4-Fluoro-N-((2 syn,3S)-2-hydroxy-4-phenyl-3-((R)-tetrahydrofuran-3-yloxycarbonylamino)-butyl)-N-isobutyl-benzenesulfonamide (compound 93);

N-(4-(((syn)-2-Hydroxy-(S)-4-phenyl-3-((tetrahydrofuran-(R)-3-yl)-oxycarbonylamino)-butyl)-isobutyl-sulfamoyl)-phenyl)-acetamide (compound 94);

4-Fluoro-N-(2 syn,3S)-2-hydroxy-4-phenyl-3-((tetrahydro-furan-(R)-3-ylmethoxycarbonylamino)-butyl)-N-isobutyl-benzenesulfonamide and 4-Fluoro-N-(2 syn,3S)-2-hydroxy-4-phenyl-3-((tetrahydro-furan-(S)-3-ylmethoxycarbonylamino)-butyl)-N-isobutyl-benzenesulfonamide (compounds 97);

4-Fluoro-N-((2 syn,3S)-2-hydroxy-4-phenyl-3-(pyridin-3-yl-methoxycarbonylamino)-butyl)-N-isobutyl-benzenesulfonamide (compound 98);

4-Chloro-N-((2 syn,3S)-2-hydroxy-4-phenyl-3-((S)-tetrahydrofuran-3-yloxycarbonylamino)-butyl)-isobutyl-benzenesulfonamide (compound 99);

N-((2 syn,3S)-2-Hydroxy-4-phenyl-3-((S)-tetrahydrofuran-3-yloxycarbonylamino)-butyl)-N-isobutyl-4-methoxy-benzenesulfonamide (compound 100);

4-Fluoro-N-(2-(syn)-hydroxy-3-((2-oxazolidon-(S)-4-yl)-methoxycarbonylamino)-4-(S)-phenyl-butyl)-N-isobutyl-benzenesulfonamide (compound 109);

Benzene-1,3-disulfonic acid 1-amide 3-((2 syn,3S)-2-hydroxy-4-phenyl-3-(3-(S)-tetrahydrofuran-3-yloxycarbonylamino)-butyl)-isobutyl-amide (compound 112);

Furan-3-sulfonic acid (2 syn,3S)-2-hydroxy-4-phenyl-3-((S)-tetrahydrofuran-3-yloxycarbonylamino)-butyl)-isobutyl-amide (compound 113);

N-((3-Allyloxycarbonylamino)-(2 syn,3S)-2-hydroxy-4-phenyl-butyl)-N-cyclopentylmethyl-4-fluoro-benzenesulfonamide (compound 114);

N-Cyclopentylmethyl-N-((3-ethoxycarbonylamino)-(2 syn, 3S)-2-hydroxy-4-phenyl-butyl)-4-fluoro-benzenesulfonamide (compound 115);

4-Chloro-N-cyclopentylmethyl-N-((2 syn,3S)-2-hydroxy-4-phenyl-3-((S)-tetrahydrofuran-3-yloxycarbonylamino)-butyl)-benzenesulfonamide (compound 116);

4-Chloro-N-cyclopentylmethyl-N-((2 syn,3S)-2-hydroxy-4-phenyl-3-(pyridin-3yl-methoxycarbonyl)-butyl)-benzenesulfonamide (compound 118);

N-(4-(Cyclopentylmethyl-((2 syn,3S)-2-hydroxy-4-phenyl-3-((S)-tetrahydrofuran-3-yloxycarbonylamino)-butyl)-sulfamoyl)-phenyl)-acetamide (compound 125);

3-Chloro-N-((2 syn,3S)-2-hydroxy-4-phenyl-3-((S)-tetrahydrofuran-3-yloxycarbonylamino)-butyl)-N-isobutyl-benzenesulfonamide (compound 138);

4-Chloro-N-cyclopentylmethyl-N-(2-(syn)-hydroxy-3-((2-oxazolidon-4-(S)-yl-methyl)-oxycarbonylamino)-4-phenyl-butyl)-benzenesulfonamide (compound 139);

N-cyclopentylmethyl-N-((2 syn,3S)-2-hydroxy-4-phenyl-3-((S)-tetrahydrofuran-3-yloxycarbonylamino)-butyl)-4-methoxy-benzenesulfonamide (compound 140);

N-((3-allyloxycarbonylamino)-(2 syn,3S)-2-hydroxy-4-phenyl-butyl)-N-cyclopentylmethyl-4-methoxy-benzenesulfonamide (compound 141);

N-Cyclopentylmethyl-N-((2 syn,3S)-2-hydroxy-4-phenyl-3-(3-pyridin-3-yl-methoxycarbonylamino)-butyl-4-methoxy-benzenesulfonamide (compound 142);

Pyridine-3-sulfonic acid ((2 syn,3S)-2-hydroxy-4-phenyl-3-((S)-tetrahydrofuran-3-yloxycarbonylamino)-butyl)-isobutyl-amide, trifluoroacetic acid salt (compound 144);

5-Isoxazol-3-yl-thiophene-2-sulfonic acid ((2 syn,3S)-2-hydroxy-4-phenyl-3-((S)-tetrahydrofuran-3-yloxycarbonylamino)-butyl)-isobutyl-amide (compound 145);

N-(4-((3-(Allyloxycarbonylamino)-(2 syn,3S)-2-hydroxy-4-phenyl-butyl)-cyclopentylmethylsulfamoyl)-phenyl)-acetamide (compound 146);

N-(4-(Cyclopentylmethyl-((2 syn,3S)-2-hydroxy-4-phenyl-3-(pyridin-3-yl-methoxycarbonylamino)-butyl)-sulfamoyl)-phenyl)-acetamide (compound 147);

N-Cyclopentylmethyl-N-((2 syn,3S)-2-hydroxy-4-phenyl-3-((S)-tetrahydrofuran-3-yloxycarbonylamino)-butyl)-benzenesulfonamide (compound 148);

Pyridine-3-sulfonic acid cyclopentylmethyl-((2 syn,3S)-2-hydroxy-4-phenyl-3-((S)-tetrahydrofuran-3-yloxycarbonylamino)-butyl)-amide (compound 149);

Piperidine-1-sulfonic acid ((2 syn,3S)-2-hydroxy-4-phenyl-3-((S)-tetrahydrofuran-3-yloxycarbonylamino)-butyl)-isobutyl-amide (compound 150);

N-4-((2-(syn)-Hydroxy-3-((2-methoxymethyl-allyloxycarbonylamino)-4-(S)-phenyl-butyl)-isobutyl-sulfamoyl)-phenyl)-acetamide (compound 155);

1-Acetyl-2,3-dihydro-1H-indole-6-sulfonic acid ((allyloxycarbonylamino)-(2 syn,3S)-2-hydroxy-4-phenyl-butyl)-cyclopentylmethyl-amide (compound 156);

1-Acetyl-2,3-dihydro-1H-indole-6-sulfonic acid cyclopentylmethyl-((2 syn,3S)-2-hydroxy-4-phenyl-3-((S)-tetrahydrofuran-3-yloxycarbonylamino)-butyl)-amide (compound 157);

N-Cyclohexylmethyl-N-((2 syn,3S)-2-hydroxy-4-phenyl-3-((S)-tetrahydrofuran-3-yloxycarbonylamino)-butyl)-4-methoxy-benzenesulfonamide (compound 158);

N-Cyclohexylmethyl-4-fluoro-N-((2 syn,3S)-2-hydroxy-4-phenyl-3-((S)-tetrahydrofuran-3-yloxycarbonylamino)-butyl)-benzenesulfonamide (compound 159);

N-(4-(Cyclohexylmethyl)-((2 syn,3S)-2-hydroxy-4-phenyl-3-((S)-tetrahydrofuran-3-yloxycarbonylamino)-butyl)-sulfamoyl-phenyl)-acetamide (compound 160);

N-((2 syn,3S)-2-Hydroxy-4-phenyl-3-(pyridin-4-yl-methoxycarbonylamino)-butyl)-N-isobutyl-4-methoxy-benzenesulfonamide (compound 163);

N-((2 syn,3S)-2-Hydroxy-4-phenyl-3-((syn)-tetrahydrofuran-3-yloxycarbonylamino)-butyl)-N-isobutyl-4-methyl-benzenesulfonamide (compound 165);

N-cyclopentylmethyl-4-hydroxy-N-((2 syn,3S)-2-hydroxy-4-phenyl-3-(pyridin-3-yl-methoxycarbonylamino)-butyl)-benzenesulfonamide (compound 166);

N-((2 syn,3S)-2-Hydroxy-4-phenyl-3-((S)-tetrahydrofuran-3-yloxycarbonylamino)-butyl)-N-isobutyl-4-nitro-benzenesulfonamide (compound 167);

4-Amino-N-((2 syn,3S)-2-Hydroxy-4-phenyl-3-((S)-tetrahydrofuran-3-yloxycarbonylamino)-butyl)-N-isobutyl-benzenesulfonamide (compound 168);

N-Cyclopentylmethyl-4-hydroxy-N-((2 syn,3S)-2-hydroxy-4-phenyl-3-((S)-tetrahydrofuran-3-yloxycarbonylamino)-butyl)-benzenesulfonamide (compound 169);

N-Cyclopentylmethyl-N-((2 syn,3S)-2-hydroxy-4-phenyl-3-((S)-tetrahydrofuran-3-yloxycarbonylamino)-butyl)-4-nitro-benezensulfonamide (compound 170);

4-Amino-N-cyclopentylmethyl-N-((2 syn,3S)-2-hydroxy-4-phenyl-3-((S)-tetrahydrofuran-3-yloxycarbonylamino)-butyl)-benzenesulfonamide (compound 171);

2,4-Diamino-N-cyclopentylmethyl-N-((2 syn,3S)-2-hydroxy-4-phenyl-3-((S)-tetrahydrofuran-3-yloxycarbonylamino)-butyl)-benzenesulfonamide (compound 173);

4-Hydroxy-N-(2 syn,3S)-2-hydroxy-4-phenyl-3-((S)-tetrahydrofuran-3-yloxycarbonylamino)-butyl)-N-isobutyl-benzenesulfonamide (compound 175);

N-Cyclopentylmethyl-4-fluoro-N-((2 syn,3S)-2-hydroxy-4-phenyl-3-((S)-tetrahydrofuran-3-yloxycarbonylamino)-butyl)-benzenesulfonamide (compound 182);

3,4-Dichloro-N-cyclopentylmethyl-N-((2 syn,3S)-2-hydroxy-4-phenyl-3-((S)-tetrahydrofuran-3-yloxycarbonylamino)-butyl)-benzenesulfonamide (compound 183);

Benzyloxycarbonyl-(L)-isoleucine-N-(5-((3-amino-(2 syn, 3S)-2-hydroxy-4-phenyl-butyl)-isobutyl-sulfamoyl)-2-fluoro-phenyl)-acetamide (compound 187);

N-((4S,2S)-4-Cyclohexyl-2-hydroxy-3-((syn)-tetrahydrofuran-3-yloxycarbonylamino)-butyl)-N-cyclopentylmethyl-4-methoxy-benzenesulfonamide (compound 195);

N-(4-(((2 syn,3S)-3-(t-Butyldicarbonylamino)-2-hydroxy-4-phenyl-butyl)-isobutyl-sulfamoyl)-phenyl)-acetamide (compound 1001);

N-(4-(((2 syn,3S)-2-Hydroxy-4-phenyl-3-((R)-2-pyrrolidinone-4-ylmethylcarbonylamino)-butyl)-isobutyl-sulfamoyl)-phenyl)-acetamide (compound 1002);

Pyridine-3-sulfonic acid ((2 syn,3S)-2-hydroxy-4-phenyl-3-((S)-tetrahydrofuran-3-yloxycarbonylamino)-butyl)-isobutyl-amide (compound 1003);

3-Amino-4-hydroxy-N-(2 syn,3S)-2-hydroxy-4-phenyl-3-((S)-tetrahydrofuran-3-yloxycarbonylamino)-butyl)-N-isobutyl-benzenesulfonamide (compound 1004);

N-((2 syn,3S)-2-Hydroxy-4-phenyl-3-((S)-tetrahydrofuran-3-yloxycarbonylamino)-butyl)-4-methoxy-N-methylbenzenesulfonamide (compound 1005);

N-((2 syn,3S)-2-Hydroxy-4-phenyl-3-((S)-tetrahydrofuran-3-yloxycarbonylamino)-butyl)-4-methoxy-N-(2-methylpropen-2-yl)benzenesulfonamide (compound 1006);

N-((2 syn,3S)-2-Hydroxy-4-phenyl-3-((S)-tetrahydrofuran-3-yloxycarbonylamino)-butyl)-N-tetrahydrofuran-2-ylmethyl-4-methoxy-benzenesulfonamide (compound 1007);

N-Furan-2-ylmethyl-N-((2 syn,3S)-2-hydroxy-4-phenyl-3-((S)-tetrahydrofuran-3-yloxycarbonylamino)-butyl)-4-methoxy-benzenesulfonamide (compound 1008);

N-2,2-Dimethyl-3-hydroxypropyl-N-((2 syn,3S)-2-hydroxy-4-phenyl-3-((S)-tetrahydrofuran-3-yloxycarbonylamino)-butyl)-4-methoxy-benzenesulfonamide (compound 1009);

N-2-hydroxy-2-methylpropyl-N-((2 syn,3S)-2-hydroxy-4-phenyl-3-((S)-tetrahydrofuran-3-yloxycarbonylamino)-butyl)-4-methoxy-benzenesulfonamide (compound 1010);

N-((2 syn,3S)-2-Hydroxy-4-phenyl-3-((S)-tetrahydrofuran-3-yloxycarbonylamino)-butyl)-N-piperidin-4-yl-4-methoxy benzenesulfonamide (compound 1011);

N-((2 syn,3S)-2-Hydroxy-4-phenyl-3-((S)-tetrahydrofuran-3-yloxycarbonylamino)-butyl)-N-3-acetylpiperidin-4-yl-4-methoxy benzenesulfonamide (compound 1012);

N-((2 syn,3S)-2-Hydroxy-4-phenyl-3-((S)-tetrahydrofuran-3-yloxycarbonylamino)-butyl)-N-piperidin-4-ylmethyl-4-methoxy benzenesulfonamide (compound 1013);

N-((2 syn,3S)-2-Hydroxy-4-phenyl-3-((S)-tetrahydrofuran-3-yloxycarbonylamino)-butyl)-N-piperidin-4-ylethyl-4-methoxy benzenesulfonamide (compound 1014); and 3,4-Diamino-N-((2 syn,3S)-2-Hydroxy-4-phenyl-3-((S)-tetrahydrofuran-3-yloxycarbonylamino)-butyl)-N-isobutyl-benzenesulfonamide (compound 1015).

8. The compound according to claim 1, wherein said compound has a molecular weight less than or equal to about 700 g/mol.

9. A compound according to claim 8, wherein said compound has a molecular weight less than or equal to about 600 g/mol.

10. A pharmaceutical composition comprising a pharmaceutically effective amount of a compound according to any one of claims 1–3 and a pharmaceutically acceptable carrier, adjuvant or vehicle.

11. A method for treating or preventing a viral disease in a mammal caused by a virus that requires an aspartyl protease for an obligatory life cycle event, said method comprising the step of administering to said mammal a compound according to any one of claims 1–3.

12. The method according to claim 11, wherein said virus is HIV-1, HIV-2, or HTLV.

13. A method for preventing HIV infection in a mammal comprising the step of administering to said mammal a pharmaceutically effective amount of a pharmaceutical composition according to claim 10.

14. A method for treating HIV infection in a mammal comprising the step of administering to said mammal a pharmaceutically effective amount of a pharmaceutical composition according to claim 10.

15. The method according to claim 13 or 14, wherein said step of administering comprises oral administration or administration by injection.

16. The compound according to claim 1, wherein:

$R^1$ is —O—C(O)—;

each D' is independently selected from the group consisting of $C_1$–$C_4$ alkyl substituted with one to two groups selected from $C_3$–$C_6$ cycloalkyl, —O—$R^7$ or $R^7$, and optionally substituted with one additional —$OR^2$ or —$R^3$; $C_2$–$C_4$ alkenyl substituted with one to two groups selected from $C_3$–$C_6$ cycloalkyl, —O—$R^7$ or $R^7$, and optionally substituted with an additional —$O^2$ or —$R^3$; $C_3$–$C_6$ cycloalkyl, which is optionally substituted with or fused with $R^7$; and $C_5$–$C_6$ cycloalkenyl, which is optionally substituted with or fused with $R^7$; and E is a 5-membered saturated or unsaturated heterocycle, containing one S and optionally containing N as an additional heteroatom, wherein said heterocycle may optionally be benzofused; and wherein any member of said heterocycle may be optionally substituted with one to two substituents independently selected from the group consisting of oxo, —$OR^2$, —$R^2$, —$N(R^2)(R^2)$, —$R^2$—OH, —CN, —$CO_2R$, —C(O)—$N(R^2)(R^2)$, —$S(O)_2$—$N(R^2)(R^2)$, —$N(R^2)$—C(O)—$R_2$, —C(O)—$R^2$, —$S(O)_n$—$R^2$, —$OCF_3$, —$S(O)_n$—$R^7$, methylenedioxy, —$N(R^2)$—$S(O)_2(R^2)$, halo, —$CF_3$, —$NO_2$, $R^7$ and —O—$R^7$.

17. The compound according to claim 16, wherein said compound is:

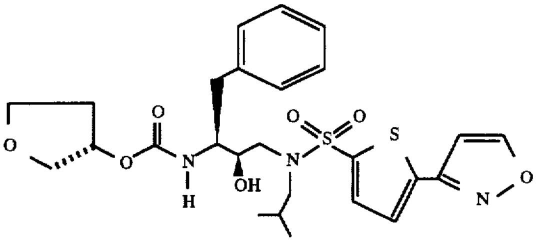

5-Isoxazol-3-yl-thiophene-2-sulfonic acid ((2 syn,3S)-2-hydroxy-4-phenyl-3-((S)-tetrahydrofuran-3-yloxycarbonylamino)-butyl)-isobutyl-amide (compound 145).

18. The pharmaceutical composition according to claim 10, wherein the viral infection is HIV 1 or HIV 2.

* * * * *

UNITED STATES PATENT AND TRADEMARK OFFICE

CERTIFICATE OF CORRECTION

PATENT NO. : 5,783,701

DATED : July 21, 1998

INVENTOR(S) : Roger D. Tung, Mark A. Murcko and Govinda Rao Bhisetti

It is certified that error appears in the above-indentified patent and that said Letters Patent is hereby corrected as shown below:

Column 159, line 13 , cancel beginning with "4-Fluoro-" to and including "(compound 44);" in column 15a, line 22.

Column 159, line 25, cancel beginning with "N-(4-(((2 syn,3S)" to and including "(compound 144);" in column 160, line 46.

Column 160, line 49, cancel beginning with ";" to and including "(compound 1015)" in column 162, line 42.

Signed and Sealed this

Eighth Day of June, 1999

Attest:

Q. TODD DICKINSON

Attesting Officer

*Acting Commissioner of Patents and Trademarks*

UNITED STATES PATENT AND TRADEMARK OFFICE

CERTIFICATE OF CORRECTION

PATENT NO. : 5,783,701
DATED : July 21,1998
INVENTOR(S) : Tung et al.

It is certified that error appears in the above-identified patent and that said Letters Patent is hereby corrected as shown below:

On title page, item [56], under OTHER PUBLICATIONS, in "M. Cushnman", delete "Delvelopment" and substitute therefor -- Development --.

On page 2, item [56], under OTHER PUBLICATIONS, in "G. Fontenot", delete "form" and substitute therefor -- from --.

On page 2, item [56], under OTHER PUBLICATIONS, in "K.P. Manfredi", delete "Specificty" and substitute therefor -- Specificity --.

Column 1, line 38, delete "case,of" and substitute therefor -- case of --.

Column 3, line 64, delete "a".

Column 5, line 11, delete "inhbitor" and substitute therefor -- inhibitor --.

Column 5, line 26, delete "DRAWINGS" and substitute therefor -- INVENTION --.

Column 7, line 29, delete "or" and substitute therefor -- of --.

Column 7, line 59, delete "cyclopentaneprqpionate," and substitute therefor -- cyclopentanepropionate, --.

Column 8, line 35, delete "-NR-C(O)-" and substitute therefor -- $-NR^2-C(O)-$ --.

UNITED STATES PATENT AND TRADEMARK OFFICE

CERTIFICATE OF CORRECTION

PATENT NO. : 5,783,701

DATED : July 21, 1998

INVENTOR(S) : Tung et al.

It is certified that error appears in the above-identified patent and that said Letters Patent is hereby corrected as shown below:

Column 9, line 32, delete "-C(O)-$NHR^7$," and substitute therefor -- -C(O)-$NHR^7$, --.

Column 9, line 52, delete "cycloalkehyl;" and substitute therefor -- cycloalkenyl; --.

Column 63, line 11, immediately after "therein." insert -- ) --.

Column 67, line 31, delete "be." and substitute therefor -- be --.

Column 67, line 32, delete "functionalites" and substitute therefor -- functionalities --.

Column 68, line 53, delete "nonhyro-" and substitute therefor -- nonhydro- --.

Column 72, line 4, delete "inhbitor" and substitute therefor -- inhibitor --.

Column 74, line 7, delete "confomrations" and substitute therefor -- conformations --.

Column 75, line 43, immediately after "period" insert -- of --.

Column 81, line 62, delete "9d,2H);" and substitute therefor -- (9d,2H); --.

Column 82, line 26, delete "2,75" and substitute therefor -- 2.75 --.

Column 83, line 63, delete "((syn," and substitute therefor -- ((syn) --.

UNITED STATES PATENT AND TRADEMARK OFFICE
CERTIFICATE OF CORRECTION

PATENT NO. : 5,783,701
DATED : July 21,1998
INVENTOR(S) : Tung et al.

It is certified that error appears in the above-identified patent and that said Letters Patent is hereby corrected as shown below:

Column 84, line 19, delete "sequentialled" and substitute therefor -- sequentially --.

Column 85, line 10, delete "738" and substitute therefor -- 7.38 --.

Column 86, line 26, immediately after "35" insert -- % --.

Column 86, line 34, delete "hydoxypropyl" and substitute therefor -- hydroxypropyl --.

Column 91, line 8, delete "(2-" and substitute therefor -- 2- --.

Column 92, line 48, delete "ps B. Compound 35".

Column 92, line 49, immediately before "A solution" insert -- B. Compound 35 --.

Column 94, line 49, delete "41" and substitute therefor -- 42 --.

Column 95, line 21, delete "pyidinecarbinol" and substitute therefor -- pyridinecarbinol --.

Column 95, line 45, delete "diethyl.ether" and substitute therefor -- diethyl ether --

Column 97, line 24, delete "(2.97 g," and substitute therefor -- (2.97g), --.

Column 97, line 32, delete "is".

Column 98, line 15, delete "hydroxyltetrahydrofuryl" and substitute therefor -- hydroxyl-tetrahydrofuryl --.

Column 99, line 2, delete "in".

UNITED STATES PATENT AND TRADEMARK OFFICE
CERTIFICATE OF CORRECTION

PATENT NO. : 5,783,701
DATED : July 21,1998
INVENTOR(S) : Tung et al.

It is certified that error appears in the above-identified patent and that said Letters Patent is hereby corrected as shown below:

Column 99, line 18, delete "Of" and substitute therefor -- of --.

Column 99, line 28, delete "of mixture was purified by preparative reversed-."

Column 99, line 29, delete "phase $C_{18}$ HPLC using a linear gradient".

Column 99, line 31, delete "$CH_2Cl_2$" and substitute therefor -- $CH_2Cl_2$. --.

Column 101, line 41, delete "(Dimethylamino)" and substitute therefor -- ((Dimethylamino) --.

Column 101, line 49, immediately after "removed" insert -- and --.

Column 103, line 33, immediately after "$CH_2Cl_2$" insert -- ; --.

Column 103, line 50, delete "was" and substitute therefor -- as --.

Column 105, line 12, delete "To a" and substitute therefor -- A --.

Column 106, line 21, delete "$MgsO_4$" and substitute therefor -- $MgSO_4$ --.

Column 108, line 43, delete "and".

Column 108, line 64, delete "butoxycaronyl," and substitute therefor -- butoxycarbonyl, --.

Column 112, line 1, delete "was".

Column 113, line 41, immediately after "To" insert -- a --.

UNITED STATES PATENT AND TRADEMARK OFFICE
CERTIFICATE OF CORRECTION

PATENT NO. : 5,783,701
DATED : July 21,1998
INVENTOR(S) : Tung et al.

It is certified that error appears in the above-identified patent and that said Letters Patent is hereby corrected as shown below:

Column 116, line 37, delete second occurrence of "was" and substitute therefor -- and --.

Column 116, line 38, immediately after "copious" insert -- amounts --.

Column 118, line 57, delete "Rt=13.9%" and substitute therefor -- Rt=13.9 --.

Column 122, line 36, delete "3,4" and substitute therefor -- 3,4- --.

Column 123, line 6, delete "liner" and substitute therefor -- linear --.

Column 124, line 12, immediately after "$CH_2Cl_2$" insert -- . --.

Column 124, line 17, immediately before "a saturated solution" insert -- by --.

Column 126, line 28, delete "(isobutenyl," and substitute therefor -- isobutenyl, --.

Column 127, line 27, delete "(3:97" and substitute therefor -- 3:97 --.

Column 128, line 64, delete "the" and substitute therefor -- then --.

Column 129, line 18, delete "the" and substitute therefor -- The --.

Column 130, line 41, delete "EtAOc" and substitute therefor -- EtOAc --.

UNITED STATES PATENT AND TRADEMARK OFFICE

CERTIFICATE OF CORRECTION

PATENT NO. : 5,783,701
DATED : July 21,1998
INVENTOR(S) : Tung et al.

It is certified that error appears in the above-identified patent and that said Letters Patent is hereby corrected as shown below:

Column 133, line 13, delete "the" and substitute therefor -- The --.

Column 133, line 23, delete "A tert" and substitute therefor -- A=tert --.

Column 134, line 21, delete "nigrogen" and substitute therefor -- nitrogen --.

Column 134, line 56, immediately before "ambient" insert -- at --.

Column 136, line 4, delete "reastion." and substitute therefor -- reaction. --

Column 136, line 15, delete "70%" and substitute therefor -- 7% --.

Column 136, line 31, immediately after "35" insert -- % --.

Column 139, line 25, delete "$CH^3CN/H_2O)$" and substitute therefor -- $CH^3CN/H_2O$ --.

Column 140, line 11, delete "5" and substitute therefor -- 5% --.

Column 142, line 53, delete "a".

Column 143, line 52, immediately after "compound" insert -- of --.

UNITED STATES PATENT AND TRADEMARK OFFICE

CERTIFICATE OF CORRECTION

PATENT NO. : 5,783,701

DATED : July 21,1998

INVENTOR(S) : Tung et al.

It is certified that error appears in the above-identified patent and that said Letters Patent is hereby corrected as shown below:

Column 144, line 7 delete "ps".

Column 145, line 11, delete "disopropylethylamine" and substitute therefor -- diisopropylethylamine --.

Column 145, line 31, delete "diioprophylethylamine" and substitute therefor -- diisopropylethylamine--.

Column 145, line 43, immediately before "added" insert -- was --.

Column 146, line 48, delete "dicarboante" and substitute therefor -- dicarbonate --.

Column 147, line 67, delete "in".

Column 148, line 4, delete "$CH_2OH$".

Column 148, line 25, delete "$Ch_3CN/H_2O$" and substitute therefor -- $CH_3CN/H_2O$ --.

Column 149, line 15, delete "(25,3RS)" and substitute therefor -- ((25,3RS) --.

Column 150, line 57, delete "was" and substitute therefor -- as --.

Column 152, line 60, delete "$CH_2CL_2$" and substitute therefor -- $CH_2Cl_2$ --.

Column 158, line 34, delete "presents" and substitute therefor -- present, --.

Column 162, line 53, delete "or preventing".

UNITED STATES PATENT AND TRADEMARK OFFICE

CERTIFICATE OF CORRECTION

PATENT NO. : 5,783,701

DATED : July 21,1998

INVENTOR(S) : Tung et al.

It is certified that error appears in the above-identified patent and that said Letters Patent is hereby corrected as shown below:

Column 162, lines 60-63, cancel claim 13.

Column 163, lines 12, delete "$-O^2$" and substitute therefor -- $-OR^2$ --.

Column 163, line 24, delete "$-CO_2R$," and substitute therefor -- $-CO_2R^2$ --.

Signed and Sealed this

Twenty-second Day of May, 2001

Attest:

NICHOLAS P. GODICI

*Attesting Officer*

*Acting Director of the United States Patent and Trademark Office*